United States Patent
Platten et al.

(10) Patent No.: US 8,536,429 B2
(45) Date of Patent: Sep. 17, 2013

(54) POLYNUCLEOTIDES ENCODING A NAX2 POLYPEPTIDE AND METHODS FOR ENHANCING SALINITY TOLERANCE IN PLANTS

(75) Inventors: John Damien Platten, Metro Manila (PH); Caitlin Byrt, Wallsend (AU); Wolfgang Spielmeyer, Gundaroo (AU); Evans Lagudah, Ngunnawal (AU); Richard Alexander James, Royalia (AU); Rana Ellen Munns, Reid (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 694 days.

(21) Appl. No.: 12/309,157

(22) PCT Filed: Jul. 12, 2007

(86) PCT No.: PCT/AU2007/000975
§ 371 (c)(1),
(2), (4) Date: Aug. 23, 2010

(87) PCT Pub. No.: WO2008/006169
PCT Pub. Date: Jan. 17, 2008

(65) Prior Publication Data
US 2010/0313289 A1 Dec. 9, 2010

(51) Int. Cl.
*C07K 1/00* (2006.01)
*C12N 15/82* (2006.01)
*A01H 1/04* (2006.01)
*A01H 5/00* (2006.01)

(52) U.S. Cl.
USPC ........ 800/320.3; 800/260; D01/126; D01/129

(58) Field of Classification Search
None
See application file for complete search history.

(56) References Cited

U.S. PATENT DOCUMENTS

| | | |
|---|---|---|
| 4,945,050 A | 7/1990 | Sanford et al. |
| 5,004,863 A | 4/1991 | Umbeck et al. |
| 5,104,310 A | 4/1992 | Saltin et al. |
| 5,141,131 A | 8/1992 | Miller et al. |
| 5,159,135 A | 10/1992 | Umbeck et al. |
| 5,177,010 A | 1/1993 | Goldman et al. |
| 5,362,865 A | 11/1994 | Austin et al. |
| 5,384,253 A | 1/1995 | Krzyzek et al. |
| 5,416,011 A | 5/1995 | Hinchee et al. |
| 5,451,513 A | 9/1995 | Maliga et al. |
| 5,463,174 A | 10/1995 | Moloney et al. |
| 5,472,869 A | 12/1995 | Krzyzek et al. |
| 5,518,908 A | 5/1996 | Corbin et al. |
| 5,545,818 A | 8/1996 | McBride et al. |
| 5,569,834 A | 10/1996 | Hinchee et al. |
| 5,589,617 A | 12/1996 | Nehra et al. |
| 5,859,347 A | 1/1999 | Brown et al. |
| 5,877,402 A | 3/1999 | Maliga et al. |
| 5,925,517 A | 7/1999 | Tyagi et al. |
| 5,932,479 A | 8/1999 | Daniell et al. |
| 6,100,447 A | 8/2000 | Wu et al. |
| 6,541,257 B2 | 4/2003 | Lemaux et al. |
| 2006/0123505 A1 | 6/2006 | Kikuchi et al. |
| 2008/0028480 A1* | 1/2008 | Lindsay et al. ............... 800/260 |

FOREIGN PATENT DOCUMENTS

| | | | |
|---|---|---|---|
| AU | 61781/94 | | 9/1994 |
| AU | 667939 | | 4/1996 |
| CA | 2092588 | | 9/1994 |
| CN | 1618804 A | * | 11/2003 |
| EP | A-239400 | | 8/1994 |
| EP | 0465572 | | 6/1995 |
| WO | WO 84/02913 | | 8/1984 |
| WO | WO 87/06614 | | 11/1987 |
| WO | WO 92/09696 | | 6/1992 |
| WO | WO 93/21335 | | 10/1993 |
| WO | WO 97/20936 | | 6/1997 |
| WO | WO 97/48814 | | 12/1997 |
| WO | WO 99/05265 | | 2/1999 |
| WO | WO 99/14314 | | 3/1999 |
| WO | WO 99/32619 | | 7/1999 |
| WO | WO 99/49029 | | 9/1999 |
| WO | WO 99/53050 | | 10/1999 |
| WO | WO 01/34815 | | 5/2001 |
| WO | WO 2005/120214 | | 12/2005 |

OTHER PUBLICATIONS

Davenport et al (Plant Physiology Mar. 2005, vol. 137 pp. 807-818).*
Gao et al. Paddy rice potassium, sodium ion transport gene and its application. Chinese Patent CN 1618804. Machine English Translation. 2003.*
Lindsay et al. A locus for sodium exclusion (Nax1), a trait for salt tolerance mapped in durum wheat. Functional Plant Biology. 2004. 31(11): 1105-1114.*
International Search Report issued by the International Searching Authority (ISA/AU) on Sep. 3, 2007 in connection with International Application No. PCT/AU2007/000975.
NCBI GenBank Accession No. DQ646332, Jun. 30, 2007.
NCBI GenBank Accession No. DQ646333, Jun. 30, 2007.
NCBI GenBank Accession No. DQ646334, Jun. 30, 2007.
NCBI GenBank Accession No. DQ646336, Jun. 30, 2007.
NCBI GenBank Accession No. DQ646337, Jun. 30, 2007.
NCBI GenBank Accession No. DQ646338, Jun. 30, 2007.
Byrt CS, et al. HKT1;5-Like Cation Transporters Linked to $Na^+$ Exclusion Loci in Wheat, *Nax2* and *Kna1*. Plant Physiology, Apr. 2007, vol. 143, pp. 1918-1928.

(Continued)

*Primary Examiner* — Cathy Kingdon Worley
*Assistant Examiner* — Ashley K Buran
(74) *Attorney, Agent, or Firm* — John P. White; Gary J. Gershik; Cooper & Dunham LLP

(57) ABSTRACT

The present invention relates to polypeptides, and polynucleotides encoding therefor, with cation transporter activity. In particular, the present invention relates to methods for producing, identifying, and/or breeding transgenic or non-transgenic plants, especially wheat or barley plants, with enhanced tolerance to saline and/or sodic soils, and/or reduced sodium accumulation in an aerial part of the plant. Also provided are plants produced using these methods.

17 Claims, 37 Drawing Sheets

(56) References Cited

OTHER PUBLICATIONS

Figure 1:
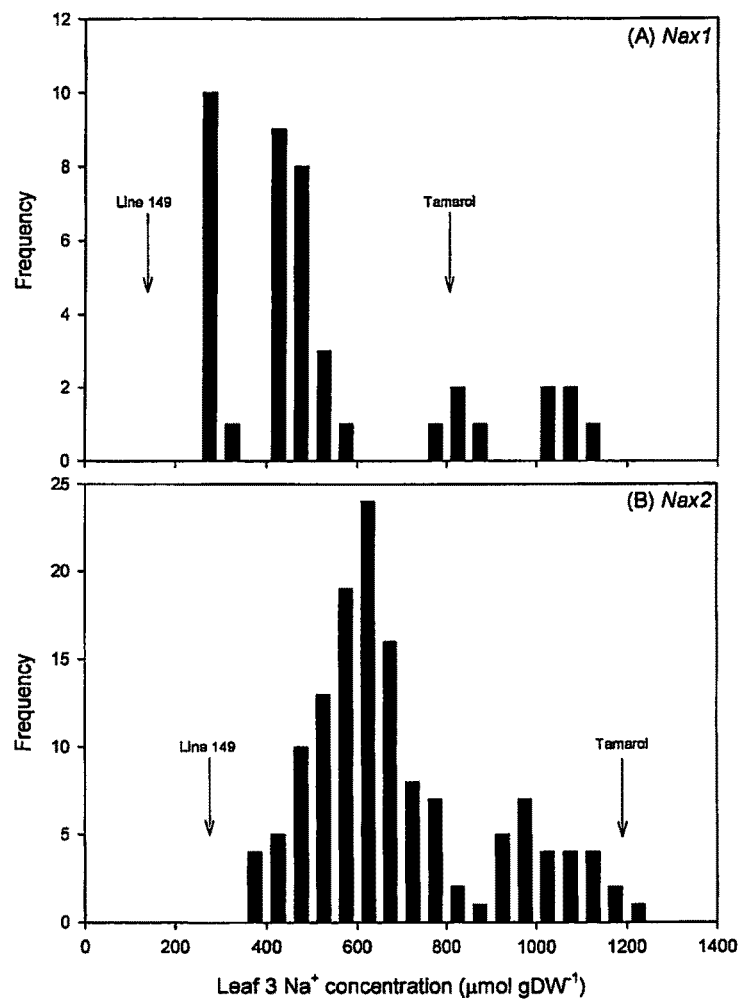

NCBI GenBank Accession No. DQ 148410, Nov. 3, 2005.
WO 2006/045829 A1 (CROPDESIGN N. V.), May 4, 2006.
James RA, et al. Physiological Characterization of Two Genes for Na$^+$ Exclusion in Durum Wheat, *Nax1* and *Nax2*. Plant Physiology, Dec. 2006. vol. 142. pp. 1537-1547.
Colmer TD. et al. Use of wild relatives to improve salt tolerance in wheat. Journal of Experimental Botany. 2006, vol. 57. No. 5. pp. 1059-1078.
US 5,962,233, 10/1999, Livak et al. (withdrawn).
The Supplementary European Search Report and Preliminary Opinion of the Examiner issued on Aug. 18, 2009 in connection with European Patent Application No. 07784642.6.
European Examination Report issued Nov. 12, 2009 in connection with European Patent Application No. 07784642.6.
Response to Examination Report filed on Sep. 2, 2010 in connection with European Patent Application No. 07784642.6.
European Examination Report issued Aug. 30, 2011 in connection with European Patent Application No. 07784642.6.
Response Examination Report filed on Jun. 28, 2012 in connection with European Patent Application No. 07784642.6.
Australian Examination Report issued Jul. 6, 2012 in connection with Australian Patent Application No. 2007272314.
Abdullah et al. (1986) "Efficient Plant Regeneration from Rice Protoplasts Through Somatic Embryogenesis" Biotechnology 4:1087.
Almeida and Allshire (2005) "RNA silencing and genome regulation" TRENDS Cell Biol 15: 251-258.
Bonnett et al. (2005) "Strategies for efficient implementation of molecular markers in wheat breeding" Molecular Breeding, 15: 75-85.
Bourque (1995) "Antisense strategies for genetic manipulation in plants" Plant Sci. 105: 125-149.
Byrt et al. (2007) "HKT1;5-Like Cation Transporters Linked to Na$^+$ Exclusion Loci in Wheat, Nax2 and Kna1$^{1(O4)}$" Plant Physiol.
Cheng at al. (1996) "Production of fertile transgenic peanut (*Arechis hypogaea* L.) plants using *Agrobacterium tumefaciens*" Plant Cell Rep. 15:653-657.
Clapp (1993) "The 16-Kilodalton N-Terminal Fragment of Human Prolactin is a Potent Inhibitor of Angiogenesis" Clin. Perinatol. 20:155-168.
Comai et al. (2004) "Efficient discovery of DNA polymorphisms in natural populations by Ecotilling" Plant J 37: 778-786.
Curiel et al. (1992) "High efficiency gene transfer mediated by adenovirus coupled to DNA-polylysine complexes via an antibody bridge" Hum. Gene Ther. 3:147-154.
Czechowski et al. (2005) "Genome-Wide Identification and Testing of Superior Reference Genes for Transcript Normalization in *Arabidopsis*" Plant Physiol. 139: 5-17.
Davenport et al. (2005) "Control of Sodium Transport in Durum Wheat" Plant Physiol 137: 807-818.
Dubcovsky et al. (1996) "Mapping of the K$^+$/Na$^+$ discrimination locus Kna1 in wheat" Theoretical and Applied Genetics 92: 448-454.
Durell et al. (1999) "Structural Models of the KtrB, TrkH, and Trk1,2 Symporters Based on the Structure of the KcsA K$^+$ Channel" Channel. Biophys. J. 77: 789-807.
Dvořák and Gorham (1992) "Methodology of gene transfer by homoeologous recombination into *Triticum turgidum*: transfer of K$^+$/Na$^+$ discrimination from *Triticum aestivum*" Genome 35: 639-646.
Dvořák et al. (1994) "Enhancement of the salt tolerance of *Triticum turgidum* L. by the Kna1 locus transferred from the *Triticum aestivum* L. chromosome 4D by homeologous recombination" Theoretical and. Applied Genetics 87: 872-877.
Eagles et al. (2001) "Implementation of markers in Australian wheat breeding" Aust. J. Agric. Res. 52:1 349-1356.
Endo and Gill (1996) "The Deletion Stocks of Common Wheat" J Heredity 87: 295-307.

Francois et al. (1986) "Effect of Salinity on Grain Yield and Quality, Vegetative Growth, and Germination of Semi-Dwarf and Durum Wheat" Agronomy Journal 78:1053-1058.
Garciadeblas et al. (2003) "Sodium transport and HKT transporters : the rice model" Plant J. 34: 788-801.
Garthwaite et al. (2005) "Salt tolerance in wild Hordeum species is associated with restricted entry of Na$^+$ and Cl$^-$ into the shoots" J Experimental Botany 56:2365-2378.
Gleave (1992) "A versatile binary vector system with a T-DNA organisational structure conducive to efficient integration of cloned DNA into the plant genome" Plant Mol. Biol. 20: 1203-1207.
Gorham et al. (1987) Theoretical and Applied Genetics 74:584-548.
Gorham et al. (1997) "Genetic analysis and physiology of a trait for enhanced K$^+$/Na$^+$ discrimination in wheat" New Phytol, 137, 109-116.
Gorham et al. (1990) "Partial characterization of the trait for enhanced K$^+$-Na$^+$ discrimination in the D genome of wheat" Planta 180, 590-597.
Grant et al. (1995) "Transformation of peas (*Pisum sativum* L.) using immature cotyledons" Plant Cell Rep. 15:254-258.
Harayama (1998) "Artificial evolution by DNA shuffling" Trends Biotechnol 16: 76-82.
Haseloff and Gerlach (1988) "Simple RNA enzymes with new and highly specific endoribonuclease activities" Nature 334:585-591.
Henikoff et al. (2004) "TILLING. Traditional Mutagenesis Meets Functional Genomics" Plant Physiol 135: 630-636.
Husain et al. (2003) "Effect of sodium exclusion train on chlorophyll retention and growth of durum wheat in saline soil" Australian Journal of Agricultural Research 54:589-597.
Jacoby (1964) "Function of Bean Roots and Stems in Sodium Retention" Plant Physiol 39: 445-449.
James et al. (2006) "Physiological Characterization of Two Genes for Na+ Exclusion in Durum Wheat, Nax1 and Nax2" Plant Physiology 142:1537-1547.
Johanson and Cheeseman (1983) "Uptake and Distribution of Sodium and Potassium by Corn Seedlings'" Plant Physiol 73: 153-158.
Koornneef and Stam (2001) "Changing Paradigms in Plant Breeding" Plant Physiology 125:156-159.
Koziel et al. (1996) "Optimizing expression of transgenes with an emphasis on post-transcriptional events" Plant Molecular Biology 32:393-405.
Kramer (1983) "The possible role of transfer cells in the adaptation of plants to salinity" Physiol. 58:549-555.
Kramer et al. (1977) "Transfer Cells in Roods of *Phaseolus coccineus*: Ultrastructure and Possible Function in Exclusion of Sodium from Shoot" Ann. Bot. 41:1031-1040.
Kumar et al. (2004) "MEGA3: Integrated software for Molecular Evolutionary Genetics Analysis and sequence alignment" Briefings in Bioinformatics 5(2)150-163.
Lacan and Durand (1996) "Na$^+$-K$^+$ Exchange at the Xylem/Symplast Boundary" Plant Physiol 110: 705-711.
Lacerda et al. (2003) "Solute accumulation and distribution during shoot and leaf development in two sorghum genotypes under salt stress" Env Exp Bot 49: 107-120.
Lagudah et al. (1991) "The Nor-D3 locus of *Triticum tauschii*: natural variation and genetic linkage to markers in chromosome 5" Genome, 34: 387-395.
Langridge et al. (2001) "Trends in genetic and genome analysis in wheat: a review" Aust J Agric Res 52: 1043-1077.
Law et al. (1981) "Intraspecific chromosome manipulation" Phil. Trans. R. Soc. Lond. B 292:509-518.
Lemieux (2000) "High Throughput Single Nucleotide Polymorphism Genotyping Technology" Current Genomics 1: 301-311.
Lindsay et al. (2004) "A locus for sodium exclusion (Nax1), a trait for salt tolerance, mapped in durum wheat" Functional Plant Biology 31: 1105-1114.
Liu et al. (1992) "Nonhomoeologous translocations between group 4, 5 and 7 chromosomes within wheat and rye" Theoretical and Applied Genetics, 83: 305-312.
Lu et al. (1993) "High Efficiency Retroviral Mediated Gene Transduction into Single Isolated Immature and Replatable CD$^{3+}$ Hematopoietic Stem/Progenitor Cells from Human Umbilical Cord Blood" J. Exp. Med. 178:2089-2096.

Maas and Grieve (1990) "Spike and Leaf Development in Salt-Stressed Wheat" Crop Science 30:1309-1313.

Mäser et al. (2002) "Glycine residues in potassium channel-like selectivity filters determine potassium selectivity in four-loop-per-subunit HKT transporters from plants" Proc. Natl. Acad. Sci. USA 99: 6428-6433.

Matsushita and Matoh (1991) "Characterization of $Na^+$ exclusion mechanisms of salt-tolerant reed plants in comparison with salt-sensitive rice plants" Physiol Plant 83: 170-176.

Millar and Waterhouse (2005) "Plant and animal microRNAs: similarities and differences" Funct Integr Genomics 5:129-135.

Munns et al. (1995) "The Significance of a Two-phase Growth Response to Salinity in Wheat and Barley" Australian Journal of Plant Physiology 22:561-569.

Munns et al. (2000) "Genetic variation for improving the salt tolerance of durum wheat" Australian Journal of Agricultural Research 51: 69-74.

Munns et al. (2002) "Avenues for increasing salt tolerance of crops, and the role of physiologically based selection traits" Plant and Soil 247:93-105.

Munns et al. (2003) "Genetic control of sodium exclusion in durum wheat" Australian Journal of Agricultural Research 54: 627-635.

Munns et al. (2006) "Approaches to increasing the salt tolerance of wheat and other cereals" Journal of Experimental Botany 57(5):1025-1043.

Munns and James (2003) "Screening methods for salinity tolerance: a case study with tetraploid wheat" Plant and Soil 253:201-218.

Murray et al. (2004) "Comparison of *Agrobacterium*-mediated transformation of four barley cultivars using the GFP and GUS reporter genes" Plant Cell Rep. 22: 397-402.

Needleman and Wunsch (1970) "A General Method Applicable to the Search for Similarities in the Amino Acid Sequence of Two Proteins" J. Mol. Biol. 48:443-453.

Nicholas et al. (1997) "GeneDoc Analysis and Visualization of Genetic Variation" EMBNEW.NEWS 4:14.

Pasquinelli et al. (2005) "MicroRNAs: a developing story" Curr Opin Genet Develop 15: 200-205.

Pellegrineschi et al. (2002) "Identification for highly transformable wheat genotypes for mass production of fertile transgenic plants" Genome 45:421-430.

Perriman et al. (1992) "Extended target-site specificity for a hammerhead ribozyme" Gene 113: 157-163.

Platten et al. (2006) "Nomenclature for HKT transporters, key determinants of plant salinity tolerance" TRENDS Plant Sci 11:372-374.

Rawson et al. (1988) "An Examination of Selection Criteria for Salt Tolerance in Wheat, Barley and Triticale Genotypes" Australian Journal of Agricultural Research 39:759-772.

Ren et al. (2005) "A rice quantitative trait locus for salt tolerance encodes a sodium transporter" Nat Genet 37: 1141-1146.

Rengasamy (2002) "Transient salinity and subsoil constraints to dryland farming in Australian sodic soils: an overview" Austrsalian Journal of Experimental Agriculture 42:351-361.

Rivelli et al. (2002) "Transient salinity and subsoil constraints to dryland farming in Australian sodic soils: an overview" Functional Plant Biology 29:1065-1074.

Roder et al. (1998) "A Microsatellite Map of Wheat" Genetics, 149: 2007-2023.

Rose et al. (2003) "CODEHOP (COnsensus-DEgenerate Hybrid Oligonucleotide Primer) PCR primer design" Nucleic Acids Res 31: 3763-3766.

Rus et al. (2004) "AtHKT1 Facilitates Na1 Homeostasis and K1 Nutrition in Planta" Plant Physiology 136: 2500-2511.

Schachtman et al. (1992) "The expression of salt tolerance from *Triticum tauschii* in hexaploid wheat" Theor Appl Genet 84: 714-719.

Schaefer (1995) "Revolutions in Rapid Amplification of cDNA Ends: New Strategies for Polymerase Chain Reaction Cloning of Full-Length cDNA Ends" Anal Biochem 227: 255-273.

Senior (1998) "Uses of Plant Gene Silencing" Biotech. Genet. Engin. Revs. 15: 79-119.

Shah et al. (1987) "Salt Tolerance in the Triticeae: The Contribution of the D Genome to Cation Selectivity in Hexaploid Wheat" Journal of Experimental Botany 38:254-269.

Sharp et al. (2001) "Validation of molecular markers for wheat breeding" Aust J Agric Res 52: 1357-1366.

Shippy et al. (1999) "The Hairpin Ribozyme" Mol. Biotech. 12: 117-129.

Shone et al. (1969) "The Absorption and Translocation of Sodium by Maize Seedlings" Planta 86: 301-314.

Slade and Knauf (2005) "TILLING moves beyond functional genomics into crop improvement" Transgenic Res 14: 109-115.

Smith et al. (2000) "Total silencing by intron-spliced hairpin RNAs" Nature 407: 319-320.

Somers et al. (2004) "A high-density microsatellite consensus map for bread wheat (*Triticum aestivum* L.)" Theor Appl Genet 109:1105-1114.

Storey (1995) "Salt Tolerance, Ion Relations and the Effect of Root Medium on the Response of Citrus to Salinity" Aust J Plant Physiol 22: 101-114.

Tester and Davenport (2003) "$Na^+$ Tolerance and $Na^+$ Transport in Higher Plants" Ann Bot (Lond) 91: 503-527.

Thompson et al. (1997) "The CLUSTAL_X windows interface: flexible strategies for multiple sequence alignment aided by quality analysis tools" Nucl. Acids Res. 25: 4876-4882.Toriyama et al. (1986) Theor. Appl. Genet. 205:34.

Wagner et al. (1992) "Coupling of adenovirus to transferrin-polylysine/DNA complexes greatly enhances receptor-mediated gene delivery and expression of transfected genes" Proc. Natl. Acad. Sci. USA 89:6099-6103.

Waterhouse et al. (1998) "Virus resistance and gene silencing in plants can be induced by simultaneous expression of sense and antisense RNA" Proc. Natl. Acad. Sci. USA 95: 13959-13964.

Accession AAA52749, Schachtman and Schroeder, (1994) 1 page.
Accession AAF68393, Uozumi et al. (2000) 1 page.
Accession AAM46870, Ghareyazie and Bennett (2002) 1 page.
Accession AAM77581, Anderson et al. (2002) 1 page.
Accession BAB93392, Sasaki et al. (2002) 3 pages.
Accession CAD37197, Rodriguez-Navarro (2002) 2 pages.
Accession CK193616.1, Crosby (2003) 2 pages.
Accession DQ148410, Lin et al. (2005) 2 pages.
Accession DR734861.1, Gulick (2005) 2 pages.
Accession DQ646342, Platten et al. (2007) 3 pages.

Platten et al. "Nomenclature for HKT transporters, key determinants of plant salinity tolerance" TRENDS in Plant Science vol. 11, No. 8, 372-374.

Summons to Attend Oral Proceedings issued in connection with European Patent Application No. 07784642.6.

Platten et al. "Nomenclature for HKT transporters, key determinants of plant salinity tolerance" Trends in Plant Science vol. 11 No. 8, 372-374.

* cited by examiner

|            |   | *          20          *          40          *          60          *          |     |
|------------|---|---------------------------------------------------------------------------------|-----|
| TmHKT8     | : | MGS-LHVESNATQHSKEERASQELVEEVHETVLQEEYEVSISFFGLVILEALYMNESTVPREMLDLIEM           | 69  |
| TaHKT8D    | : | MGS-LHVESSATQHSKEERASQELVEEVHETVLQEEYEVSISFFGLEILEALUMEESTVPREMLDLIEE           | 69  |
| TtHKT8B2   | : | MGSLLHVSFSATQHSKEHRASQELEESVEETLQEEYEVSISFFGEIILEEENEIG---MEVELDEIEE            | 67  |
| TtHKT8B1   | : | MGS-LHVECSTTQHSKEQEVEQELEESVEEPEVELHEEYEVTISFLGEEELEALEEMEESMVSREEELEEEE        | 69  |
| OsHKT8     | : | MSS---EDAETPRYDEFKEIEHEFLEEAEEEELQEEYEFESLLGEEMLEALEMEESMVPREMLDLEIEE           | 67  |
| OsHKT7     | : | MPE----ERRELAGGAES--------------HHEAEELAESCLEEGLEGVEKVEEPG-AAERRIDRFEE          | 51  |
|            |   | M 3   s       l r y l    fh hpfw6  1YF6 IS  G   6LkaLp64t       P d6DliFt      |     |

|            |   | *          80          *          100          *          120          *          140 |     |
|------------|---|----------------------------------------------------------------------------------------|-----|
| TmHKT8     | : | EVSAETVSSMEEVEMEEFSNEQLLLLTLLMLLGGEVEESMLGEHEEVESEKEEAQAPHDHDEGD-KGKE                   | 138 |
| TaHKT8D    | : | EVSAETVSSMEEVEMEEFSNEQLLLLTLLMLLGGEVEESMLGEHEEVESEKEEAQAPHDHDEGD-KGKE                   | 138 |
| TtHKT8B2   | : | EVSAETVSSMEEVEMEEFSNEQLLLLTLLMLLGGEVEESMLGEHEEELESETEEAQAPHEHDEAD-KGKE                  | 136 |
| TtHKT8B1   | : | EVSAETVSSMEEVEMEEFSNEQLLLLTILMLLGGEVEESMLGEYEEEIESEKE--EAPHDHGEGGGKVEE                  | 137 |
| OsHKT8     | : | EVSAETVSSMEEVEMEEFSMEQLLLITLMLLGGEVEESILGEYENAEYSSEMIATLPEDDEHGGSEKE                    | 137 |
| OsHKT7     | : | AVSAAETVSSNESTVEMEEVSSHGELVVLTVLMLLGGEVEVSLVGEASKEESELESDAMDRSRRVESHGDVALA              | 121 |
|            |   | sVSAtTVSSMvaVEMEsFSN QL666T6LMLLGGEVFtS66GL ft   K    k               d       p        |     |

|            |   | *          160          *          180          *          200          *          |     |
|------------|---|-------------------------------------------------------------------------------------|-----|
| TmHKT8     | : | AESC------SEKEAATECEED----------VERVEQEFK------------DQPRYDEAFLEEE                  | 176 |
| TaHKT8D    | : | AESS------SEEEAVTEGEED----------VERVEQEFK------------DQPRYDEAFLEEE                  | 176 |
| TtHKT8B2   | : | AESS------SEQETATECEED----------VERVEQEFK------------DQPRYDEAFLEEE                  | 174 |
| TtHKT8B1   | : | AES-------SEEEPATEPEEDSTA-------QEQEMEQEENK----------EQPRYGEAFLEEE                  | 178 |
| OsHKT8     | : | PEPETSPSSTLEEEELAPPEEVVVVNPTTTATTHEEVELELGRRNKRGCTCTTTHTSSSSSASETTTEEE               | 207 |
| OsHKT7     | : | DIDG-------GDEENPESSGE----------EAASRRRP------------MDADTLEHNAVEA                   | 157 |
|            |   | p          6    t md              e g                        4   tRl               |     |

|            |   | *          220          *          240          *          260          *          280 |     |
|------------|---|-----------------------------------------------------------------------------------------|-----|
| TmHKT8     | : | LEFIVLEEVVHLEGELMEEYLEVSGEGEELTEEELELEETESEETVSTEAECGFEPNEGMVAFEE                        | 246 |
| TaHKT8D    | : | LEFIVLEEVVHLEGELMEEYLEVSGEGEELTEEELELEETESEETVSTEAECGFEEENEGMEAEEE                       | 246 |
| TtHKT8B2   | : | LLFIVLDEEVVHLEGEYEEEYLEVSGEAREELAEEEISLEETESEETVSTEAECGFEENEEMVAFEE                      | 244 |
| TtHKT8B1   | : | LLFIVLEEEVVHLEGEYEEEYLEVSGEAREELAEEEISLEETESEETVSTEAECGFEENEEGMVVEEE                     | 248 |
| OsHKT8     | : | LMFVVEGEEAVVHVEGETAEEEEEVYLEAEGEAGEEVAEEEESAETEAEETVSTEEECGFEEPTEEGMVSFEE                | 277 |
| OsHKT7     | : | LEFYIVLEAIFAVVHVVEAVAEAAEEVLASPEAERRTEGDESENTWEEAEETVSTESECGFEETHENEVVEER                | 227 |
|            |   | L   56V6gyh VVH6aGy   6    Y6s  v  GA  av6  gKg6s  hTF   FTvVSTFaN GF P  NE M6 F4s      |     |

A
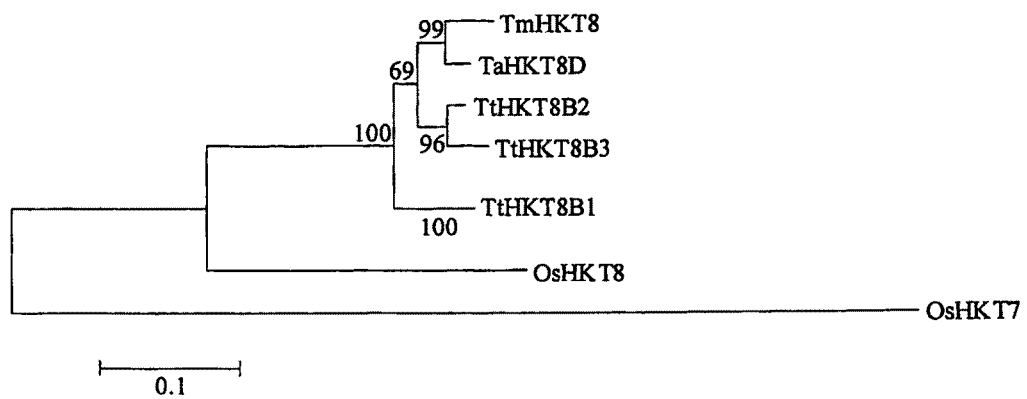
B
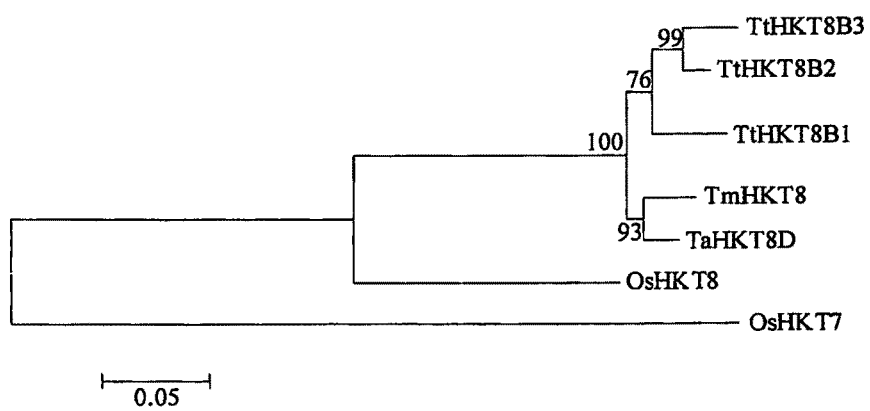
Figure 19

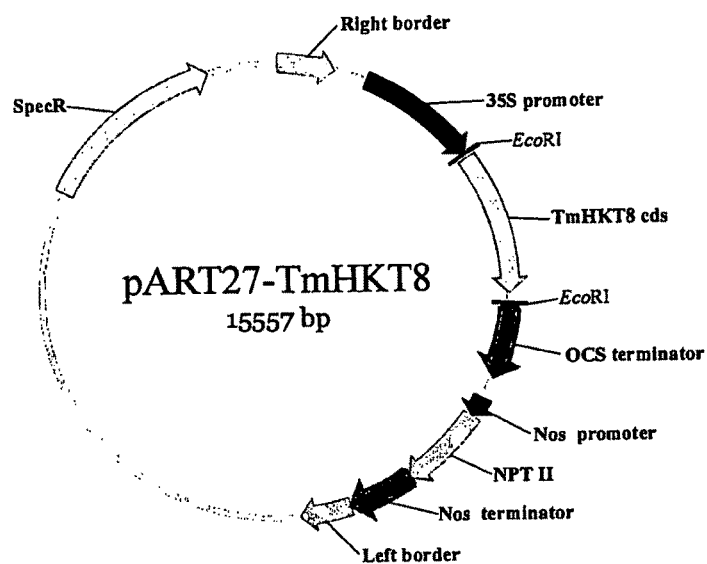
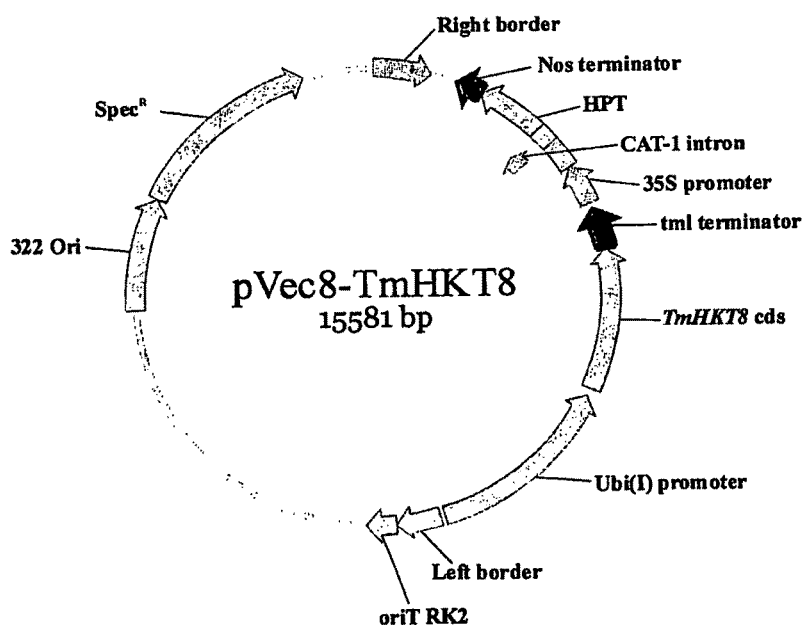
Figure 23

```
                         *↓
               860        880
TmHKT8    : SLHTESVFTVVSTFANCGFVPNNEGM
TaHKT8-   : SLHTESVFTVVSTFANCGFVPNNEGM
TtHKT8-B1 : SLHTESVFTVVSTFANGGFVPNNEGM
TtHKT8-B2 : SLHTESVFTVVSTFANGGFMPNNEEM
TtHKT8-B3 : SLHTESAFTVVSTFANGGFAPNNEGM
OsHKT8    : SAHTEAIFTVVSTFANGGFVPTNEGM
TtHKT7    : SVWTEAVFTTVSTFSSGGFMPNNENM
OsHKT7    : NTWTEAVFTTVSTFSNGGFMPTNENM
TmHKT6    : GLFIESVFTAISSVANGGFTPVNENM
OsHKT6    : GIIVESVFTAISSVGNGGFTPVNENM
TtHKT4    : KMWTESIFTAVSSFANGGFTPLNDSM
OsHKT5    : KIWTESIFTAVSSFANGGFTPVNDNM
OsHKT4    : NMYTECIFTAVSSFANGGFTPLNSNM
AtHKT1    : SPLTESVFTTVSTFANGGFVPTNENM
EcHKT2    : KMMTESIFTTVSTFASGGFVPTNENM
EcHKT1    : KMVTESVFTTVSTFASGGFVPTNENM
SmHKT1    : KTFTESIFSVVSTFASGGFTPTNENM
McHKT2    : KSITEAIFTSVSTFSSGGFVPTNENM
PtHKT1    : KIQTESVFTTVSTFSNGGFVPTNENM
McHKT1    : EMHLESLFVTVSTFSNGGFIPTNENM
HvHKT1    : NIVLFSLSVTVASIANGLVPTNENM
TaHKT1    : NIVLFSLSVTVASCANAGLVPTNENM
PaHKT1    : NVALFSVSVTVSSFANGGLVPTNENM
OsHKT2    : NIALFSFSVTVSSFAN.GLVPTNENM
OsHKT1    : NIALFSFSVTVSSFANVGLVPTNENM
TmHKT9    : NTMLFSISVTVSSFTNGGLIPTNESM
TaHKT9-2  : NTMLFSISVTVSSFTNGGLIPTNESM
TaHKT9-1  : NTMLFSISVTVSSFTNGGLIPTNESM
TtHKT9    : NTMLFSISVTVSSFTNGGLIPTNESM
OsHKT9    : NKALFSISVTVSSFTNGGLLPTNESM
OsHKT3    : NKALFSISVTVSSFTNGGLLPTNESM
```

Figure 25

```
TmHKT1;5     : GY HLLTSRHTWF
TaHKT1;5D    : GY HLLTSRHTWF
TtHKT1;5B2   : GY HLLTSRHTCF
TtHKT1;5B3   : ------------
TtHKT1;5B1   : GYGHLLTSRHTCF
OsHKT1;5Ko   : GYHHLLPSSRTRF
OsHKT1;5NB   : GY HLLPSSRTRF
OsHKT1;4     : GY AHLMPARRCWM
TtHKT1;4     : GYYHLLPARRCAM
SmHKT1;1     : EYHHLLSSKHSRF
McHKT1;2     : AYHHLLPTKHSKY
EcHKT1;2     : GYKHLLPSLYSSL
EcHKT1;1     : GYKHLLPSLYSSL
PtHKT1;1     : GYGHLLSFSHSCL
McHKT1;1     : GYGLFFSQVDALL
AtHKT1;1     : GYSHLLSVRLCVL
OsHKT1;3     : GYKHLMSTRESVY
OsHKT1;2     : GYRYLQLQKNSVN
OsHKT1;1     : GYKHLHVRRNSVY
TtHKT1;1.1   : GYRHLQPHKNSVQ
TtHKT1;1.2   : GYRHLQPHKNSVQ
OsHKT2;4     : GFSHLLPNLQTIF
OsHKT2;3     : GFSHLLPNLQTIF
OsHKT2;2     : QYDYLLPKLPTAF
OsHKT2;1     : QYDYLLPKLPTAF
TaHKT2;1     : RFANLLARLPTVF
HvHKT2;1     : HFGNLLPRLPTVF
```

Figure 28

```
CLUSTAL W (1.83) multiple sequence alignment

Aet110664      ATGGGTTCTTTGCATGTCTCCTCGAGTGCCACTCAACATAGCAAGCTTGAGAGGGCTTAC
Aet18913       ATGGGTTCTTTGCATGTCTCCTCGAGTGCCACTCAACATAGCAAGCTTGAGAGGGCTTAC
Chinese        ATGGGTTCTTTGCATGTCTCCTCGAGTGCCACTCAACATAGCAAGCTTGAGAGGGCTTAC
Aet18905       ATGGGTTCTTTGCATGTCTCCTCGAGTGCCACTCAACATATCAAGCTTGAGAGGGCTTAC
               **************************************** *******************

Aet110664      CAACTCCTGGTTTTCCATGTGCACCCGTTCTGGCTCCAGCTCTTGTACTTTGTATCCATC
Aet18913       CAACTCCTGGTTTTCCATGTGCACCCGTTCTGGCTCCAGCTCTTGTACTTTGTATCCATC
Chinese        CAACTCCTGGTTTTCCATGTGCACCCGTTCTGGCTCCAGCTCTTGTACTTTGTATCCATC
Aet18905       CAACTCCTGGTTTTCCATGTGCACCCGTTCTGGCTCCAGCTCTTGTACTTTGTATCCATC
               ************************************************************

Aet110664      TCCTTCTTCGGTTTGGTGATCCTCAAAGCCCTCCCCATGAAGACCAGCACGGTCCCGAGG
Aet18913       TCCTTCTTCGGTTTGGTGATCCTCAAAGCCCTCCCCATGAAGACCAGCACGGTCCCGAGG
Chinese        TCCTTCTTCGGTTTGGTGATCCTCAAAGCCCTCCCCATGAAGACCAGCACGGTCCCGAGG
Aet18905       TCCTTCTTCGGTTTGGTGATCCTCAAAGCCCTCCCCATGAAGACCAGCACGGTCCCGAGG
               ************************************************************

Aet110664      CCCATGGATTTGGACCTGATCTTCACGTCGGTCTCGGCGACCACGGTGTCGAGCATGGTG
Aet18913       CCCATGGATTTGGACCTGATCTTCACGTCGGTCTCGGCGACCACGGTGTCGAGCATGGTG
Chinese        CCCATGGATTTGGACCTGATCTTCACGTCGGTCTCGGCGACCACGGTGTCGAGCATGGTG
Aet18905       CCCATGGATTTGGACCTGATCTTCACGTCGGTCTCGGCGACCACGGTGTCGAGCATGGTG
               ************************************************************

Aet110664      GCCGTGGAGATGGAGTCCTTCTCCAACCCCCAGCTCCTACTCCTGACCCTCCTCATGCTC
Aet18913       GCCGTGGAGATGGAGTCCTTCTCCAACCCCCAGCTCCTACTCCTGACCCTCCTCATGCTC
Chinese        GCCGTGGAGATGGAGTCCTTCTCCAACCCCCAGCTCCTACTCCTGACCCTCCTCATGCTC
Aet18905       GCCGTGGAGATGGAGTCCTTCTCCAACCCCCAGCTCCTACTCCTGACCCTCCTCATGCTC
               ************************************************************

Aet110664      CTCGGCGGCGAGGTGTTCACGAGCATGCTTGGCCTGCACTTCACCTACGTCAAGTCCAAG
Aet18913       CTCGGCGGCGAGGTGTTCACGAGCATGCTTGGCCTGCACTTCACCTACGTCAAGTCCAAG
Chinese        CTCGGCGGCGAGGTGTTCACGAGCATGCTTGGCCTGCACTTCACCTACGTCAAGTCCAAG
Aet18905       CTCGGCGGCGAGGTGTTCACGAGCATGCTTGGCCTGCACTTCACCTACGTCAAGTCCAAG
               ************************************************************

Aet110664      AAGAAAGAAGCACAAGCACCCCACGACCATGACGATGGTGACAAAGGCAAACCAGCACCA
Aet18913       AAGAAAGAAGCACAAGCACCCCACGACCATGACGATGGTGACAAAGGCAAACCAGCACCA
Chinese        AAGAAAGAAGCACAAGCACCCCACGACCATGACGATGGTGACAAAGGCAAACCAGCACCA
Aet18905       AAGAAAGAAGCACAAGCACCCCACGACCATGACGATGGTGACAAAGGCAAACCAGCACCA
               ************************************************************

Aet110664      TCATCTAGCCTAGAGCTCGCTGTTACCACCGGCATGGATGACGTCGATCGTGTGGAGCAA
Aet18913       TCATCTAGCCTAGAGCTCGCTGTTACCACCGGCATGGATGACGTCGATCGTGTGGAGCAA
Chinese        TCATCTAGCCTAGAGCTCGCTGTTACCACCGGCATGGATGACGTCGATCGTGTGGAGCAA
Aet18905       TCATCTAGCCTAGAGCTCGCTGTTACCACCGGCATGGATGACGTCGATCGTGTGGAGCAA
               ************************************************************

Aet110664      GGGTTTAAGGACCAGCCCCGTTACAATCGCGCCTTCCTCACCAGGTTGCTTCTGTTCATA
Aet18913       GGGTTTAAGGACCAGCCCCGTTACAATCGCGCCTTCCTCACCAGGTTGCTTCTGTTCATA
Chinese        GGGTTTAAGGACCAGCCCCGTTACGATCGCGCCTTCCTCACCAGGTTGCTTCTGTTCATA
Aet18905       GGGTTTAAGGACCAGCCCCGTTACGATCGCGCCTTCCTCACCAGGTTGCTTCTGTTCATA
               ************************ ***********************************
```

Figure 30a

```
Aet110664    GTGCTGGGCTATCACGTGGTGGTGCACCTCGCCGGCTACTCCTTGATGCTGGTCTACCTG
Aet18913     GTGCTGGGCTATCACGTGGTGGTGCACCTCGCCGGCTACTCCTTGATGCTGGTCTACCTG
Chinese      GTGCTGGGCTATCACGTGGTGGTGCACCTCGCCGGCTACTCCTTGATGCTGGTCTACCTG
Aet18905     GTGCTGGGCTATCACGTGGTGGTGCACCTCGCCGGCTACTCCTTGATGCTGGTCTACCTG
             ************************************************************

Aet110664    AGCGTGGTCTCCGGCGCGAGGGCTGTGCTCACCGGCAAGGGGATCAGCCTGCACACCTTC
Aet18913     AGCGTGGTCTCCGGCGCGAGGGCTGTGCTCACCGGCAAGGGGATCAGCCTGCACACCTTC
Chinese      AGCGTGGTCTCCGGCGCGAGGGCTGTGCTCACCGGCAAGGGGATCAGCCTGCACACCTTC
Aet18905     AGCGTGGTCTCCGGCGCGAGGGCTGTGCTCACCGGCAAGGGGATCAGCCTGCACACCTTC
             ************************************************************

Aet110664    TCCGTCTTCACCGTCGTCTCGACGTTCGCCAACTGCGGCTTCGTCCCGAACAACGAAGGG
Aet18913     TCCGTCTTCACCGTCGTCTCGACGTTCGCCAACTGCGGCTTCGTCCCGAACAACGAAGGG
Chinese      TCCGTCTTCACCGTCGTCTCGACGTTCGCCAACTGCGGCTTCGTCCCGAACAACGAAGGG
Aet18905     TCCGTCTTCACCGTCGTCTCGACGTTCGCCAACTGCGGCTTCGTCCCGAACAACGAAGGG
             ************************************************************

Aet110664    ATGATCGCCTTCCGGTCCTTCCCGGGCCTCCTGCTCCTAGTCATGCCGCACGTCCTCCTC
Aet18913     ATGATCGCCTTCCGGTCCTTCCCGGGCCTCCTGCTCCTAGTCATGCCGCACGTCCTCCTC
Chinese      ATGATCGCCTTCCGGTCCTTCCCGGGCCTCCTGCTCCTAGTCATGCCGCACGTCCTCCTC
Aet18905     ATGATCGCCTTCCGGTCCTTCCCGGGCCTCCTGCTCCTAGTCATGCCGCACGTCCTCCTC
             ************************************************************

Aet110664    GGCAACACACTCTTCCCCGTCTTCCTCAGGCTGGCCATCTGGGCTCTCCGGAGAGTCACC
Aet18913     GGCAACACACTCTTCCCCGTCTTCCTCAGGCTGGCCATCTGGGCTCTCCGGAGAGTCACC
Chinese      GGCAACACACTCTTCCCCGTCTTCCTCAGGCTGGCCATCTGGGCTCTCCGGAGAGTCACC
Aet18905     GGCAACACACTCTTCCCCGTCTTCCTCAGGCTGGCCATCTGGGCTCTCCGGAGAGTCACC
             ************************************************************

Aet110664    AGGAGGCCCGAGCTCGGTGAGCTGAGGAGCATCGGCTACGACCACCTGCTGACGAGCCGG
Aet18913     AGGAGGCCCGAGCTCGGTGAGCTGAGGAGCATCGGCTACGACCACCTGCTGACGAGCCGG
Chinese      AGGAGGCCCGAGCTCGGTGAGCTGAGGAGCATCGGCTACGACCACCTGCTGACGAGCCGG
Aet18905     AGGAGGCCCGAGCTCGGTGAGCTGAGGAGCATCGGCTACGACCACCTGCTGACGAGCCGG
             ************************************************************

Aet110664    CACACGTGGTTCTTGGCTTTCACCGTGGCGGCGTTCGTGCTAGCGCAGCTGTCGCTCTTC
Aet18913     CACACGTGGTTCTTGGCTTTCACCGTGGCGGCGTTCGTGCTAGCGCAGCTGTCGCTCTTC
Chinese      CACACGTGGTTCTTGGCTTTCACCGTGGCGGCGTTCGTGCTAGCGCAGCTGTCGCTCTTC
Aet18905     CACACGTGGTTCTTGGCTTTCACCGTGGCGGCGTTCGTGCTAGCGCAGCTGTCGCTCTTC
             ************************************************************

Aet110664    TGCGCCATGGAGTGGGGCTCCAACGGGCTGCGCGGGCTCACCGCCGTGCAGAAGCTCGTT
Aet18913     TGCGCCATGGAGTGGGGCTCCAACGGGCTGCGCGGGCTCACCGCCGTGCAGAAGCTCGTT
Chinese      TGCGCCATGGAGTGGGGCTCCAACGGGCTGCGCGGGCTCACCGCCGTGCAGAAGCTCGTT
Aet18905     TGCGCCATGGAGTGGGGCTCCAACGGGCTGCGCGGGCTCACCGCCGTGCAGAAGCTCGTT
             ************************************************************

Aet110664    GCGGGACTGTTCATGTCGGTCAACTCCAGGCACACCGGTGAGATGGTGGTGGACCTTTCC
Aet18913     GCGGGACTGTTCATGTCGGTCAACTCCAGGCACACCGGTGAGATGGTGGTGGACCTTTCC
Chinese      GCGGGACTGTTCATGTCGGTCAACTCCAGGCACACCGGTGAGATGGTGGTGGACCTTTCC
Aet18905     GCGGGACTGTTCATGTCGGTCAACTCCAGGCACACCGGTGAGATGGTGGTGGACCTTTCC
             ************************************************************
```

Figure 30b

```
Aet110664    ACCGTGTCGTCGGCCCTCGTGGTGCTCTATGTGGTCATGATGTACCTACCACCTTACACT
Aet18913     ACCGTGTCGTCGGCCCTCGTGGTGCTCTATGTGGTCATGATGTACCTACCACCTTACACT
Chinese      ACCGTGTCGTCGGCCCTCGTGGTGCTCTATGTGGTCATGATGTACCTACCACCTTACACT
Aet18905     ACCGTGTCGTCGGCCCTCGTGGTGCTCTATGTGGTCATGATGTACCTACCACCTTACACT
             ************************************************************

Aet110664    ACATTTCTACCAGTGGAAGACGACAGTGACCAACAAGTGGGAGCAGATCAGCGCGACCAG
Aet18913     ACATTTCTACCAGTGGAAGACGACAGTGACCAACAAGTGGGAGCAGATCAGCGCGACCAG
Chinese      ACATTTCTACCAGTGGAAGACGACAGTGACCAACAAGTGGGAGCAGATCAGCGCGACCAG
Aet18905     ACATTTCTACCAGTGGAAGACGACAGTGACCAACAAGTGGGAGCAGATCAGCGCGACCAG
             ************************************************************

Aet110664    AAAAGGATAACAAGCATGTGGCGGAAGCTGCTCATGTCGCCGCTCTCGTGCTTGGCCATC
Aet18913     AAAAGGATAACAAGCATGTGGCGGAAGCTGCTCATGTCGCCGCTCTCGTGCTTGGCCATC
Chinese      AAAAGGATAACAAGCATGTGGCGGAAGCTGCTCATGTCGCCGCTCTCGTGCTTGGCCATC
Aet18905     AAAAGGATAACAAGCATGTGGCGGAAGCTGCTCATGTCGCCGCTCTCGTGCTTGGCCATC
             ************************************************************

Aet110664    TTCATCGCCGTGGTGTGCATCACGGAGCGGCGGCAGATCTCCGATGACCCCCTCAACTTC
Aet18913     TTCATCGCCGTGGTGTGCATCACGGAGCGGCGGCAGATCTCCGATGACCCCCTCAACTTC
Chinese      TTCATCGCCGTGGTGTGCATCACGGAGCGGCGGCAGATCTCCGATGACCCCCTCAACTTC
Aet18905     TTCATCGCCGTGGTGTGCATCACGGAGCGGCGGCAGATCTCCGATGACCCCCTCAACTTC
             ************************************************************

Aet110664    AACGTCCTCAACATCACCGTCGAGGTTATCAGTGCGTACGGAAACGTGGGGTTCAGCACC
Aet18913     AACGTCCTCAACATCACCGTCGAGGTTATCAGTGCGTACGGAAACGTGGGGTTCAGCACC
Chinese      AACGTCCTCAACATCACCGTCGAGGTTATCAGTGCGTACGGAAACGTGGGGTTCAGCACC
Aet18905     AACGTCCTCAACATCACCGTCGAGGTTATCAGTGCGTACGGAAACGTGGGGTTCAGCACC
             ************************************************************

Aet110664    GGGTACAGCTGTGGCCGGCAGGTGACGCCCGACGGCGGCTGCAGGGACACGTGGGTTGGC
Aet18913     GGGTACAGCTGTGGCCGGCAGGTGACGCCCGACGGCGGCTGCAGGGACACGTGGGTTGGC
Chinese      GGGTACAGCTGTGGCCGGCAGGTGACGCCCGACGGCGGCTGCAGGGACACGTGGGTTGGC
Aet18905     GGGTACAGCTGTGGCCGGCAGGTGACGCCCGACGGCGGCTGCAGGGACACGTGGGTTGGC
             ************************************************************

Aet110664    TTCTCTGGGAAGTGGAGTTGGCAAGGGAAGCTGGCTCTCATTGCTGTCATGTTCTACGGC
Aet18913     TTCTCTGGGAAGTGGAGTTGGCAAGGGAAGCTGGCTCTCATTGCTGTCATGTTCTACGGC
Chinese      TTCTCTGGGAAGTGGAGTTGGCAAGGGAAGCTGGCTCTCATTGCTGTCATGTTCTACGGC
Aet18905     TTCTCTGGGAAGTGGAGTTGGCAAGGGAAGCTGGCTCTCATTGCTGTCATGTTCTACGGC
             ************************************************************

Aet110664    AGGCTCAAGAAGTTCAGCATGCATGGTGGCGAGGCATGGAGGATAGTATAA
Aet18913     AGGCTCAAGAAGTTCAGCATGCATGGTGGCGAGGCATGGAGGATAGTATAA
Chinese      AGGCTCAAGAAGTTCAGCATGCATGGTGGCGAGGCATGGAGGATAGTATAA
Aet18905     AGGCTCAAGAAGTTCAGCATGTATGGTGGCGAGGCATGGAGGATAGTATAA
             ********************* ******************************
```

Figure 30c

```
CLUSTAL W (1.83) multiple sequence alignment

Aet110664       MGSLHVSSSATQHSKLERAYQLLVFHVHPFWLQLLYFVSISFFGLVILKALPMKTSTVPR
Aet18913        MGSLHVSSSATQHSKLERAYQLLVFHVHPFWLQLLYFVSISFFGLVILKALPMKTSTVPR
Chinese         MGSLHVSSSATQHSKLERAYQLLVFHVHPFWLQLLYFVSISFFGLVILKALPMKTSTVPR
Aet18905        MGSLHVSSSATQHIKLERAYQLLVFHVHPFWLQLLYFVSISFFGLVILKALPMKTSTVPR
LOC_Os01g20160  MSSLDATT--PRYDEFKRIYHLFLFHAHPFWLQLLYFLFISLLGFLMLKALPMKTSMVPR
                *.**..:: .:: :::* *:*::**.********** **::*:::******** ***

Aet110664       PMDLDLIFTSVSATTVSSMVAVEMESFSNPQLLLLTLLMLLGGEVFTSMLGLHFTYVK-S
Aet18913        PMDLDLIFTSVSATTVSSMVAVEMESFSNPQLLLLTLLMLLGGEVFTSMLGLHFTYVK-S
Chinese         PMDLDLIFTSVSATTVSSMVAVEMESFSNPQLLLLTLLMLLGGEVFTSMLGLHFTYVK-S
Aet18905        PMDLDLIFTSVSATTVSSMVAVEMESFSNPQLLLLTLLMLLGGEVFTSMLGLHFTYVK-S
LOC_Os01g20160  PMDLDLIFTSVSATTVSSMVAVEMESFSNSQLLLITLLMLLGGEVFTSILGLYFTNAKYS
                *****************************.****:************:***:** .* *

Aet110664       KKKEAQAPHDHDDGDKGKPAPSSS--------LELA---------VTTGMDDVDRVEQGF
Aet18913        KKKEAQAPHDHDDGDKGKPAPSSS--------LELA---------VTTGMDDVDRVEQGF
Chinese         KKKEAQAPHDHDDGDKGKPAPSSS--------LELA---------VTTGMDDVDRVEQGF
Aet18905        KKKEAQAPHDHDDGDKGKPAPSSS--------LELA---------VTTGMDDVDRVEQGF
LOC_Os01g20160  SKMIATLPDDDDHGGSGKPPPPTTSPSSTLVELELAPPMDVVVVNPTTTATTHDEVELGL
                .*  *  *.*.*.*..***.*.::        ****         **    *.** *:

Aet110664       KDQPR--------------YNRAFLTRLLLFIVLGYHVVVHLAGYSLMLVYLSVVSGAR
Aet18913        KDQPR--------------YNRAFLTRLLLFIVLGYHVVVHLAGYSLMLVYLSVVSGAR
Chinese         KDQPR--------------YDRAFLTRLLLFIVLGYHVVVHLAGYSLMLVYLSVVSGAR
Aet18905        KDQPR--------------YDRAFLTRLLLFIVLGYHVVVHLAGYSLMLVYLSVVSGAR
LOC_Os01g20160  GRRNKRGCTCTTTHTSSSSSASKTTTTRLLMFVVMGYHAVVHVAGYTAIVVYLSAVGGAG
                 : :               .:: ****:*:***.***:***:*:  :****.*.**

Aet110664       AVLTGKGISLHTFSVFTVVSTFANCGFVPNNEGMIAFRSFPGLLLLVMPHVLLGNTLFPV
Aet18913        AVLTGKGISLHTFSVFTVVSTFANCGFVPNNEGMIAFRSFPGLLLLVMPHVLLGNTLFPV
Chinese         AVLTGKGISLHTFSVFTVVSTFANCGFVPNNEGMIAFRSFPGLLLLVMPHVLLGNTLFPV
Aet18905        AVLTGKGISLHTFSVFTVVSTFANCGFVPNNEGMIAFRSFPGLLLLVMPHVLLGNTLFPV
LOC_Os01g20160  AVVAGKGISAHTFAIFTVVSTFANCGFVPTNEGMVSFRSFPGLLLLVMPHVLLGNTLFPV
                **::.**** ***::************** ****::********************

Aet110664       FLRLAIWALRRVTRRPELGELRS-------IGYDHLLTSRHTWFLAFTVAAFVLAQLSLF
Aet18913        FLRLAIWALRRVTRRPELGELRS-------IGYDHLLTSRHTWFLAFTVAAFVLAQLSLF
Chinese         FLRLAIWALRRVTRRPELGELRS-------IGYDHLLTSRHTWFLAFTVAAFVLAQLSLF
Aet18905        FLRLAIWALRRVTRRPELGELRS-------IGYDHLLTSRHTWFLAFTVAAFVLAQLSLF
LOC_Os01g20160  FLRLAIAALERVTGWPELGELLIRRRGGGEGYHHLLPSSRTRFLALTVAVLVVAQLALF
                ****** **.*** ******  .       **:***.*:* ***:***.:*:***:**

Aet110664       CAMEWGSNGLRGLTAVQKLVAGLFMSVNSRHTGEMVVDLSTVSSALVVLYVVMMYLPPYI
Aet18913        CAMEWGSNGLRGLTAVQKLVAGLFMSVNSRHTGEMVVDLSTVSSALVVLYVVMMYLPPYI
Chinese         CAMEWGSNGLRGLTAVQKLVAGLFMSVNSRHTGEMVVDLSTVSSALVVLYVVMMYLPPYI
Aet18905        CAMEWGSNGLRGLTAVQKLVAGLFMSVNSRHTGEMVVDLSTVSSALVVLYVVMMYLPPYI
LOC_Os01g20160  CAMEWGSDGLRGLTAGQKLVGALFMAVNSRHSGEMVLDLSTVSSAVVVLYVVMMYLPPYI
                *******:*******.****..***:****:****:********:**************:
```

Figure 31a

```
Aet110664       TFLPVEDDSDQQVGADQRDQKRITSMWRKLLMSPLSCLAIFIAVVCITERRQISDDPLNF
Aet18913        TFLPVEDDSDQQVGADQRDQKRITSMWRKLLMSPLSCLAIFIAVVCITERRQISDDPLNF
Chinese         TFLPVEDDSDQQVGADQRDQKRITSMWRKLLMSPLSCLAIFIAVVCITERRQISDDPLNF
Aet18905        TFLPVEDDSDQQVGADQRDQKRITSMWRKLLMSPLSCLAIFIAVVCITERRQISDDPLNF
LOC_Os01g20160  TFVPVQDKHQQTGAQSGQEGSSSSSIWQKLLMSPLSCLAIFIVVICITERRQIADDPINY
                **:**:*. :*   . . :: .   :*:*:**************.*:********:***:*:

Aet110664       NVLNITVEVISAYGNVGFSTGYSCGRQVTPDGGCRDTWVGFSGKWSWQGKLALIAVMFYG
Aet18913        NVLNITVEVISAYGNVGFSTGYSCGRQVTPDGGCRDTWVGFSGKWSWQGKLALIAVMFYG
Chinese         NVLNITVEVISAYGNVGFSTGYSCGRQVTPDGGCRDTWVGFSGKWSWQGKLALIAVMFYG
Aet18905        NVLNITVEVISAYGNVGFSTGYSCGRQVTPDGGCRDTWVGFSGKWSWQGKLALIAVMFYG
LOC_Os01g20160  SVLNIVVEVISAYGNVGFSTGYSCARQVRPDGSCRDLWVGFSGKWSKQGKLTLMAVMFYG
                .****.******************.*** ***.*** ********.****:*:******

Aet110664       RLKKFSMHGGEAWRIV
Aet18913        RLKKFSMHGGEAWRIV
Chinese         RLKKFSMHGGEAWRIV
Aet18905        RLKKFSMYGGEAWRIV
LOC_Os01g20160  RLKKFSLHGGQAWKIE
```

Figure 31b

POLYNUCLEOTIDES ENCODING A NAX2 POLYPEPTIDE AND METHODS FOR ENHANCING SALINITY TOLERANCE IN PLANTS

This application is a §371 national stage of PCT International Application No. PCT/AU2007/000975, filed Jul. 12, 2007, and claims the benefit of U.S. Provisional Application Nos. 60/847,765, filed Sep. 27, 2006 and 60/830,754, filed Jul. 12, 2006, the contents of all of which are hereby incorporated by reference into this application.

This application Incorporates-by-reference nucleotide and/or amino acid sequences which are present in the file named "130415_2251_76632_A_PCT_US_Sequence_Listing_REB.txt", which is 160 kilobytes in size, and which was created Apr. 15, 2013 in the IBM-PC machine format, having an operating system compatibility with MS-Windows, which is contained in the text file filed Apr. 15, 2013 as part of this application.

FIELD OF THE INVENTION

The present invention relates to polypeptides, and polynucleotides encoding therefor, with cation transporter activity. In particular, the present invention relates to methods for producing, identifying, and/or breeding transgenic or non-transgenic plants, especially wheat or barley plants, with enhanced tolerance to saline and/or sodic soils, and/or reduced sodium accumulation in an aerial part of the plant. Also provided are plants produced using these methods.

BACKGROUND OF THE INVENTION

Soil salinity causes significant reductions in plant productivity, and consequent economic losses associated with reduced grain quality and yield of agricultural crops (Pitman and Läuchli, 2002). Over 6% of the world's land is affected by either salinity or sodicity. A large proportion of the Australian wheat belt is at risk of salinisation due to rising water tables, and a further and larger part has soils that are sodic, and underlain with subsoil salinity (Rengasamy, 2002). This subsoil salinity is formed in semi-arid zones (with annual rainfall less than 450 mm), and is transient in nature as it moves in and out of the root zone according to soil wetting and drying cycles (Rengasamy, 2002).

Cultivars of *durum* wheat are more salt sensitive than bread wheat (Gorham et al. 1990; Rawson et al. 1988), and may yield less when grown on saline soils (Francois et al. 1986; Maas and Grieve, 1990). The usual high price of *durum* wheat on the international market can bring a better return to farmers than bread wheat and other crops, so, breeding new cultivars of *durum* wheat with improved salt tolerance can allow growers more options in dealing with subsoil salinity. Marker assisted selection is potentially the most efficient approach to developing cultivars that can tolerate saline soils.

There are three avenues by which to introduce salt-tolerance into *durum* wheat: traditional breeding techniques using physiologically-based phenotyping, marker-assisted selection, and through transformation of genes known to improve $Na^+$ exclusion or tissue tolerance. To increase salt tolerance of crops in terms of yield increases and associated economic gains, there is great potential for the introduction of salt tolerance traits into *durum* wheat using marker-assisted selection (Munns et al. 2002). This approach has successfully been used to introduce various agronomic traits into cereals, and overcomes the problems associated with wheat transformation and market acceptance (Koorneef and Stam, 2001).

Plant breeding using marker-assisted selection has a proven track-record of successfully incorporating a stable trait into the genome of the target species. However, marker development is dependent on accurate phenotyping, requiring a quantitative measure of a specific trait. An understanding of physiological mechanisms is needed to identify such a trait.

Salt tolerance in the Tritiaceae is associated with sodium exclusion, which limits the entry of sodium into the plant and its transport to leaves. Sodium exclusion from the transpiration stream reaching the leaves is controlled at three stages: (1) selectivity of the root cells taking up cations from the soil solution, (2) selectivity in the loading of cations into the xylem vessels in the roots, and (3) removal of sodium from the xylem in the upper part of the roots and the lower part of the shoot (Munns et al. 2002; Tester and Davenport 2003).

Bread wheat (hexaploid) cultivars are able to exclude $Na^+$ from the leaves, however, *durum* wheat (tetraploid) cultivars lack this trait (Dubcovsky et al. 1996). The Kna1 locus on chromosome 4DL of hexaploid wheat is linked to $Na^+$ exclusion and $K^+/Na^+$ discrimination, and subsequently, improved salt tolerance (Dvořák et al. 1994; Shah et al. 1987). Hexaploid wheat has three genomes, A, B and D, but tetraploid wheat has only the A and B genomes. A homoeologue of the Kna1 locus has not yet been found on the A or B genomes.

Recently, a novel source of $Na^+$ exclusion was identified in a *durum* landrace (Munns et al. 2000). The landrace had very low rates of $Na^+$ accumulation in the leaf blade, as low as bread wheat cultivars, and maintained a high rate of $K^+$ accumulation, with consequent high $K^+/Na^+$ discrimination. The low-$Na^+$ *durum* landrace had a $K^+/Na^+$ ratio of 17 whereas the *durum* cultivars Wollaroi, Tamaroi and Langdon had $K^+/Na^+$ ratios of 1.5, 0.7 and 0.4 respectively (Munns et al. 2000). The bread wheat cultivars Janz and Machete had $K^+/Na^+$ ratios of 10 and 8 respectively. The low $Na^+$ trait was shown to confer a significant yield advantage at moderate soil salinity (Husain et al. 2003), indicating that this novel germplasm provides the opportunity to improve the salt tolerance of cultivated *durum* wheat. Markers for identifying the Nax1 locus from *durum* landrace wheat which is partially responsible for the sodium exclusion phenotype have recently been described (WO 2005/120214).

Methods for selection of $Na^+$ excluding individuals in wheat breeding populations are time-consuming and expensive. In one case, the method involves growing plants in pots using a sub-irrigation system to provide a gradual and uniform exposure to NaCl to the plant, and the harvesting of a given leaf for $Na^+$ accumulation. Although this screening method is very reproducible, it is labour intensive and requires a controlled environment. It is not possible to screen plants in the field or with large numbers of individual lines using this method. QTL mapping and marker-assisted selection is a technique that has many advantages over phenotypic screening as a selection tool. Marker-assisted selection is non-destructive and can provide information on the genotype of a single plant without exposing the plant to the stress. The technology is capable of handling large numbers of samples. Although developing a QTL map is laborious, the markers identified may prove to be sufficiently robust to use as the sole selection tool for a specific trait in a breeding program. PCR-based molecular markers have the potential to reduce the time, effort and expense often associated with physiological screening. In order to use marker-assisted selection in breeding programs, the markers must be closely linked to the trait, and work across different genetic backgrounds.

There is a need for the identification of further genes and/or markers thereof which can be used to produce plants, particularly wheat or barley plants, with enhanced tolerance to saline and/or sodic soils, and/or reduced sodium accumulation in an aerial part of the plant.

SUMMARY OF THE INVENTION

The present inventors have identified a family of wheat and barley genes which encode cation transporters. At least some alleles of these genes have been shown to confer upon a wheat or barley plant enhanced tolerance to saline and/or sodic soils.

In a first aspect, the present invention provides a substantially purified and/or recombinant polypeptide comprising amino acids having a sequence as provided in any one of SEQ ID NOs: 1 to 9 or 83 to 89, a biologically active fragment thereof, or an amino acid sequence which is at least 67% identical to any one or more of SEQ ID NOs: 1 to 9 or 83 to 89, wherein the polypeptide has cation transporter activity when produced in a cell.

In a preferred embodiment, the polypeptide has amino acids in a sequence at least 90% identical to SEQ ID NO:1 and/or SEQ ID NO:6.

In one embodiment, the polypeptide is from or in wheat or barley.

In a further embodiment, the cation is sodium and/or potassium.

In an embodiment, the polypeptide comprises at least one membrane spanning domain. In another embodiment, the polypeptide comprises at least four membrane spanning domains. In a further embodiment, the polypeptide comprises eight membrane spanning domains. In a preferred embodiment, the polypeptide comprises four regions each of two membrane spanning domains flanking a pore loop domain, as shown schematically in FIG. 26.

In yet another embodiment, the polypeptide comprises a cysteine residue at a position corresponding to amino acid number 232 of SEQ ID NO:1 and/or an aspartic acid residue at a position corresponding to amino acid number 294 of SEQ ID NO:1.

In a further preferred embodiment, the polypeptide transports sodium across a cell membrane and out of the xylem of a plant to a greater extent than it transports potassium. More preferably the sodium transport is out of the xylem and into xylem parenchyma cells, thus reducing sodium ion concentration in the xylem fluid. Preferably, the polypeptide comprises amino acids having a sequence as provided in any one of SEQ ID NOs: 1, 6 to 9, a biologically active fragment thereof, or an amino acid sequence which is at least 67% identical to any one or more of SEQ ID NOs: 1 or 6 to 9.

Preferably the cell is a plant cell, and more preferably in a cereal plant cell. In one embodiment, the cell is a root cell. In another embodiment, the cell is a xylem parenchyma cell.

In a further embodiment, the polypeptide is a fusion protein further comprising at least one other polypeptide sequence.

The at least one other polypeptide may be, for example, a polypeptide that enhances the stability of a polypeptide of the present invention, or a polypeptide that assists in the purification of the fusion protein.

In another aspect, the present invention provides an isolated and/or exogenous polynucleotide comprising nucleotides having a sequence as provided in or complementary to any one of SEQ ID NOs: 10 to 18 or 90 to 96, a sequence which is at least 65% identical to any one or more of SEQ ID NOs: 10 to 18 or 90 to 96, a sequence which hybridizes to any one or more of SEQ ID NOs: 10 to 18 or 90 to 96, or a sequence which encodes a polypeptide of the invention.

Preferably, the polynucleotide comprises nucleotides having a sequence which hybridizes to any one or more of SEQ ID NOs: 10 to 18 or 90 to 96 under stringent conditions.

Preferably, the polynucleotide is operably linked to a promoter capable of directing expression of the polynucleotide in a cell, preferably a plant cell and more preferably in a cereal plant. In one embodiment, the cell is a root cell. In another embodiment, the cell is a xylem parenchyma cell.

In another embodiment, the promoter comprises nucleotides having a sequence as provided in or complementary to SEQ ID NO:97 and/or SEQ ID NO:98, a sequence which is at least 65% identical to SEQ ID NO:97 and/or SEQ ID NO:98, a sequence which hybridizes to SEQ ID NO:97 and/or SEQ ID NO:98, or a biologically active fragment of any one thereof capable of directing gene expression in the cell.

Preferably, the polynucleotide encodes a polypeptide having cation transporter activity when expressed in a cell.

The present inventors have also identified new promoters which can be used to drive transcription of a transgene in a recombinant cell. The promoters are tissue specific and useful for producing chimeric DNAs that can function to improve salt tolerance of the cell. Thus, in yet another aspect, the present invention provides an isolated and/or exogenous polynucleotide capable of promoting gene transcription in a cell, the polynucleotide comprising nucleotides having a sequence as provided in or complementary to SEQ ID NO:97 and/or SEQ ID NO:98, a sequence which is at least 65% identical to SEQ ID NO:97 and/or SEQ ID NO:98, a sequence which hybridizes to SEQ ID NO:97 and/or SEQ ID NO:98, or a biologically active fragment of any one thereof.

Preferably, the cell is a root cell of a cereal plant. In a further embodiment, the polynucleotide confers expression to an operably linked second polynucleotide preferentially in the root of a cereal plant relative to at least one other tissue or organ of said cereal plant.

In another embodiment, the cell is a xylem parenchyma cell.

In a further aspect, the present invention provides a method of producing the polypeptide of the invention, comprising expressing in a cell the polynucleotide of the invention.

In one embodiment, the cell is a recombinant cell. In another embodiment, the cell is non-recombinant.

Preferably, the cell is a plant cell.

Preferably, the cell is comprised in a plant which may be growing in the field under saline and/or sodic conditions.

In a further aspect, the present invention provides an isolated and/or exogenous polynucleotide which, when present in a cell of a cereal plant, decreases the expression of at least one polynucleotide of the invention corresponding to a cell of a cereal plant that lacks said polynucleotide.

This aspect of the invention is particularly useful when it is desirable to preferentially express a Nax2 gene that confers enhanced tolerance to saline and/or sodic soils to a cereal plant, and/or reduced sodium accumulation in an aerial part of a cereal plant, and at the same time down-regulate mRNA levels of a Nax2 gene family member that does not confer one or both of these traits. Thus, in an embodiment, the polynucleotide does not confer enhanced tolerance to saline and/or sodic soils to a cereal plant, and/or reduced sodium accumulation in an aerial part of a cereal plant.

Preferably, the polynucleotide of this aspect is operably linked to a promoter capable of directing expression of the polynucleotide in a cell of a cereal plant.

Preferably, the polynucleotide of this aspect is an antisense polynucleotide, a sense polynucleotide, a catalytic polynucleotide, an artificial microRNA or a duplex RNA molecule.

In an embodiment, the promoter comprises nucleotides having a sequence as provided in or complementary to SEQ ID NO:97 and/or SEQ ID NO:98, a sequence which is at least 65% identical to SEQ ID NO:97 and/or SEQ ID NO:98, a sequence which hybridizes to SEQ ID NO:97 and/or SEQ ID NO:98, or a biologically active fragment of any one thereof capable of directing gene expression in the cell.

In an embodiment, the at least one polynucleotide comprises nucleotides having a sequence as provided in any one of SEQ ID NOs: 11 to 15, or a sequence which is at least 95% identical to any one or more of SEQ ID NOs: 11 to 15.

In a further aspect, provided is a vector comprising a polynucleotide of the invention.

Preferably, the polynucleotide is operably linked to a promoter, which may be any promoter. In one embodiment, the promoter confers expression of the polynucleotide preferentially in the root of a cereal plant relative to at least one other tissue or organ of said cereal plant. In another embodiment, the promoter confers expression of the polynucleotide preferentially in xylem parenchyma cells of a cereal plant.

In another embodiment, the promoter comprises nucleotides having a sequence as provided in or complementary to SEQ ID NO:97 and/or SEQ ID NO:98, a sequence which is at least 65% identical to SEQ ID NO:97 and/or SEQ ID NO:98, a sequence which hybridizes to SEQ ID NO:97 and/or SEQ ID NO:98, or a biologically active fragment of any one thereof capable of directing gene expression in the cell.

In yet another aspect, the present invention provides, a vector comprising the polynucleotide of the invention which is a promoter.

Also provided is a cell comprising a polypeptide of the invention, a polynucleotide of the invention, or a vector of the invention.

In an embodiment, the polypeptide, polynucleotide or vector was introduced into the cell or a progenitor of the cell. Examples of such cells include, but are not limited to, a bacterial cell, plant cell or animal cell.

In an embodiment, the cell is an *E. coli* cell, an *Agrobacterium* cell or a cereal plant cell.

In an embodiment, the polynucleotide is integrated into the genome of the cell.

In a further embodiment, the cell comprises a polynucleotide of the invention encoding at least one Nax2 gene that confers enhanced tolerance to saline and/or sodic soils, to a cereal plant and a polynucleotide which, when present in a cell of a cereal plant, decreases the expression of at least one Nax2 gene family member which does not confer one of these phenotypes relative to a cell of a cereal plant that lacks said polynucleotide. As noted above, this embodiment of the invention is particularly useful when it is desirable to preferentially express a Nax2 gene that confers enhanced tolerance to saline and/or sodic soils to a cereal plant, and/or reduced sodium accumulation in an aerial part of a cereal plant, and at the same time down-regulate mRNA levels of a Nax2 gene family member that does not confer one or both of these traits.

In a further aspect, the present invention provides a plant comprising the cell according to the invention. Preferably all of the cells of the plant comprise the polypeptide, polynucleotide or vector of the invention.

Preferably, the plant is a cereal plant. More preferably, the plant is a wheat or barley plant.

In one embodiment, the wheat plant is of the species *Triticum aestivum* ssp *aestivum*.

In another embodiment, the wheat plant is of the species *Triticum turgidum* ssp. *durum*.

In another embodiment, the *durum* wheat plant has a genetic background comprising less than 50% of the genetic complement of *durum* Line 149, 5049 or of the cultivar Tamaroi. In another embodiment, the *durum* wheat plant has a genetic background comprising less than 50% of the genetic complement of *durum* cultivar Marrocos.

In a further embodiment, the plant comprises a non-transgenic Nax2 gene on the A genome that confers enhanced tolerance to saline and/or sodic soils to the plant, and/or reduced sodium accumulation in an aerial part of the plant.

In yet another embodiment, the gene is on the A genome. More preferably, the gene is on chromosome 5A or chromosome 4A. More preferably the plant is homozygous for Nax2, optionally further comprising another salt tolerance gene such as the Nax1 gene.

In a further embodiment, the gene encodes a polypeptide which comprises a cysteine residue at a position corresponding to amino acid number 232 of SEQ ID NO:1 and/or an aspartic acid residue at a position corresponding to amino acid number 294 of SEQ ID NO:1.

Preferably, the gene encodes a polypeptide that transports sodium across a cell membrane and out of the xylem of a plant to a greater extent than it transports potassium. Preferably, the polypeptide comprises amino acids having a sequence as provided in any one of SEQ ID NOs: 1 or 6 to 9, a biologically active fragment thereof, or an amino acid sequence which is at least 67% identical to any one or more of SEQ ID NOs: 1 or 6 to 9.

In yet another embodiment, the plant has enhanced tolerance to saline and/or sodic soils, and/or reduced sodium accumulation in an aerial part of the plant, relative to a corresponding plant lacking said cell or said polypeptide, polynucleotide or vector of the invention.

In a further aspect, the present invention provides a method of producing the cell of the invention, the method comprising the step of introducing a polynucleotide of the invention, or a vector of the invention, into a cell. Preferably, this embodiment further comprises the step of regenerating a transgenic plant from the cell.

In a further aspect, the present invention provides for the use of a polynucleotide of the invention or a vector of the invention to produce a recombinant cell. The polynucleotides may be used in a screening method to test the function of the polynucleotides or the polypeptides they encode, optionally with a step of selecting an active polynucleotide.

In yet another aspect, the present invention provides a genetically modified plant having increased expression and/or activity of a polypeptide relative to a corresponding non-modified plant, wherein the polypeptide of the invention is expressed from a polynucleotide of the invention encoding said polypeptide.

In an embodiment, the expression level of at least one endogenous Nax2 gene has been increased relative to a corresponding non-modified plant.

Also provided is a wheat or barley plant which is homozygous for a Nax2 gene that confers enhanced tolerance to saline and/or sodic soils, and/or reduced sodium accumulation in an aerial part of the plant.

In one embodiment, the wheat plant is *durum* wheat. In a further embodiment, the *durum* wheat plant has a genetic background comprising less than 50% of the genetic complement of *durum* Line 149, 5049 or of the cultivar Tamaroi or Marrocos.

In another embodiment, the wheat plant is hexaploid wheat.

In yet another embodiment, the gene is on the A genome. More preferably, the gene is on chromosome 5A or chromosome 4A. More preferably the plant is homozygous for Nax2, optionally further comprising the Nax1 gene and/or the Kna1 gene.

In a further embodiment, the gene encodes a polypeptide which comprises a cysteine residue at a position corresponding to amino acid number 232 of SEQ ID NO:1 and/or an aspartic acid residue at a position corresponding to amino acid number 294 of SEQ NO:1.

In yet another embodiment, the plant further comprises an allele of a Nax1 gene which confers enhanced tolerance to saline and/or sodic soils, and/or reduced sodium accumulation in an aerial part of the plant. In a further embodiment, the plant is characterized by a sheath:blade ratio of $Na^+$ concentration in leaf 3 of at least about 1.5, more preferably at least about 2, when grown for at least 10 days in a hydroponic system using a growth medium having a NaCl concentration of 50 mM.

In a further embodiment, the wheat plant further comprises an allele of the Kna1 gene which confers enhanced tolerance to saline and/or sodic soils, and/or reduced sodium accumulation in an aerial part of the plant.

In another embodiment, the plant is characterized by a sheath:blade ratio of $Na^+$ concentration in leaf 3 of less than about 2, more preferably less than about 1.5, when grown for at least 10 days in a hydroponic system using a growth medium having a NaCl concentration of 50 mM.

Preferably, the gene encodes a polypeptide that transports sodium across a cell membrane and out of the xylem of a plant to a greater extent than it transports potassium. Preferably, the polypeptide comprises amino acids having a sequence as provided in any one of SEQ ID NOs: 1 or 6 to 9, a biologically active fragment thereof, or an amino acid sequence which is at least 67% identical to any one or more of SEQ ID NOs: 1 or 6 to 9.

In another aspect, the present invention provides a genetically modified hexaploid wheat plant comprising a Nax2 gene that confers enhanced tolerance to saline and/or sodic soils, and/or reduced sodium accumulation in an aerial part of the plant, relative to a corresponding plant not having the allele.

In one embodiment, the Nax2 gene is obtained from *durum* wheat.

In another embodiment, the Nax2 gene is expressed in xylem parenchyma cells.

In a further aspect the present invention provides a method of identifying a wheat or barley plant with enhanced tolerance to saline and/or sodic soils, the method comprising detecting a nucleic acid molecule of the plant, wherein the nucleic acid molecule is linked to, and/or comprises at least a part of, a Nax2 locus in the plant that comprises an allele that confers enhanced tolerance to saline and/or sodic soils.

Also provided is a method of identifying a wheat or barley plant having a phenotype of reduced sodium accumulation in an aerial part of the plant, the method comprising detecting a nucleic acid molecule of the plant, wherein the nucleic acid molecule is linked to, and/or comprises at least a part of, a Nax2 locus in the plant that comprises an allele that confers reduced sodium accumulation in an aerial part of the plant.

Preferably, the above two methods comprise:
i) hybridising a second nucleic acid molecule to said nucleic acid molecule which is obtained from said plant,
ii) optionally hybridising at least one other nucleic acid molecule to said nucleic acid molecule which is obtained from said plant; and
iii) detecting a product of said hybridising step(s) or the absence of a product from said hybridising step(s).

Preferably, the second nucleic acid molecule is used as a primer to reverse transcribe or replicate at least a portion of the nucleic acid molecule.

Examples of how the nucleic acid can be detected include, but are not limited to, using a technique selected from the group consisting of: restriction fragment length polymorphism analysis, amplification fragment length polymorphism analysis, microsatellite amplification and/or nucleic acid sequencing.

Preferably, the method comprises nucleic acid amplification. In an embodiment, the amplification is performed using primers pairs comprising the sequences selected from:

| i) and | CATCCCTACGCCACTCTGC | (SEQ ID NO: 28) |
|---|---|---|
| | AATGGTATCTATTCCGACCCG, | (SEQ ID NO: 29) |
| ii) and | GCTTGAGACCGGCACAGT | (SEQ ID NO: 30) |
| | CGAGACCTTGAGGGTCTAGA, | (SEQ ID NO: 31) |
| iii) and | CATCACCGTCGAGGTTATCAG | (SEQ ID NO: 32) |
| | TTGAGGTACTCGGCATA, | (SEQ ID NO: 33) |
| iv) and | CAAATTACAAACGCACAGCC | (SEQ ID NO: 72) |
| | TTTGTGCCATTGTGTGTGTG, | (SEQ ID NO: 73) | or at least one primer which is a variant of any one of said primers.

In a further embodiment, the identification methods analyse expression levels of the allele.

In another aspect, the present invention provides a method of obtaining a wheat or barley plant, the method comprising;
i) crossing two plants of the same species of which at least one plant comprises a Nax2 locus comprising an allele which confers enhanced tolerance to saline and/or sodic soils, and
ii) screening progeny plants from the cross for the presence or absence of said Nax2 locus by a method of the invention,
wherein progeny with said allele have enhanced tolerance to saline and/or sodic soils when compared to progeny lacking said allele.

In a further aspect, the present invention provides a method of obtaining a wheat or barley plant, the method comprising;
i) crossing two plants of the same species of which at least one plant comprises a Nax2 locus comprising an allele which confers reduced sodium accumulation in an aerial part of the plant, and
ii) screening progeny plants from the cross for the presence or absence of said Nax2 locus by a method of the invention,
wherein progeny with said allele have reduced sodium accumulation in an aerial part of the plant when compared to progeny lacking said allele.

In an embodiment, the above two methods further comprise the step of selecting a plant with the desired genotype or of analysing the plant for at least one other genetic marker.

In one embodiment, at least one of the wheat plants of step i) is a hexaploid wheat plant. Preferably, the cross is between a *durum* wheat plant comprising said allele and a hexaploid wheat plant lacking said allele.

In another embodiment, one of the wheat plants is *durum* wheat Line 149, *T. monococcum* C68-01, or a progenitor or progeny plant thereof comprising said allele.

In yet a further aspect, the present invention provides a method of introducing a Nax2 locus into the genome of a wheat or barley plant lacking said locus, the method comprising;

i) crossing a first parent plant with a second parent plant, wherein the second plant comprises a Nax2 locus which comprises an allele which confers enhanced tolerance to saline and/or sodic soils, and ii) backcrossing the progeny of the cross of step i) with plants of the same genotype as the first parent plant for a sufficient number of times to produce a plant with a majority of the genotype of the first parent but comprising said allele, wherein progeny plants are screened for the presence or absence of said allele by a method of the invention.

In another aspect the present invention provides a method of introducing a Nax2 locus into the genome of a wheat or barley plant lacking said locus, the method comprising;

i) crossing a first parent plant with a second parent plant, wherein the second plant comprises a Nax2 locus which comprises an allele which confers reduced sodium accumulation in an aerial part of a plant, and ii) backcrossing the progeny of the cross of step i) with plants of the same genotype as the first parent plant for a sufficient number of times to produce a plant with a majority of the genotype of the first parent but comprising said allele, wherein progeny plants are screened for the presence or absence of said allele by a method of the invention.

In a further aspect, the present invention provides a method of enhancing tolerance to saline and/or sodic soils in a cereal plant, the method comprising genetically manipulating said plant such that the production of a polypeptide is increased when compared to a wild-type plant, wherein the polypeptide has cation transporter activity.

In yet a further aspect, the present invention provides a method of reducing sodium accumulation in an aerial part of a cereal plant, the method comprising genetically manipulating said plant such that the production of a polypeptide is increased when compared to a wild-type plant, wherein the polypeptide has cation transporter activity.

Preferably, the polypeptide is a polypeptide according to the invention.

Also provided is a plant, or progeny thereof, produced using a method of the invention.

In yet another aspect, the present invention provides a wheat or barley plant, or progeny thereof, identified or obtained using a method of the invention.

In a further aspect the present invention provides a method of producing seed, the method comprising;

a) growing a plant of the invention, and
b) harvesting the seed.

Also provided is a seed of a plant of the invention.

In yet a further aspect, the present invention provides a method of producing flour, wholemeal, starch or other product obtained from seed, the method comprising;

a) obtaining seed of the invention, and
b) extracting the flour, wholemeal, starch or other product.

Also provided is a product produced from a plant of the invention.

In a further aspect the present invention provides a product produced from a seed of the invention. The product may be a food or non-food product.

Examples of food products include, but are not limited to, flour, starch, leavened or unleavened breads, pasta, noodles, animal fodder, beer, malt, breakfast cereals, snack foods, cakes, malt, beer, pastries and foods containing flour-based sauces.

Examples of non-food products include, but are not limited to, films, coatings, adhesives, building materials and packaging materials.

In a further aspect, the present invention provides a method of preparing a food product of the invention, the method comprising mixing seed, or flour, wholemeal or starch from said seed, with another ingredient.

Also provided is a method of preparing malt, comprising the step of germinating seed of the invention.

In another aspect, the present invention provides a substantially purified antibody, or fragment thereof, that specifically binds a polypeptide of the invention.

In a further aspect, the present invention provides a kit for identifying a wheat or barley plant with enhanced tolerance to saline and/or sodic soils, and/or identifying a wheat or barley plant having a phenotype of reduced sodium accumulation in an aerial part of the plant, the kit comprising at least one polynucleotide capable of being used in a method of the invention.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The invention is hereinafter described by way of the following non-limiting Examples and with reference to the accompanying figures.

BRIEF DESCRIPTION OF THE ACCOMPANYING DRAWINGS

FIG. 1. Frequency distributions for leaf (leaf 3 on the main-stem) $Na^+$ concentrations (mmol $gDW^{-1}$) of (A) Nax1 and (B) Nax2 $BC_5F_2$ populations, grown at 150 mM NaCl for 10 d. Arrows indicate parental means (n=6). For Nax1 screen, Line 149: 141±14, Tamaroi: 811±31; For Nax2 screen, Line 149: 278±37, Tamaroi: 1193±48.

Figure 2:
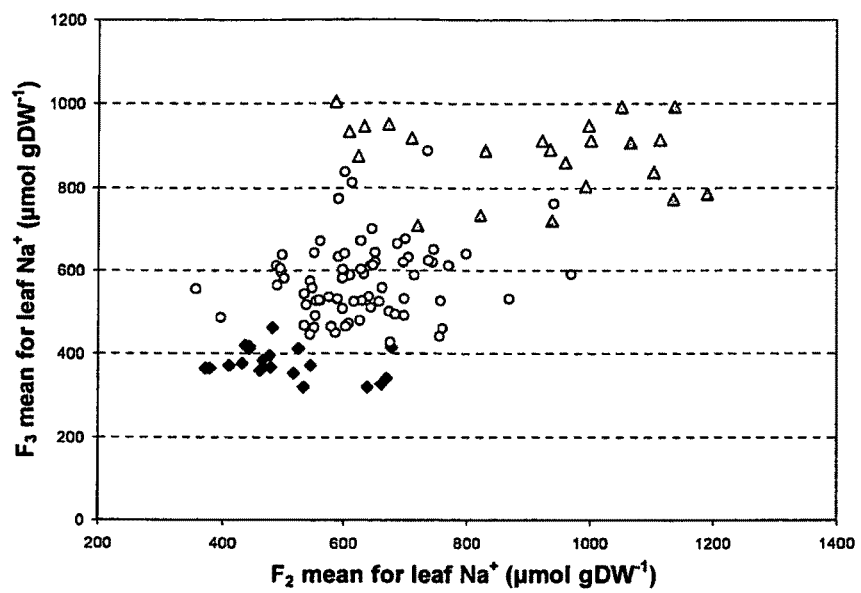

FIG. 2. Relationship between the $F_2$ and $F_{2:3}$ progeny means for $Na^+$ concentration of the $3^{rd}$ leaf in the single gene Nax2 family. Plants were grown at 150 mM NaCl for 10 days. ▲=homozygous lacking Nax2, ○=heterozygous for Nax2, ♦=homozygous for Nax2.

Figure 3:
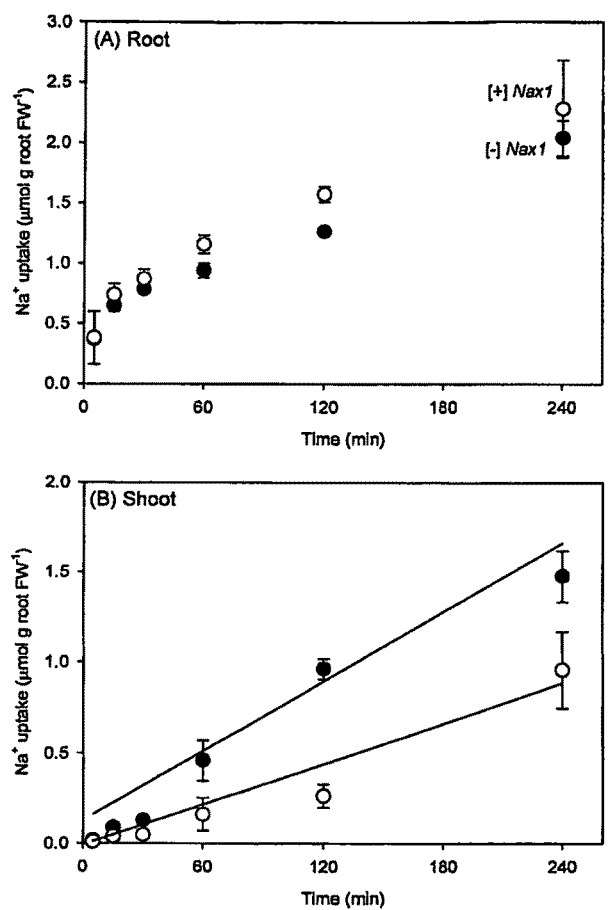

FIG. 3. $Na^+$ uptake measured as $^{22}Na^+$ accumulation in the (A) root and (B) shoot on a root fresh weight basis in Nax1 near-isogenic lines grown in 25 mM NaCl. Symbols: ○-[+]Nax1; ●-[−]Nax1. Fitted linear regressions to determine rate of $^{22}Na^+$ uptake (shoot) are described by the following equations: [+]Nax1: y=3.73×10$^{-3}$x−0.0074 ($r^2$=098); [−]Nax1: y=6.38×10$^{-3}$x+0.129 ($r^2$=0.86). Values represent means±se (n=4).

Figure 4:
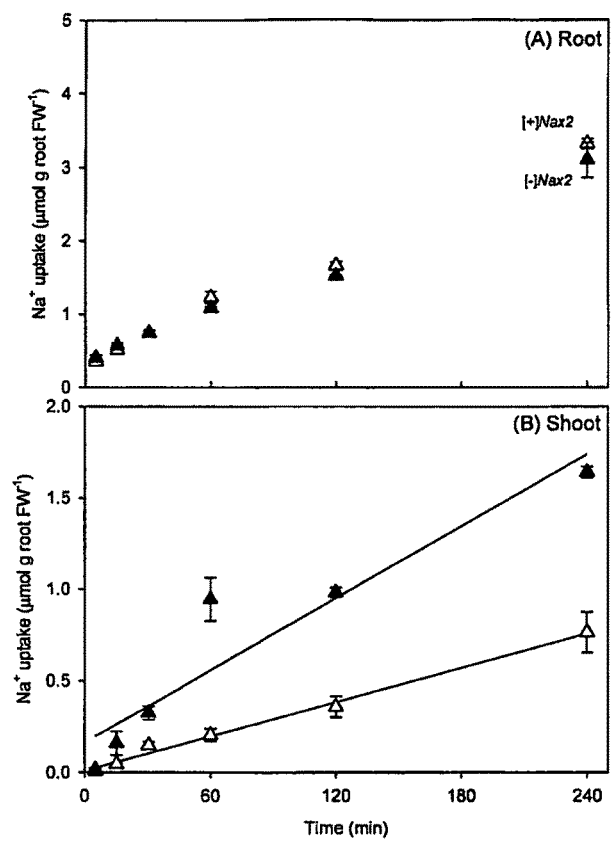

FIG. 4. $Na^+$ uptake measured as $^{22}Na^+$ accumulation in the (A) root and (B) shoot on a root fresh weight basis in Nax2 near-isogenic lines grown in 25 mM NaCl. Symbols: Δ-[+]Nax2; ▲-[−]Nax2. Fitted linear regressions to determine rate of $^{22}Na^+$ uptake (shoot) are described by the following equations: [+]Nax2: y=3.11×10$^{-3}$x+0.011 ($r^2$=0.99); [−]Nax2: y=6.55×10$^{-3}$x+0.165 ($r^2$=0.89). Values represent means±se (n=4).

Figure 5:
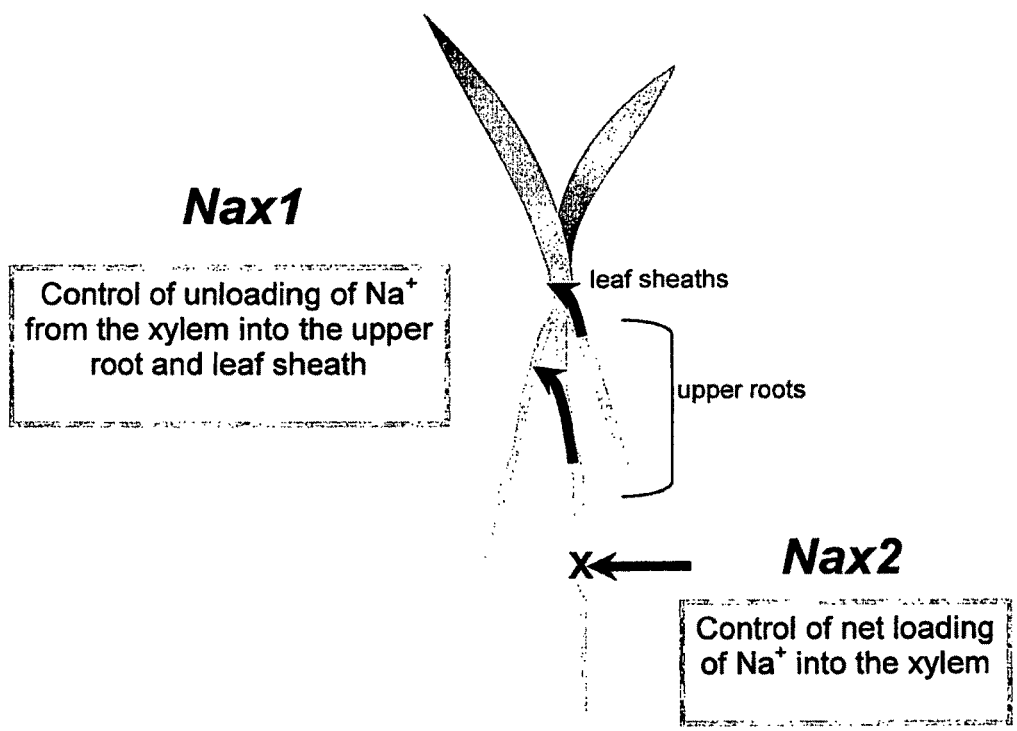

FIG. 5. Summary of differences between Nax1 and Nax2.

Figure 6:
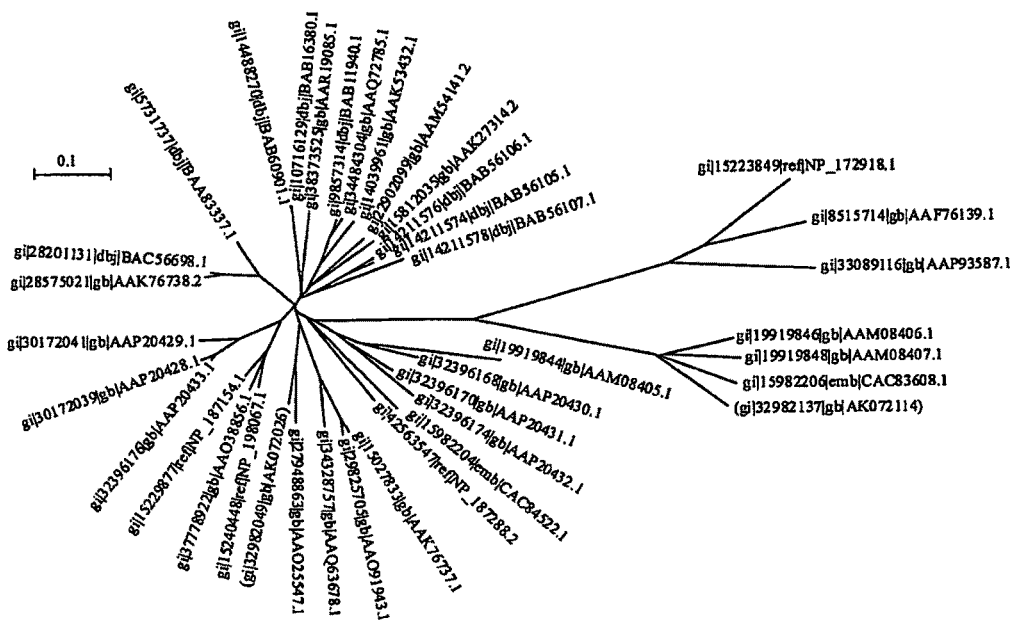

FIG. 6. Unrooted Neighbour-Joining tree of the NHX family of putative $Na^+/H^+$ antiporters obtained using CLUSTALX program. Scale bar shows 0.1 substitutions per site.

Figure 7:
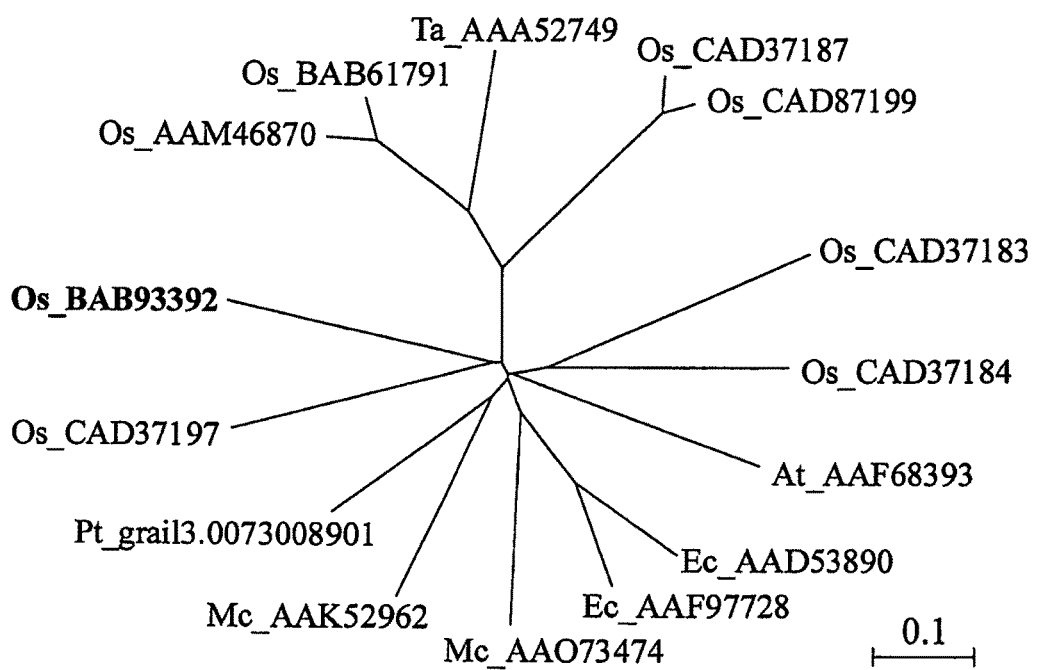

FIG. 7. Unrooted Neighbor-Joining tree of the sodium/potassium transporter gene family (HKT). The tree was constructed using the default alignment and bootstrap parameters of the ClustalX program. Scale bar shows 0.1 substitutions per site.

Figure 8:
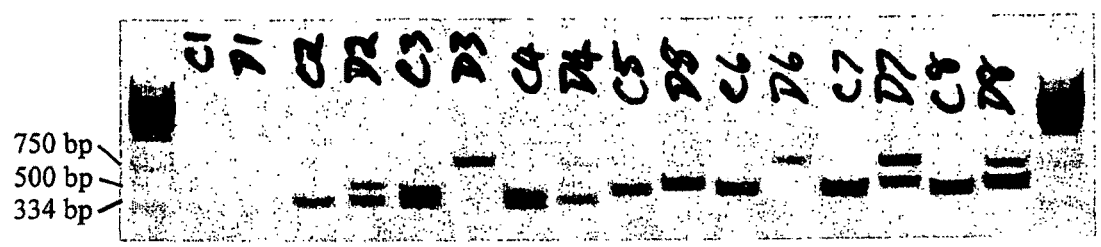

FIG. 8. Gel electrophoretogram showing the amplified fragment polymorphism between salt tolerant durum cv. Line 149 and salt sensitive cv. Tamaroi ("Tamaroi"). Template DNAs used were: Lane D1, none (negative control); D2, *T. monococcum* cDNA; D3, cv. Tamaroi cDNA; D4, Line 149 cDNA; D5, *T. monococcum* genomic DNA; D6, cv. Tamaroi genomic DNA; D7, Line 149 genomic DNA; D8, *T. aestivum* cv. Chinese Spring genomic DNA. Reactions labeled C1-C8 were from a different gene cloned at the same time and did not show a polymorphism between salt tolerant and sensitive lines.

Figure 9:
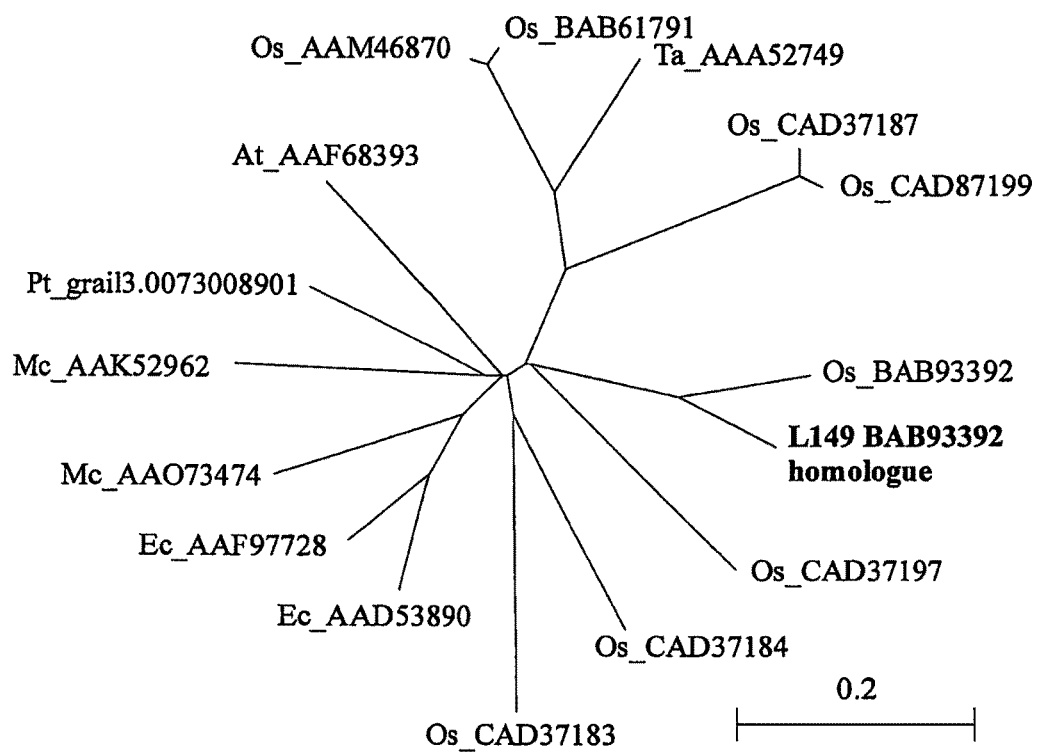

FIG. 9. Unrooted phylogenetic tree showing relationships of the fragment amplified from *T. monococcum* and *durum* cv. Line 149 with members of the sodium/potassium transporter gene family (HKT). The fragment amplified showed clear homology to the 3' end of the predicted protein corresponding to the rice gene OSJNBa0022N24.16. Scale bar shows 0.2 substitutions per site.

Figure 10:
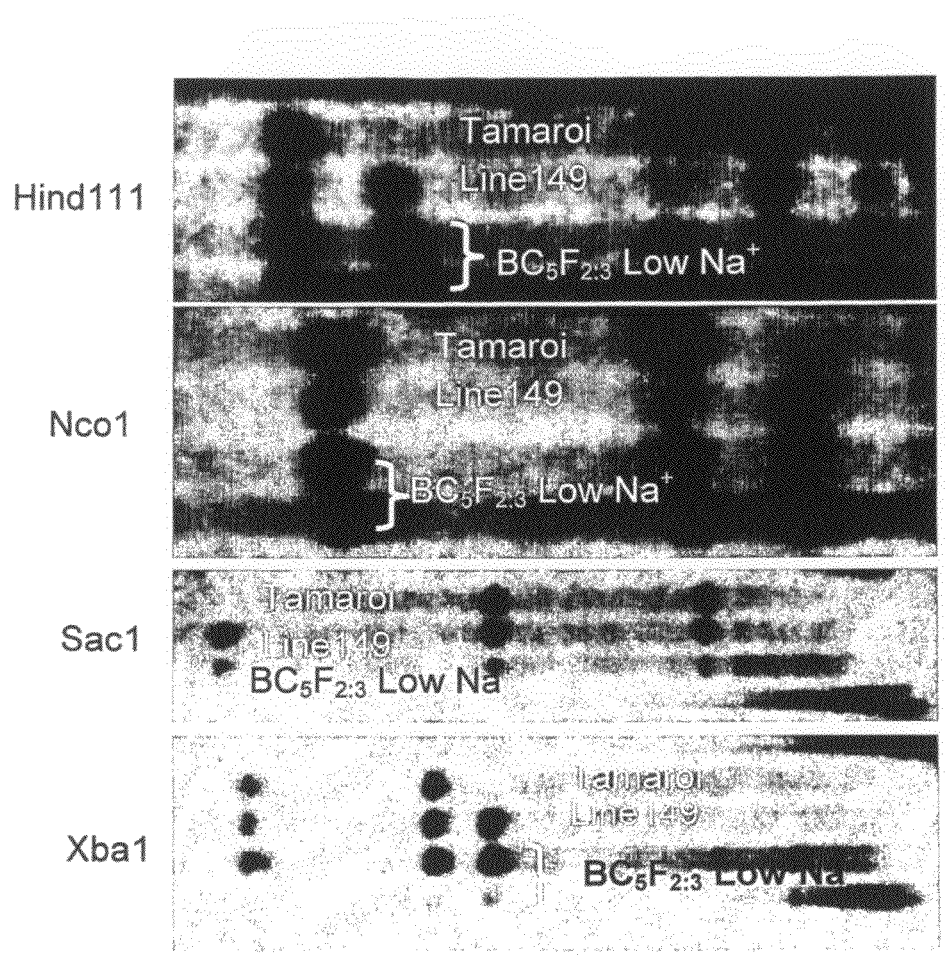

FIG. 10. Southern blot-hybridisation analysis of Tamaroi, Line 149 and six low sodium $BC_5F_{2:3}$ lines, in two hulks, when probed with the HKT8 probe. Tamaroi and Line 149 were polymorphic for a single band for each restriction enzyme digest, and the low sodium progeny had the same restriction pattern as Line 149.

Figure 11:
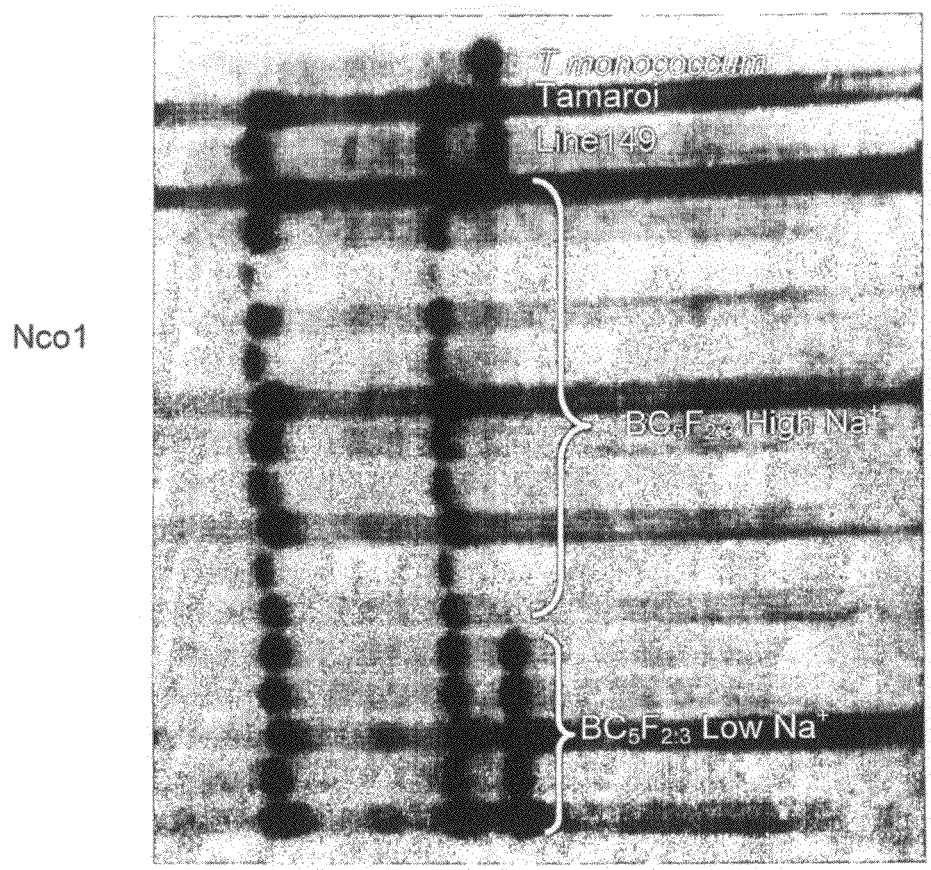

FIG. 11. Southern blot-hybridization analysis after NcoI digestion of DNA from *Triticum monococcum*, Tamaroi, Line 149, and 16 $BC_5F_{2:3}$ progeny, 11 of which had high leaf 3 $Na^+$ concentrations and 5 of which had low leaf 3 $Na^+$ concentrations. The additional hand in Line 149 and the low sodium progeny, but not Tamaroi, was also present in *T. monococcum*.

Figure 12:
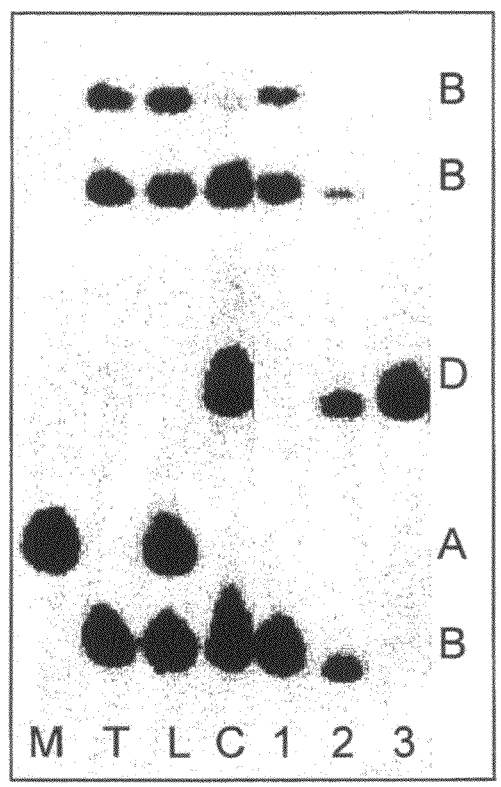

FIG. 12. Southern blot-hybridization with HKT8 probe after HindIII restriction digest of DNA from *Triticum monococcum* (M), Tamaroi (T), Line 149 (L), Chinese Spring (C), Langdon (1) and Langdon substitution lines 4D(4A) (2) and 4D(4B) (3). The genome location of the HKT8 gene members are shown on the right hand side.

Figure 13:
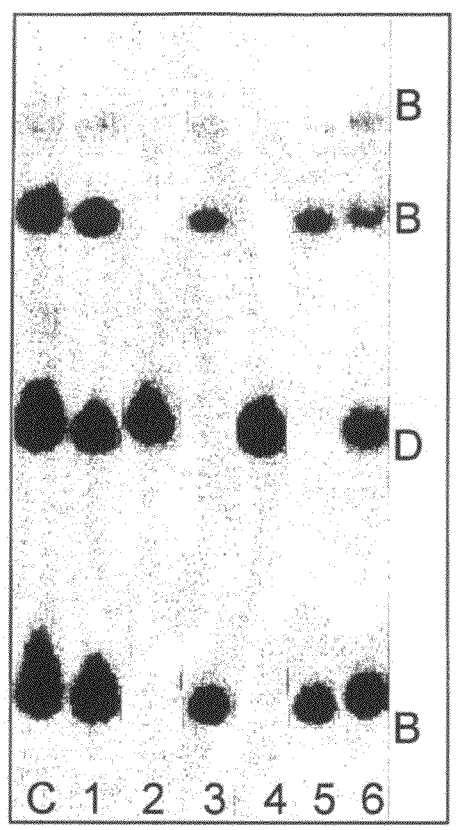

FIG. 13. Southern blot-hybridization with HKT8 probe after HindIII restriction digest of DNA from Chinese Spring (C); Chinese Spring chromosome deletion lines N4AT4B (missing chromosome 4A, four copies of 4B) (1), m4BT4A (one copy of 4B, four copies of 4A) (2), N4DT4B (missing 4D, four copies of 4B) (3); and Chinese Spring ditelomeric lines Dt4BS (missing the long arm of 4B) (4), Dt4DS (missing the long arm of 4D) (5) and Dt4DL (missing the short arm of 4D) (6). The genome location of the HKT8 gene members are shown on the right hand side.

Figure 14:
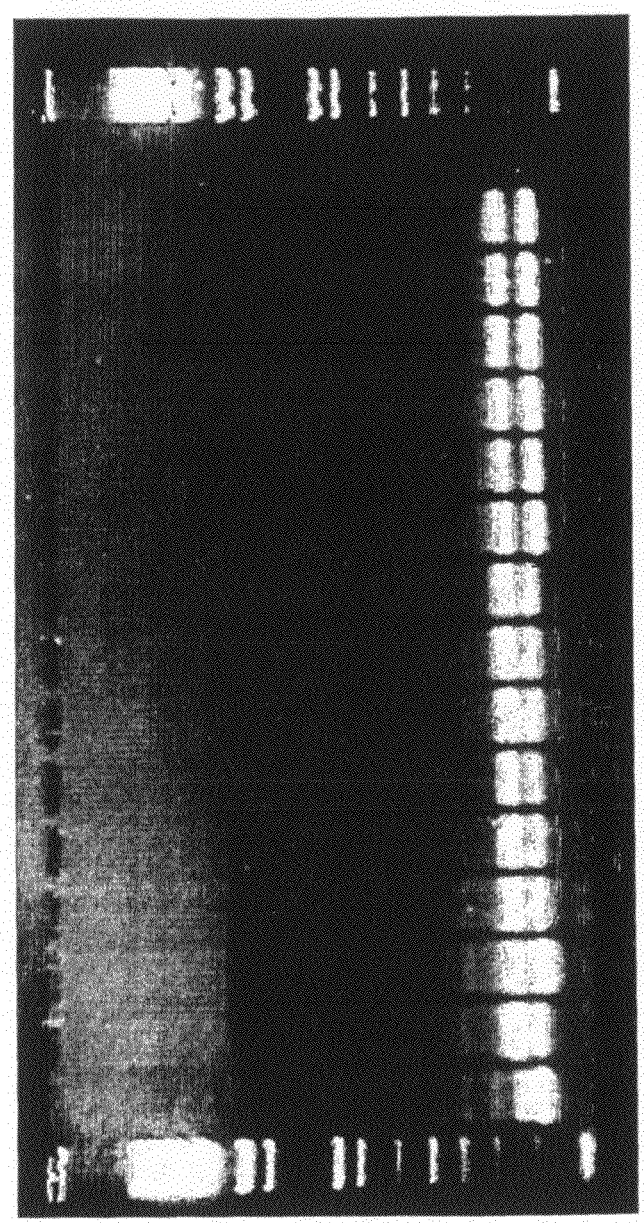

FIG. 14. PCR with the gpw2181 marker. The lower band was polymorphic between the lines with Nax2 and lines without Nax2. The lower band was smaller in Tamaroi (T) and the lines with high leaf $Na^+$ compared to *T. monococcum* (M), Line 149 (L) and the lines with low leaf $Na^+$. N=No template control. 1 $kb^+$=DNA ladder.

Figure 15:
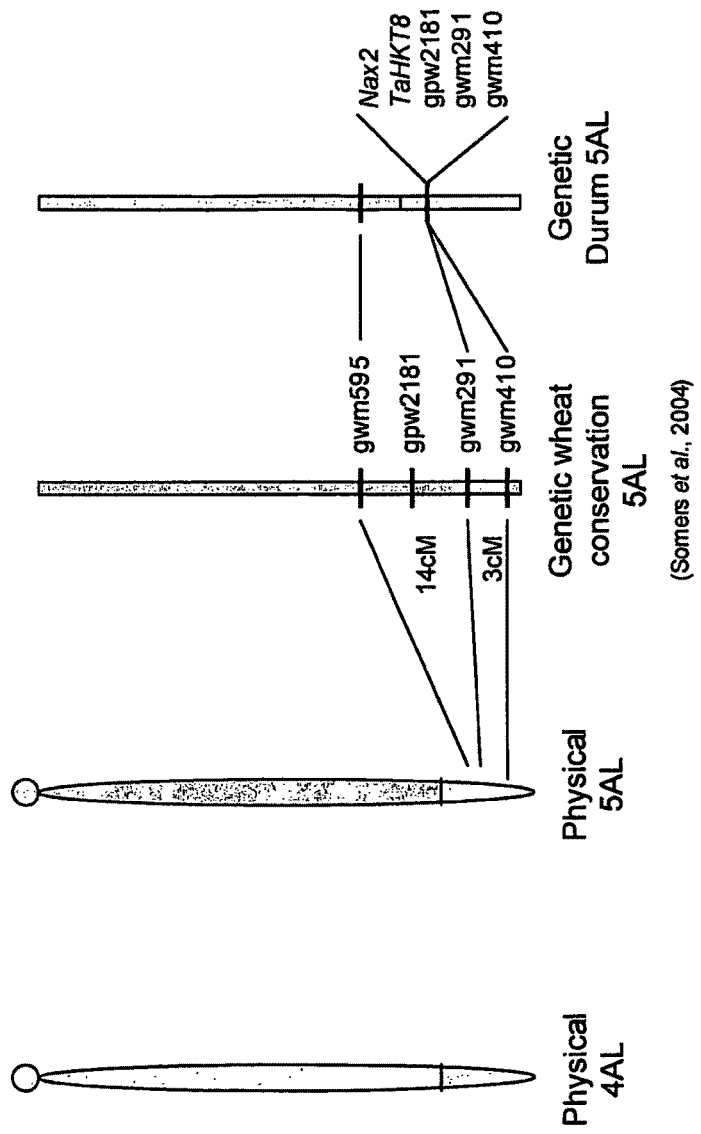

FIG. 15. Physical 5AL was found to correspond to genetic 4AL due to an ancient reciprocal translocation between the distal end of chromosome 4AL and 5AL. Genetic *Durum* 5AL depicts the fragment containing Nax2 which had been introgressed from Line 149 into the Tamaroi background in the Nax2 mapping population. Proximal to the introgression was gwm595. Nax2 was linked to gwm291, gwm410 and gpw2181.

Figure 16:
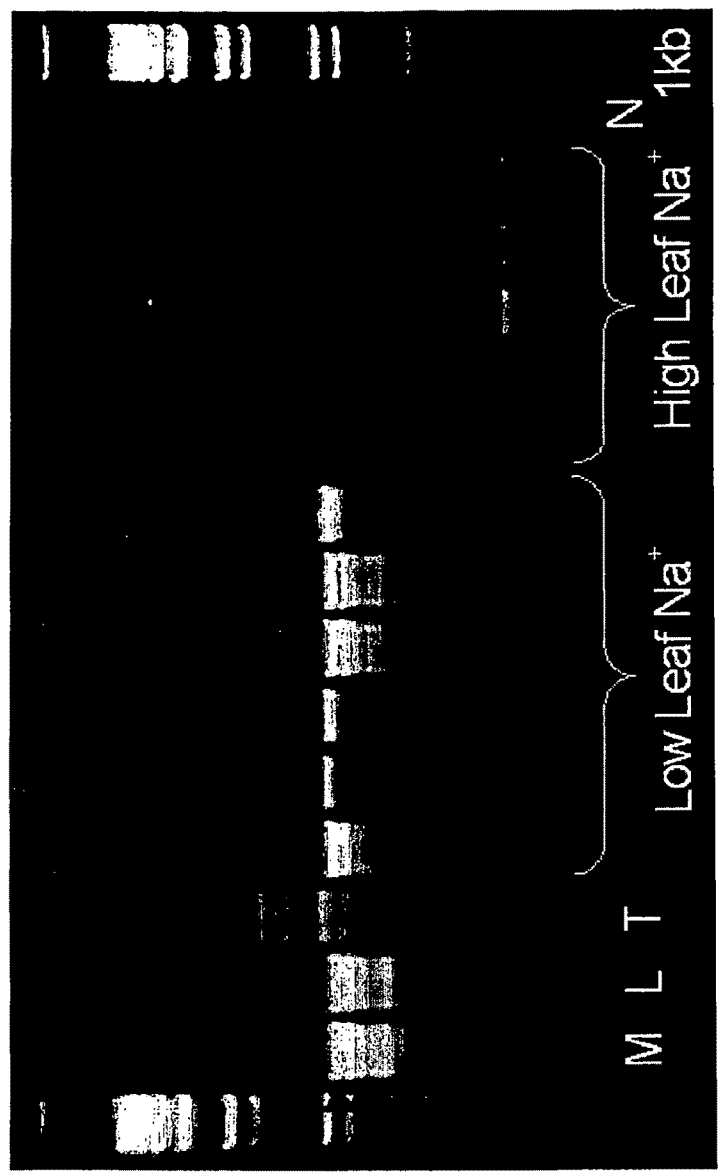

FIG. 16. PCR with the gene specific marker (HKT8-A) for Nax2. This marker was dominant for Nax2. Lines with Nax2 contained a band of 986 bp (lanes for *T. monococcum* (M), Line 149 (L) and the lines with low leaf $Na^+$). This band was absent for Tamaroi (T) and the lines with high leaf $Na^+$ compared. N=No template control. 1 kb=DNA ladder of molecular weight standards.

Figure 17B:
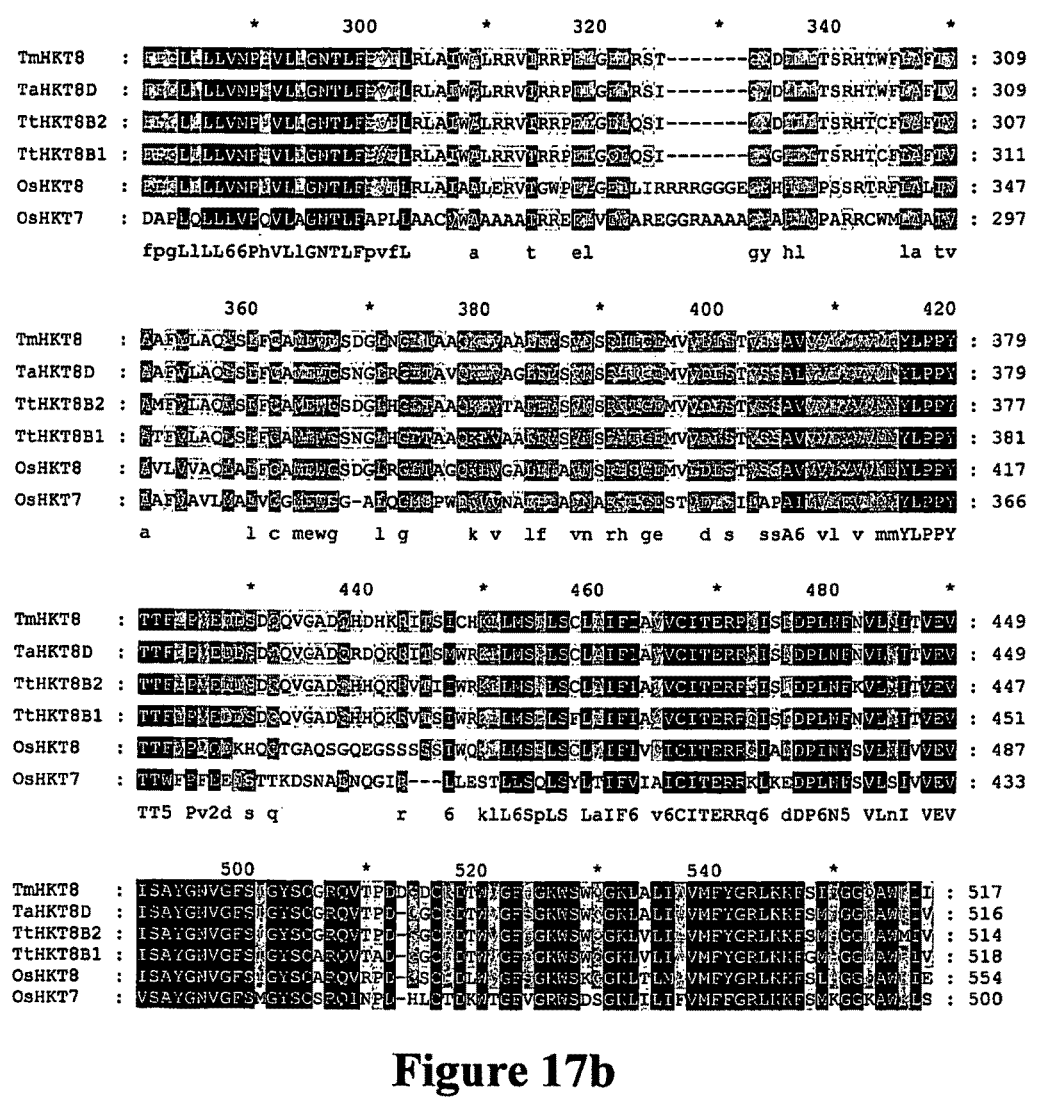

FIG. 17. Alignment of full-length predicted amino acid sequences for the *T. monococcum* (SEQ ID NO:1), *T. turgidum* ssp. *durum* cv. Tamaroi (SEQ ID NO's 2 and 3), *T. aestivum* cv. Halberd HKT8 (SEQ ID NO:6) and *Oryza sativa* OsHKT8 and OsHKT7 (SEQ ID NO's 26 and 27) genes. Only the D-genome homeologue is shown for *T. aestivum* as the B-genome genes were identical to those of *T. turgidum* ssp. *durum* cv. Tamaroi. Alignments were constructed using CLUSTALX (Thompson et al. 1997) and the default parameters. Alignments were visualised using GeneDoc (Nicholas et al. 1997).

Figure 18A:
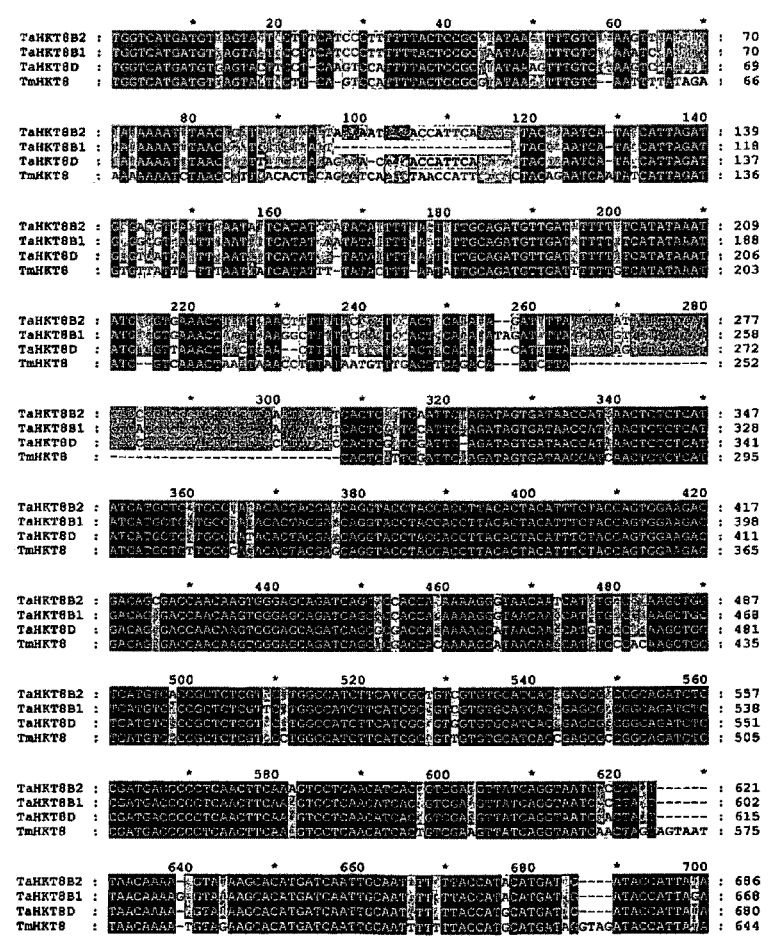
Figure 18B:
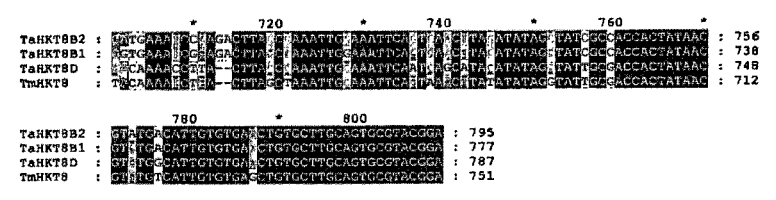

FIG. 18. Alignment of *T. monococcum*, and *T. aestivum* cv. Halberd genomic DNA sequences of HKT8 (SEQ ID NO's 99-102 respectively). The *T. turgidum* ssp. *durum* cv. Tamaroi B-genome homeologues were essentially identical in sequence to their *T. aestivum* B-genome homologues. The fragment shown spans a region from 10 bp upstream of the first intron to 10 bp downstream of the second intron, and includes the intervening second exon (nucleotide positions 381 to 611 in the alignment). Protein coding sequence corresponds to nucleotides 1-10, 381 to 611 and 800 to 809 in the alignment. Alignment was created using MEGA3 (REF) and the default parameters. Alignment was viewed using GeneDoc (REF).

FIG. 19. Unrooted minimum-evolution phylogeny of the full-length HKT8 amino acid sequences shown in FIG. 18 and cDNA nucleotide sequences. The OsHKT7 (accession CAD37197) sequence was included as an outgroup. A. Unrooted protein phylogeny. The tree was constructed using MEGA3 (Kumar et al. 2004), with the Close-Neighbour-Interchange algorithm (level 2) to calculate the tree, a Neighbour-Joining tree as the starting tree, and 10000 bootstrap replicates with a random number seed of 64238. The Dayhoff model of amino acid residue substitution was applied. Scale bar shows 0.1 substitutions per site. B. Unrooted cDNA coding sequence phylogeny. The tree was constructed using MEGA3 with the Close-Neighbour-Interchange algorithm (level 2) to calculate the tree, a Neighbour-Joining tree as the starting tree, and 10000 bootstrap replicates with a random number seed of 39306. The Kimura 2-parameter model of nucleotide substitution was applied. Scale bar shows 0.05 substitutions per site. Numbers on branches in both trees indicate percentage bootstrap support.

Figure 20:
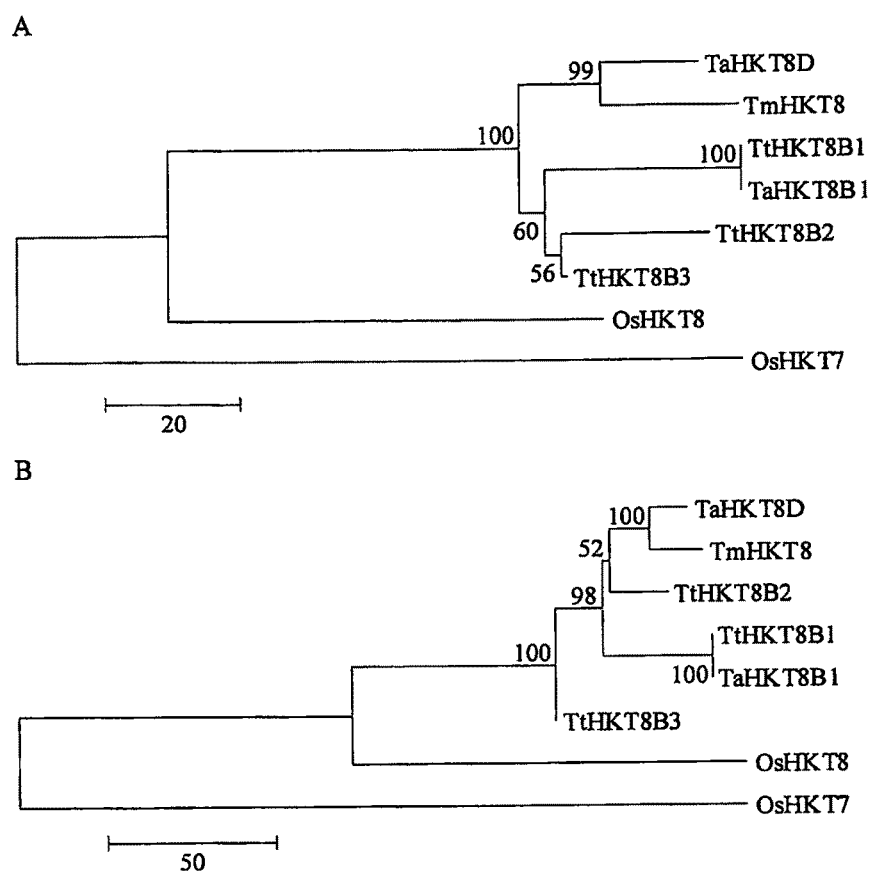

FIG. 20. Unrooted minimum-evolution phylogeny of full-length HKT8 cDNA sequences, constructed using the Nei-Gojobori method. The TaHKT8B1 sequence has been included, and the OsHKT7 (accession CAD37197) sequence is included as an outgroup. A. Tree constructed using only synonymous changes (i.e. those that do not affect protein sequence). This tree reflects the "baseline" phylogeny due simply to time since divergence. B. Tree constructed using only non-synonymous changes (i.e. those affecting amino acid sequence). The HKT8 genes from the B genome showed differences in position that could be related to selection pressure.

Figure 21:
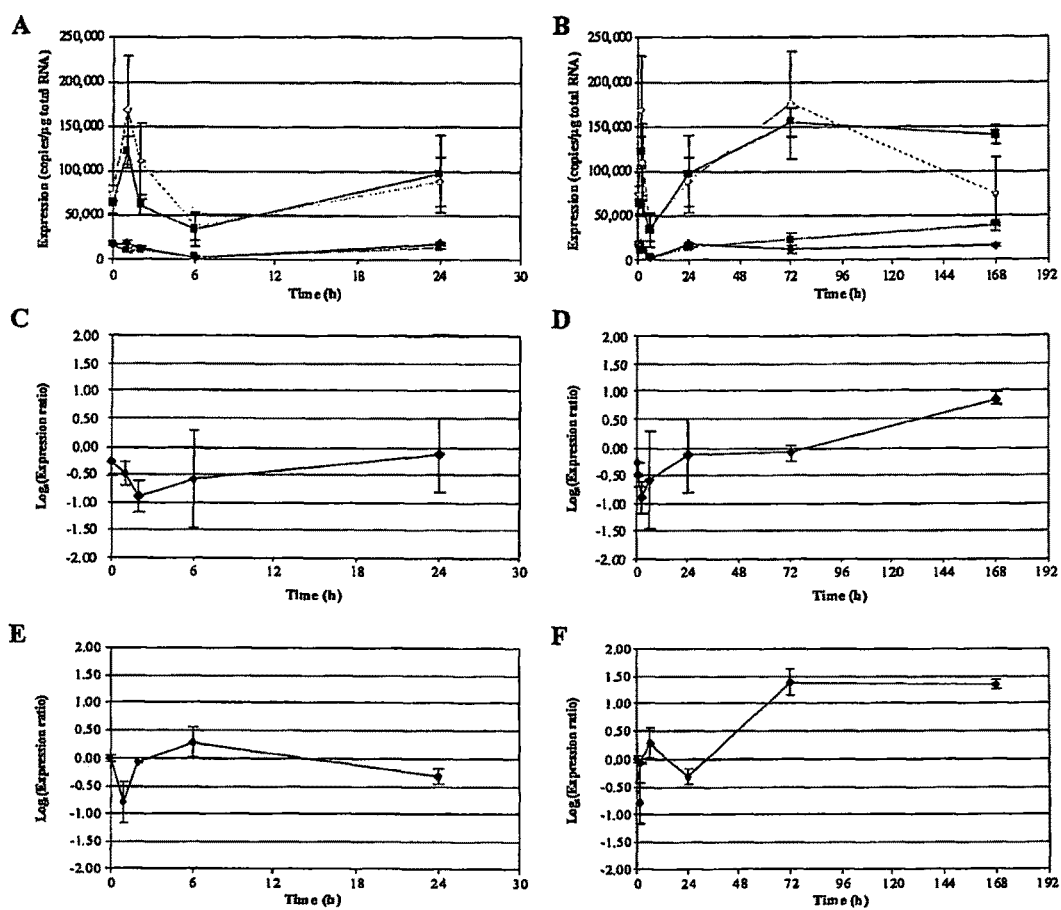

FIG. 21. Expression profile of HKT8 after treatment with 75 mM NaCl. A, B. Expression profile of HKT8 in the salt tolerant cultivar 5049 and the salt sensitive cultivar Tamaroi. Expression was normalized to the wheat homologues of ACT1, At1g13320, and At4g34270. A. Expression over the first 24 hours after exposure. B. Expression over 7 days. ──◆── cv. 5049, untreated; ──■── cv. 5049+75 mM NaCl; ──▲── cv. Tamaroi, untreated; ──●── cv. Tamaroi+75 mM NaCl. C, D. The $\log_2$ transformation of the salt treated vs. untreated HKT8 expression ratio in cv. 5049 plants. C. Expression differences over the first 24 hours after exposure. D. Expression differences over 7 days after exposure. E, F.

The log₂ transformation of the salt treated vs. untreated HKT8 expression ratio in cv. Tamaroi plants. Note the much shorter period of down-regulation after salt treatment, and the accelerated rate at which equilibrium is achieved.

Figure 22:
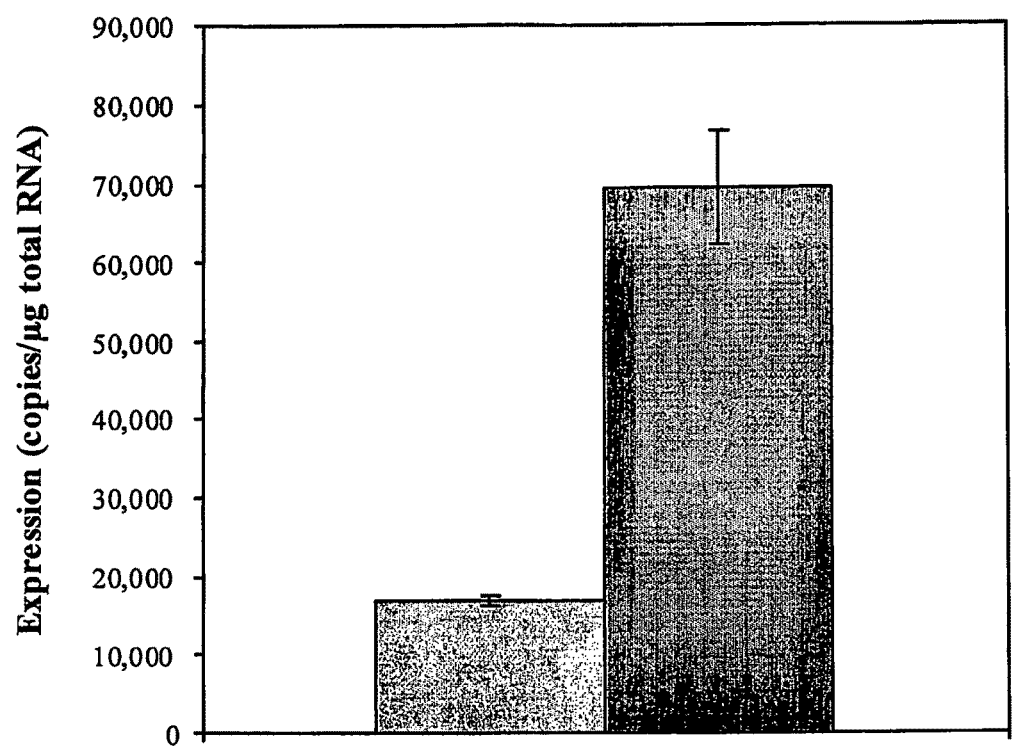

FIG. 22. Absolute expression levels in salt-sensitive cv. Tamaroi and salt tolerant cv. 5049 14d after germination under non-stressed (untreated) conditions. Salt tolerant cv. 5049 has approximately 4-fold higher expression of HKT8 than cv. Tamaroi. The ratio of expression is similar at other timepoints and after salt treatment. ▨ cv. Tamaroi; ▨ cv. 5049.

FIG. 23. A. Map of the binary construct pART27-TmHKT8 for overexpression of the TmHKT8 gene. Maps for overexpression of the TtHKT8-B1, TtHKT8-B2, TtHKT8-B3, and TaHKT8-D genes are similar but for the specific coding region inserted into the EcoRI site between the 35S promoter and OCS terminator. B. Map of the binary construct pVec8-TmHKT8 for transformation into barley and/or rice (the pWUbi-pVec8 system seems to be effective in many graminaceous species).

Figure 24:
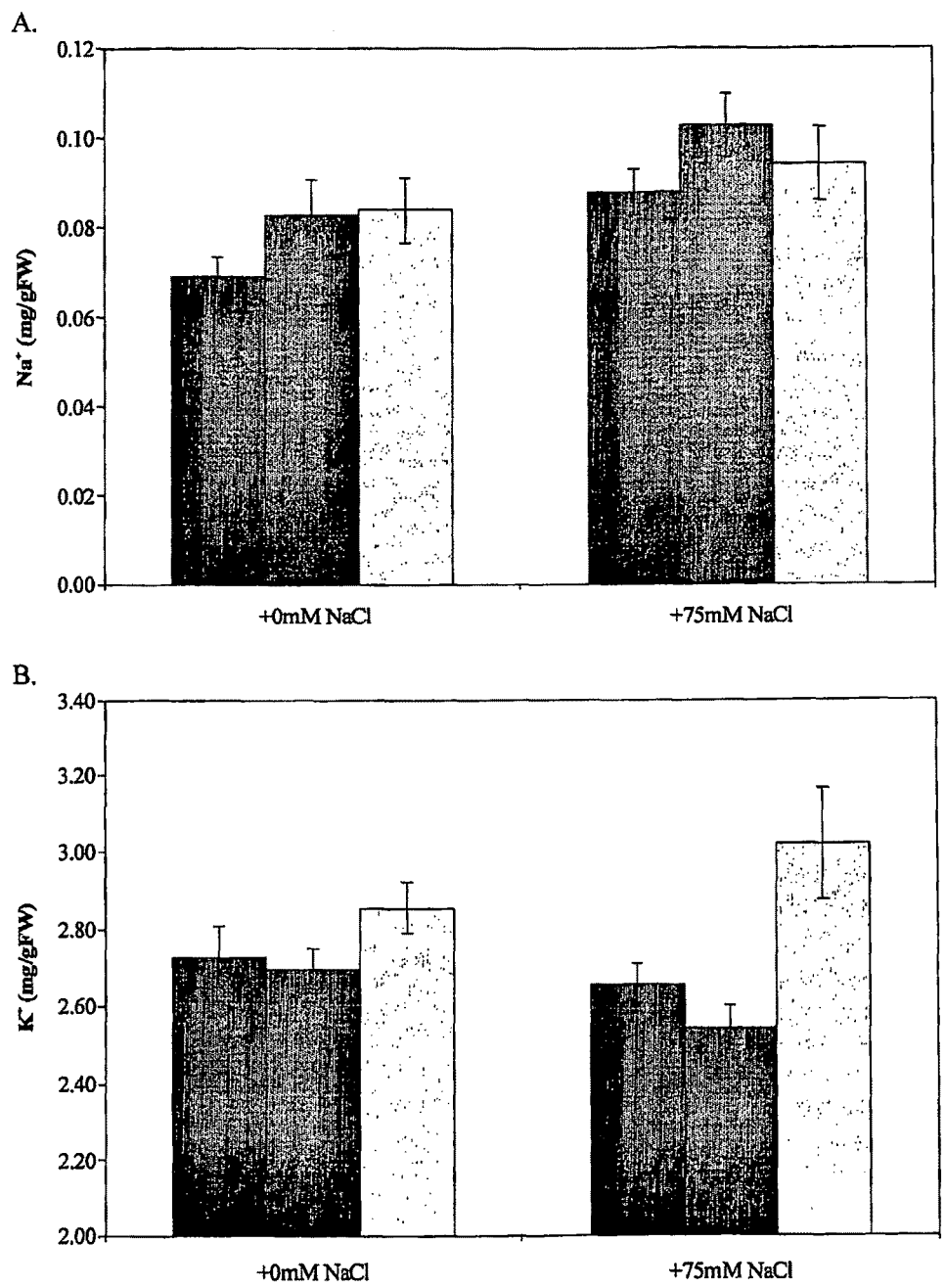

FIG. 24. A. Na$^+$ content (mg/gFW) of leaf 5 from wild-type *Arabidopsis* cv. Columbia, and plants overexpressing the TmHKT8 and TtHKT8-B1 genes. B. K$^+$ content of the same plants. Note the abbreviated scale on the y-axis. ■ wild-type cv. Columbia; ■ lines overexpressing the TmHKT8 gene; ☐ lines overexpressing the TtHKT8-B1 gene.

FIG. 25. Sequence polymorphism of B-genome HKT8 homologues (SEQ ID NO's 103 to 133 respectively). The cysteine-to-glycine substitution in HKT8 B-genome members indicated is shared with most members of subfamily 2 (brown) but is different from all other members of subfamily 1 including the A$^m$- and D-genome members. The residue in question is predicted to lie directly next to a residue in the first pore loop domain (Durell and Guy, 1999), a residue that is known to be a critical determinant of the Na$^+$/K$^+$ selectivity of the protein (Mäser et al, 2002), and is therefore highly likely to have functional consequences.

Figure 26:
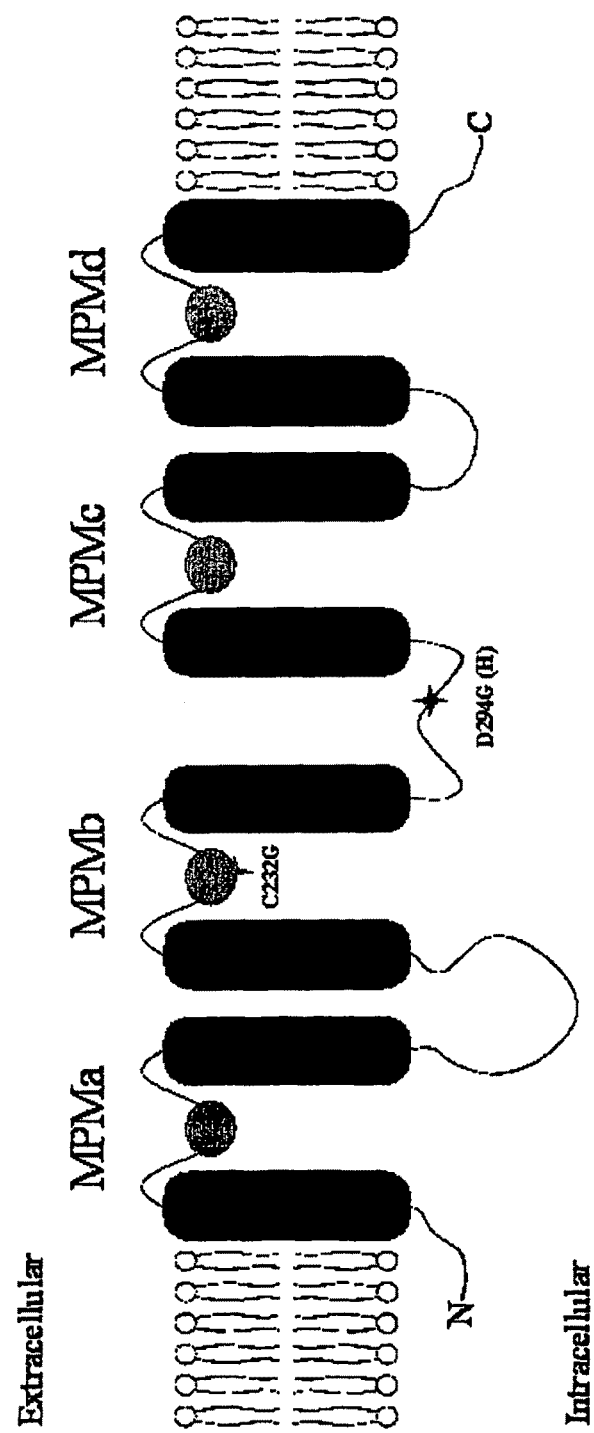

FIG. 26. Schematic diagram showing predicted relative position of transmembrane spanning domains, as well as intracellular and extracellular loops, of wheat Nax2 polypeptides. Amino acid residues which may play a role in conferring enhanced tolerance to saline and/or sodic soils are highlighted.

Figure 27:
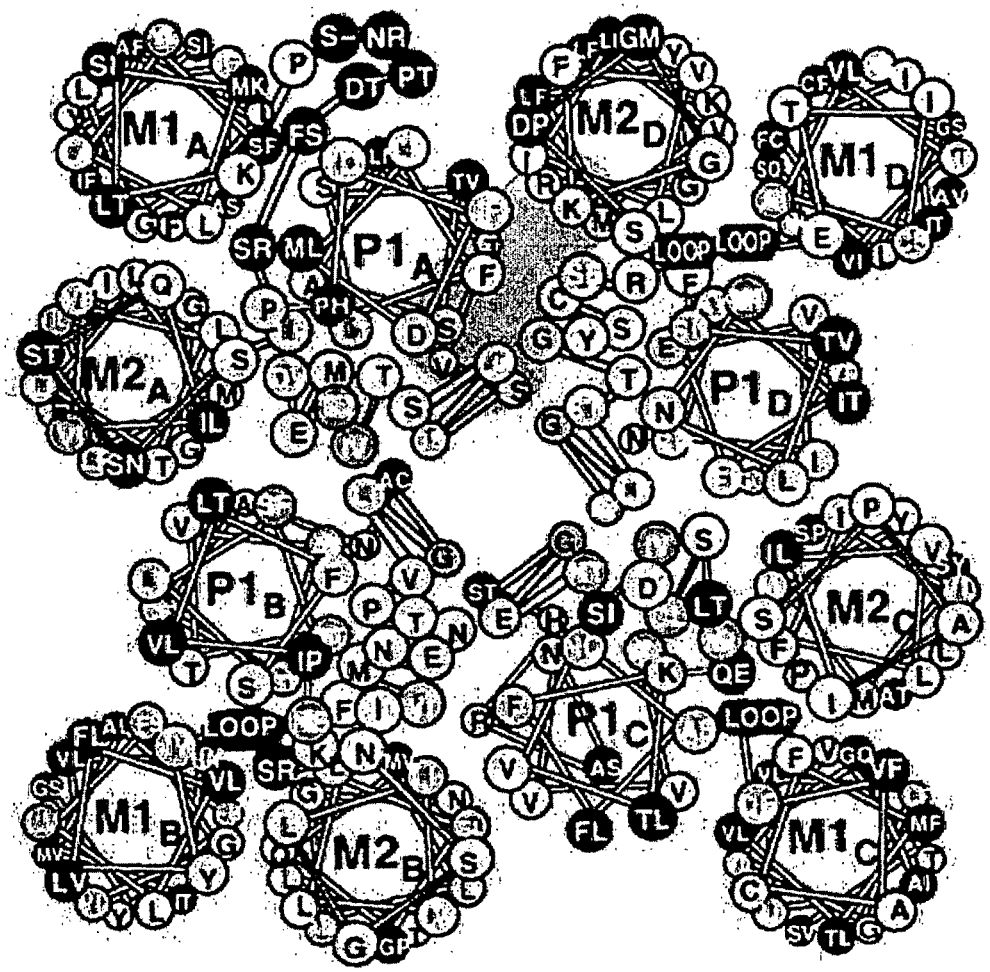

FIG. 27. Schematic representation of structure of wheat Nax2 polypeptides.

FIG. 28. Sequence polymorphism of HKT8 homologues surrounding amino acid position 294 (SEQ ID NO's 134 to 159 respectively).

Figure 29:

FIG. 29. Southern blot-hybridization with HKT8 probe after HindIII restriction digest of DNA from Chinese Spring (lane 1); and Chinese Spring chromosome deletion lines 0.86 (lane 2), 0.70 (lane 3), 0.61 (lane 4). 0.56 (lane 5). The chromosome D HKT8 gene member mapped to the most distal deletion bin. The genome location of the HKT8 gene members are shown on the right hand side.

FIG. 30. Alignment of nucleotide sequences of D genome HKT8 coding regions isolated from *Aegilops tauschii* lines Aet110664 (SEQ ID NO:16), Aet18913 (SEQ ID NO:17), and Aet18905 (SEQ ID NO:18) and Chinese Spring ("Chinese", SEQ ID NO:15).

FIG. 31. Alignment of deduced amino acid sequences of proteins encoded by D genome HKT8 genes isolated from *A. tauschii* lines Aet110664 (SEQ ID NO:7), Aet18913 (SEQ ID NO:8), and Aet18905 (SEQ ID NO:9) and Chinese Spring ("Chinese", SEQ ID NO:6), compared to the rice gene Os01g20160 (SEQ ID NO:26).

Figure 32:
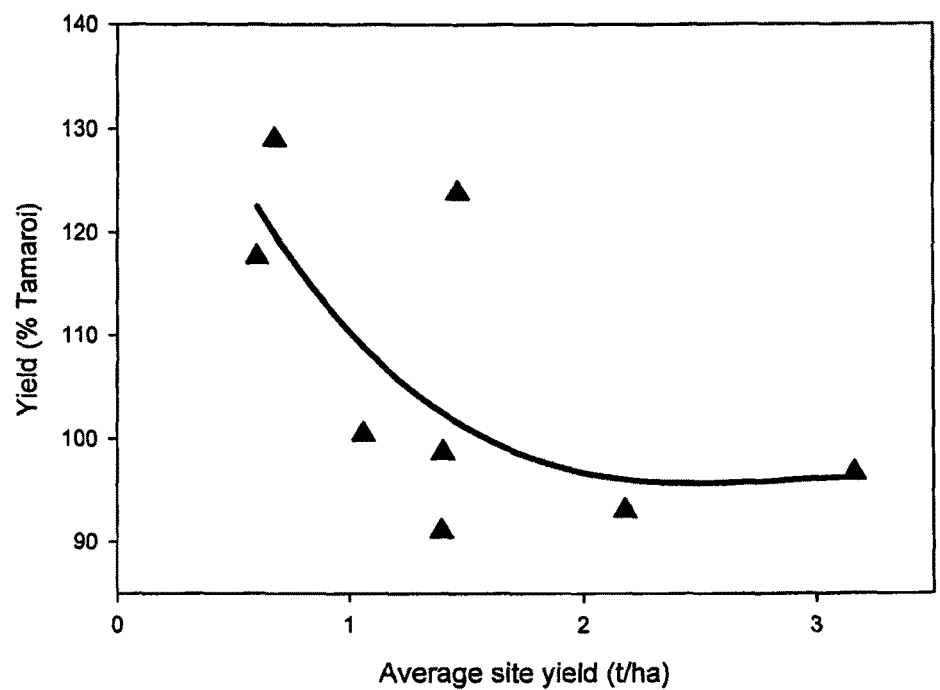

FIG. 32. Mean yield of Nax2 lines, as a percentage of recurrent parent Tamaroi, across 8 field sites in South Australia.

KEY TO THE SEQUENCE LISTING

SEQ ID NO:1—Nax2 polypeptide from *Triticum monococcum* (also referred to herein as TmHKT8 and HKT1;5).

SEQ ID NO:2—TtHKT8B1 Nax2 polypeptide from *Triticum turgidum* ssp *durum* cv. Tamaroi (also referred to herein as TtHKT1;5-B1).

SEQ ID NO:3—TtHKT8B2 Nax2 polypeptide from *Triticum turgidum* ssp *durum* cv. Tamaroi (also referred to herein as TtHKT1;5-B2).

SEQ ID NO:4—TaHKT8B1 Nax2 polypeptide from *Triticum aestivum* cv Chinese Spring.

SEQ ID NO:5—TaHKT8B2 Nax2 polypeptide from *Triticum aestivum* cv Chinese Spring.

SEQ ID NO:6—TaHKT8D Nax2 polypeptide from *Triticum aestivum* cv Chinese Spring.

SEQ ID NO:7—HKT Nax2 polypeptide from *Aegilops tauschii* line CPI 110664.

SEQ ID NO:8—HKT Nax2 polypeptide from *Aegilops tauschii* line AUS 18913.

SEQ ID NO:9—HKT Nax2 polypeptide from *Aegilops tauschii* line AUS 18905.

SEQ ID NO:10—Open reading frame encoding Nax2 polypeptide from *Triticum monococcum* (TmHKT8 or HKT1;5).

SEQ ID NO:11—Open reading frame encoding TtHKT8B1 Nax2 polypeptide from *Triticum turgidum* ssp *durum* cv. Tamaroi.

SEQ ID NO:12—Open reading frame encoding TtHKT8B2 Nax2 polypeptide from *Triticum turgidum* ssp *durum* cv. Tamaroi.

SEQ ID NO:13—Open reading frame encoding TaHKT8B1 Nax2 polypeptide from *Triticum aestivum* cv Chinese Spring.

SEQ ID NO:14—Open reading frame encoding TaHKT8B2 Nax2 polypeptide from *Triticum aestivum* cv Chinese Spring.

SEQ ID NO:15—Open reading frame encoding TaHKT8D Nax2 polypeptide from *Triticum aestivum* cv Chinese Spring.

SEQ ID NO:16—Open reading frame encoding HKT Nax2 polypeptide from *Aegilops tauschii* line CPI 110664.

SEQ ID NO:17—Open reading frame encoding HKT Nax2 polypeptide from *Aegilops tauschii* line AUS 18913.

SEQ ID NO:18—Open reading frame encoding HKT Nax2 polypeptide from *Aegilops tauschii* line AUS 18905.

SEQ ID NO:19—Full length cDNA sequence encoding Nax2 polypeptide from *Triticum monococcum* (TmHKT8).

SEQ ID NO:20—Full length cDNA sequence encoding TtHKT8B1 Nax2 polypeptide from *Triticum turgidum* ssp *durum* cv Tamaroi.

SEQ ID NO:21—Full length cDNA sequence encoding TtHKT8B2 Nax2 polypeptide from *Triticum turgidum* ssp *durum* cv. Tamaroi.

SEQ ID NO:22—Full length cDNA sequence encoding TaHKT8B1 Nax2 polypeptide from *Triticum aestivum* cv Chinese Spring.

SEQ ID NO:23—Full length cDNA sequence encoding TaHKT8B2 Nax2 polypeptide from *Triticum aestivum* cv Chinese Spring.

SEQ ID NO:24—Full length cDNA sequence encoding TaHKT8D Nax2 polypeptide from *Triticum aestivum* cv Chinese Spring.

SEQ ID NO:25—Full length cDNA sequence encoded by TtHKT8B3 Nax2 pseudogene from *Triticum turgidum* ssp *durum* cv. Tamaroi.

SEQ ID NO:26—Rice HKT8 polypeptide.
SEQ ID NO:27—Rice HKT7 polypeptide.
SEQ ID NO's 28 to 64—Oligonucleotide primers.
SEQ ID NO:65—Nucleotide sequence corresponding to part of the *T. monococcum* TmHKT8-A$^m$ gene, amplified from cDNA.
SEQ ID NO:66—Nucleotide sequence corresponding to part of the *T. monococcum* TmHKT8-A$^m$ gene, amplified from genomic DNA. The intron corresponds to bases 22 to 206 of this sequence (length=185 bp).
SEQ ID NO:67—Amino acid sequence encoded by SEQ ID NO:65 and SEQ ID NO:66 (minus intron sequence).
SEQ ID NO's 68 to 82—Oligonucleotide primers.
SEQ ID NO:83—Nax2 polypeptide from *Hordeum vulgare* cv Golden Promise (also referred to herein as HvHKT1;5-1).
SEQ ID NO:84—Partial Nax2 polypeptide sequence from *Hordeum vulgare* cv Halcyon (also referred to herein as HvHKT1;5-2).
SEQ ID NO:85—Nax2 polypeptide from *Hordeum vulgare* cv Morex (also referred to herein as HvHKT1;5-3).
SEQ ID NO:86—Partial Nax2 polypeptide sequence from *Hordeum intercedens* (also referred to herein as HiHKT1;5).
SEQ ID NO:87—Partial Nax2 polypeptide sequence from *Hordeum murinum* ssp. *glaucum* (also referred to herein as HmurHKT1;5).
SEQ ID NO:88—Partial Nax2 polypeptide sequence from *Hordeum marinum* ssp. *gussoneanum* homeologue 1 (also referred to herein as HmarHKT1;5A).
SEQ ID NO:89—Partial Nax2 polypeptide sequence from *Hordeum marinum* ssp. *gussoneanum* homeologue 2 (also referred to herein as HmarHKT1;5B).
SEQ ID NO:90—Open reading frame encoding Nax2 polypeptide from *Hordeum vulgare* cv Golden Promise.
SEQ ID NO:91—Open reading frame encoding partial Nax2 polypeptide from *Hordeum vulgare* cv Halcyon.
SEQ ID NO:92—Open reading frame encoding Nax2 polypeptide from *Hordeum vulgare* cv Morex.
SEQ ID NO:93—Open reading frame encoding partial Nax2 polypeptide from *Hordeum intercedens*.
SEQ ID NO:94—Open reading frame encoding partial Nax2 polypeptide from *Hordeum murinum* ssp. *glaucum*.
SEQ ID NO:95—Open reading frame encoding partial Nax2 polypeptide from *Hordeum marinum* ssp. *gussoneanum* homeologue 1.
SEQ ID NO:96—Open reading frame encoding partial Nax2 polypeptide from *Hordeum marinum* ssp. *gussoneanum* homeologue 2.
SEQ ID NO:97—Promoter region of TmHKT8 gene.
SEQ ID NO:98—Promoter region of the TaHKT8D gene.

DETAILED DESCRIPTION OF THE INVENTION

General Techniques

Unless specifically defined otherwise, all technical and scientific terms used herein shall be taken to have the same meaning as commonly understood by one of ordinary skill in the art (e.g., in cell culture, molecular genetics, immunology, immunohistochemistry, protein chemistry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al. Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

Selected Definitions

As used herein, the term "Nax2 gene" refers to a gene on the A genome of a wheat plant which confers enhanced tolerance to saline and sodic soils and/or reduced sodium accumulation in an aerial part of the plant comprising the gene. This gene is located on chromosome 5AL of certain diploid, tetraploid and hexaploid wheat genotypes. It is ancestrally located on chromosome 4AL. The experimental data provided herein shows that Nax2 is a HKT8 gene family member. An example of an allele of HKT8 which confers enhanced tolerance to saline and sodic soils and/or reduced sodium accumulation in an aerial part of the plant comprising the gene (namely, a Nax2 gene) is TmHKT8 (which encodes the polypeptide sequence provided as SEQ ID NO:1). Platten et al. (2006) propose to call this new gene family HKT1;5. It will readily be understood by those skilled in the art that a Nax2 gene can be introduced into cells other than wheat cells, preferably other plant cells and more preferably cereal plant cells, and such cells are said to comprise a Nax2 gene.

Homoeologues of the Nax2 gene are found on chromosomes 4DL and 4BL in wheat as described herein. The "Nax2 gene family" or "wheat HKT8 gene family" as used herein therefore refers to members of the gene family including such homoeologues encoding polypeptides (referred to herein as Nax2 polypeptides) comprising amino acids having a sequence as provided in any one of SEQ ID NOs: 1 to 9, a fragment thereof, or an amino acid sequence which is at least 67% identical to any one or more of SEQ ID NOs: 1 to 9, wherein the polypeptide has cation transporter activity when produced in a cell. As exemplified herein, members of the Nax2 gene family contribute to enhanced salt tolerance and/or reduced sodium accumulation, although some members do so to a greater extent than others. However, it is to be understood that all of the Nax2 gene family members in a plant may contribute together to the observed salt tolerance phenotype of the plant.

As used herein, a "Nax2 locus" refers to a region (locus) of the genome of a plant encompassing a Nax2 gene. Typically, this includes a region of the genome extending up to about 2 cM on either side of the Nax2 gene. An allelic variant (allele) of a Nax2 locus present on the A genome has been shown herein to be linked to enhanced tolerance to saline and sodic soils as well as reduced sodium accumulation in an aerial part of a plant. Furthermore, a homoeologous locus on wheat chromosome 4DL comprising the Kna1 gene also confers salt tolerance. Examples of markers of alleles of the Nax2 locus which confer enhanced tolerance to saline and sodic soils as well as reduced sodium accumulation, or which are genetically linked thereto, include genomic regions amplified using the primer pair CATCACCGTCGAGGTTATCAG (SEQ ID NO: 32 and TTGAGGTACTCGGCATA (SEQ ID NO: 33), as well as microsatellite markers Xgwm291, Xgwm410 and gpw2181.

As used herein, the term "cation transporter activity" refers to the ability of a polypeptide to form part of the membrane of a plant cell (especially a wheat cell) and play a role in the active transport of a cation(s), particularly sodium and/or potassium, across the cell membrane.

As used herein, the phrase "enhanced tolerance to saline and/or sodic soils" is considered as relative term. A saline soil is defined as having a high concentration of soluble salts, high enough to affect plant growth. Salt concentration in a soil is measured in terms of its electrical conductivity. As used herein a "saline soil" has an $EC_e$ of at least 1 dS/m, more preferably at least 2 dS/m, more preferably at least 3 dS/m, and even more preferably at least 4 dS/m. $EC_e$ is the electrical conductivity of the 'saturated paste extract', that is, of the solution extracted from a soil sample after being mixed with sufficient water to produce a saturated paste. Sodic soils have a low concentration of soluble salts, but a high percent of exchangeable $Na^+$; that is, $Na^+$ forms a high percent of all cations bound to the negative charges on the clay particles that make up the soil complex. Sodicity is defined in terms of the threshold ESP (exchangeable sodium percentage) that causes degradation of soil structure. As used herein a "sodic soil" has an ESP greater than 5, more preferably an ESP greater than 7, more preferably an ESP greater than 9, more preferably an ESP greater than 11, more preferably an ESP greater than 13, and even more preferably an ESP greater than 15. A wheat or barley plant with enhanced tolerance to saline and/or sodic soils is defined as a plant which is more capable of growing, and/or reproducing, in saline and/or sodic conditions when compared to a plant with the same, or similar, genotype but lacking the salt tolerance allele. Indicators of enhanced tolerance to saline and/or sodic soils linked to loci of the invention include, but are not limited to, reduced sodium uptake and/or lower levels of sodium in seeds (whether grown in saline and/or sodic soils or not).

As used herein, the term "a field under saline and/or sodic conditions" refers to an area of land where the soil is a "saline soil" and/or "sodic soil" as defined above.

As used herein, the term "reduced sodium accumulation in an aerial part of the plant" is considered a relative term. More specifically, the present inventors have identified markers of plants linked to a low rate of $Na^+$ accumulation in, for example, the leaf blade. A wheat or barley plant with "reduced sodium accumulation" is defined as a plant which accumulates less sodium in an aerial part of the plant (including any above ground part of the plant such as, for example, the stem, leaves, leaf sheaths, leaf blades, inflorescence, developing seeds and/or mature seed) when compared to a plant with the same, or similar, genotype but lacking the salt tolerance allele. "Reduced sodium accumulation" can be determined using any method known in the art, such as those described in the Examples.

An aspect of the invention relates to a method of introducing a Nax2 allele which confers enhanced tolerance of saline and/or sodic soils, and/or reduced sodium accumulation in an aerial part of a plant, into the genome of a wheat or barley species lacking said allele. The aim of this aspect is to produce a plant with a majority of the genotype of a first parent plant but comprising said Nax2 allele introduced from a second parent plant. As used in this context, the term "majority" means that the product of the breeding comprises greater than 50% of the genome of the first parent. However, the product preferably comprises at least 60%, more preferably at least 70%, more preferably at least 80%, more preferably at least 90%, more preferably at least 95%, more preferably at least 96%, more preferably at least 97%, more preferably at least 98%, and even more preferably at least 99% of the genome of the first parent. In an embodiment, the product comprising the Nax2 gene does not comprise one or more of chromosomes 1A, 2A, 3A, 4A, 6A and 7A from the second parent plant, preferably most or all of these. In a particular embodiment, the product does not contain chromosomes 1A, 2A, 3A, 4A, 6A and 7A from *durum* lines Line 149, Line 5049 or variety Tamaroi.

As used herein, the term "wheat" refers to any species of the Genus *Triticum*, including progenitors thereof, as well as progeny thereof produced by crosses with other species. Wheat includes "hexaploid wheat" which has genome organization of AABBDD, comprised of 42 chromosomes, and "tetraploid wheat" which has genome organization of AABB, comprised of 28 chromosomes. Hexaploid wheat includes *T. aestivum, T. spelta, T. macha, T. compactum, T. sphaerococcum, T. vavilovii*, and interspecies cross thereof. Tetraploid wheat includes *T. durum* (also referred to herein as *durum* wheat or *Triticum turgidum* ssp. *durum*), *T. dicoccoides, T. dicoccum, T. polonicum*, and interspecies cross thereof. In addition, the term "wheat" includes potential progenitors of hexaploid or tetraploid *Triticum* sp. such as *T. uartu, T. monococcum* or *T. boeoticum* for the A genome, *Aegilops speltoides* for the B genome, and *T. tauschii* (also known as *Aegilops squarrosa* or *Aegilops tauschii*) for the D genome. Particularly preferred progenitors are those of the A genome, even more preferably the A genome progenitor is *T. monococcum*. A wheat cultivar for use in the present invention may belong to, but is not limited to, any of the above-listed species. Also encompassed are plants that are produced by conventional techniques using *Triticum* sp. as a parent in a sexual cross with a non-Triticum species (such as rye [*Secale cereale*]), including but not limited to *Triticale*.

As used herein, the term "barley" refers to any species of the Genus *Hordeum*, including progenitors thereof, as well as progeny thereof produced by crosses with other species. It is preferred that the plant is of a *Hordeum* species which is commercially cultivated such as, for example, a strain or cultivar or variety of *Hordeum vulgare* or suitable for commercial production of grain.

The term "plant" includes whole plants, vegetative structures (for example, leaves, stems), roots, floral organs/structures, seed (including embryo, endosperm, and seed coat), plant tissue (for example, vascular tissue, ground tissue, and the like), cells and progeny of the same.

A "transgenic plant", "genetically modified plant" or variations thereof refers to a plant that contains a gene construct ("transgene") not found in a wild-type plant of the same species, variety or cultivar. A "transgene" as referred to herein has the normal meaning in the art of biotechnology and includes a genetic sequence which has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

As used herein, the term "corresponding non-modified plant" refers to a wild-type plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein. Wild-type varieties that are suitable as a reference standard include *durum* cv. Tamaroi and breadwheat cv. Westonia and Chinese Spring.

The terms "seed" and "grain" are used interchangeably herein. "Grain" generally refers to mature, harvested grain but can also refer to grain after imbibition or germination, according to the context. Mature grain commonly has a moisture content of less than about 18-20%.

"Nucleic acid molecule" refers to a oligonucleotide, polynucleotide or any fragment thereof. It may be DNA or RNA of genomic or synthetic origin, double-stranded or single-stranded, and combined with carbohydrate, lipids, protein, or other materials to perform a particular activity defined herein.

As used herein, the term "nucleic acid amplification" refers to any in vitro method for increasing the number of copies of a nucleic acid molecule with the use of a DNA polymerase. Nucleic acid amplification results in the incorporation of nucleotides into a DNA molecule or primer thereby forming a new DNA molecule complementary to a DNA template. The newly formed DNA molecule can be used a template to synthesize additional DNA molecules.

"Operably linked" as used herein refers to a functional relationship between two or more nucleic acid (e.g., DNA) segments. Typically, it refers to the functional relationship of transcriptional regulatory element (promoter) to a transcribed sequence. For example, a promoter is operably linked to a coding sequence, such as a polynucleotide defined herein, if it stimulates or modulates the transcription of the coding sequence in an appropriate cell. Generally, promoter transcriptional regulatory elements that are operably linked to a transcribed sequence are physically contiguous to the transcribed sequence, i.e., they are cis-acting. However, some transcriptional regulatory elements, such as enhancers, need not be physically contiguous or located in close proximity to the coding sequences whose transcription they enhance.

As used herein, the term "gene" is to be taken in its broadest context and includes the deoxyribonucleotide sequences comprising the protein coding region of a structural gene and including sequences located adjacent to the coding region on both the 5' and 3' ends for a distance of at least about 2 kb on either end and which are involved in expression of the gene. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region which may be interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above.

As used herein, the term "genetically linked" or similar refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the embodiment where the marker locus comprises a polymorphism that is responsible for the trait of interest (in other words the marker locus is directly "linked" or "perfectly linked" to the phenotype). In another embodiment, the marker locus and a second locus are different, yet sufficiently close on a chromosome that they will be inherited together in more than 50% of meioses. The percent of recombination observed between genetically linked loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM apart and most preferably about 0 cM apart.

An "allele" refers to one specific form of a genetic sequence (such as a gene) within a cell, an individual plant or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations".

A "polymorphism" as used herein denotes a variation in the nucleotide sequence between alleles of the loci of the invention, of different species, cultivars, strains or individuals of a plant. A "polymorphic position" is a preselected nucleotide position within the sequence of the gene. In some cases, genetic polymorphisms are reflected by an amino acid sequence variation, and thus a polymorphic position can result in location of a polymorphism in the amino acid sequence at a predetermined position in the sequence of a polypeptide. In other instances, the polymorphic region may be in a non-polypeptide encoding region of the gene, for example in the promoter region such may influence expression levels of the gene. Typical polymorphisms are deletions, insertions or substitutions. These can involve a single nucleotide (single nucleotide polymorphism or SNP) or two or more nucleotides.

As used herein, the "other genetic markers" may be any molecules which are linked to a desired trait of a cereal plant such as wheat or barley. Such markers are well known to those skilled in the art and include molecular markers linked to genes determining traits such disease resistance, yield, plant morphology, grain quality, dormancy traits such as grain colour, gibberellic acid content in the seed, plant height, flour colour and the like. Examples of such genes in wheat are stem-rust resistance genes Sr2 or Sr38, the stripe rust resistance genes Yr10 or Yr17, the nematode resistance genes such as Cre1 and Cre3, alleles at glutenin loci that determine dough strength such as Ax, Bx, Dx, Ay, By and Dy alleles, the Rht genes that determine a semi-dwarf growth habit and therefore lodging resistance (Eagles et al. 2001; Langridge et al. 2001; Sharp et al. 2001). The other gene may also confer enhanced tolerance to saline and/or sodic soils to the plant, and/or reduced sodium accumulation in an aerial part of the plant, examples of such genes include NaxI and KnaI. As shown herein, a combination of alleles of genes which enhanced tolerance to saline and/or sodic soils to the plant, and/or reduced sodium accumulation in an aerial part of the plant, can have an additive effect on these traits.

As used herein, the term "Nax1" refers to a region (locus) on the long arm of chromosome 2 of the genome of a wheat plant. An allelic variant (allele) of the Nax1 locus has been shown to be linked to enhanced tolerance to saline and sodic soils as well as reduced sodium accumulation (WO 2005/120214). Examples of markers of this region, or genetically linked thereto, include AFLP markers AFLP42-1 and AFLP27-1; RFLP markers Xspr102, XksuE16 and XksuD22, as well as microsatellite markers Xgwm249, Xgwm817, TaA, TaC, Xgwm312 (also referred to herein as gwm312) and Xwmc170 (also referred to herein as wmc170) (see the Examples section for further details). Particularly preferred markers of alleles of the Nax1 locus linked to enhanced tolerance to saline and/or sodic soils, as well as reduced sodium accumulation, are Xgwm312, Xgwm817 and Xwmc170.

As used herein, the term "Kna1" refers to a region (locus) on the long arm of chromosome 4 of the genome of a wheat plant. An allelic variant (allele) of the Kna1 locus has been shown to be linked to enhanced tolerance to saline and sodic soils as well as reduced sodium accumulation (Dvořák et al. 1994).

Polypeptides

By "substantially purified polypeptide" or "purified" we mean a polypeptide that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated.

The term "recombinant" in the context of a polypeptide refers to the polypeptide when produced by a cell, or in a cell-free expression system, in an altered amount or at an altered rate compared to its native state. In one embodiment the cell is a cell that does not naturally produce the polypeptide. However, the cell may be a cell which comprises a non-endogenous gene that causes an altered, preferably increased, amount of the polypeptide to be produced. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components.

The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

As used herein a "biologically active" fragment is a portion of a polypeptide of the invention which maintains a defined activity of the full-length polypeptide, namely be able to transport ions across a cell membrane of a plant cell, preferably $Na^+$ and/or $K^+$ ions. Biologically active fragments can be any size as long as they maintain the defined activity. Preferably, biologically active fragments are at least 100, more preferably at least 200, and even more preferably at least 350 amino acids in length.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

In an embodiment, a polypeptide of the invention is not a polypeptide encoded by a polynucleotide provided as Accession No. CK193616.1 or DR734861.1.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

Mutant (altered) polypeptides can be prepared using any technique known in the art. For example, a polynucleotide of the invention can be subjected to in vitro mutagenesis. Such in vitro mutagenesis techniques may include sub-cloning the polynucleotide into a suitable vector, transforming the vector into a "mutator" strain such as the E. coli XL-1 red (Stratagene) and propagating the transformed bacteria for a suitable number of generations. In another example, the polynucleotides of the invention are subjected to DNA shuffling techniques as broadly described by Harayama (1998). These DNA shuffling techniques may include genes related to those of the present invention, such as other HKT family members. Products derived from mutated/altered DNA can readily be screened using techniques described herein to determine if they are able to confer enhanced tolerance to saline and/or sodic soils, and/or reduced sodium accumulation in an aerial part, to a plant expressing said mutated/altered gene.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as important for function. Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, e.g., by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

TABLE 1

Exemplary substitutions

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Polynucleotides and Oligonucleotides

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. Furthermore, the term "polynucleotide" is used interchangeably herein with the term "nucleic acid".

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

With regard to the defined polynucleotides, it will be appreciated that % identity figures higher than those provided above will encompass preferred embodiments. Thus, where applicable, in light of the minimum % identity figures, it is preferred that a polynucleotide of the invention comprises a sequence which is at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

As used herein, the term "hybridizes" refers to the ability of two single stranded nucleic acid molecules being able to form at least a partially double stranded nucleic acid through hydrogen bonding.

As used herein, the phrase "stringent conditions" refers to conditions under which a polynucleotide, probe, primer and/or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel et al. (supra), Current Protocols In Molecular Biology, John Wiley & Sons, N.Y. (1989), 6.3.1-6.3.6, as well as the Examples described herein. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. In another embodiment, a nucleic acid sequence that is hybridizable to the nucleic acid molecule comprising the nucleotide sequence of SEQ ID NO's 10 to 18 or 90 to 98, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art, see, e.g., Ausubel et al. (supra), and Kriegler, 1990; Gene Transfer And Expression, A Laboratory Manual, Stockton Press, NY. In yet another embodiment, a nucleic acid that is hybridizable to the nucleic acid molecule comprising any one of the nucleotide sequences SEQ ID NO's 10 to 18 or 90 to 98, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art, see, e.g., Ausubel et al. (supra) and Kriegler, 1990, Gene Transfer And Expression, A Laboratory Manual, Stockton Press, NY, as well as the Examples provided herein.

In an embodiment, a polynucleotide of the invention is not a polynucleotide provided as Accession No. CK193616.1 or DR734861.1.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

Oligonucleotides of the present invention can be RNA, DNA, or derivatives of either. Although the terms polynucleotide and oligonucleotide have overlapping meaning, oligonucleotide are typically relatively short single stranded molecules. The minimum size of such oligonucleotides is the size required for the formation of a stable hybrid between an oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

Usually, monomers of a polynucleotide or oligonucleotide are linked by phosphodiester bonds or analogs thereof to form oligonucleotides ranging in size from a relatively short monomeric units, e.g., 12-18, to several hundreds of monomeric units. Analogs of phosphodiester linkages include: phosphorothioate, phosphorodithioate, phosphoroselenoate, phosphorodiselenoate, phosphoroanilothioate, phosphoranilidate, phosphoramidate.

The present invention includes oligonucleotides that can be used as, for example, probes to identify nucleic acid molecules, or primers to produce nucleic acid molecules. Oligonucleotide of the present invention used as a probe are typically conjugated with a detectable label such as a radioisotope, an enzyme, biotin, a fluorescent molecule or a chemiluminescent molecule.

Probes and/or primers can be used to clone homologues of the polynucleotides of the invention from other species. Furthermore, hybridization techniques known in the art can also be used to screen genomic or cDNA libraries for such homologues.

A variant of an oligonucleotide described herein includes molecules of varying sizes of, and/or are capable of hybridising to the genome close to that of, the specific oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise the target region. In addition, variants may readily be designed which hybridise close (for example, but not limited to, within 50 nucleotides) to the region of the genome where the specific oligonucleotides defined herein hybridise.

Antisense Polynucleotides

The term "antisense polynucleotide" shall be taken to mean a DNA or RNA, or combination thereof, molecule that is complementary to at least a portion of a specific mRNA molecule encoding a polypeptide of the invention and capable of interfering with a post-transcriptional event such as mRNA translation. The use of antisense methods is well known in the art (see for example, G. Hartmann and S. Endres, Manual of Antisense Methodology, Kluwer (1999)). The use of antisense techniques in plants has been reviewed by Bourque, 1995 and Senior, 1998. Bourque, 1995 lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior, 1998 states that antisense methods are now a very well established technique for manipulating gene expression.

An antisense polynucleotide of the invention will hybridize to a target polynucleotide under physiological conditions. As used herein, the term "an antisense polynucleotide which hybridises under physiological conditions" means that the polynucleotide (which is fully or partially single stranded) is at least capable of forming a double stranded polynucleotide with mRNA encoding a protein, such as those provided in any one or more of SEQ ID NO's 1 to 9 or 83 to 89 under normal conditions in a cell, preferably a wheat or barley cell.

Antisense molecules may include sequences that correspond to the structural genes or for sequences that effect control over the gene expression or splicing event. For example, the antisense sequence may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilize the molecule.

Catalytic Polynucleotides

The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are the hammerhead ribozyme (Haseloff and Gerlach, 1988, Perriman et al. 1992) and the hairpin ribozyme (Shippy et al. 1999).

The ribozymes of this invention and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. Accordingly, also provided by this invention is a nucleic acid molecule, i.e., DNA or cDNA, coding for a catalytic polynucleotide of the invention. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense polynucleotides described herein, catalytic polynucleotides of the invention should also be capable of hybridizing a target nucleic acid molecule (for example an mRNA encoding a polypeptide provided as any one or more of SEQ ID NO's 1 to 9 or 83 to 89 under "physiological conditions", namely those conditions within a cell (especially conditions in a plant cell such as a wheat or barley cell).

RNA Interference

RNA interference (RNAi) is particularly useful for specifically inhibiting the production of a particular protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof, in this case an mRNA encoding a polypeptide according to the invention. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

Preferred small interfering RNA ('siRNA") molecules comprise a nucleotide sequence that is identical to about 19-21 contiguous nucleotides of the target mRNA. Preferably, the target mRNA sequence commences with the dinucleotide AA, comprises a GC-content of about 30-70%

(preferably, 30-60%, more preferably 40-60% and more preferably about 45%-55%), and does not have a high percentage identity to any nucleotide sequence other than the target in the genome of the plant (preferably wheat or barley) in which it is to be introduced, e.g., as determined by standard BLAST search.

microRNA

MicroRNA regulation is a clearly specialized branch of the RNA silencing pathway that evolved towards gene regulation, diverging from conventional RNAi/PTGS. MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005; Pasquinelli et al. 2005; Almeida and Allshire, 2005).

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to WO 97/20936 and EP 0465572 for methods of implementing co-suppression approaches.

Nucleic Acid Constructs, Vectors and Host Cells

The present invention includes the production of various transgenic plants. These include, but are not limited to, i) plants that express a polynucleotide of the invention which encodes a polypeptide having cation transporter activity, ii) plants where the expression level of at least one endogenous Nax2 gene has been increased relative to a corresponding non-transgenic plant, and iii) plants that express a polynucleotide which, when present in a cell of a cereal plant, down-regulates the level of Nax2 activity in the cell when compared to a cell that lacks said polynucleotide.

Nucleic acid constructs useful for producing the above-mentioned transgenic plants can readily be produced using standard techniques.

When inserting a region encoding an mRNA the construct may comprise intron sequences. These intron sequences may aid expression of the transgene in the plant. The term "intron" is used in its normal sense as meaning a genetic segment that is transcribed but does not encode protein and which is spliced out of an RNA before translation. Introns may be incorporated in a 5'-UTR or a coding region if the transgene encodes a translated product, or anywhere in the transcribed region if it does not. However, in a preferred embodiment, any polypeptide encoding region is provided as a single open reading frame. As the skilled addressee would be aware, such open reading frames can be obtained by reverse transcribing mRNA encoding the polypeptide.

To ensure appropriate expression of the gene encoding an mRNA of interest, the nucleic acid construct typically comprises one or more regulatory elements such as promoters, enhancers, as well as transcription termination or polyadenylation sequences. Such elements are well known in the art.

The transcriptional initiation region comprising the regulatory element(s) may provide for regulated or constitutive expression in the plant. Preferably, expression at least occurs in cells of the root. More preferably, expression at least occurs in xylem parenchyma cells. The regulatory elements may be selected be from, for example, root-specific promoters, or promoters not specific for root cells.

A number of constitutive promoters that are active in plant cells have been described. Suitable promoters for constitutive expression in plants include, but are not limited to, the cauliflower mosaic virus (CaMV) 35S promoter, the Figwort mosaic virus (FMV) 35S, the sugarcane bacilliform virus promoter, the commelina yellow mottle virus promoter, the light-inducible promoter from the small subunit of the ribulose-1,5-bis-phosphate carboxylase, the rice cytosolic triose-phosphate isomerase promoter, the adenine phosphoribosyl-transferase promoter of Arabidopsis, the rice actin 1 gene promoter, the mannopine synthase and octopine synthase promoters, the Adh promoter, the sucrose synthase promoter, the R gene complex promoter, and the chlorophyll $\alpha/\beta$ binding protein gene promoter. These promoters have been used to create DNA vectors that have been expressed in plants; see, e.g., PCT publication WO 8402913. All of these promoters have been used to create various types of plant-expressible recombinant DNA vectors.

An example of a root specific promoter is the promoter for the acid chitinase gene. Expression in root tissue could also be accomplished by utilizing the root specific subdomains of the CaMV 35S promoter that have been identified The promoter may be modulated by factors such as temperature, light or stress. Ordinarily, the regulatory elements will be provided 5' of the genetic sequence to be expressed. The construct may also contain other elements that enhance transcription such as the nos 3' or the ocs 3' polyadenylation regions or transcription terminators.

The 5' non-translated leader sequence can be derived from the promoter selected to express the heterologous gene sequence of the polynucleotide of the present invention, and can be specifically modified if desired so as to increase translation of mRNA. For a review of optimizing expression of transgenes, see Koziel et al. (1996). The 5' non-translated regions can also be obtained from plant viral RNAs (Tobacco mosaic virus, Tobacco etch virus, Maize dwarf mosaic virus, Alfalfa mosaic virus, among others) from suitable eukaryotic genes, plant genes (wheat and maize chlorophyll a/b binding protein gene leader), or from a synthetic gene sequence. The present invention is not limited to constructs wherein the non-translated region is derived from the 5' non-translated sequence that accompanies the promoter sequence. The leader sequence could also be derived from an unrelated promoter or coding sequence. Leader sequences useful in context of the present invention comprise the maize Hsp70 leader (U.S. Pat. No. 5,362,865 and U.S. Pat. No. 5,859,347), and the TMV omega element.

The termination of transcription is accomplished by a 3' non-translated DNA sequence operably linked in the chimeric vector to the polynucleotide of interest. The 3' non-translated region of a recombinant DNA molecule contains a polyadenylation signal that functions in plants to cause the addition of adenylate nucleotides to the 3' end of the RNA. The 3' non-translated region can be obtained from various genes that are expressed in plant cells. The nopaline synthase 3' untranslated region, the 3' untranslated region from pea small subunit Rubisco gene, the 3' untranslated region from soybean 7S seed storage protein gene are commonly used in this capacity. The 3' transcribed, non-translated regions containing the polyadenylate signal of *Agrobacterium* tumor-inducing (Ti) plasmid genes are also suitable.

Typically, the nucleic acid construct comprises a selectable marker. Selectable markers aid in the identification and screening of plants or cells that have been transformed with the exogenous nucleic acid molecule. The selectable marker gene may provide antibiotic or herbicide resistance to the wheat or barley cells, or allow the utilization of substrates such as mannose. The selectable marker preferably confers hygromycin resistance to the wheat or barley cells.

Preferably, the nucleic acid construct is stably incorporated into the genome of the plant. Accordingly, the nucleic acid comprises appropriate elements which allow the molecule to be incorporated into the genome, or the construct is placed in an appropriate vector which can be incorporated into a chromosome of a plant cell.

One embodiment of the present invention includes a recombinant vector, which includes at least one polynucleotide molecule of the present invention, inserted into any vector capable of delivering the nucleic acid molecule into a host cell. Such a vector contains heterologous nucleic acid sequences, that is nucleic acid sequences that are not naturally found adjacent to nucleic acid molecules of the present invention and that preferably are derived from a species other than the species from which the nucleic acid molecule(s) are derived. The vector can be either RNA or DNA, either prokaryotic or eukaryotic, and typically is a virus or a plasmid.

A number of vectors suitable for stable transfection of plant cells or for the establishment of transgenic plants have been described in, e.g., Pouwels et al. Cloning Vectors: A Laboratory Manual, 1985, supp. 1987; Weissbach and Weissbach, Methods for Plant Molecular Biology, Academic Press, 1989; and Gelvin et al., Plant Molecular Biology Manual, Kluwer Academic Publishers, 1990. Typically, plant expression vectors include, for example, one or more cloned plant genes under the transcriptional control of 5' and 3' regulatory sequences and a dominant selectable marker. Such plant expression vectors also can contain a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion. A recombinant cell may remain unicellular or may grow into a tissue, organ or a multicellular organism. Transformed nucleic acid molecules of the present invention can remain extrachromosomal or can integrate into one or more sites within a chromosome of the transformed (i.e., recombinant) cell in such a manner that their ability to be expressed is retained. Preferred host cells are plant cells, more preferably cells of a cereal plant, more preferably barley or wheat cells, and even more preferably a wheat cell.

Transgenic Plants

Plants contemplated for use in the practice of the present invention include both monocotyledons and dicotyledons. Target plants include, but are not limited to, the following: cereals (for example, wheat, barley, rye, oats, rice, sorghum and related crops); beet (sugar beet and fodder beet); pomes, stone fruit and soft fruit (apples, pears, plums, peaches, almonds, cherries, strawberries, raspberries and black-berries); leguminous plants (beans, lentils, peas, soybeans); oil plants (rape, mustard, poppy, olives, sunflowers, coconut, castor oil plants, cocoa beans, groundnuts); cucumber plants (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, turf, bananas and natural rubber plants, as well as ornamentals (flowers, shrubs, broad-leaved trees and evergreens, such as conifers). Preferably, the plant is a cereal plant, more preferably wheat or barley, even more preferably wheat.

Transgenic plants, as defined in the context of the present invention include plants (as well as parts and cells of said plants) and their progeny which have been genetically modified using recombinant techniques to cause production of at least one polypeptide of the present invention in the desired plant or plant organ. Transgenic plants can be produced using techniques known in the art, such as those generally described in A. Slater et al., Plant Biotechnology—The Genetic Manipulation of Plants, Oxford University Press (2003), and P. Christou and H. Klee, Handbook of Plant Biotechnology, John Wiley and Sons (2004).

In a preferred embodiment, the transgenic plants are homozygous for each and every gene that has been introduced (transgene) so that their progeny do not segregate for the desired phenotype. The transgenic plants may also be heterozygous for the introduced transgene(s), such as, for example, in F1 progeny which have been grown from hybrid seed. Such plants may provide advantages such as hybrid vigour, well known in the art.

Four general methods for direct delivery of a gene into cells have been described: (1) chemical methods (Graham et al. 1973); (2) physical methods such as microinjection (Capecchi, 1980); electroporation (see, for example, WO 87/06614, U.S. Pat. No. 5,472,869, U.S. Pat. No. 5,384,253, WO 92/09696 and WO 93/21335); and the gene gun (see, for example, U.S. Pat. No. 4,945,050 and U.S. Pat. No. 5,141, 131); (3) viral vectors (Clapp, 1993; Lu et al. 1993; Eglitis et al. 1988); and (4) receptor-mediated mechanisms (Curiel et al. 1992; Wagner et al. 1992).

Acceleration methods that may be used include, for example, microprojectile bombardment and the like. One example of a method for delivering transforming nucleic acid molecules to plant cells is microprojectile bombardment. This method has been reviewed by Yang et al., Particle Bombardment Technology for Gene Transfer, Oxford Press, Oxford, England (1994). Non-biological particles (microprojectiles) that may be coated with nucleic acids and delivered into cells by a propelling force. Exemplary particles include those comprised of tungsten, gold, platinum, and the like. A particular advantage of microprojectile bombardment, in addition to it being an effective means of reproducibly transforming monocots, is that neither the isolation of protoplasts, nor the susceptibility of *Agrobacterium* infection are required. An illustrative embodiment of a method for delivering DNA into *Zea mays* cells by acceleration is a biolistics α-particle delivery system, that can be used to propel particles coated with DNA through a screen, such as a stainless steel or Nytex screen, onto a filter surface covered with corn cells cultured in suspension. A particle delivery system suitable for use with the present invention is the helium acceleration PDS-1000/He gun is available from Bio-Rad Laboratories.

For the bombardment, cells in suspension may be concentrated on filters. Filters containing the cells to be bombarded are positioned at an appropriate distance below the microprojectile stopping plate. If desired, one or more screens are also positioned between the gun and the cells to be bombarded.

Alternatively, immature embryos or other target cells may be arranged on solid culture medium. The cells to be bombarded are positioned at an appropriate distance below the microprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus that express the exogenous gene product 48 hours post-bombardment often range from one to ten and average one to three.

In bombardment transformation, one may optimize the pre-bombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids. It is believed that pre-bombardment manipulations are especially important for successful transformation of immature embryos.

In another alternative embodiment, plastids can be stably transformed. Method disclosed for plastid transformation in higher plants include particle gun delivery of DNA containing a selectable marker and targeting of the DNA to the plastid genome through homologous recombination (U.S. Pat. No. 5,451,513, U.S. Pat. No. 5,545,818, U.S. Pat. No. 5,877,402, U.S. Pat. No. 5,932,479, and WO 99/05265.

Accordingly, it is contemplated that one may wish to adjust various aspects of the bombardment parameters in small scale studies to fully optimize the conditions. One may particularly wish to adjust physical parameters such as gap distance, flight distance, tissue distance, and helium pressure. One may also minimize the trauma reduction factors by modifying conditions that influence the physiological state of the recipient cells and that may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art (see, for example, U.S. Pat. No. 5,177,010, U.S. Pat. No. 5,104,310, U.S. Pat. No. 5,004,863, U.S. Pat. No. 5,159,135). Further, the integration of the T-DNA is a relatively precise process resulting in few rearrangements. The region of DNA to be transferred is defined by the border sequences, and intervening DNA is usually inserted into the plant genome.

Modern *Agrobacterium* transformation vectors are capable of replication in *E. coli* as well as *Agrobacterium*, allowing for convenient manipulations as described (Klee et al., In: Plant DNA Infectious Agents, Hohn and Schell, eds., Springer-Verlag, New York, pp. 179-203 (1985). Moreover, technological advances in vectors for *Agrobacterium*-mediated gene transfer have improved the arrangement of genes and restriction sites in the vectors to facilitate construction of vectors capable of expressing various polypeptide coding genes. The vectors described have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant varieties where *Agrobacterium*-mediated transformation is efficient, it is the method of choice because of the facile and defined nature of the gene transfer.

A transgenic plant formed using *Agrobacterium* transformation methods typically contains a single genetic locus on one chromosome. Such transgenic plants can be referred to as being hemizygous for the added gene. More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants for the gene of interest.

It is also to be understood that two different transgenic plants can also be mated to produce offspring that contain two independently segregating exogenous genes. Selfing of appropriate progeny can produce plants that are homozygous for both exogenous genes. Back-crossing to a parental plant and out-crossing with a non-transgenic plant are also contemplated, as is vegetative propagation. Descriptions of other breeding methods that are commonly used for different traits and crops can be found in Fehr, In: Breeding Methods for Cultivar Development, Wilcox J. ed., American Society of Agronomy, Madison Wis. (1987).

Transformation of plant protoplasts can be achieved using methods based on calcium phosphate precipitation, polyethylene glycol treatment, electroporation, and combinations of these treatments. Application of these systems to different plant varieties depends upon the ability to regenerate that particular plant strain from protoplasts. Illustrative methods for the regeneration of cereals from protoplasts are described (Fujimura et al. 1985; Toriyama et al. 1986; Abdullah et al. 1986).

Other methods of cell transformation can also be used and include but are not limited to introduction of DNA into plants by direct DNA transfer into pollen, by direct injection of DNA into reproductive organs of a plant, or by direct injection of DNA into the cells of immature embryos followed by the rehydration of desiccated embryos.

The regeneration, development, and cultivation of plants from single plant protoplast transformants or from various transformed explants is well known in the art (Weissbach et al., In: Methods for Plant Molecular Biology, Academic Press, San Diego, Calif., (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene is well known in the art. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired exogenous nucleic acid is cultivated using methods well known to one skilled in the art.

Methods for transforming dicots, primarily by use of *Agrobacterium tumefaciens*, and obtaining transgenic plants have been published for cotton (U.S. Pat. No. 5,004,863, U.S. Pat. No. 5,159,135, U.S. Pat. No. 5,518,908); soybean (U.S. Pat. No. 5,569,834, U.S. Pat. No. 5,416,011); *Brassica* (U.S. Pat. No. 5,463,174); peanut (Cheng et al. 1996); and pea (Grant et al. 1995).

Methods for transformation of cereal plants such as wheat and barley for introducing genetic variation into the plant by introduction of an exogenous nucleic acid and for regeneration of plants from protoplasts or immature plant embryos are well known in the art, see for example, Canadian Patent Application No. 2,092,588, Australian Patent Application No 61781/94, Australian Patent No 667939, U.S. Pat. No. 6,100,447, International Patent Application PCT/US97/10621, U.S. Pat. No. 5,589,617, U.S. Pat. No. 6,541,257, and other methods are set out in Patent specification WO99/14314. Preferably, transgenic wheat or barley plants are produced by *Agrobacterium tumefaciens* mediated transformation procedures. Vectors carrying the desired nucleic acid construct may be introduced into regenerable wheat cells of tissue cultured plants or explants, or suitable plant systems such as protoplasts.

The regenerable wheat cells are preferably from the scutellum of immature embryos, mature embryos, callus derived from these, or the meristematic tissue.

To confirm the presence of the transgenes in transgenic cells and plants, a polymerase chain reaction (PCR) amplification or Southern blot analysis can be performed using methods known to those skilled in the art. Expression products of the transgenes can be detected in any of a variety of ways, depending upon the nature of the product, and include Western blot and enzyme assay. One particularly useful way to quantitate protein expression and to detect replication in different plant tissues is to use a reporter gene, such as GUS. Once transgenic plants have been obtained, they may be grown to produce plant tissues or parts having the desired phenotype. The plant tissue or plant parts, may be harvested, and/or the seed collected. The seed may serve as a source for growing additional plants with tissues or parts having the desired characteristics.

Marker Assisted Selection

Marker assisted selection is a well recognised method of selecting for heterozygous plants required when backcrossing with a recurrent parent in a classical breeding program. The population of plants in each backcross generation will be heterozygous for the gene of interest normally present in a 1:1 ratio in a backcross population, and the molecular marker can be used to distinguish the two alleles of the gene. By extracting DNA from, for example, young shoots and testing with a specific marker for the introgressed desirable trait, early selection of plants for further backcrossing is made whilst energy and resources are concentrated on fewer plants. To further speed up the backcrossing program, the embryo from immature seeds (25 days post anthesis) may be excised and grown up on nutrient media under sterile conditions, rather than allowing full seed maturity. This process, termed "embryo rescue", used in combination with DNA extraction at the three leaf stage and analysis of at least one Nax2 gene or allele that confers enhanced tolerance to saline and/or sodic soils to the plant, and/or reduced sodium accumulation in an aerial part of the plant, allows rapid selection of plants carrying the desired trait, which may be nurtured to maturity in the greenhouse or field for subsequent further backcrossing to the recurrent parent.

Any molecular biological technique known in the art which is capable of detecting alleles of a Nax2 gene can be used in the methods of the present invention. Such methods include, but are not limited to, the use of nucleic acid amplification, nucleic acid sequencing, nucleic acid hybridization with suitably labeled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof (see, for example, Lemieux, 2000; Langridge et al. 2001). The invention also includes the use of molecular marker techniques to detect polymorphisms linked to alleles of (for example) a Nax2 gene which confers enhanced tolerance to saline and/or sodic soils to the plant, and/or reduced sodium accumulation in an aerial part of a plant. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis, as reviewed by Langridge et al. (2001).

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (Ed. M. J. McPherson and S. G Moller (2000) BIOS Scientific Publishers Ltd, Oxford). PCR can be performed on cDNA obtained from reverse transcribing mRNA isolated from plant cells expressing a Nax2 gene or allele which confers enhanced tolerance to saline and/or sodic soils to the plant, and/or reduced sodium accumulation in an aerial part of the plant. However, it will generally be easier if PCR is performed on genomic DNA isolated from a plant.

A primer is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Multiplex PCR systems contain multiple sets of primers that result in simultaneous production of more than one amplicon. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al. (supra) and Sambrook et al. (supra). Sequencing can be carried out by any suitable method, for example, dideoxy sequencing, chemical sequencing or variations thereof. Direct sequencing has the advantage of determining variation in any base pair of a particular sequence.

Hybridization based detection systems include, but are not limited to, the TaqMan assay and molecular beacons. The TaqMan assay (U.S. Pat. No. 5,962,233) uses allele specific (ASO) probes with a donor dye on one end and an acceptor dye on the other end such that the dye pair interact via fluorescence resonance energy transfer (FRET). A target sequence is amplified by PCR modified to include the addition of the labeled ASO probe. The PCR conditions are adjusted so that a single nucleotide difference will effect binding of the probe. Due to the 5' nuclease activity of the Taq polymerase enzyme, a perfectly complementary probe is cleaved during PCR while a probe with a single mismatched base is not cleaved. Cleavage of the probe dissociates the donor dye from the quenching acceptor dye, greatly increasing the donor fluorescence.

An alternative to the TaqMan assay is the molecular beacon assay (U.S. Pat. No. 5,925,517). In the molecular beacon assay, the ASO probes contain complementary sequences flanking the target specific species so that a hairpin structure is formed. The loop of the hairpin is complimentary to the target sequence while each arm of the hairpin contains either donor or acceptor dyes. When not hybridized to a donor sequence, the hairpin structure brings the donor and acceptor dye close together thereby extinguishing the donor fluorescence. When hybridized to the specific target sequence, however, the donor and acceptor dyes are separated with an increase in fluorescence of up to 900 fold. Molecular beacons can be used in conjunction with amplification of the target sequence by PCR and provide a method for real time detection of the presence of target sequences or can be used after amplification.

Tilling

Plants of the invention can be produced using the process known as TILLING (Targeting Induced Local Lesions IN Genomes). In a first step, introduced mutations such as novel single base pair changes are induced in a population of plants by treating seeds (or pollen) with a chemical mutagen, and then advancing plants to a generation where mutations will be stably inherited. DNA is extracted, and seeds are stored from all members of the population to create a resource that can be accessed repeatedly over time.

For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as Cel I, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique.

TILLING is further described in Slade and Knauf, 2005, and Henikoff et al. (2004).

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al. 2004).

Each SNP is recorded by its approximate position within a few nucleotides. Thus, each haplotype can be archived based on its mobility. Sequence data can be obtained with a relatively small incremental effort using aliquots of the same amplified DNA that is used for the mismatch-cleavage assay. The left or right sequencing primer for a single reaction is chosen by its proximity to the polymorphism. Sequencer software performs a multiple alignment and discovers the base change, which in each case confirmed the gel band.

Ecotilling can be performed more cheaply than full sequencing, the method currently used for most SNP discovery. Plates containing arrayed ecotypic DNA can be screened rather than pools of DNA from mutagenized plants. Because detection is on gels with nearly base pair resolution and background patterns are uniform across lanes, bands that are of identical size can be matched, thus discovering and genotyping SNPs in a single step. In this way, ultimate sequencing of the SNP is simple and efficient, made more so by the fact that the aliquots of the same PCR products used for screening can be subjected to DNA sequencing.

Antibodies

The invention also provides monoclonal or polyclonal antibodies to polypeptides of the invention or fragments thereof. Thus, the present invention further provides a process for the production of monoclonal or polyclonal antibodies to polypeptides of the invention.

The term "binds specifically" refers to the ability of the antibody to bind to a polypeptide of the present invention but not other known proteins, for example, cation transporters such as those from rice. It is preferred that an antibody of the invention does not bind other polypeptides found in a wheat and/or barley cell producing the polypeptide (with the exception of related polypeptides that have cation transporter activity).

As used herein, the term "epitope" refers to a region of a polypeptide of the invention which is bound by the antibody. An epitope can be administered to an animal to generate antibodies against the epitope, however, antibodies of the present invention preferably specifically bind the epitope region in the context of the entire polypeptide.

If polyclonal antibodies are desired, a selected mammal (e.g., mouse, rabbit, goat, horse, etc.) is immunised with an immunogenic polypeptide such as that provided as any one of SEQ ID NO's 1 to 9 or 83 to 89. Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides peptides of the invention or fragments thereof haptenised to another peptide for use as immunogens in animals.

Monoclonal antibodies directed against polypeptides of the invention can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; i.e., for isotype and epitope affinity.

An alternative technique involves screening phage display libraries where, for example the phage express scFv fragments on the surface of their coat with a large variety of complementarity determining regions (CDRs). This technique is well known in the art.

For the purposes of this invention, the term "antibody", unless specified to the contrary, includes fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanised antibodies, for example as described in EP-A-239400.

Antibodies of the invention may be bound to a solid support and/or packaged into kits in a suitable container along with suitable reagents, controls, instructions and the like.

Preferably, antibodies of the present invention are detectably labeled. Exemplary detectable labels that allow for direct measurement of antibody binding include radiolabels, fluorophores, dyes, magnetic beads, chemiluminescers, colloidal particles, and the like. Examples of labels which permit indirect measurement of binding include enzymes where the substrate may provide for a coloured or fluorescent product. Additional exemplary detectable labels include covalently bound enzymes capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art. Further exemplary detectable labels include biotin, which binds with high affinity to avidin or streptavidin; fluorochromes (e.g., phycobiliproteins, phycoerythrin and allophycocyanins; fluorescein and Texas red), which can be used with a fluorescence activated cell sorter; haptens; and the like. Preferably, the detectable label allows for direct measurement in a plate luminometer, e.g., biotin. Such labeled antibodies can be used in techniques known in the art to detect polypeptides of the invention.

EXAMPLES

Example 1

Materials and Methods

Growth Conditions and the Gravel-Based Hydroponic Method for Growing Plants

Seeds were selected by weight, surface sterilised with 1% hypochlorite for 15 min, and germinated in Petrie dishes for 3 days. Germinated seeds were planted (one plant per pot) into 6.5×15.8 cm pots containing coarse quartz gravel, in a 90 L plastic moulded tray containing 153 pots. Seedlings were watered with either saline or non-saline nutrient solution using an automatic subirrigation system (Munns et al. 1995, Munns and James, 2003), whereby solutions were pumped into trays and then drained into holding tanks every 30 min. Seedlings were watered with half strength modified Hoagland's solution, then at 6 d after emergence (DAE), 25 mM NaCl was added twice a day to a final concentration of 50 mM. Supplemental $Ca^{2+}$ was also added as $CaCl_2$ to give a final $Na^+$:$Ca^{2+}$ ratio of 15:1. Plants were grown in a controlled environment chamber with a 10 h photoperiod and a maximum PPFD of 800 µmol $m^{-2}$ $s^{-1}$, provided by 10 1000-W metal arc and 24 60-W incandescent lamps. The air temperature was controlled at 25° C. during the day and 18° C. during the night. Each harvest consisted of 6 reps of each genotype after 6 and 10 d in 50 mM NaCl. Shoots were separated into leaf blades and leaf sheaths. Roots were washed in a cold solution of 10 mM $Ca(NO_3)_2$ for 10-15 s, blotted and weighed. All plant material was then dried at 70° C. for 3 days, weighed and extracted in 500 mM $HNO_3$ at 80° C. for 1.5 h and analysed for $Na^+$ and $K^+$ by an Inductively Coupled Plasma—Atomic Emission Spectrometer (Varian Vista Pro, Melbourne, Australia). Net $Na^+$ and $K^+$ transport rates (roots to shoots) were calculated on a root fresh weight basis according to Pitman (1988) and Storey (1995). Transpiration rates were estimated from the measured leaf area and whole plant water loss of a corresponding set of seedlings grown in pots containing coarse sand which were watered and flushed daily with 50 mM NaCl in half strength modified Hoagland's solution.

In other experiments to measure salinity tolerance, seedlings were watered initially with tap water, then half strength nutrient solution was introduced 2 days after emergence (DAE), and increased to full strength at 3 DAE. Commencing at 4-6 DAE, 25 mM NaCl was added to the irrigation solution twice daily over three days to a final concentration of 150 mM. Supplemental $Ca^{2+}$ was added (as $CaCl_2$) to bring the total concentration of $Ca^{2+}$ to 10 mM, and the molar ratio of $Na^+$:$Ca^{2+}$ to 15:1. Phosphate was reduced to 50 µM. Control treatments always had 1 mM NaCl added to the nutrient solution. The pH was measured twice weekly and adjusted as needed to pH 6.0 with HCl. Root temperature was controlled using condensers in the solution reservoirs and monitored every 5 min using thermocouples. Experiments were conducted in a glasshouse with natural light and controlled air temperature. In a typical experiment, average daily PAR was 43.6 mol $m^{-2}$ $d^{-1}$ and the daily glasshouse air temperature ranged between 32° C. (day) and 20° C. (night).

These gravel culture growth conditions were preferred to other forms of hydroponic culture because roots were supported, each plant was a separate replicate, the frequent subirrigation and drainage avoided hypoxia, and there was no breakage of lateral roots as occurs in unsupported hydroponics when the solution was changed (Miller, 1987). The nutrient solution at full strength was Hoagland and Arnon solution No 2, containing 4 mM $Ca^{2+}$ and 1 mM P.

Salinity tolerance was calculated as shoot dry weight as a percentage of control shoot dry weight.

$Na^+$ Accumulation Assays

To measure $Na^+$ accumulation in the plants, leaf 3 of each seedling was harvested 10 days after its appearance, coinciding with approximately 10 days of salt treatment. Parental lines were replicated 10 times. $Na^+$ levels were measured according to the method of Munns et al. (2000), briefly as follows. Leaf material was harvested, washed in distilled water, dried at 70° C. for 2 days, extracted in 500 mM HCl at 80° C. for 1 hour, and $Na^+$ concentrations in the extracts measured by atomic absorption spectrometry (Varian Spectra AA-300). Alternatively, dried leaf material was extracted in 0.5M $H_2NO_3$ at 80° C. and $Na^+$ concentrations measured by inductively coupled plasma analysis (Varian Vista ProICP-AES).

Leaf 3 was chosen for analysis as it was the first leaf to have fully developed after the salt treatment was initiated. Preliminary experiments had indicated that genotypic differences were greatest for leaf 3 after 10 days. However, any subsequent leaf at any stage of development would probably have shown the same genotypic differences and could have been used. Subsequent leaves have lower concentrations than early leaves, but the genetic differences remain the same (Rivelli et al. 2002).

To measure biomass production and thereby evaluate salt tolerance, shoots of the plants were harvested at 28 days after emergence (DAE, coinciding with 24 days of treatments) and dry weights determined.

Radiotracer Experiments: $Na^+$ Uptake $Na^+$ uptake to the root and shoot was measured using $^{22}Na^+$ as described previously (Davenport et al. 2005). Seeds were germinated and then transferred to microcentrifuge tubes with the base removed and suspended over hydroponic solution. Seedlings were exposed to ½ strength modified Hoagland's solution (P concentration reduced from 1 mM to 100 µM) for 5 days and then transferred to ½ modified Hoagland's plus 25 mM or 50 mM NaCl for 5 days before experiments.

$Na^+$ Retranslocation $^{22}Na^+$ retranslocation into roots was measured with a split root system. Three day old seedlings were grown in ¼ strength Hoagland's solution for 3 d, and then transferred to 25 mM NaCl and 2 mM $CaCl_2$ in ½ strength modified Hoagland's solution. After 7 days in the salt treatment they were relocated into a split pot system with roots divided evenly into 2 darkened and covered connected beakers, each containing 120 ml of pre-treatment solution (containing 25 mM NaCl, 2 mM $CaCl_2$ in ½ strength modified Hoagland's solution). The shoot was supported in an upright position. This was placed on a rotating shaker under a light bank for 20 h to adjust to the new growth conditions, before solutions were refreshed with pre-treatment solution on one side and influx solution (containing $^{22}Na^+$) on the other side. Labeled and unlabeled roots and shoots were harvested after 48 h and $^{22}Na^+$ was measured as described above. The radioactivity in the solution on the non-labeled side was also counted.

Withdrawal of $Na^+$ by Upper Roots

Seedlings were grown as described for $Na^+$ uptake and transferred to a horizontal chamber with 2 unequal-sized compartments separated by a movable Perspex barrier pierced with a hole for the root. The plant was placed in the larger compartment so that the shoot was upright and the apical portion of a single root was sealed into the smaller compartment with silicon grease. The small compartment was filled with 5 ml solution and the rest of the root system was covered in filtered paper wetted with the same solution (identical to the saline growth solution). Both compartments were sealed to maintain high humidity. Plants were placed under a light bank on a slowly rotating shaker and allowed to recover for an hour before the 5 ml solution was replaced with $^{22}Na^+$-labelled solution of the same composition. After 2 h of labeling the labeled root was cut on either side of the barrier. The labeled apical portion was rinsed briefly in deionised water, blotted and weighed. The rest of the same root ('unlabelled root') was excised from the rest of the root system, blotted and weighed separately. The shoot was excised near the seed and weighed. Leakage between compartments was checked by measuring radioactive counts in the rest of the root system; any replicates with high counts in the rest of the root system were excluded from analysis.

Southern Blot Hybridisation Analysis

Restriction endonuclease digestion and Southern blot hybridizations were performed according to standard methods (Sambrook et al. 1989). After restriction digestion and gel electrophoresis, gels were stained with ethidium bromide and photographed. The DNA was denatured for 30 min in a solution containing 0.5N NaOH and 1.5M NaCl (pH 7.4) and then the gel was neutralized using 0.5M Tris-HCl, 2.5M NaCl pH7.4. DNA was blotted onto a positively charged nylon membrane (Amersham Hybond-$N^+$) using capillary transfer and immobilized by UV cross-linking (BIO-RAD GS Gene Linker). For stringent hybridizations, the membrane was pre-hybridized at 65° C. for 3 h and then hybridized with the radiolabelled probe overnight using the prehybridization and hybridization solutions as described in Sambrook et al. (1989). The membrane was washed for 20 min in 0.2% sodium sodium citrate solution (SSC) containing 0.1% sodium dodecyl sulphate (SDS) followed by further washes (0.1% SSC and 0.1% SDS) until the membranes registered 5-10 counts per minute on a Geiger counter. The membrane was exposed to X-ray film (Kodak BioMax MS).

Microsatellite Markers

All amplifications for microsatellite markers were performed in 20 µl aliquots containing 1.5 mM $MgCl_2$, 200 µM dNTP, 200 µM 1×PCR buffer (Boehringer Mannheim), 2 U Taq DNA polymerase and 100 ng genomic DNA. Genomic DNA was amplified using a step-down PCR program: 95° C./4 min, 15 cycles of 94° C./30 s, 65° C.-50° C./30 s decreasing by 1° C./cycle, 72° C./80 s, 30 cycles of 94° C./15 s, 72° C./45 s, followed by a 4° C. holding step. The PCR products were separated using 1.8% metaphor agarose gels.

Screening for the Presence of Nax1 Using the Molecular Marker gwm312

The presence or absence of the Nax1 gene in wheat plants was determined by using the tightly linked marker gwm312 as described in WO2005/120214. The PCR reactions used standard conditions with the primers: 312F 5'-ATCGCAT-GATGCACGTAGAC-3' (SEQ ID NO:70) and 312R 5'-ACATGCATGCCTACCTAATGG-3' (SEQ ID NO:71). The PCR cycling conditions were: 1 cycle of 95° C. 15 min; 5 cycles of 94° C. 1 min, 55° C. 1 min, 72° 2 min; 30 cycles of 94° C. 30 sec, 55° C. 30 sec, 72° C. 50 sec; 1 cycle of 25° C. 1 min. The observed product size in cv. Tamaroi, which lacked Nax1, was about 200 bp while a smaller fragment was observed for Line 149 and plants which comprised Nax1.

Example 2

Separation of Nax1 and Nax2 and Development of Single Gene Families

Durum wheat (*Triticum turgidum* ssp. *durum*) is more salt sensitive than bread wheat (*Triticum aestivum* L.) and yields less than bread wheat when grown on salt-affected soils, probably because of its poorer ability to exclude $Na^+$ from the leaf blade (Gorham et al. 1990). An unusual source of $Na^+$ exclusion trait was identified in a *durum* landrace from a collection of 64 tetraploid wheat landraces representing five subspecies, using a screening technique for leaf blade $Na^+$ accumulation as described in Example 1. One line, which we designated Line 149, (corresponding to Accession No. AUS17045, Australian Winter Cereals Collection, Tamworth, NSW, Australia) had an unusually low sodium concentration, as low as bread wheat, compared to the other tetraploid lines tested.

Genetic analysis of a cross between Line 149 and the *durum* cultivar Tamaroi indicated two genes of major effect for Na$^+$ exclusion (Munns et al. 2003). A QTL (Quantitative Trait Locus) for low Na$^+$ concentration in leaf blades was mapped to the distal region on the long arm of chromosome 2A and named Nax1 (Na$^+$ exclusion). This QTL accounted for 38% of the phenotypic variation in the F$_2$ generation, suggesting that it was associated with one of the two major genes. A microsatellite marker, gwm312, was closely linked to the trait (Lindsay et al. 2004; WO 2005/120214).

The presence of a second gene for Na$^+$ exclusion in Line 149 was suggested from the observation that some plants without the Line 149 allele of gwm312 belonged to the low Na$^+$ class. A second gene independent of Nax1 was suggested to contribute to the full expression of the Na$^+$ exclusion trait. We designated this second gene as Nax2.

From the F$_2$ family derived from a cross between Line 149 and Tamaroi, individuals with leaf Na$^+$ concentrations as low as the parent Line 149 were selected and backcrossed to Tamaroi four times. Each backcross was selfed, and individual F$_2$ plants with the lowest leaf Na$^+$ concentrations were used for the next backcross. The BC$_4$F$_2$ family of 100 individuals was used to isolate the Nax1 and Nax2 genes into separate BC$_5$F$_2$ single gene families. Selections were based on the allelic variation of the gwm312 marker, in combination with a Na$^+$ phenotype screen. The presence of Nax2 was evident in lines that carried the Tamaroi allele for gwm312 but were intermediate for Na$^+$. While plants that were homozygous for the Line 149 gwm312 allele usually had a low Na$^+$ phenotype, some plants were intermediate for Na$^+$ indicating the possible absence of Nax2.

To develop families containing only Nax1, BC$_4$F$_2$ individuals were selected that were homozygous for the Line 149 allele of gwm312 but had an intermediate Na$^+$ concentration. To develop lines containing only Nax2, BC$_4$F$_2$ individuals were selected that were homozygous for the Tamaroi allele of gwm312 but had an intermediate Na$^+$ concentration. These selections were backcrossed to the recurrent parent Tamaroi and selfed in the BC$_5$F$_1$. The resulting BC$_5$F$_2$ families were scored for leaf Na$^+$ concentration as described in Example 1.

Homozygous BC$_5$F$_3$ low and high Na$^+$ near-isogenic Nax1 and Nax2 lines used in Na$^+$ uptake studies were given the annotations, [+]Nax1, [−]Nax1 and [+]Nax2, [−]Nax2, respectively.

Single-gene Nax1 families showed a 1:2:1 distribution (FIG. 1, upper panel), indicating the segregation of a single co-dominant gene, whereas putative Nax2 families showed a 3:1 distribution (FIG. 1, lower panel), indicating the segregation of a single partially or fully dominant gene. Progeny testing of the BC$_5$F$_3$ lines validated the single plant F$_2$ phenotype. For example, in the Nax2 families the segregation of a single partially or fully dominant gene was confirmed by comparison of the F$_2$ and F$_{2:3}$ progeny means for Na$^+$ concentration of the 3$^{rd}$ leaf (FIG. 2). The segregation of the Nax2 sodium exclusion trait in 125 F$_{2:3}$ lines fitted the expected ratio for a single major gene (Expected 94:31; Observed 96:29; $\chi^2$=0.171, P$_{0.05}$=3.84).

To compare the effectiveness of the two genes in these near-isogenic lines in controlling Na$^+$ transport to the leaf blades, Na$^+$ concentrations in leaf blades, leaf sheaths and roots were measured after growth of plants in 50 mM NaCl for 10 days. Both genes greatly reduced the accumulation of Na$^+$ in the leaf blade, although neither on its own reduced the Na$^+$ concentration as much as when present together in the parent Line 149 (Table 2). The data suggested that the physiological mechanisms by which the two genes achieved low Na$^+$ concentrations in the blade differed.

The Nax1 gene reduced Na$^+$ concentrations in the shoot as a whole. Total shoot Na$^+$ concentration of [+]Nax1 lines was about half that of [−]Nax1 lines (Table 2). Nax1 was responsible for retention of Na$^+$ at the base of the leaf, and the sheath:blade ratio of Na$^+$ concentration was the same as that in Line 149, being greater than 2. This feature was characteristic of Nax1. Nax1 was also associated with a higher root Na$^+$ concentration, as was Line 149 (Table 2).

TABLE 2

Na$^+$ concentrations in plant parts of Nax1 and Nax2 near-isogenic BC$_5$F$_3$ plants compared to parental lines Line 149 and Tamaroi.

| | | Na$^+$ concentration (μmol gDW$^{-1}$) | | | | |
|---|---|---|---|---|---|---|
| Category | Line | Leaf blades | Leaf sheaths | Sheath: blade | Total shoot | Roots |
| Parents | Line 149 | 104 ± 7 | 271 ± 12 | 2.6 | 160 ± 9 | 983 ± 23 |
| | Tamaroi | 579 ± 17 | 559 ± 15 | 1.0 | 572 ± 16 | 811 ± 26 |
| Nax1 | [+]Nax1 | 183 ± 6 | 427 ± 8 | 2.3 | 260 ± 6 | 886 ± 17 |
| lines | [−]Nax1 | 599 ± 15 | 581 ± 21 | 1.0 | 593 ± 16 | 836 ± 17 |
| Nax2 | [+]Nax2 | 210 ± 8 | 209 ± 20 | 1.0 | 209 ± 11 | 819 ± 20 |
| lines | [−]Nax2 | 583 ± 18 | 529 ± 12 | 0.9 | 565 ± 16 | 805 ± 13 |

Values are means ± s.e. (n = 6)

The Nax2 gene reduced Na$^+$ concentrations in the shoot to a greater extent than Nax1 (Table 2). There was no preferential retention of Na$^+$ in the leaf sheath, so the reduced Na$^+$ uptake into the leaf blade was determined predominantly by the roots. Therefore, the Nax1 locus appeared to be solely responsible for preferential partitioning of Na$^+$ into the leaf sheath, a trait originally identified in Line 149 (Davenport et al. 2005). The combination of sheath partitioning and root control of Na$^+$ transport in [+]Nax1 together delivered lower leaf blade Na$^+$ concentrations than [+]Nax2.

K$^+$ concentrations were also measured in the same plant parts (Table 3). K$^+$ concentration in the shoot was enhanced by the presence of both Neal and Nax2 (Table 3). In the blade, the presence of both genes had a greater effect on K$^+$ concentration than either alone, but in the sheath, Nax2 alone produced as high a K$^+$ concentration as Line 149 with both genes. Thus, the Nax2 gene promoted a greater transport of K$^+$ to the total shoot than did Nax1. The K$^+$/Na$^+$ discrimination ratio, therefore, was enhanced by both genes in leaf and sheath, with Nax2 having a greater effect in the sheath than Nax1 (Table 3).

TABLE 3

K+ concentration and K:Na ratio in leaf blades and leaf sheaths, and roots in
Line 149 (low Na+) and Tamaroi (high Na+) and in low Na+ and high Na+ Nax1 and Nax2
near-isogenic families grown in 50 mM NaCl for 10 d. Values are means ± s.e. (n = 6)

| Plant material | Category | K concentration ($\mu$mol K:Na ratio gDW$^{-1}$) | | | |
| --- | --- | --- | --- | --- | --- |
| | | Leaf blades | Leaf sheaths | Leaf blades | Leaf sheaths |
| Parents | Line 149 | 1390 ± 14 | 1386 ± 16 | 13.8 ± 1.0 | 5.2 ± 0.3 |
| | Tamaroi | 941 ± 15 | 1099 ± 20 | 1.6 ± 0.0 | 2.0 ± 0.1 |
| Nax1 families | [+]Nax1 | 1180 ± 18 | 1217 ± 17 | 6.5 ± 0.2 | 2.9 ± 0.1 |
| | [−]Nax1 | 901 ± 11 | 1072 ± 12 | 1.5 ± 0.0 | 1.9 ± 0.1 |
| Nax2 families | [+]Nax2 | 1110 ± 19 | 1324 ± 20 | 5.4 ± 0.2 | 6.5 ± 0.6 |
| | [−]Nax2 | 874 ± 19 | 1075 ± 12 | 1.5 ± 0.1 | 2.0 ± 0.1 |

It is important to note that neither Nax1 nor Nax2 alone gave the Na$^+$ exclusion capability present in the parent, Line 149, indicating that both genes interacting together were required to give a greater expression of Na$^+$ exclusion in the total shoot and leaf blades. The phenotype of Nax1 was quite different from the phenotype of Na$^+$ exclusion in hexaploid wheat. The latter has no ability to retain Na$^+$ in the sheath, and shows a sheath:blade ratio no greater than about 1. There appears no counterpart of the Nax1 gene in bread wheat or the D genome as shown in synthetic wheat.

However, the phenotype of Nax2 *durum* plants was similar to that of salt tolerant hexaploid wheat, with a higher K$^+$ and lower Na$^+$ in leaves, and a resultant high K/Na$^+$ ratio (Table 3). This was similar to the enhanced K$^+$/Na$^+$ discrimination trait (Gorham et al. 1990) conferred by the Kna1 locus on chromosome 4DL (Dubcovsky et al. 1996). Like Kna1, Nax2 resulted in low Na$^+$ and high K$^+$ concentrations in the leaf blade of plants growing in 50 mM NaCl.

Example 3

Physiological Mechanisms Controlling Na$^+$ Uptake and Transport in Wheat

Results

To compare the physiological mechanisms underlying the phenotypes conferred by Nax1 and Nax2, the homozygous BC$_5$F$_3$Na$^+$ near-isogenic Nax1 and Nax2 plants generated as described in Example 2 (annotated [+]Nax1, [−]Nax1 and [+]Nax2, [−]Nax2) were further characterised in Na$^+$ uptake and flux studies. The parental control lines used in these experiments were Line 149 and Tamaroi. Radiotracer experiments using radiolabelled $^{22}$Na$^+$ in the presence of 25 mM NaCl were carried out as described in Example 1.

Initial uptake rates of $^{22}$Na$^+$ into the roots, measured at 5 min, did not differ between parents or between [+/−]Nax1 and [+/−]Nax2 lines (FIGS. 3 and 4), indicating that the unilateral (inward) flux of Na$^+$ into the roots did not differ between these lines. Longer term radiotracer experiments using $^{22}$Na$^+$ up to 30 min showed no differences in net root uptake with either Nax1 or Nax2, and only in Nax1 lines were there differences after this time (FIGS. 3 and 4), with [+]Nax1 roots showing slightly higher rates of uptake. This difference was consistent with the root total Na$^+$ concentrations shown in Table 2, with [+]Nax1 roots containing slightly more Na$^+$ than [−]Nax1. These data show that the Nax genes must control the loading of Na$^+$ into the xylem, rather than the uptake from the soil solution into the roots.

Time course experiments on the appearance of $^{22}$Na$^+$ in the shoots were carried out on plants grown in the presence of 50 mM NaCl to determine if there were differences in the rate of transport from roots to shoots. $^{22}$Na$^+$ appeared in the shoots after 15 min, and after 30 min the uptake by the [+]Nax1 and [−]Nax1 lines differed significantly (FIG. 3B). At 4 h, the calculated Na$^+$ uptake rate of [+]Nax1 shoots (3.7 nmol g$_{root}$FW$^{-1}$ min$^{-1}$) was about half that of [−]Nax1 shoots (6.4 nmol g$_{root}$FW$^{-1}$ min$^{-1}$). The rapid appearance of $^{22}$Na$^+$ in the shoot indicated a rapid labelling of the root cytoplasmic pool with the external solution, leading to a steady rate of efflux to the shoot. If maintained over 10 days, this would completely account for the differences in total shoot Na$^+$ concentration between Nax1 lines (Table 2). Differences in shoot Na$^+$ uptake between the Nax1 lines could be due to either a tighter control of xylem loading or a higher rate of withdrawal of Na$^+$ from the transpiration stream into the older parts of the roots. A higher rate of withdrawal is consistent with the observed withdrawal of Na$^+$ from the xylem stream into leaf sheaths and the higher root Na$^+$ concentrations. Evidence for xylem retrieval of Na$^+$ in the roots of Nax1 plants was obtained in a separate 'compartmental loading' experiment. When the apical part of the root was exposed to $^{22}$Na$^+$, [+]Nax1 plants translocated 21% less $^{22}$Na$^+$ to the upper part of the root and retrieved more of the translocated $^{22}$Na$^+$ into the upper roots than [−]Nax1 plants (88% versus 51%). This resulted in a four-fold higher shoot Na$^+$ uptake in [−]Nax1 plants.

In the Nax2 lines, root $^{22}$Na$^+$ uptake rates were the same for the [+]Nax2 and [−]Nax2 lines over the whole period studied (FIG. 4A), which was consistent with them having the same total Na$^+$ concentrations after 10 d in 50 mM NaCl. Shoot uptake of $^{22}$Na$^+$ was apparent at 15 min, by which time [+]Nax2 had a lower rate of uptake than [−]Nax2. This difference was quite clear at 30 min and thereafter (FIG. 4B) and was sufficient to account for differences in shoot Na$^+$ concentrations (Table 2). As the rates of root Na$^+$ uptake were identical in both Nax2 lines, differences in shoot uptake were due to the net rate of xylem loading.

The inventors concluded that the reduction in shoot Na$^+$ accumulation in Nax$^+$ plants was due to differences in the rate of net loading of Na$^+$ into the xylem, thus this is exclusion from the xylem rather than exclusion from the root as a whole.

Uptake of Na$^+$ and K$^+$ Along the Leaf in the [+]Nax1 Family

As the retention of Na$^+$ in the leaf sheath conferred by the Nax1 gene was unique, the distribution of Na$^+$ along the length of the leaf was measured to determine whether the Na$^+$ retention phenomenon was confined to cells in the sheath, or whether the ligule could act as a barrier to Na$^+$ movement in the xylem. Analysis of sheath and leaf blade segments after 2 d and 5 d in 50 mM NaCl showed a gradient of Na$^+$ concentrations, decreasing from the base of the sheath to the leaf tip. This indicated that the xylem parenchyma cells in the leaf sheath did not differ from those in the blade in the ability to withdraw Na$^+$ from the xylem, and showed clearly that there was no barrier to Na$^+$ movement at the ligule. After 5 d in 50 mM NaCl, Na$^+$ concentrations in successive lower sheath segments appeared to level off at about 250 mM, possibly indicating a threshold in the storage capacity of that tissue.

rate from root to shoot. C68-101 had the same low Na$^+$ concentrations in leaves as Line 149, the same high K$^+$/Na$^+$ discrimination and the high sheath:blade ratio characteristic of the Nax1 gene. It also had the Line 149 allele of gwm312. Marrocos had a sheath:blade ratio of 1:1. It was concluded that C68-101 was the donor of both Nax genes to Line 149.

TABLE 4

Na$^+$ and K$^+$ net transport rates to the shoot, Na$^+$ and K$^+$ concentration in the xylem stream and percentage exclusion of Na$^+$ by the roots in Line 149, Tamaroi and Nax1 and Nax2 near-isogenic lines grown in 50 mM NaCl. Values are calculated over a 6 to 10 d period, from two experiments and are means ± s.e. (n = 12).

| Plant material | Category | Shoot transport rate (μmol $g_{root}FW^{-1} d^{-1}$) | | Ion concentration in xylem (mM) | | Exclusion by roots (%) |
|---|---|---|---|---|---|---|
| | | Na$^+$ | K+ | Na$^+$ | K+ | Na$^+$ |
| Parents | Line 149 | 6.0 ± 0.6 | 45 ± 3 | 0.9 ± 0.1 | 6.7 ± 0.3 | 98.3 ± 0.2 |
| | Tamaroi | 22.7 ± 0.8 | 41 ± 3 | 2.8 ± 0.1 | 5.0 ± 0.4 | 94.4 ± 0.3 |
| Nax1 lines | [+]Nax1 | 6.5 ± 0.3 | 35 ± 3 | 1.0 ± 0.1 | 5.2 ± 0.3 | 98.0 ± 0.1 |
| | [−]Nax1 | 22.5 ± 1.5 | 37 ± 3 | 2.8 ± 0.3 | 4.7 ± 0.5 | 94.4 ± 0.6 |
| Nax2 lines | [+]Nax2 | 8.7 ± 0.9 | 42 ± 2 | 1.3 ± 0.1 | 6.3 ± 0.4 | 97.4 ± 0.2 |
| | [−]Nax2 | 17.9 ± 1.3 | 33 ± 3 | 2.5 ± 0.1 | 4.5 ± 0.3 | 95.0 ± 0.2 |

Measurements of K$^+$ in leaves at 2 and 5 d indicated that K$^+$ displaced Na$^+$ over time. K$^+$ was initially at high concentrations (400 mM) in all part of the sheath and blade, but decreased over time as Na$^+$ increased. The greater decrease in the leaf sheath over time, while Na$^+$ increased, indicating that K$^+$ was either entering the xylem in exchange for Na$^+$ and moving towards the leaf tip, or entering the phloem and moving out of the leaf. No such gradient was found across the leaf in lines without Nax1.

Net Na$^+$ and K$^+$ Transport Rates from Root to Shoot, and Xylem Concentrations Total Na$^+$ and K$^+$ transport rates to the shoot were calculated from the increase in roots and shoots between 6 and 10 d after exposure to 50 mM NaCl. High Na$^+$ uptake rates, similar to the recurrent parent Tamaroi, were evident in [−]Nax1 and [−]Nax2 lines (Table 4). There was less variation in K$^+$ transport rates between genotypes, however the highest K$^+$ transport rates were found in Line 149 and [+]Nax2, indicating that the Nax2 locus may be associated with the exchange of K$^+$ and Na$^+$ in net xylem loading in the root.

Given that the extent of retranslocation was relatively small, Na$^+$ concentrations in the xylem were calculated from the ion transport rate and the transpiration rate. Na$^+$ concentrations in the xylem were about 1 mM for lines containing either or both Nax1 and Nax2, and 2.5 mM or over if either gene was lacking (Table 4). Relating the Na$^+$ xylem concentration to the external salinity, plants containing either Nax1 or Nax2 excluded 98% of the Na$^+$ from the external solution, yet those without these genes still excluded 94% (Table 4). This shows that relatively small percentage differences in Na$^+$ exclusion capability led to profound differences in the accumulation of Na$^+$ into the shoot.

Origin of Nax1 and Nax2

The *durum* Line 149 was derived from a cross between a *durum* cultivar Marrocos and an accession of the wheat progenitor, *Triticum monococcum*, C68-101 (The, 1973). Na$^+$ concentrations in leaf blades of such plants were measured. C68-101 had the same low levels as Line 149, whereas Marrocos had a high Na$^+$ concentration. In experiments similar to those described above, Na$^+$ transport rates in C68-101 were similar to Line 149, but Marrocos had a much higher transport Discussion The two genes for Na$^+$ exclusion in Line 149 were both shown to function in reducing unidirectional Na$^+$ transport from root to shoot, however the two genes had different additional functions that suggested they acted via different mechanisms. Both Nax1 and Nax2 reduced the rate of Na$^+$ accumulation in the leaf blade, and enhanced the K$^+$ concentration, but differed in two ways. Firstly, Nax1 had a higher rate of deposition of Na$^+$ in the leaf sheath than Nax2, and as a consequence a higher ratio of Na$^+$ concentration in sheath:blade. Secondly, Nax1 had a lower rate of K$^+$ transport from root to shoot than Nax2, but the displacement of K$^+$ in the sheath led to an equal deposition in the leaf blade. Thus, both Nax1 and Nax2 lead to Na$^+$ exclusion from the leaf blade, and a high K/Na$^+$ ratio, but by different mechanisms (FIG. 5).

Nax1 Mechanism—Retention of Na$^+$ at the Leaf Base

The mechanism conferred by Nax1, which was characterised by the deposition of Na$^+$ in the base of the leaf, is not confined to wheat germplasm containing the Nax1 gene. Preferential deposition of Na$^+$ in the leaf base has been described for rice and the reed plant *Phragmites communis* (Matsushita and Matoh, 1991) and sorghum (Lacerda et al. 2003).

The gradients in Na$^+$ and K$^+$ concentration along the leaf, and their change over time, indicated that the cells lining the xylem were removing Na$^+$ from the xylem stream, storing it in parenchyma cells in the sheath, and causing a displacement of the K$^+$ there. It was possible to explain the gradient of Na$^+$ along the leaf with a model incorporating the passive movement of Na$^+$ from the xylem and possibly a subsequent active scavenging of Na$^+$ as the concentration falls. Na$^+$ can move passively from the xylem into the xylem parenchyma cells, against a concentration gradient, due to the electrical potential of the cells which might be about −100 to −200 mV. Na$^+$ in the xylem could initially move passively via a Na$^+$ permeable channel or a Na$^+$ uniporter into the xylem parenchyma in the basal sheath tissue, leading to high rates of retrieval in these cells compared to the cells in the upper sheath and leaf blade which would experience progressively lower Na$^+$ concentrations in the xylem stream, and subsequently lower rates of Na$^+$ retrieval. Active uptake might be necessary to scavenge the Na$^+$ at very low concentrations, depending on the cytosolic concentration of cells near the leaf tip.

This Nax1 mechanism of removal of Na$^+$ (and displacement of K$^+$) was not restricted to the leaf as the transport of Na$^+$ to the shoot as a whole was lower in the [+]Nax1 than the [−]Nax1 family, indicating that this same process probably occurred in the root as well. That Na$^+$ can be withdrawn from the xylem in the roots was shown by the apical feeding with $^{22}$Na$^+$.

Nax2 Mechanism—Control of Net Loading of Na$^+$ in Root Xylem

The Nax2 mechanism was confined to the roots, and had the effect of reducing the transport of Na$^+$ from root to shoot while increasing the transport of K$^+$. This resulted in an "exchange" of Na$^+$ for K$^+$. Re-absorption of Na$^+$ from the xylem in the upper part of the root system has been described for maize (Shone et al. 1969; Johanson and Cheeseman, 1983), for soybean (Lacan and Durand, 1996), and for beans, both *Phaseolus vulgaris* (Jacoby, 1964) and *Phaseolus coccineus* (Kramer et al. 1977). The studies with soybean indicated an exchange of K$^+$ for Na$^+$, energised by H$^+$-ATPases, and the authors suggested that Na$^+$/H$^+$ and K$^+$/H$^+$ antiporters at the plasma membrane of the xylem parenchyma might be involved (Lacan and Durand, 1996). Na$^+$-selective HKTs have been implicated in Na$^+$ withdrawal from the xylem with a concomitant enhancement of K$^+$ uptake to the shoot, but it is not clear whether the HKTs affect K$^+$ transport directly or via an influence on cation homeostasis (Rus et al. 2004; Ren et al. 2005). The Na$^+$ reabsorption from the xylem in the upper part of *P. coccineus* roots was associated with cells having the appearance of "transfer cells". These are xylem parenchyma cells with a wall labyrinth that increases the surface area of the plasma membrane suggesting a function in transport processes (Kramer et al. 1977). Transfer cells have been described in the roots of other species (Kramer, 1983) but have not been found in wheat.

The mechanism may be similar to that described above for Nax1, that is, the removal of Na$^+$ from the xylem by the upper part of the root and a consequent influx of K$^+$ into the xylem to restore the electrical potential. This would result in an "exchange" of Na$^+$ for K$^+$. Alternatively, it is possible that the converse occurs, that is, an enhanced loading of K$^+$ into the xylem by the upper parts of the roots which results in a removal of Na$^+$. Thirdly, there could be control of loading of the xylem in the roots with a high selectivity for K$^+$ over Na$^+$.

Example 4

Cloning of Wheat Homologues of Cation Transporter Genes

In order to clone wheat homologues of genes related to salt tolerance, the available literature was searched for genes known to confer salt tolerance, mediate cation transport, or both, in various species of plants including *Arabidopsis* and rice. In this way, a non-redundant list of 397 candidate genes comprising around 20 distinct gene families was compiled. Protein sequences corresponding to the genes from this list were retrieved from public databases, for example Genbank, and the entire set used to query all wheat EST sequences available from the Genbank database as of 18 Aug. 2004, using the BLAST program with default parameters. By this, 1540 unique wheat ESTs were identified that encoded amino acid sequences that were significantly similar to one or more of the query protein sequences, each having a BLAST E value of less than approximately 0.001. The batch BLAST results were then analysed to retrieve the most similar query gene for each of the 1540 wheat EST sequences, so that each of these could be classified as related to the homologue of that particular cation transporter or salt tolerance gene.

Further, sequence relationships were confirmed by performing multiple sequence alignments of the known and predicted amino acid sequences using the CLUSTALX program (Thompson et al. 1997). Amino acid sequences were used in these analyses rather than the nucleotide sequences as the percent identities were generally higher for the former. For example, nucleotide sequences were often less than 50% identical even for members within families of clear homologues, while the corresponding amino acid sequences were at least 50% identical and typically at least 60% identical. Phylogenetic (Neighbour-Joining) trees for related amino acid sequences were therefore generated with CLUSTALX using the default parameters (random number seed 111, bootstrap replicates=1000, gaps not excluded) to determine the broad relationships between the various members of each family. From this information a list of wheat ESTs having similarity to each cation transporter gene or salt tolerance gene family was compiled. This resulted in around 20 distinct gene families being identified, which could be further subdivided into subfamilies. Table 5 shows the number of wheat ESTs identified for each family of candidate genes. FIG. 6 shows an example of one of the phylogenetic trees, for the so-called Na+/H+-antiporter family (NHX family in Table 5).

As part of this process and as an example of it, the database was searched for ESTs encoding amino acid sequences similar to one family of known and putative sodium/potassium transporter genes (HKT in Table 5). This family included the wheat high-affinity potassium uptake transporter U16709 (protein accession AAA52749), the *Arabidopsis* sodium transporter AF237672 (protein accession AAF68393) and similar sequences. Nine genes from this family have been described in rice (Garciadeblas et al. 2003). These were included in the batch BLAST along with homologues from a variety of other species. FIG. 7 shows the phylogenetic tree created by CLUSTALX for the members of this family. The rice genes were found to fall into 3 subfamilies, each with 2 subdivisions. The subfamilies were essentially equidistant on the phylogenetic tree. Analyses of the batch BLAST results revealed 6 wheat ESTs with similarity to the wheat gene U16709, and 1 to each of the rice genes AF500082, AJ491853 and OSJNBb0022N24.16 (protein accessions AAM46870, CAD37197 and BAB93392 respectively). These ESTs are listed in Table 6. A single wheat EST (CK193616) was identified that showed stronger homology to the rice OSJNBb0022N24.16 gene than any other wheat EST.

TABLE 5

Number of wheat ESTs identified corresponding to each family of candidate genes.

| Superfamily | Function | Family | No. of ESTs |
|---|---|---|---|
| CHX | Cation-hydrogen antiporters, all or mostly for monovalent and divalent cations | CHX | 6 |
| | | KEA | 44 |
| | | MHX | 4 |
| | | NHA | 6 |
| | | NHD | 4 |
| | | NHX | 53 |
| | | SOS1 | 10 |
| CNGC | Proteins in the CNGC family are thought to be non-selective cation channels, while members of the KAT family are thought to be K$^+$ channels. Both have domains for regulation by cyclic nucleotides. | CNGC | 117 |
| | | KAT | 247 |

TABLE 5-continued

Number of wheat ESTs identified corresponding to each family of candidate genes.

| Superfamily | Function | Family | No. of ESTs |
|---|---|---|---|
| KC | Thought to be K+ channels of varying affinity, but research is suggesting roles for the HKTs in transporting sodium. | HAK | 212 |
|  |  | HKT | 9 |
|  |  | KCO | 72 |
| Various | Putative non-selective cation channels; similar to animal glutamate receptor proteins. | GLR | 41 |
|  | Putative non-selective cation channels; unknown. | LCT | 26 |
|  | Vacuolar H+-pyrophosphatases. | AVP | 191 |
|  |  | HAL2 | 84 |
|  |  | HAL3 | 7 |
|  | Mechanosensitive ion channels | MIC | 36 |
|  | Protein kinases | SOS2 | 228 |
|  | GTP-binding proteins | SOS3 | 143 |
|  | Total: |  | 1540 |

TABLE 6

List of wheat ESTs matching members of the HKT gene family. Match lengths are given as the number of amino acids.

| Query Gene | Protein Accession No of Query | Wheat EST Accession No | BLAST output parameters | | | Match length |
|---|---|---|---|---|---|---|
|  |  |  | Score | E-value | % Identity |  |
| OsHKT1 | AAM46870 | CA611947 | 100 | 7.10E−28 | 75 | 70 |
| TaHKT1 | AAA52749 | BE428877 | 268 | 3.60E−71 | 100 | 133 |
|  |  | CA700881 | 243 | 9.40E−64 | 100 | 117 |
|  |  | CA649725 | 111 | 7.20E−28 | 100 | 55 |
|  |  | CA663666 | 107 | 6.20E−23 | 59 | 98 |
|  |  | CA646680 | 77 | 6.8E−14 | 80 | 40 |
|  |  | CA653018 | 75 | 3.4E−13 | 77 | 40 |
| OsHKT7 | CAD37197 | BE604162 | 237 | 6.20E−62 | 82 | 139 |
| OsHKT8 | BAB93392 | CK193616 | 163 | 3.3E−42 | 81 | 90 |

In order to isolate gene fragments corresponding to many of the wheat ESTs for microarray experiments (Example 8), primers were designed internal to many of the ESTs, PCR amplifications carried out, and the resultant PCR products cloned into the pGEMT-easy vector (Promega Corporation, Madison USA). More than 125 wheat EST fragments were cloned in this way. For example, the primers for CK193616 were HKT8For01 (5'-CATCACCGTCGAGGTTATCAG-3', SEQ ID NO: 34) and HKT8Rev01 (5'-TTGAGGTACTCG-GCATA-3'; SEQ ID NO: 35). These primers were used in polymerase chain reactions (PCR) using standard conditions with the following cycling protocol: 95° C., 7 min; then 5 cycles of 95° C., 1 min; 61°-57° C. (reducing 1° per cycle), 1 min; 72° C., 3 min; followed by 35 cycles of 95° C., 45 sec; 56° C., 30 sec; 72° C., 3 min; and finally 72° C. for 5 min. The PCR reactions used template DNA from several wheat lines including both salt tolerant and salt sensitive lines.

Fortuitously, it was noticed that the PCR for the wheat EST CK193616 produced a polymorphism between two salt tolerant lines and a salt sensitive variety. The PCR reactions produced fragments of 332 bp and 517 bp from the cDNA of the salt tolerant lines *Triticum monococcum* and *T. turgidum* ssp. *durum* cv. Line 149, but not from the salt sensitive variety *T. turgidum* ssp. *durum* cv. Tamaroi ("Tamaroi"; see FIG. 8). When genomic DNAs were used as the templates in the PCR reactions, similar patterns of amplified fragments were seen (FIG. 8). A PCR product of approximately 750 bp was also amplified from *durum* wheat lines Line 149 and Tamaroi but sequencing of the product revealed it to be unrelated to the OSJNBb0022N24.16 homologue. This product presumably resulted from a secondary priming site for one of the primer pair in *durum* wheat.

The PCR products obtained from *T. monococcum* and *T. turgidum* ssp. *durum* cv. Line 149 cDNA and genomic DNA and corresponding to CK193616 were ligated into pGEMT-easy, transformed into DH5α electrocompetent cells and positive (white on XGal medium) colonies containing the PCR products identified. The plasmid containing the *T. monococcum* fragment was designated D4.1. The inserts from the plasmids were sequenced using BigDye Terminator version 3.1 according to the suppliers instructions. Sequencing results confirmed that the fragments, which were identical for *T. monococcum* and Line 149 cDNA, were from a wheat homologue of OSJNBb0022N24.16. This was confirmed by phylogenetic analysis (FIG. 9). Since the gene of which this fragment was a part was a member of the HKT family, the gene in *T. monococcum* was designated TmHKT8-A$^m$. The sequencing also showed the presence of a 185 bp intron in the 517 bp fragment, confirming that the 332 bp and 517 bp fragments corresponded to cDNA and genomic DNA portions of TmHKT8-A$^m$, respectively. The nucleotide sequences are given as SEQ ID NOs: 65 and 66, respectively, and the predicted amino acid sequence as SEQ ID NO: 67. The intron sequence corresponds to nucleotides 22 to 206.

The amplified fragment polymorphism therefore provided a molecular marker that could be used to distinguish Line 149 and Tamaroi. As described below in Example 5, the marker was tested for co-segregation with the Nax2 locus and found to be tightly linked with the locus.

Example 5

Genetic Mapping of the Nax2 Gene in *Durum* Wheat

Introduction

As described in Example 2, analysis of *durum* wheat plants from a cross between Line 149 and Tamaroi allowed separation of the Nax1 and Nax2 genes in near isogenic BC$_5$F$_3$ families. Several molecular markers, each based on one of a series of families of cation transporter-related genes as described in Example 4, were tested for linkage to the Nax2 gene in segregating populations or by bulked segregant analysis. One of these markers, based on the wheat HKT8 gene, showed linkage to Nax2 as described in this example.

Results
Phenotyping of the Nax2 Mapping Population

A population of 30 $BC_5F_{2:3}$ lines containing the Nax2 gene but not the Nax1 gene was used for testing the linkage of molecular markers to Nax2. Phenotyping of plants was carried out as described in Example 1 by measuring Na+ levels in leaf 3 after growth of the plants in solutions containing 150 mM Na+. Individual $F_2$ plants having either the low, intermediate or high Na+ accumulation levels were selected and selfed. The families of $F_{2:3}$ progeny of this mapping population were also phenotyped for sodium accumulation and the $F_2$ phenotypes confirmed in the $F_3$ generation. This also confirmed the homozygosity or heterozygosity of the $F_2$ plants. The number of $F_{2:3}$ seed tested per family was nine for progeny of $F_2$ plants with a low sodium phenotype (approximately $\leq 500$ μmmol Na+ $gDW^{-1}$) and five for $F_2$ plants with a medium or high sodium accumulation phenotype (approximately $\geq 500$ μmol $gDW^{-1}$). These numbers were based upon recommended population sizes required in biparental populations having segregating loci, to ensure that at least one homozygous genotype was obtained in later generations, as recommended by Bonnett et al. (2005). The observed Na+ levels in the $F_2$ and $F_3$ plants and parental lines are summarized in Table 7, including the number of plants or lines tested for each group.

TABLE 7

Observed Na+ levels in the $F_2$ and $F_3$ plants and parental lines.

| Generation | Germplasm | Mean and s.e. | Range |
|---|---|---|---|
| $P_1$ | Line 149 (n = 10) | 216 ± 7 | 171-254 |
| $P_2$ | Tamaroi (n = 10) | 832 ± 68 | 699-1431 |
| $BC_5F_2$ | Low Na+ selections (20) | 450 ± 10 | 358-502 |
| $BC_5F_2$ | High Na+ selections (20) | 1068 ± 15 | 976-1201 |
| $BC_5F_{2:3}$ | Low Na+ selections (19) | 462 ± 23 | 360-637 |
| $BC_5F_{2:3}$ | High Na+ selections (11) | 927 ± 16 | 837-1006 |

Genotyping

For genotyping plants in this population, plants grown in salt tanks for phenotyping were transplanted into soil and allowed to grow for approximately four weeks prior to DNA extraction. A single plant was retained from each of the $F_3$ families. For families with a homozygous low sodium accumulation phenotype, the plant with the lowest leaf sodium concentration was used. The plant with the highest leaf sodium was used from families with a homozygous high sodium accumulation phenotype. For half of those families with a heterozygous phenotype, the lowest of the low sodium accumulating plants was used, and for the other half of the families with a heterozygous phenotype, the highest of the high sodium accumulating plant was used. Leaf material from plants was harvested and DNA extracted as per Lagudah et al. (1991).

To prepare an HKT8 probe, a 332 bp fragment was amplified from the HKT8 region from the plasmid D4.1 by PCR using primers HKT8For01 and HKT8Rev01 (Example 4). The PCR was conducted under standard conditions with the following cycling protocol: 95° C., 15 min; then 5 cycles at 94° C., 1 min; 55° C., 1 min; 72° C., 1 min 20 sec; followed by 30 cycles of 94° C., 30 sec; 55° C., 30 sec; and finally 72° C., 2 min. After gel electrophoresis of the PCR products, a band of 332 bp was excised from the gel and the DNA isolated using a QIAquick Gel Extraction Kit (Qiagen) according to the manufacturer's instructions. This fragment was radio-labeled with $^{32}$P-CTP using the Megaprime DNA Labeling System (Amersham), according to the manufacturer's instructions. The probe was then purified through a column of G50 sephadex beads equilibrated in Tris-EDTA.

Co-Segregation of HKT8 Gene Marker with Nax2

In an initial experiment using the RFLP technique, DNA from 12 $BC_5F_{2:3}$ lines, each obtained from low sodium $F_2$ parents, was pooled into four bulks with DNA from three plants in each bulk. Samples of the bulked DNA and from the parental lines (Line 149 and Tamaroi) and *T. monococcum* (AUS#90382) were digested individually with NcoI, HindIII, EcoRI, EcoRV, SacI, XbaI. After gel electrophoresis, the gels were blotted and probed with the HKT8 probe as described in Example 1. Tamaroi and Line 149 were found to be polymorphic for each of the restriction enzyme digests when probed with the HKT8 probe (FIG. 10). HindIII and NcoI digested better than the other enzymes and gave clearer restriction patterns. All four bulked $BC_5F_{2:3}$ DNA samples gave the same hybridization pattern as the low sodium parent, Line 149. These patterns were different to the pattern obtained for Tamaroi in that they contained an additional band. This was a preliminary indication of co-segregation of the HKT8 marker and Nax2.

In a second experiment, DNA samples from 19 $BC_5F_{2:3}$ plants, each homozygous for the low sodium phenotype, and from 11 $BC_5F_{2:3}$ plants, each homozygous for the high sodium phenotype, were tested individually by the same RFLP method. Each of the 19 low sodium lines provided the same restriction pattern as Line 149, while each of the 11 high sodium lines provided the same restriction pattern as the high sodium parent, Tamaroi (for example see FIG. 11). This confirmed that the HKT8 marker co-segregated with the Nax2 gene and was closely linked to Nax2 in *durum* wheat. Indeed, this HKT8 sequence was a candidate for Nax2 itself.

The HKT8 probe hybridized to a single restriction fragment from the *T. monococcum* DNA when it was digested with either HindIII or NcoI, suggesting a single HKT8 gene member in the diploid wheat which contains an A genome. When DNA was digested with HindIII, the HKT8 probe hybridized to three different restriction fragments from Tamaroi, suggesting three different gene members, and four different restriction fragments in Line 149, suggesting four HKT8 gene members (FIG. 10). Line 149 and Tamaroi had three of the four fragments in common. The fourth fragment from Line 149 was of the same size as that from *T. monococcum*, suggesting that the fourth gene member in Line 149 might be sourced from *T. monococcum* and therefore be present in the A genome.

Chromosomal Location of Nax2

In similar Southern blot hybridization/RFLP analyses using the HKT8 probe, DNA from hexaploid wheat (cv. Chinese Spring) digested with HindIII gave four bands, indicating the presence of at least four members of the HKT8 gene family in hexaploid wheat (FIG. 12). To determine the chromosomal locations of these gene members and on which genome(s) they occurred, DNA samples from Langdon substitution lines (FIG. 12) and wheat nullisomic-tetrasomic lines and ditelomeric lines in a Chinese Spring background were also screened with the HKT8 RFLP marker as described above (FIG. 13). Furthermore, Chinese Spring chromosome deletion lines were used to localize the gene (Law et al. 1987; Law et al. 1981). The RFLP autoradiograms showed that the Chinese Spring lines which lacked chromosome 4L also lacked one or more hybridizing bands. By this analysis, HKT8 mapped to the distal end of chromosome 4L in Chinese Spring. HKT8 gene members were found to be present on both of the B and D genomes in Chinese Spring, three on the B genome and a single gene member on the D genome. No HKT8 members were found on the A genome of Chinese Spring under stringent hybridisation conditions.

This suggested that the single HKT8 gene member in *T. monococcum* (TmHKT8-A$^m$) and one of the members in *durum* Line 149 would be present on chromosome 4L, corresponding to 4AL of hexaploid wheat. To establish the chromosome location of Nax2 (and therefore the linked HKT8, see above) in *durum* Line 149 and test this, microsatellite markers were used. A group of 470 wheat microsatellite markers were used to screen DNA from the parental lines, Tamaroi and Line 149, for polymorphisms (Roder et al. 1998). Twenty-five were found to be polymorphic between Line 149 and Tamaroi (Table 8). These were then tested on bulked DNA samples from the BC$_5$F$_{2:3}$ lines, two bulks each containing pooled DNA from ten low sodium lines and two bulks each pooled from ten high-sodium lines. Three wheat microsatellite markers co-segregated with Nax2, namely Xgwm291-5A (5'-CATCCCTACGCCACTCTGC-3' (SEQ ID NO:28) and 5'-AATGGTATCTATTCCGACCCG-3' (SEQ ID NO:29)), Xgwm410 (5'-GCTTGAGACCGGCA-CAGT-3' (SEQ ID NO:30) and 5'-CGAGACCT-TGAGGGTCTAGA-3' (SEQ ID NO:31)) and gpw2181 (5'-CAAATTACAAACGCACAGCC-3' (SEQ ID NO:72) 5'-TTTGTGCCATTGTGTGTGTG-3') (SEQ ID NO:73)). These had been mapped previously to the distal end of chromosome 5AL (Roder et al. 1998), not 4AL.

To confirm co-segregation of these markers with Nax2, 19 BC$_5$F$_{2:3}$ plants with a homozygous low sodium phenotype were tested for genotype with respect to markers gwm291, gwm410 (data not shown) and gpw2181 (FIG. 14). All 19 homozygous low sodium phenotype plants had the same genotype as Line 149. In contrast, 11 BC$_5$F$_{2:3}$ plants which had a homozygous high sodium phenotype all had the same genotypic pattern with gwm291, gwm410 and gpw2181 as Tamaroi. This confirmed close linkage of these markers with Nax2. The gpw2181 marker is co-dominant where as both gwm291 and gwm410 are dominant for Tamaroi, they do not distinguish heterozygous genotype from homozygous for Nax2.

Members of HKT8 gene family identified by the TmHKT8-A$^m$ marker were thus located on the long arm of chromosome 4B and 4D in Chinese Spring and the long arm of chromosome 5A in *durum* wheat Line 149. Three other members in Line 149 could be presumed to be on chromosome 4B, corresponding to those in Chinese Spring. The *durum* gene fragment on chromosome A was identical to that in *T. monococcum*, which has an A genome, and could be presumed to have come from *T. monococcum* by introgression.

The difference in chromosomal positions, chromosome 4 for the B and D genomes and chromosome 5 for the A genome, might have been due to an ancient translocation between 4AL and 5AL, possibly formed during the hybridization event that resulted in the formation of tetraploid wheat from the A and B genome progenitors. The terminal segment of 5AL has been shown to be homologous to 4BL and 4DL (Liu et al. 1992). We therefore explain the 5AL location of the HKT8 gene and the linked Nax2 gene in *T. monococcum* and Line 149 as occurring by a 4AL/5AL translocation at the diploid level before or during the polyploidization of wheat (FIG. 15). It was concluded that HKT8 and Nax2 map to this translocated segment.

TABLE 8

Microsatellite markers polymorphic between Line 149 or P04973 and Tamaroi.

| WMS Number | Dominance | Chromosome | Position [cM] | Fragment sizes Line 149 | Fragment sizes Tamaroi |
|---|---|---|---|---|---|
| WMS4090 | codominant | 1A, 5B | 89.7; 247.6 | 192, 214 | 216, 240 |
| WMS0784 | codominant | 1B | 98.6 | 222 | 208 |
| WMS4106 | codominant | 1B | 105.5 | 190 | 192 |
| WMS1521 | codominant | 1B | 141.9 | 125, 173, 187 | 125, 177, 187 |
| WMS4096 | codominant | 1B | 156.8 | 230, 238 | 238 |
| WMS0153 | codominant | 1B | 168.3 | 187, 199, 213, 227 | 199, 227 |
| WMS0274 | codominant | 1B | 170.9 | 140, 160, 182, 186 | 140, 160, 182 |
| WMS0124 | dominant | 1B | 176.5 | 199, 205 | 205 |
| WMS0268 | codominant | 1B | 176.5 | 204, 212, 224 | 204 |
| WMS0077 | codominant | 3B | 168.1 | 137, 143 | 137 |
| WMS0637 | codominant | 4A | 145.9 | 146 | 144 |
| WMS0260 | codominant | 7A | 197.8 | 152, 170 | 170 |
| WMS0731 | codominant | 4A | 48.1 | 91, 131 | 93, 131 |
| WMS4445 | codominant | 4A | 54 | 186, 220 | 188, 220 |
| WMS0610 | codominant | 4A | 65.6 | 165 P04973 | 167 |
| WMS1342 | dominant | 5A | 173.9 | 0 | 156, 185 |
| WMS0291 | dominant | 5A | 247.2 | 0 | 171 |
| WMS0132 | dominant | 6B | 43.6 | 135, 149, 156 | 135, 0, 0 |
| WMS3085 | dominant | 1A | 63.9 | 0 | 200 |
| WMS0095 | dominant | 2A | 165 | 99, 111, 123 | 99, 111, 0 |
| WMS0685 | dominant | 3B | 163.1 | 116, 120 | 0, 120 |
| WMS3144 | dominant | 3B | 205.7 | 167, 176 | 0, 176 |
| WMS4063 | dominant | 4A | 55.1 | 0 | 148 |
| WMS0410 | dominant | 5A | — | — | — |
| WMS1694 | dominant | 4A | 238 | 0, 170, 177 | 157, 170, 177 |

Sequence polymorphism (see Example 6) between the HKT8 A and B gene members was used to develop a PCR marker (HKT8-A marker) specific for the A gene member, very likely to be Nax2, i.e. one that could distinguish the A and B genome members in a breeding population. Primer sequences were: For AI 5'-GAGTGGGGCTC-CGACGGGCTGAA-3' (SEQ ID NO:68) and RevAI 5'-GC-CGGCCGTCCACTGCGGACTGC-3' (SEQ ID NO:69). PCR was conducted under standard conditions with the following cycling protocol: 95° C., 15 min; then 5 cycles at 94° C., 1 min; 60° C., 1 min; 72° C., 1 min; followed by 30 cycles of 94° C., 30 sec; 60° C., 30 sec; and 72° C., 50 sec. A band of the expected size (986 bp) was observed for all lines with Nax2 and none of those without Nax2 (FIG. 16). The genetic distance between the co-dominant gpw2181 marker and Nax2 was not determined although they would be tightly linked. Therefore if gpw2181 was used as a genetic marker for the locus in plant breeding there remained a low possibility of recombination between gpw2181 and Nax2. The HKT8-A marker was therefore preferred. However, use of the combination of the gpw2181 with the HKT8-A marker in a breeding program to track Nax2 is even more preferred.

Conclusion

A genetic marker based on the HKT8 gene was developed that showed co-segregation with the Nax2 gene, which was known to confer salt tolerance to *durum* wheat. The marker was based on a primer pair designed from the sequence of a wheat EST (accession CK193616) which showed homology to a putative rice cation-transporter gene (OSJNBb0022N24.16, protein ID BAB93392.1). This primer pair was found to amplify a 517-bp fragment of genomic DNA from lines showing the Nax2-mediated exclusion of sodium from the aerial portions of tolerant lines, but did not amplify the fragment from lines showing no Nax2-mediated exclusion. The amplified fragment polymorphism was found to show perfect co-segregation with the trait in all plants so far tested. The primer pair thus provided a dominant RFLP marker for the presence/absence of the Nax2 locus. The co-dominant marker gpw2181 was found to be linked to Nax2 and mapped to the Nax2 locus. This PCR based marker may be used in combination with the dominant PCR based gene specific marker for Nax2 in plant breeding.

Example 6

Cloning of Full-Length HKT8 Coding Regions

In view of the observed genetic linkage of the TmHKT8 allele with the Nax2 salt tolerance locus in Line 149 as described above, it was of interest to characterise TmHKT8 further as a candidate for Nax2. To do this, full-length transcribed regions were cloned and their nucleotide sequences obtained of TmHKT8 alleles from Line 149, its salt-tolerant progenitor *T. monococcum* and the salt-sensitive *durum T. turgidum* ssp *durum* cv. Tamaroi as follows.

The inventors attempted to clone the 5' and 3' ends of the salt-tolerant allele from Line 149 via 5'- and 3'-RACE (Schaefer, 1995) using the sequence of the cloned fragment in plasmid D4.1. 5'- and 3'-RACE cDNA was prepared from Line 149 and cv. Tamaroi root RNA using the GeneRacer kit (Invitrogen) and the manufacturer's protocol. Primers HKT8_5'Rev01 and HKT8_5'Rev02 (Table 9) were designed internal to the D4.1 fragment for use in 5'-RACE with the following touchdown protocol: 95° C. 6 min; 5 cycles of 95° C. 1 min, T1° C. 1 min, 72° C. 5 min; X # cycles of 95° C. 1 min, T2° C. 1 min, 72° C. 5 min, with a touchdown of –1° C./cycle; then 30 cycles of 95° C. 45 sec, T3° C. 30 sec, 72° C. 5 min; 72° C. 10 min, 4° C. hold. Sequences, compatible RACE primers, and cycling parameters are given in Tables 9 and 10. Since the primers supplied in the kit were predicted to have multiple false priming sites within the D4.1 sequence, modified RACE primers were designed used which did not appear to have this disadvantage relative to the known sequence. However, the initial attempt at 5'-RACE was unsuccessful, possibly due to the length of product required from the RACE PCR. RACE PCR is known to be highly sensitive to amplicon length, with efficiency declining rapidly as amplicon length exceeds 1500 bp. The predicted amplicons required from these RACE reactions were in excess of 1800 bp.

An extension of the fragment in D4.1 was sought in a modified approach to clone the full-length genes. To obtain this, gene-specific cDNA was synthesised with the HKT8Rev01 primer using the SuperScript III reverse-transcriptase kit (Invitrogen) according to the manufacturer's protocol. This reduced the complexity of the cDNA used as PCR template, thereby greatly enhancing the performance of other primers in the subsequent PCR steps. A degenerate CODEHOP forward primer (sequence 5'-GTGCTGATGCT-GCTGGGNGGNGARGT-3' (SEQ ID NO:55), see Rose et al. 2003) was designed based on the rice HKT7 and HKT8 protein sequences. This was used together with the HKT8_5'Rev01 reverse primer in a PCR to amplify a longer fragment of the gene, using standard conditions and the following cycling protocol: 95° C. 7 min; 7 cycles of 95° C. 1 min, 65° C. 1 min, 72° C. 3 min with a touchdown of –1° C./cycle; 35 cycles of 95° C. 45 sec, 55° C. 30 sec, 72° C. 3 min; 72° C. 5 min, 4° C. hold. By this means a fragment of the gene was obtained comprising about 70% of the protein coding sequence of the TmHKT8 allele, lacking only the first 30%.

Primers designed within this coding region (HKT8For02: 5'-CCTGCACACCTTCTCCGTCTTCAC-3' (SEQ ID NO:56) and HKT8_5'Rev01) were also found to amplify fragments of HKT8 homologues from cv. Tamaroi using genomic DNA and the cycling protocol 95° C. 4 min; 10 cycles of 95° C. 1 min, 70° C. 1 min, 72° C. 4 min with a touchdown of –1° C./cycle; 40 cycles of 95° C. 45 sec, 61° C. 30 sec, 72° C. 4 min; 72° C. 10 min, 4° C. hold. After cloning amplified fragments into a vector and determining their nucleotide sequences, two distinct genomic sequences were identified, coming from genes that were designated as TtHKT8B1 and TtHKT8B2. When the same primer pair was used in PCR reactions with genomic DNA from bread wheat (*T. aestivum* cv. Chinese Spring) three distinct sequences were amplified, two of which closely matched the TtHKT8B1 and TtHKT8B2 sequences. The corresponding Chinese Spring genes were therefore designated TaHKT8B1 and TaHKT8B2. The third sequence was distinct from these and the TmHKT8 sequence. The gene from which this sequence was derived was designated TaHKT8D because it was likely this member was present on the D genome in bread wheat.

TABLE 9

Primers used in 5' and 3'-RACE.

| Primer name | Sequence (5'-3') | Tm (° C.) | Compatible RACE primer | T1 (° C.) | X # cycles | T2 (° C.) | T3 (° C.) |
|---|---|---|---|---|---|---|---|
| GeneRacer3'_4 Rev01 | GCTGTCAACGATACGCTACG-TAAC (SEQ ID NO: 36) | 73.1 | | | | | |
| GeneRacer3'_4 Rev02 | CGCTACGTAACGGCATGACAGT (SEQ ID NO: 37) | 75.6 | | | | | |
| GeneRacer5'_4 For01 | CGACTGGAGCACGAGGACACT (SEQ ID NO: 38) | 76.5 | | | | | |
| GeneRacer5'_4 For04 | CTGGAGCACGAGGACACTGAC (SEQ ID NO: 39) | 74.8 | | | | | |
| HKT8_3'For01 | TCATAGTGCTGGGCTATCA (SEQ ID NO: 40) | 66.3 | GeneRacer3'_4Rev01 | 65 | 6 | 76 | 59 |

TABLE 9-continued

Primers used in 5' and 3'-RACE.

| Primer name | Sequence (5'-3') | Tm (° C.) | Compatible RACE primer | T1 (° C.) | X # cycles | T2 (° C.) | T3 (° C.) |
|---|---|---|---|---|---|---|---|
| HKT8_3'For02 | TGGTCGCCTTCCGGTCTTT (SEQ ID NO: 41) | 76.5 | GeneRacer3'_4Rev01 | 71 | 9 | 71 | 62 |
| HKT8_5'Rev01 | TGAGCCTGCCGTAGAACA (SEQ ID NO: 42) | 70.5 | Invitrogen 5'F outer primer | 70 | 5 | 70 | 65 |
| HKT8_5'Rev02 | CCAGAGAAGCCAACCCAC (SEQ ID NO: 43) | 70.6 | Invitrogen 5'F nested primer | 70 | 5 | 70 | 65 |
| HKT8_5'Rev03 | CACGACGGCTGACGACAC (SEQ ID NO: 44) | 74.3 | GeneRacer5'_4For01 | 70 | 5 | 70 | 65 |
| HKT8_5'Rev04 | CTCCGGAGAGCCCAGAT (SEQ ID NO: 45) | 70.3 | GeneRacer5'_4For01 | 70 | 6 | 70 | 65 |
| HKT8_5'Rev05 | CGTGATAGCCCAGCACTATGA (SEQ ID NO: 46) | 72.4 | GeneRacer5'_4For04 | 70 | 6 | 70 | 65 |

TABLE 10

Primers used to amplify full-length HKT8 coding sequences from T. monococcum, bread and durum wheats.

| Gene/homologue | Primer name | Sequence (5'-5') | Tm (° C.) | T1 (° C.) | X # cycles | T2 (° C.) |
|---|---|---|---|---|---|---|
| TmHKT8 | TMHKT8F01 | AGGCCAAGAAGTCTCTACACA (SEQ ID NO: 47) | 65.1 | 61 | 6 | 55 |
|  | TmHKT8R01 | AGGTACTCGGCATAATGAA (SEQ ID NO: 48) | 61.7 |  |  |  |
| TtHKT8B1 | TtHKT8B1F01 | ARGCCAAGAASTCTCTAC (SEQ ID NO: 49) | 57.5 | 56 | 2 | 55 |
|  | TtHKT8B1R01 | AGGTACTTGCATAATGAA (SEQ ID NO: 50) | 56.3 |  |  |  |
| TtHKT8B2 | TaHKT8B2F03 | AGAASTCTCTADAATACTTG (SEQ ID NO: 51) | 51.5 | 55 | 5 | 50 |
|  | TaHKT8B2R01m | AATATGTTCAGATGGTTTTTG (SEQ ID NO: 52) | 63.1 |  |  |  |
| TaHKT8D | TmHKT8F01 | AGGCCAAGAAGTCTCTACACA (SEQ ID NO: 53) | 67.9 | 60 | 10 | 50 |
|  | HKT8Rev01 | TTGAGGTACTCGGCATA (SEQ ID NO: 54) | 61.9 |  |  |  |

To obtain a full-length cDNA for TmHKT8 including the 5' and 3' UTRs, new primers compatible with the 5'- and 3'-RACE were designed within the additional sequence obtained from the genomic sequences. Gene-specific 5'-RACE cDNA was synthesised from Line 149 root total RNA using the HKT8Rev01 primer. Nested 5'-RACE PCR was performed on this cDNA using the protocols outlined in Table 9. The primary PCR was performed using the HKT8_5'Rev03 primer and associated parameters, and subsequent nested PCR reactions were performed using primers in ascending numeric order. At each stage, 1 µL of PCR product from the previous nesting was used as template, along with 1 µL of the cDNA in a companion reaction. 3'-RACE was conducted in a similar manner, but due to its nature it was not possible to construct gene-specific cDNA. Therefore, total 3'-RACE cDNA was synthesised from Line 149 root total RNA as per the manufacturer's instructions. Nested PCR was then performed on cDNA in a similar manner.

These 5'- and 3'-RACE reactions yielded products approximating to the expected sizes. The products were gel-purified to remove contaminating bands, and ligated into pGEM-T easy (Invitrogen) as per the manufacturer's instructions. Ligation products were transformed into electrocompetent E. coli DH5α cells, and the bacteria plated onto LB medium containing ampicillin and XGa1. White colonies were selected, picked to replicate plates and inserts in the plasmids of these clones amplified with M13 Forward and Reverse primers. Sequencing of the PCR products was also performed with these primers.

Both of the RACE reactions were found to have amplified the 5' and 3' cDNA ends, including the UTRs, having nucleotide sequences with homology to corresponding regions of OsHKT8. From overlapping regions between the TmHKT8, TtHKT8B1 and TtHKT8B2 genes, it was determined that all of the 5' and 3' cDNA clones derived from Line 149 were from the TmHKT8 homoeologue.

Similar RACE reactions were also performed on root RNA from cv. Tamaroi, and again clones were obtained with homology to OsHKT8. In this instance, the clones were found to be 5' and 3' cDNA fragments of the TtHKT8B1 gene.

Primers were next designed based on the sequence of the 5'- and 3'-untranslated regions (UTRs) of the genes thus obtained. These primers were used to amplify the full-length genomic and cDNA genes, including the protein coding regions of these two genes, using HotStart polymerase (BIO-LINE) and the following touchdown cycling protocol: 95° C. 6 min; X # cycles of 95° C. 1 min, T1° C. 1 min, 72° C. 5 min, with a touchdown of −1° C./cycle; 30 cycles of 95° C. 45 sec, T2° C. 30 sec, 72° C. 5 min; 72° C. 10 min, 4° C. hold. Primers and cycling parameters used are given in Table 10.

Full-length cDNA (corresponding to the transcribed region) and genomic clones of the TmHKT8 gene were thus obtained using *T. monococcum* genomic DNA and root cDNA as templates. Additionally, a gene identical in nucleotide sequence was amplified from Line 149, consistent with the hypothesis that the salt tolerance gene had been introgressed into this line from *T. monococcum*. Full-length clones of the HKT8B1 gene were also obtained from *durum* cv. Tamaroi cDNA and genomic DNA (TtHKT8B1), and from *T. aestivum* cv. Chinese Spring genomic DNA (TaHKT8B1). In all cases, identity of the clones was confirmed by sequencing.

During the sequencing of clones derived from the TaHKT8B1 gene from cv. Chinese Spring, one clone was found that showed greater sequence similarity with the corresponding sequence of the TtHKT8B2 gene than with either TtHKT8B1 or TaHKT8B1. Using polymorphisms in the 5'- and 3'-UTRs of this clone, it was possible to design allele-specific forward and reverse primers flanking the entire coding region. The TaHKT8B2R01 primer (5'-AATATGTTCA-GATGGTTTTTG-3') ID NO: 52) was used to synthesise gene-specific cDNA containing only transcripts from HKT8B2 from total root RNA from *durum* wheat cv. Tamaroi and bread wheat cv. Halberd. The full-length coding region of the HKT8B2 gene was then amplified from this gene-specific cDNA. Interestingly, it was found that the majority of clones from both species corresponded to unspliced sequences, containing both introns common to the family. In the case of bread wheat, more than 90% of HKT8B2 clones corresponded to unspliced sequences, with only 3 of 92 clones representing fully spliced mRNA transcripts. It was not known whether these clones were derived from unspliced pre-mRNA transcripts, or from genomic DNA present as a contaminant in the RNA preparations and carried over in the cDNA synthesis reaction.

Of the approximately 90 clones sequenced from *durum* wheat, 32 represented correctly spliced mRNA transcripts and 54 represented unspliced transcripts/carry-over genomic DNA. In addition, however, 4 clones represented a different gene, most closely related to HKT8B2 but clearly distinct from it. This gene was most likely a pseudogene since it had a deletion of a substantial portion of conserved sequence in the middle of the gene, which was replaced by a relatively short sequence of no particular homology to known HKT genes. This insert shifted the reading frame which would have produced a truncated protein of about half the length compared to proteins from the other genes. This third gene from *durum* wheat has been designated TtHKT8B3.

Since the HKT8 EST sequence represented in the GenBank database (accession CK193616) matched the known partial sequence of a putative D-genome member of HKT8 from bread wheat, it was hypothesised that the 3'-UTR of this EST represented the 3'-UTR of the TaHKT8D gene. The HKT8Rev01 primer from this 3'-UTR region was specific for the D-genome gene, and this forming the basis for the polymorphism identified as described in Example 4. Therefore, this primer was used to synthesise gene-specific cDNA for the D-genome member from *T. aestivum* cv. Halberd total root RNA. This primer was then used in PCR together with three forward primers in an attempt to clone the 5'-UTR of the D-genome member cDNA. The primer combinations tested were as follows: TmHKT8FullFor01-HKT8Rev01; TtHKT8B1FullFor01m-HKT8Rev01; and TtHKT8B2FullFor03-HKT8Rev01. The Tm for the final 3-step cycling was lowered to 50° C. to facilitate binding of the forward primer in case there were a few mismatches in the priming site.

The primer combinations involving the TmHKT8FullFor01 and TtHKT8B1FullFor01m forward primers amplified a band of the right size, approximately 1700 bp, from the gene-specific cDNA. This band was gel-purified from each reaction and ligated into the pCR-XL vector (Invitrogen) according to the manufacturer's instructions. Ligation products were transformed into *E. coli* DH5α cells, and transformed cells selected on LB-Kanamycin agar. 72 single colonies of the TmHKT8FullFor01 reaction were picked, and insert PCR performed using M13 forward and reverse primers. Sequencing of these clones showed that all represented the same gene and covered the full coding region. This gene showed exact matches to the known EST corresponding to the partial TaHKT8D gene.

Thus, full-length sequences were obtained for one HKT8 gene from Line 149/*T. monococcum* corresponding to the salt-tolerance allele, 3 genes from *durum* wheat (predicted on the B genome, see below), and one from the D-genome of bread wheat. The number of amino acids in the predicted proteins were: TmHKT8, 517; TtHKTB1, 518; TtHKTB2, 514; TtHKT8B3, 415; TaHKT8D, 516, compared to OsHKT8, 554 amino acids.

The nucleotide and predicted protein sequences were compared and their relatedness determined by phylogenetic-tree analysis. An alignment of the amino acid sequences is shown in FIG. 17, whereas alignments for the nucleotides are provided in FIG. 18. Alignment of full-length protein and cDNA sequences showed that all of the genes were more closely related to the OsHKT8 gene than to the OsHKT7 or other genes in the HKT gene family (see FIG. 19). Interestingly, it was noticed that the position of the TtHKT8B1 sequence within the wheat HKT8 Glade differed depending on whether the phylogenetic tree was constructed with protein or cDNA coding sequence (FIG. 19). This indicated that there were more nucleotide variations within the TtHKT8B1 cDNA sequence that changed the amino acid sequence than expected, and that at least some of these changes were likely to be functionally significant.

This was supported by phylogenetic trees constructed using only synonymous (silent) or only non-synonymous (amino acid-altering) substitutions (FIG. 20). A tree constructed based only on synonymous substitutions (FIG. 20A) was topologically equivalent to the cDNA based tree shown in FIG. 19. This tree should theoretically reflect the time since the various sequences diverged, and indeed was found to be equivalent to trees based on non-coding (intron) sequences. In contrast, the tree constructed on non-synonymous substitutions (FIG. 20B) showed several notable changes in the branching. This tree suggested that the TtHKT8B2 gene retained the most similarity to the homoeologues from *T. monococcum* and the *T. aestivum* D-genome which are presumed to be functional. On the other hand, the TtHKT8B1 and TtHKT8B3 genes, which were more closely related to the TtHKT8B2 gene based on synonymous and non-coding substitution data, had more non-synonymous substitutions, with TtHKT8B3 (a presumed pseudogene, see above) the most divergent. This was consistent with the notion of a decrease in selection pressure on these genes or even a positive selection for divergence.

The identity, similarity and differences of wheat HKT8 protein sequences compared to OsHKT8 are provided in Table 11.

TABLE 11

Identity, similarity and differences of wheat HKT8 protein sequences compared to OsHKT8.

|  |  | TmHKT8 | TaHKT8D | TtHKT8B2 | TtHKT8B3 | TtHKT8B1 | OsHKT8 |
|---|---|---|---|---|---|---|---|
| TmHKT8 | Identity | 517 | 94% | 91% | 73% | 86% | 64% |
|  | Similarity | 0 | 97% | 94% | 75% | 92% | 75% |
|  | Differences | 0 | 0% | 0% | 20% | 1% | 7% |
| TaHKT8D | Identity | 490 | 516 | 92% | 74% | 87% | 64% |
|  | Similarity | 503 | 0 | 94% | 75% | 92% | 75% |
|  | Differences | 1 | 0 | 0% | 19% | 1% | 7% |
| TtHKT8B2 | Identity | 472 | 476 | 514 | 77% | 88% | 63% |
|  | Similarity | 487 | 488 | 0 | 77% | 92% | 73% |
|  | Differences | 5 | 4 | 0 | 19% | 2% | 8% |
| TtHKT8B3 | Identity | 379 | 383 | 398 | 415 | 71% | 50% |
|  | Similarity | 389 | 392 | 400 | 0 | 74% | 58% |
|  | Differences | 104 | 103 | 99 | 0 | 21% | 26% |
| TtHKT8B1 | Identity | 451 | 458 | 462 | 372 | 518 | 63% |
|  | Similarity | 481 | 482 | 483 | 391 | 0 | 75% |
|  | Differences | 9 | 8 | 12 | 111 | 0 | 7% |
| OsHKT8 | Identity | 362 | 360 | 355 | 279 | 355 | 554 |
|  | Similarity | 418 | 422 | 412 | 325 | 420 | 0 |
|  | Differences | 43 | 42 | 46 | 145 | 40 | 0 |

Example 7

Cloning of Genomic Sequences

As part of the cloning of full-length sequences from the various HKT8 alleles, clones were obtained corresponding to the genomic DNA from each allele. These clones were obtained using the same primers and amplification conditions as described in Example 6.

Allele-specific molecular markers can readily be designed based on polymorphisms in the genomic sequences, particularly the intron regions. Preferred markers are co-dominant markers based on size differences, i.e. where the PCR primers span deletions or insertions of one allele relative to another.

Example 8

Expression Studies on Wheat HKT8 Genes

In order to further examine the relationship between the *Triticum monococcum* homeologue of HKT8 and salt tolerance in *durum* wheat, expression studies comparing *durum* cultivars Tamaroi and 5049 were carried out. Initial attempts with a cDNA microarray suggested the expression level of the gene was at the lower detection limit of the scanner available, and reliable data could not be obtained. Studies were therefore carried out using quantitative real-time PCR (QPCR).

*Durum* wheat cv. Tamaroi and 5049 seeds were surface-sterilised and sown on moistened filter paper in 150 mm diameter plastic petri dishes. Seeds were stratified for 48 h. at 4° C. in the dark and then transferred to room temperature in the dark to germinate. Once the emerging coleoptile had reached a length of around 10 mm, seedlings were transplanted to a supported hydroponics medium consisting of well-washed ($Na^+$-free) quartz gravel, bathed every 20 min with a solution of modified half-strength Hoagland's #2 solution (3.25 mM $KNO_3$, 2.0 mM $Ca(NO_3)_2.4H_2O$, 50 µM $NH_4H_2PO_4$, 1.0 mM $MgSO_4.7H_2O$, 2.3 µM $H_3BO_3$, 0.25 µM $MnCl_2.4H_2O$, 0.1 µM $ZnSO_4.7H_2O$, 0.05 µM $(NH_4)_6Mo_7O_{24}.4H_2O$, 0.1 µM $CuSO_4.5H_2O$, 22.5µ $FeCl_3$, pH adjusted with KOH pellets). Prior to planting, gravel was washed repeatedly with $CaCl_2$ and de-ionised water to remove $Na^+$ contamination on the gravel surface until the conductivity of washes remained at 1-2 $\mu S \cdot cm^{-1}$, corresponding to a maximum $Na^+$ concentration of 20 µM, for 24 hours. Plants were grown in a controlled-environment cabinet illuminated by a mixed incandescent/halogen lamp system delivering a total fluence-rate of around 600 $\mu mol \cdot m^{-2} \cdot s^{-1}$ at soil level. Once leaf 3 had begun emerging (approximately 14 days after germination), half the tanks were treated with 75 mM NaCl supplemented with 3 mM $CaCl_2$ to compensate for the lower activity of $Ca^{2+}$ in the presence of $Na^+$.

Root material was harvested at the following timepoints after $Na^+$ treatment: 0 h (just before $Na^+$ treatment), 1 h, 2 h, 6 h, 24 h, 72 h, and 7d. Three replicate samples with 4 plants per sample were harvested for each genotype-timepoint-salt treatment combination. Total RNA was extracted using a modified phenol-chloroform extraction method as follows. Tissue was finely ground in a mortar and pestle under liquid nitrogen. Ground tissue was then mixed with an equal volume of phenol:chloroform:iso-amyl alcohol (24:24:1) and of NTES buffer (0.1M NaCl, 10 mM Tris pH 8.0, 1 mM EDTA, 1% SDS). This mixture was once again ground in the mortar and pestle until a homogenous suspension with a runny texture was produced. This suspension was kept on ice for 15 min, then centrifuged at maximum speed (5100 rpm in a Sigma 4K15C centrifuge with a #11150 rotor and #13350 sample holders) for 20 min. The upper (aqueous) phase was removed, and an equal volume of 4M LiCl/10 mM EDTA added. RNA was left to precipitate at −20° C. for 12-18 h. RNA was then pelleted by centrifuging at maximum speed (5100 rpm) for 45 min. The supernatant was removed, and the pellet washed with 1-5 mL of −20° C. 70% ethanol. The pellet was centrifuged again for 10 min at maximum speed, and resuspended in 360 µL DEPC-treated milliQ water. The first ethanol precipitation was performed by adding 40 µL 3M sodium acetate (NaOAc; pH 5.8) and 1 mL −20° C. 100% ethanol. The solution was vortexed and precipitated at −20° C. for a minimum of 2 hours. RNA was pelleted by centrifuging at maximum speed for 10 min at 4° C. The supernatant was removed and the pellet washed with 1 mL −20° C. 70% ethanol, centrifuging for 10 min at maximum speed. The supernatant was removed, and the pellet air-dried for 30 min. The pellet was then resuspended in 250 μL DEPC-treated water. A sub-optimal precipitation was performed to remove excess carbohydrate by adding 3.5 μL 3M NaOAc and 125 μL −20° C. 100% ethanol. The sample was vortexed, and centrifuged for 10 min at 4° C. The supernatant (containing the RNA) was removed to a separate tube, and precipitated with 21.5 μL 3M NaOAc and 375 μL −20° C. 100% ethanol. RNA was precipitated at −20° C. for 1 hour, and pelleted and washed as before. The pellet was resuspended in 40 μL DEPC-treated water and RNA quantified on a spectrophotometer.

For QPCR, 50 μg total RNA was treated with RQ1 DNase (Promega) according to the suppliers instructions. 25 μg of the DNase-treated total RNA was then reverse-transcribed using the SuperScript III reverse transcriptase (Invitrogen) and an oligo-dT$_{23}$V primer in a total volume of 40 μL. cDNA was diluted to a nominal concentration of 25 ng/μL. QPCR was performed by adding 4 μL of cDNA template (25 ng/μL) to 6 μL of a master mix containing Jumpstart 2×SYBR Green readymix (Sigma-Aldrich), water and primers in the recommended concentrations. Primers to amplify HKT8 were designed based on the consensus cDNA sequence of all 5 *T. monococcum*, *T. turgidum* ssp. *durum* and *T. aestivum* HKT8 homeologues. Primers used were HKT8cFor01 5'-CCTAC-CACCTTACACTACATT-3' (SEQ ID NO:57) and HKT8cRev01: 5'-TTTCCGTACGCACTGATAAC-3' (SEQ ID NO:58). These primers amplified a 240-bp fragment from the cDNA of all 5 homeologues, but failed to amplify a fragment from genomic DNA due to the reverse primer lying across the boundary of intron 2. There were no mutations between any homeologues within either priming site. QPCR was performed on a Corbett Research Rotor-Gene 2000 with the following cycling parameters: 95° C. 5 min; 55 cycles of 95° C. 30 s, 57° C. 20 s, 72° C. 25 s; 50° C. 5 min; 55° C.-95° C. holding 60 s on first step then 5 s on each remaining step, rising in 0.5° C. increments. Data was acquired after each 72° C. extension, and after each step in the melt determination. To correct for differences in loading of total RNA and efficiency of reverse-transcription, QPCR was also performed on wheat homologues of ACT1, At1g13320 and At4g34270 (Czechowski et al. 2005). Primers to amplify these are given in Table 12. Cycling conditions were as for HKT8. Each QPCR run contained both no-template (negative) controls and plasmid (positive) controls of known concentration. A minimum of 4 replicate reactions were done for each sample and control template. For analysis, an average was taken of all three reference genes relative to the first sample to give a loading control for each sample. The HKT8c value was then divided by this loading control to give the normalized level of expression. The HKT8c expression level was then averaged across the three biological replicates.

TABLE 12

Primers used in quantitative real-time PCR.

| Gene | Forward primer (5'-3') | Reverse primer (5'-3') | cDNA product length (bp) |
|---|---|---|---|
| ACT1 | TCAGCCGAGCGGGAAATTGT (SEQ ID NO: 59) | CCTCTCTGCGCCAATCGT (SEQ ID NO: 60) | 156 |
| At1G13320 | AGTTCTGCAGTCGCTTGTA (SEQ ID NO: 61) | GGCCTGGTTTGCATAGTATC (SEQ ID NO: 62) | 121 |
| At4g34270 | TCCTTACAGCGCGAGTGAG (SEQ ID NO: 63) | CAAGATTCGGGTCTGCGTAT (SEQ ID NO: 64) | 237 |

Expression studies thus carried out in the salt tolerant 5049 cultivar revealed a strong circadian-like regulation of HKT8 expression (FIG. 21). The 0 h timepoint was harvested approximately 4 hours after subjective dawn. The expression increased to 1 hour after salt treatment in both control and treated plants, followed by a decrease in expression at 2 hours from the peak, which continued out to 6 hours. By 24 hours (harvested at the same time of day as the 0 hour timepoint) the expression was comparable. A ratio of expression in treated and untreated plants showed an initial down-regulation of HKT8 expression after salt treatment, reaching a minimum after 2 hours, followed by a gradual recovery between 2 and 24 hours (FIG. 21C, D). This was followed by a gradual and prolonged trend towards increased expression in salt-treated plants that continued for at least 7 days (FIG. 21C, D). The expression profile of HKT8 in cv. Tamaroi was similar to that in 5049 (FIGS. 21A and B). The ratio of expression levels in salt treated vs. untreated cv. Tamaroi plants showed a similar initial down-regulation of expression following salt treatment, but this down-regulation showed a reduced duration compared to cv. 5049; in 5049 the down-regulation continued to a minimum after 2 hours and persisted through at least 6 hours, whereas in Tamaroi the minimum ratio was achieved after just 1 hour, and had recovered completely by 2 hours (FIG. 21E, F). The gradual increase in the expression ratio between salt stressed and unstressed plants was also seen in cv. Tamaroi, but in cv. Tamaroi plants this increase was much more rapid, reaching a maximum ratio of just over 2-fold higher expression in salt treated plants after only 72 hours of treatment 5049 plants, on the other hand, showed a much more gradual increase, not reaching the maximum ratio of just under 2-fold higher in salt treated plants until the 7-day timepoint (FIG. 21C, D).

Comparison of absolute levels of HKT8 expression in the cultivars Tamaroi and 5049 revealed that the salt tolerant cv. 5049 had a much higher level of HKT8 expression than the salt-sensitive cv. Tamaroi. At the 0-hour timepoint, HKT8 levels were 4.1-fold higher in the salt tolerant cultivar, with an absolute expression level of 70,000±7,000 copies/μg total RNA (mean±standard error) in cv. 5049 and 17,000±750 copies/μg total RNA in cv. Tamaroi (FIG. 22). This ratio was relatively constant irrespective of developmental stage (timepoint harvested), circadian patterns and salt treatment.

These results are consistent with the hypothesis that HKT8 is involved in salt stress responses in plants. Comparison of salt stressed and unstressed plants indicated an initial down-regulation of around 2-fold in salt stressed plants, which may have been due to initial osmotic stresses due to addition of 75 mM NaCl to the growth medium. Alternatively, this could be a mechanism to limit loading of $Na^+$ into the xylem stream in the case of a rapid and transient salt challenge. This was followed by a gradual up-regulation of expression to a maximum of around 2-fold higher in salt treated plants after prolonged salt stress. This indicated a role for HKT8 in adaptation responses by the plant to $Na^+$ stress. It was interesting to note that these changes were accelerated in cv. Tamaroi (salt-sensitive) plants. These plants accumulated $Na^+$ approximately twice as fast as cv. 5049 plants at the whole-plant level (Davenport et al. 2005). Therefore the accelerated progression of the expression profile and the somewhat higher expression ratio achieved in cv. Tamaroi could have been due to feedback from shoot material to the roots resulting in accelerated changes in HKT8 expression. The nature and mechanism of such feedback is currently unknown.

Aside from differences in the rate of progression, the expression profiles of HKT8 between the salt tolerant and salt sensitive cultivars were similar. Both showed evidence of a circadian-like regulation of expression, both showed an initial down-regulation after salt challenge, and both showed a long-term increase in expression under salt stress. However, the cultivars differed remarkably in the absolute level of HKT8 expression, with the salt tolerant cv. 5049 having 4.1× the level of HKT8 expressed even under control (unstressed) conditions. This expression difference was remarkably stable, being observed at every timepoint and condition tested. Analysis of melt curves and amplified clones suggested that the predominant homeologue expressed in cv. 5049 plants was the A-genome homeologue derived from *T. monococcum*. Therefore it appeared that that this homeologue had a higher basal level of expression than all of the B-genome homeologues combined, and that introgression of this gene from *T. monococcum* had therefore conferred a much higher level of HKT8 expression than was present in current commercial cultivars of *durum* wheat. Since the expression evidence presented suggested a role for HKT8 in plant responses to salt stress, and since the HKT genes are known to transport $Na^+$ and $K^+$ (e.g. Mäser et al 2002, Ren et al. 2005), it appears that a higher level of HKT8 expression enhanced the ability of plants to exclude $Na^+$ from aerial tissues and therefore increased the tolerance of plants to $Na^+$ stress. Therefore, differences in basal HKT8 expression alone or in combination with variations in the amino acid sequences relative to the A and B-genome HKT8 homeologues could explain the salt tolerance of cv. 5049.

Example 9

Constructs for Transgenic Expression of Wheat HKT8 Genes in Heterologous Species To further examine the function of HKT8, experiments were performed to express the coding region in heterologous species. Two model plant species were chosen for this purpose: the dicotyledonous plant *Arabidopsis thaliana* due to its ease of transformation and the monocotyledonous plant barley (*Hordeum vulgare*) which is more closely related to wheat and therefore was expected to respond similarly to wheat. Transformation systems for barley are routine, for example using *Agrobacterium*, and while barley was considered relatively salt-tolerant compared to wheat, it appeared to lack the $Na^+$-exclusion mechanism mediated by the Nax2 locus. These model plants could therefore be used to characterise the 5 identified HKT8 homologues from wheat and compare their function.

*Arabidopsis* expression constructs were produced based on the pART7 and pART27 vector systems (Gleave, 1992). The coding sequences of each homologue/homeologue including native translation start and termination codons were amplified from cDNA clones by PCR using primers in the 5'- and 3'-UTRs as described above. PCR products were cloned into standard cloning vectors such as pGEMT-easy and sequenced to identify clones free from PCR-induced errors. Gene inserts having error-free coding sequences were excised from the cloning vectors using flanking EcoRI restriction sites, and introduced into the EcoRI site within the multiple cloning region of the pART7 vector. In some cases both the cloning vector and pART7 carried ampicillin selectable markers and therefore the inserts were first cloned into a chloramphenicol-resistant version of pBluescript (Invitrogen). Once the coding regions were subcloned into pART7, the orientation of the insert relative to the promoter was determined via restriction digests and clones with the coding region in the forward (sense) orientation were identified. The 35S promoter-coding region-OCS terminator cassette was then excised with NotI and ligated into the NotI site in the multiple cloning region of the pART27 binary vector. The orientation of the insert was again determined with restriction digests, and clones with the cassette in the forward orientation were purified. These were used to transform *Agrobacterium* cells of the GV3101 strain via an electroporation method. Transformed cells were selected on LB-rifampicin-spectinomycin media and grown at 28° C. Several colonies were picked and cultured in liquid medium. To confirm that the correct plasmid had been introduced and that no rearrangements or deletions had occurred, plasmid DNA was extracted using standard protocols, transformed into *E. coli* and tested with restriction digests and sequencing to confirm the correct structures within the vector. *Agrobacterium* colonies thus identified were grown up and used for transformation. An example of a map of a pART27 binary vector used for overexpression is given in FIG. 23A.

*Arabidopsis* plants of the ecotype Columbia were used for transformation. Plants were grown under standard conditions until approximately 1 week after the first flower buds began to open. Transformation was carried out with via the floral dip method. $T_1$ seed thus produced was plated on MS-kanamycin medium to select transformants. PCR was performed on DNA extracted from tissue samples of these plants to confirm the presence of the HKT8 transgene and/or the $Kan^R$ selectable marker. $T_2$ seed was collected and sown to produce transgenic progeny which were used to assay $Na^+$ and $K^+$ uptake.

Barley transformation was carried out using the pWUbi-pVec8 vector system (Murray et al. 2004). Coding regions of the *T. monococcum* HKT8 and *T. turgidum* HKT8-B1 were excised with EcoRI and ligated into the EcoRI site of pWUbi as described previously for pART7. The expression cassette was then excised with NotI and ligated into the appropriate site of pVec8. Correctly oriented (sense) clones were electrotransformed into *Agrobacterium* strain AGL0, and colonies with plasmids of the correct structure identified as described above. An example of a map of a pVec8 binary vector driving the overexpression of the TmHKT8 gene under the control of the maize Ubiquitin promoter is given in FIG. 23B. Tissue culture and transformation was carried out using tissue from immature embryos of barley as described (Murray et al 2004) using hygromycin as the selection agent, based on the presence of a hygromycin resistance selectable marker gene on pVec8.

Arabidopsis and barley transformants were obtained. $Na^+$ and $K^+$ uptake was measured in Arabidopsis $T_2$ segregating families overexpressing the TmHKT8 and TtHKT8-B1 genes under the control of the 35S promoter. Under control conditions (soil-grown plants, no salt applied), 4 week old plants overexpressing both genes showed an increased $Na^+$ content in leaf 5 compared to wild-type plants of cv. Columbia (FIG. 24A), but there was no significant difference between the lines overexpressing the TmHKT8 and TtHKT8-B1 genes. After addition of 75 mM NaCl supplemented with 3 mM $CaCl_2$ to the growth medium for 24 hours, all lines showed an increase in the $Na^+$ content of the leaf Columbia and the TmHKT8 overexpressing lines accumulated approximately 25% more $Na^+$ than untreated plants, while lines overexpressing the TtHKT8-B1 gene accumulated approximately half the amount (13%) more $Na^+$. This preliminary data indicated that both genes encoded proteins having cation transporter activity and that there was a reduced rate of $Na^+$ flux through the TtHKT8-B1 transporter protein compared to the TmHKT8 protein.

As expected, wild-type cv. Columbia plants accumulated less $K^+$ in the presence of NaCl stress (FIG. 24B), consistent with previous work showing a negative correlation between $Na^+$ uptake and $K^+$ content. Lines overexpressing the TmHKT8 coding sequence showed a reduced $K^+$ content relative to Columbia under both control and NaCl-treated conditions, consistent with the slightly higher $Na^+$ content of these lines due to the transgene. In contrast, lines overexpressing the TtHKT8-B1 coding region showed a significant increase in total $K^+$ content even though they had a higher overall $Na^+$ content. This was seen under both control and salt-stressed conditions. This suggested the TtHKT8-B1 transporter may have altered cation selectivity relative to TmHKT8. The TmHKT8 transporter appeared to preferentially affect $Na^+$ uptake, with $K^+$ uptake being altered only as a consequence of the altered $Na^+$ content. The TtHKT8-B1 transporter on the other hand seemed to be conducting $K^+$ as well as, or instead of, $Na^+$, and indeed the increased $K^+$ content in NaCl-treated plants over the control could indicate $Na^+$—$K^+$ co-uptake by this transporter. This mechanism has been proposed for the unrelated (in terms of gene sequence) TaHKT1 gene in subfamily 2 of the HKT gene family (see Mäser et al. 2002; for phylogenetic relationships see Platten et al., 2006). Indeed, the endogenous B-genome homoeologues of HKT8 which were observed not to confer salt tolerance in wheat shared a particular polymorphism with various members of subfamily 2 that was not seen in any other known members of subfamily 1 (FIGS. 25 and 26). This polymorphism was located at the centre of the second pore loop domain, in a region that lay directly beside a residue in the first pore loop domain that has been shown previously to be a critical determinant of the $Na^+/K^+$ selectivity of the transporter (Mäser et al. 2002; for structural homologies see Durell and Guy 1999) (FIG. 27). There was therefore reason to expect a difference in transport properties between the TmHKT8 and TtHKT8-B1 proteins, and the latter might be expected to show characteristics more like members of subfamily 2 than subfamily 1.

A second notable polymorphism can be found at position 294 (FIGS. 26 and 28) where alleles of Nax2 genes which appear to confer enhanced tolerance to saline and/or sodic soils often encode an aspartic residue at this position whereas alleles that do not seem to confer this trait have other residues such as histidine, tyrosine or glycine. This may result in an inverted loop structure.

After continued growth in the presence of NaCl, some Arabidopsis transformants overexpressing the TtHKT8-B1 gene developed a chlorotic phenotype that was not observed in cv. Columbia or lines overexpressing the TmHKT8 gene. Many of these plants subsequently died prior to setting seed. While plants overexpressing the TtHKT8-B1 gene accumulated less $Na^+$ than TmHKT8-overexpressing lines 24 hours after treatment, the former lines apparently continued accumulating $Na^+$ to a final concentration that was higher than in the latter.

Overexpression of the wheat TmHKT8 gene (also known more recently as HKT1;5) in A. thaliana under the control of the strong, constitutive CaMV 35S promoter indicated that the homoeologue from Triticum monococcum caused an increase in $Na^+$ content in leaves of transgenic plants relative to null segregants and the wild-type parent, consistent with its role as encoding a cation transporter with ability to transport $Na^+$. Transgenic plants overexpressing the TtHKT8-B1 (TtHKT1;5-B1) and TtHKT8-B2 (TtHKT1;5-B2) genes, on the other hand, displayed little or no difference in $Na^+$ content relative to null segregants. However, they had significantly increased $K^+$ content in their leaves. This suggested that the B-genome homoeologues from wheat had switched their ion selectivity or preference from $Na^+$ to $K^+$, and therefore had reduced ability to exclude $Na^+$ ions from leaves. The $A^m$-genome homoeologue on the other hand seemed to retain the (probably ancestral) $Na^+$ transport function, and therefore could still confer the $Na^+$ exclusion phenotype seen in the Nax2[+] lines.

Example 10

HKT8 is a Candidate Gene for the Kna1 Locus in Bread Wheat

Durum wheat is more sensitive than bread wheat to salinity, probably because it lacks the D genome and the Kna1 locus. Bread wheat is a moderately salt tolerant crop. It has low $Na^+$ accumulation and the "enhanced $K^+/Na^+$ discrimination trait" on chromosome 4D (Gorham et al. 1990). The locus, named Kna1, has been shown to improve the salt tolerance of durum wheat by homoeologous transfer, and has been mapped to the distal end of chromosome 4DL (Dubcovsky et al. 1996).

The durum Line 149 had very low rates of $Na^+$ accumulation in the leaf blade and maintained a high rate of $K^+$ accumulation, with consequent high $K^+/Na^+$ discrimination. Line 149 had a $K^+/Na^+$ ratio of 17 whereas the durum cultivars Wollaroi, Tamaroi and Langdon had $K^+/Na^+$ ratios of 1.5, 0.7 and 0.4 respectively (Munns et al. 2000). The bread wheat cultivars Janz and Machete had $K^+/Na^+$ ratios of 10 and 8 respectively (Munn et al. 2000).

In contrast to the Nax1 gene, the Nax2 locus was found to confer a similar phenotype to the Kna1 locus, as described in Example 3. This included low rates of transport of $Na^+$ to the shoot in both leaf blade and leaf sheath, high rates of transport of $K^+$ to the shoot, and consequently high ratios of $K^+/Na^+$ in the shoot. Nax2 has been mapped to the distal region of chromosome 5A (Example 5). This region is homoeologous to the distal region of chromosome 4D to which Kna1 has been mapped (Dubcovsky et al. 1996). We considered the possibility that Nax2 was homoeologous to Kna1 and that HKT8 was a candidate gene for Kna1.

Seeds of the Chinese Spring lines carrying deletions on chromosome arm 4DL (Endo and Gill, 1996) were germinated in "salt tanks" and exposed to 50 mM NaCl as described in previous examples, and the $Na^+$ and $K^+$ concentration in the blade of leaf 3 was measured after 10 d (Table 13). DNA was extracted. The location of genes for $Na^+$ exclusion and enhanced $K^+/Na^+$ discrimination in Chinese Spring were clearly confined to the most distal deletion bin, that is, on the distal 14% of the chromosome arm, as the character was not present on the remaining 86%. Likewise, the HKT8 probe (prepared as described in Example 5) identified the presence of a gene in the D genome of Chinese Spring, located on the distal 14% of chromosome 4. Thus, the HKT8 probe identified a gene in the same chromosomal region as Kna1 (FIG. 29). It was concluded from this observation and the similarity of the phenotypes conferred by Nax2 and Kna1 that the D genome member of the HKT8 family was a likely candidate gene for Kna1.

Example 11

Crossing of Sodium-Exclusion Allele of Nax2 into Hexaploid Wheat

The sodium exclusion alleles of Nax1 and Nax2 from landrace Line 149 were introduced into representative hexaploid wheat varieties by backcrossing. The hexaploid varieties were chosen as representative of the genetic backgrounds of bread wheats currently grown across the Australian wheat belt. Bread wheats generally have lower $Na^+$ uptake than *durum* wheats and therefore have superior salt tolerance. However, there is about a 2-fold variation in $Na^+$ uptake in varieties of bread wheat, which was also represented in the varieties used. Nax1 (on chromosome 2A) conferring salt tolerance was introduced into bread wheat because the genes controlling the retention of $Na^+$ in the leaf sheath were previously lacking in bread wheat. The presence of this gene may be particularly important where salinity is associated with waterlogging or any soil abiotic/biotic stress that impairs root function. Nax2 (on chromosome 5A) was also introduced to test its effect in bread wheat, even though a salt tolerance gene with similar mechanism was already known to exist in many varieties of bread wheat, Kna1 (on chromosome 4D—Dvorak et al. 1994).

TABLE 13

Salt concentrations in blade of leaf 3 of Chinese Spring chromosome 4DL deletion lines.

| Deletion[a] | Name | Na ($\mu$mol $gDW^{-1}$) | K ($\mu$mol $gDW^{-1}$) | K/Na | HKT8[b] |
| --- | --- | --- | --- | --- | --- |
| 1.00 | Chinese Spring | 172 | 1250 | 7.5 | + |
| 0.86 | 4DL-14 | 632 | 972 | 1.6 | − |
| 0.71 | 4DL-12 | 846 | 897 | 1.1 | − |
| 0.70 | 4DL-2 | 795 | 889 | 1.1 | − |
| 0.61 | 4DL-11 | 771 | 867 | 1.1 | − |
| 0.56 | 4DL-13 | 815 | 751 | 0.9 | − |
| 0.53 | 4DL-8 | 736 | 793 | 1.1 | − |
| 0.46 | 4DL-1 | 853 | 840 | 1.0 | − |
| 0.41 | 4DL-7 | 776 | 828 | 1.1 | − |
| 0.38 | 4DL-6 | 746 | 789 | 1.1 | − |
| 0.31 | 4DL-9 | 814 | 739 | 0.9 | − |
| 0.09 | 4DL-5 | 836 | 723 | 0.9 | − |

[a]indicates the percentage of 4DL remaining in each deletion line.
[b](+), presence of D genome member of HKT8; (−), absence of D genome member of HKT8.

Initial crosses were made between the hexaploid cultivars Chara, Camm, Carnamah and Westonia and the tetraploid line P01819 (CSIRO Plant Industry, seed catalogue no. P01819) which was a backcrossed ($BC_1F_3$) selection having a low $Na^+$ phenotype identical to that of Line 149 and known to contain both $Na^+$ exclusion genes. $F_1$ pentaploids from one of these direct crosses (P02901) were backcrossed with Westonia (male) to produce $BC_1F_1$ plants, and the progeny then selfed.

The $BC_1F_2$ seedlings were screened for the presence of the $Na^+$ exclusion allele from the tetraploid parent using the Xgwm312 marker. Initially, the Xgwm312 primers as described in WO2005/120214 were used in the PCR reactions together with analysis on high percentage agarose gels with long run times. Under these conditions, subtle shifts in band position of the PCR products were observed, allowing us to distinguish homozygous material with a reasonable degree of certainty. Later, more robust analyses including those in the Westonia background were performed using the Xgwm31 mod primers as described in WO2005/120214.

Three positive lines were identified and selected from two $BC_1F_2$ populations (P03980 & P03982). These were selfed to produce $BC_1F_3$ seed. Ears of all 3 selections were determined not to be pentaploid due to full ear fertility and hexaploid status. This was confirmed using a D-genome specific marker (D-gas). These hexaploid $BC_1F_3$ selections containing the tetraploid $Na^+$ exclusion allele were backcrossed again into Westonia and also top-crossed with the hexaploid cultivars Sunstate, Carnamah and Chara. Further backcross/topcrosses were completed without selection using $BC_2F_1$ plants, and additional top crosses performed into the hexaploid cultivars Janz and Yitpi. $BC_3F_2$ populations of these crosses were screened using the Xgwm312 marker and selections made, thus generating $BC_3F_3$ homozygous families containing the tetraploid $Na^+$ exclusion allele in 6 different hexaploid backgrounds.

The homozygous lines are tested in both greenhouse and field trials under saline and non-saline conditions for Na accumulation in leaf and grain, growth rate, biomass accumulation and grain yield. For example, $Na^+$ uptake in cultivars was substantially decreased in the presence of the Na exclusion alleles from the tetraploid parent, and associated with improved salt tolerance and yield. When $Na^+$ concentration was measured in leaf 3 after 10 days growth of the plants in the hydroponic system in medium containing 50 mM NaCl (Example 1), the following average data was obtained:

| [+]Nax1 families: | 110 $\mu$mol $gDW^{-1}$ |
| --- | --- |
| [−]Nax1 families: | 161 $\mu$mol $gDW^{-1}$ |
| Westonia: | 195 $\mu$mol $gDW^{-1}$ |

Partitioning of $Na^+$ between leaf sheath and leaf blade in leaf 2 after 10 d in 50 mM NaCl was determined, giving the following average sheath:blade ratios:

| [+]Nax1 families: | 3.50 ± 0.10 |
| --- | --- |
| [−]Nax1 families: | 2.14 ± 0.10 |
| Westonia: | 2.06 ± 0.14 |

Lines known to lack Nax1 as confirmed with the Xgwm312 marker were tested for the presence or absence of the $Na^+$ excluding allele of Nax2 using the HKT8 marker as described in Example 4. Measurement of $Na^+$ concentration ($\mu$mol $g^{-1}$ DW) in the blade of leaf 3 after 10 d in 50 mM NaCl revealed a significant reduction of $Na^+$ accumulation in lines containing Nax2:

| [+Nax2], | 149 ± 6 µmol gDW$^{-1}$ |
| [−Nax2], | 173 ± 13 µmol gDW$^{-1}$ |
| Westonia, | 195 ± 16 µmol gDW$^{-1}$ |

This result was surprising considering the presence of Kna1 which already functions to provide salt tolerance in bread wheat, and indicated that further improvement could be obtained by the presence of the salt tolerance Nax2 allele from Line 149.

Example 12

HKT8 Homologs from the D Genome of the Diploid Progenitor and Allohexaploid of Common Wheat (*Triticum aestivum*)

As described in Example 10, chromosome deletion series of wheat 4D placed the Kna1 locus on the most distal deletion bin of the long arm of wheat chromosome 4D. In bread wheat, homologs of the HKT8 gene family were located on homoeologous group 4 chromosomes, in particular 4B and 4D. While three HKT8 members were present in 4B, there was only one gene member present in the D genome. The HKT8 D genome member was located in the same 4DL deletion bin as the Kna1 locus. Therefore, full length genomic and cDNA clones were isolated from the wheat cv. Chinese Spring. Equivalent genes were also isolated from a BAC clone of the *Aegilops tauschii* accession, AUS 18913 (diploid D genome progenitor) and directly from two other *Ae. tauschii* genotypes (accessions CPI 110664 and AUS18905). The amino acid sequences of the proteins encoded by these HKT8 D genome members were deduced from the nucleotide sequences of the clones.

Sequence alignment/comparisons (FIGS. 30 and 31) revealed that the proteins encoded by the HKT8 gene members in the diploid *Ae. tauschii* were essentially identical, with at most 1-2 amino acid substitutions, compared to that of the D genome of Chinese Spring.

Experiments with reconstituted wheat ("synthetic wheat") which involved the production of allohexaploids derived from crosses between tetraploid wheat (*Triticum turgidum*) and *Ae tauschii* (Schachtman et al. 1992) showed that levels of sodium ion accumulation were the same as levels found in common hexaploid wheat. It was concluded that the introduction of the Kna1 gene from *Ae. tauschii* in the crosses with tetraploid wheat produced synthetic hexaploids with essentially the same salt tolerance characteristics as bread wheat.

A rice homolog, Os01g20160, of HKT8 located on rice chromosome 1, also referred to as SKC1, has been shown to control sodium exclusion. Overall the deduced protein of SKC1 was 66% identical (75% similar) in amino acid sequence compared to the HKT8 D genome encoded proteins. The nucleotide sequences of the coding regions of the cDNAs from the D genome were 84% identical to the rice Os01g20160 gene.

Example 13

Role of HKT8 (HKT1;5) Homologues in *Hordeum* Species

Cultivated barley (*Hordeum vulgare*) is known to lack the Na$^+$ exclusion mechanisms seen in salt-tolerant *durum* wheat that are mediated by the Nax1 (HKT7, also designated HKT1;4) and Nax2 (HKT8, also designated HKT1;5) loci/genes. However, a screen of several wild *Hordeum* species showed that most of these had active Na$^+$ exclusion mechanisms (Garthwaite et al. 2005).

The *Hordeum vulgare* HKT1;5 gene was cloned from a BAC library derived from the cultivar Morex using probes made from TmHKT8 and hybridization under high stringency conditions. Primers designed to amplify the gene showed that this gene was not expressed, at least in the cultivar Golden Promise, with no spliced cDNA clones being amplified from root tissue by RT-PCR. In addition, the coding sequence of the gene contained a number of unusual substitutions including ones in the pore residues of the first MPM domain.

Primers to highly conserved regions of the gene from wheat and barley were used to amplify the majority of the coding sequence of the HKT1;5 gene from several wild *Hordeum* species. The primers used were: Forward: TTTCCATGTGCACCCGTTCTG-3' (SEQ ID NO:74), Reverse: 5'-CTTGAGCCTGCCGTAGAACATGAC-3' (SEQ ID NO:75). PCR conditions were: 95° C. for 6 min; 11 cycles of 95° C. for 1 min, 72° C. for 1 min decreasing 1° per cycle, 72° C. for 3 min 30 sec; followed by 40 cycles of 95° C. for 45 sec, 61° C. for 30 sec, 72° C. for 3 sec; 72° C. for 10 min.

This revealed that a full-length HKT1;5 gene was present and expressed in most of the wild species, with the exception of *H. patagonicum* ssp. *santacrucense*, which had a large deletion in the middle of the gene. In the latter case, the gene was expressed, suggesting that this deletion is a relatively recent occurrence and the gene has not yet fully devolved into a pseudogene. In addition, *H. murinum* ssp. *glaucum* had several unusual sequence polymorphisms shared with *H. vulgare*, though unlike the latter species the gene was expressed. Comparison with the Na$^+$ exclusion results in Garthwaite et al. (2005) showed that of the species examined, *H. murinum* ssp. *glaucum* showed Na$^+$ exclusion ability that was little better than *H. vulgare* at high concentrations of NaCl in the growth medium. In addition, *H. patagonicum* ssp. *santacrucense* displayed a higher percentage of dead leaf matter and somewhat higher leaf Na$^+$ concentrations than other wild species at both intermediate and high Na$^+$ concentrations. This therefore fitted well with the observed variation in the HKT1;5 homologues.

Sequencing of a partial HKT1;5 gene from 16 barley cultivars, amplified using the same primers used on wild *Hordeum* species, revealed 3 distinct groups of alleles. Pairwise comparisons of nucleotides and predicted amino acid sequences with the wheat genes are provided in Table 14, showing that the *Hordeum* HKT8 proteins were 72-90% identical in their amino acid sequences to TmHKT8. The most common allele was present in 10 of the 16 cultivars (Golden Promise, Incheon Naked, Harrington, Chebec, ChameII, Bohemian, Sloop, Sik and Olli). Allele 2 was found in Halcyon, Igri and Sonya, while allele 3 (the most divergent of the 3) was found in Tongeon Covered, Morex and Steptoe. Restriction polymorphisms (defined by the presence or absence of restriction enzyme sites) can be identified between the 3 alleles, such as those summarised in Table 15. Any of the polymorphisms between the genes, preferably restriction polymorphisms, can be used to track these alleles in crosses between barley cultivars, e.g. for mapping and breeding purposes.

Example 14

Field Trials on *Durum* and Hexaploid Wheat Containing Nax2

No Yield Penalty of Nax2 Under Non-Saline Field Conditions

To determine the field performance of both *durum* and hexaploid wheat lines containing Nax2, BC$_5$F$_4$ *durum* seed for lines that were homozygous for Nax2, from the cross between Line 149 and Tamaroi, were sown at Ginninderra Experimental Station (GES). Similarly, Westonia (hexaploid) $BC_3F_4$ seed for plants that were homozygous for Nax2 were sown at the same location. Recurrent parents, Tamaroi and Westonia were also sown for a yield comparison with a line lacking Nax2. Soils at GES were of low salinity and therefore this trial was used to assess the yield potential of lines containing Nax2.

The field plots were harvested and grain yield was measured. Yield data was summarised in Table 16. The yield of the *durum* $BC_5F_4$ lines which contained Nax2 was on average not different to recurrent parent Tamaroi. Mean yield (t/ha) for the Nax2 containing lines was 3.56 compared to 3.67 for Tamaroi, with the small decrease in yield of the Nax2 lines (0.11 t/ha) not significantly different from Tamaroi. Likewise, the yield potential of the bread wheat cultivar Westonia was unaffected by the presence of Nax2. Mean yield of the Westonia $BC_3F_4$ lines containing Nax2 was 4.52 t/ha compared to 4.34 t/ha for Westonia. From this it was concluded that Nax2 does not carry a yield penalty in non-saline conditions.

TABLE 14

Pairwise comparisons of *Hordeum* and wheat HKT8 genes.

Protein sequences, pairwise percent identity or similarity

| | | TaHKT8-D | TmHKT8 | TtHKT8-B1 | TtHKT8-B2 | TtHKT8-B3* | HvHKT8-Chebec |
|---|---|---|---|---|---|---|---|
| TaHKT8-D | Identity | 100% | 94% | 88% | 92% | 71% | 82% |
| | Similarity | 100% | 96% | 92% | 94% | 73% | 87% |
| TmHKT8 | Identity | | 100% | 87% | 91% | 71% | 82% |
| | Similarity | | 100% | 91% | 94% | 73% | 86% |
| TtHKT8-B1 | Identity | | | 100% | 89% | 69% | 81% |
| | Similarity | | | 100% | 92% | 72% | 87% |
| TtHKT8-B2 | Identity | | | | 100% | 74% | 82% |
| | Similarity | | | | 100% | 75% | 87% |
| TtHKT8-B3 | Identity | | | | | 100% | 62% |
| | Similarity | | | | | 100% | 66% |

| | | HvHKT8-Olli | HvHKT8-Sik | HvHKT8-Harrington | HvHKT8-incheon Naked | HvHKT8-Chamell | HvHKT8-Sloop |
|---|---|---|---|---|---|---|---|
| TaHKT8-D | Identity | 81% | 80% | 83% | 85% | 85% | 83% |
| | Similarity | 86% | 85% | 88% | 90% | 90% | 88% |
| TmHKT8 | Identity | 81% | 80% | 83% | 85% | 85% | 83% |
| | Similarity | 85% | 85% | 87% | 90% | 89% | 87% |
| TtHKT8-B1 | Identity | 80% | 79% | 82% | 84% | 83% | 82% |
| | Similarity | 85% | 85% | 88% | 90% | 89% | 87% |
| TtHKT8-B2 | Identity | 81% | 80% | 83% | 85% | 85% | 83% |
| | Similarity | 86% | 85% | 88% | 90% | 90% | 88% |
| TtHKT8-B3 | Identity | 61% | 60% | 63% | 65% | 64% | 63% |
| | Similarity | 65% | 64% | 67% | 69% | 69% | 67% |

| | | HvHKT8-Sonya | HvHKT8-Mor | HvHKT8-Steptoe | HvHKT8-Tongeon covered | H-int-HKT8 | H-mar-guss-HKT8-A |
|---|---|---|---|---|---|---|---|
| TaHKT8-D | Identity | 85% | 85% | 85% | 72% | 85% | 85% |
| | Similarity | 90% | 90% | 90% | 77% | 89% | 90% |
| TmHKT8 | Identity | 85% | 84% | 84% | 72% | 84% | 84% |
| | Similarity | 90% | 90% | 90% | 76% | 88% | 89% |
| TtHKT8-B1 | Identity | 83% | 83% | 83% | 71% | 84% | 83% |
| | Similarity | 89% | 89% | 89% | 77% | 89% | 89% |
| TtHKT8-B2 | Identity | 85% | 85% | 85% | 72% | 84% | 84% |
| | Similarity | 90% | 90% | 90% | 77% | 89% | 90% |
| TtHKT8-B3 | Identity | 64% | 64% | 64% | 52% | 64% | 64% |
| | Similarity | 69% | 69% | 69% | 56% | 68% | 69% |

| | | HvHKT8-Bohemian | HvHKT8-GP | H-mar-guss-HKT8-B | H-mur-gl-HKT8 | H-mar-guss-HKT8-B | H-mur-gl-HKT8 |
|---|---|---|---|---|---|---|---|
| TaHKT8-D | Identity | 85% | 85% | 84% | 90% | 84% | 90% |
| | Similarity | 90% | 90% | 89% | 94% | 89% | 94% |
| TmHKT8 | Identity | 85% | 85% | 84% | 89% | 84% | 89% |
| | Similarity | 90% | 90% | 89% | 94% | 89% | 94% |
| TtHKT8-B1 | Identity | 84% | 84% | 83% | 83% | 83% | 83% |
| | Similarity | 90% | 90% | 89% | 90% | 89% | 90% |
| TtHKT8-B2 | Identity | 85% | 85% | 84% | 88% | 84% | 88% |
| | Similarity | 90% | 90% | 89% | 93% | 89% | 93% |
| TtHKT8-B3 | Identity | 65% | 65% | 64% | 68% | 64% | 68% |
| | Similarity | 69% | 69% | 69% | 72% | 69% | 72% |

TABLE 14-continued

Pairwise comparisons of *Hordeum* and wheat HKT8 genes.

Nucleotide coding sequence identity: pairwise percent identity

|  | TaHKT8-D | TmHKT8 | TtHKT8-B1 | TtHKT8-B2 | TtHKT8-B3* | HvHKT8-Chebec |
|---|---|---|---|---|---|---|
| TaHKT8-D | 100% | 95% | 90% | 93% | 74% | 74% |
| TmHKT8 |  | 100% | 89% | 92% | 73% | 73% |
| TtHKT8-B1 |  |  | 100% | 91% | 72% | 73% |
| TtHKT8-B2 |  |  |  | 100% | 76% | 74% |
| TtHKT8-B3 |  |  |  |  | 100% | 57% |

|  | HvHKT8-Olli | HvHKT8-Sik | HvHKT8-Harrington | HvHKT8-Incheon Naked | HvHKT8-Chamell | HvHKT8-Sloop |
|---|---|---|---|---|---|---|
| TaHKT8-D | 72% | 72% | 74% | 76% | 76% | 74% |
| TmHKT8 | 72% | 72% | 74% | 76% | 76% | 74% |
| TtHKT8-B1 | 72% | 71% | 74% | 76% | 75% | 74% |
| TtHKT8-B2 | 72% | 72% | 74% | 76% | 76% | 74% |
| TtHKT8-B3 | 56% | 55% | 58% | 60% | 59% | 58% |

|  | HvHKT8-Sonya | HvHKT8-Mor | HvHKT8-Steptoe | HvHKT8-Tongeon covered | H-int-HKT8 | H-mar-guss-HKT8-A |
|---|---|---|---|---|---|---|
| TaHKT8-D | 76% | 77% | 77% | 69% | 87% | 86% |
| TmHKT8 | 76% | 77% | 77% | 69% | 86% | 86% |
| TtHKT8-B1 | 75% | 77% | 77% | 69% | 87% | 86% |
| TtHKT8-B2 | 76% | 77% | 77% | 69% | 86% | 86% |
| TtHKT8-B3 | 60% | 60% | 60% | 52% | 68% | 68% |

|  | HvHKT8-Bohemian | HvHKT8-GP | HvHKT8-Halcyon | HvHKT8-Igri | H-mar-guss-HKT8-B | H-mur-gl-HKT8 |
|---|---|---|---|---|---|---|
| TaHKT8-D | 76% | 76% | 74% | 74% | 86% | 91% |
| TmHKT8 | 76% | 76% | 74% | 74% | 86% | 91% |
| TtHKT8-B1 | 76% | 76% | 73% | 73% | 86% | 87% |
| TtHKT8-B2 | 76% | 76% | 74% | 74% | 86% | 91% |
| TtHKT8-B3 | 60% | 60% | 58% | 57% | 68% | 72% |

*TtHKT8-B3 is a pseudogene, the sequence of which has not been provided.

TABLE 15

Restriction polymorphisms identified between HvHKT1; 5 alleles.

| Enzyme | Recognition site | Allele 1 # cuts | Allele 2 # cuts | Allele 3 # cuts |
|---|---|---|---|---|
| AloI | |N$_5$|N$_7$GAACN$_6$TCC (SEQ ID NO: 160) | 1 (376) | 0 | 1 (376) |
| BaeI | |N$_5$|N$_{10}$ACNNNNGTAYC (SEQ ID NO: 161) | 1 (1396) | 1 (1396) | 0 |
| BbvCI | CC|TCA|GC | 0 | 0 | 1 (1281) |
| BcgI | |NN|N$_{10}$CGANNNNNNTGC (SEQ ID NO: 162) | 2 (317, 484) | 2 (317, 484) | 0 |
| Bpu10I | CC|TNA|GC | 1 (476) | 1 (476) | 2 (476, 1281) |
| BsaXI | |NNN|N$_9$ACNNNNNCTCC (SEQ ID NO: 163) | 0 | 2 (143, 521) | 0 |
| BsmAI | GTCTCN|NNNN| (SEQ ID NO: 164) | 2 (559, 1235) | 2 (559, 1235) | 0 |
| BstNI | CC|W|GG | 2 (400, 446) | 2 (400, 446) | 1 (400) |
| PpiI | |N$_5$|N$_7$GAACNNNNNCTC (SEQ ID NO: 165) | 1 (376) | 0 | 1 (376) |
| PspGI | |CCWGG| | 2 (398, 444) | 2 (398, 444) | 1 (398) |
| PstI | C|TGCA|G | 2 (1089, 1475) | 2 (1089, 1475) | 1 (1089) |
| SfcI | C|TRYA|G | 2 (1085, 1471) | 2 (1085, 1471) | 1 (1085) |
| TatI | W|GTAC|W | 2 (210, 1391) | 2 (210, 1391) | 1 (210) |
| Tsp509I | |AATT| | 1 (1453) | 1 (1320) | 2 (1316, 1320) |

TABLE 16

Yield of durum wheat and hexaploid wheat with Nax2 grown at Ginninderra Experimental Station (GES), ACT. Contrasts are supplied for comparison of the mean difference in yield between Nax2 lines and recurrent parent.

| Wheat type | Genotype | No. | Mean yield (t/ha) | Contrast estimate (t/ha) | Contrast LSD |
|---|---|---|---|---|---|
| Durum wheat | Tamaroi | | 3.67 | | |
| | [+] Nax2 BC$_5$F$_4$ lines | (n = 19) | 3.56 | −0.11$^{ns}$ | 0.24 |
| Bread wheat | Westonia | | 4.34 | | |
| | [+] Nax2 BC$_3$F$_4$ lines | (n = 4) | 4.52 | 0.18$^{ns}$ | 0.41 |

Yield Advantage of Nax2 Under Saline Conditions

To determine the impact of Nax2 on yield at saline sites, initial trials of two *durum* Nax2 lines (5004, 5042, BC$_4$F$_5$ Tamaroi background) included in a range of *durum* breeding lines containing Nax1, were conducted at a moderately saline field site (Two Wells) in South Australia. Lines 5004 and 5042 were ranked 1$^{st}$ and 2$^{nd}$ in yield of all the lines included in the trial, yielding about 30-60% more than Tamaroi.

Further field trials on these *durum* Nax2 lines were also carried out at sites with saline soils. Comparisons for yield at 8 saline sites ranging from moderate yielding (3.2 t/ha) low salinity sites (e.g. Winulta) to low yielding (0.6 t/ha) high salinity sites (e.g. Port Pine), showed that the presence of Nax2 provided a yield benefit with increasing soil salinity (FIG. 32). Nax2 lines yielded similarly to recurrent parent Tamaroi at the moderately yielding sites, but there was a strong trend towards higher yields relative to Tamaroi, at the lower yielding, more saline sites. At three of these sites (Buckleboo, Pt Pine & Red Hill), Nax2 lines had yields that were between 18-30% greater than Tamaroi. It was concluded that Nax2 provides a significant yield advantage to *durum* wheat under moderate to high salinities. Nax2 will therefore provide similar yield advantages for hexaploid wheat grown under moderate to highly saline conditions.

Example 15

Silencing Kna1 (TaHKT8-D) in Wheat

The Kna1 gene confers on hexaploid wheat a phenotype of low leaf Na$^+$ and a high leaf K$^+$ to Na$^+$ ratio. Langdon substitution lines with and without the Kna1 region were different in their leaf K$^+$ to Na$^+$ ratio (Dvorak and Gorham, 1992). Plants with Kna1 had leaf K$^+$ to Na$^+$ ratios six to eight times higher than those without Kna1 (Gorham et al., 1987; Gorham et al., 1990).

As shown in Example 10, Kna1 and the TaHKT8-D gene were co-located to the distal end of chromosome 4DL on the D genome of breadwheat, and TaHKT8-D was therefore a strong candidate gene for Kna1. Loss of the region containing TaHKT8-D in Chinese Spring deletion lines corresponded to an increase in average Na$^+$ concentrations in the leaf blade and a six fold decrease in the K$^+$ to Na$^+$ ratio from 7.5 to 1.2.

To test whether reduction of the expression of TaHKT8-D (corresponding to Accession No. DQ646342) by post-transcriptional gene silencing of its mRNA resulted in loss of the Kna1 phenotype, two RNA interference (duplex RNA) constructs designed to reduce the expression of TaHKT8-D were made and introduced into bread wheat (cv. Bob White). The fragments of TaHKT8-D used in the constructs were amplified by PCR under standard conditions. Fragment 1 consisted of 600 basepairs corresponded to nucleotides 1121-1702 of SEQ ID NO: 24 with an additional 18 nucleotides 3', while fragment 2 of 559 bp corresponded to nucleotides 1135-1693 of SEQ ID NO: 24. Both fragments included the region at the 3' end of the cDNA, in the region where the D allele was least similar to the B genome alleles. However, because of the high degree of identity even in this region, it was expected that the B genome alleles will also be down-regulated to some extent in the transgenic wheat plants.

Fragments 1 and 2 were ligated individually into pENTR-D-TOPO (Invitrogen) as per the manufacturers' instructions, and transformed into *E. coli*. Purified plasmid pENTR-D-TOPO DNA containing each of the fragments was sequenced to confirm the insert, and then used in a Gateway Recombinase reaction as per the manufacturers instructions to transfer the insert into Gateway-enabled pSTARGATE (provided by Dr Peter Waterhouse, CSIRO Plant Industry, Can berra, Australia). In both cases, this resulted in the insertion of two copies of the insert, one in sense orientation and the other in antisense orientation, under the control of a single Ubi1 promoter. When transcribed from the promoter, the chimeric DNA constructs will express a self-complementary RNA where the sense and antisense sequences can hybridize to form a hairpin RNA having a 600 bp, or 559 bp, respectively, duplex region. Plasmid DNA of pSTARGATE with each of the fragments present was purified, referred to as pSTARGATE RNA insert 1 and pSTARGATE RNA insert 2.

Plasmid DNA of pSTARGATE RNA insert 1, pSTARGATE RNA insert 2 or pSTARGATE without inserts were co-bombarded with a marker gene construct (pNEO1 plasmid DNA with the NPTII gene) into immature wheat (cv. Bob White) embryos when the embryos are about 1 mm in length via biolistics techniques according to Pellegrineschi et al. (2002). After bombardment, actively growing calli from the embryos were transferred every 2½ weeks onto fresh regeneration medium and those that survived and grew on regeneration medium containing Geneticin (50 µg/L) as selective agent (to select for cells transformed with the NPTII selectable marker gene) were maintained until roots had grown and 3 or 4 leaves had grown. Healthy green plants were then transferred to soil mixture in peat cups in a mist chamber and then at leaf 5 or 6 stage transferred in pots and grown to maturity.

T$_1$ seed from these plants will be used in an experiment to test whether the mRNA transcript levels of TaHKT8-D are significantly reduced and whether there is a difference in leaf Na$^+$ concentration between plants that contain each of the RNA interference constructs and those in which the RNA interference construct has segregated away.

Example 16

Heterologous Expression of HKT8

The TaHKT8-D full protein coding sequence used for heterologous expression experiments was amplified from pBLUESCRIPT which had the coding sequence as an insert. The full cDNA insert was isolated from a Chinese Spring cDNA library as follows. The library was constructed using mRNA isolated and purified from drought stressed root tissue at full tillering. Approximately 120 000 clones of the mass excised phagemid library were plated and screened with the partial TmHKT8 probe (Byrt et al., 2007) according to standard protocols (Sambrook, 1989). Eleven colonies hybridised to the probe. These were grown at 37° C. overnight in Luria broth (Sambrook, 1989) and plasmid DNA was isolated using a Qiaspin miniprep Kit® according to the manufacturer's instructions (Qiagen). Plasmid DNA was digested with EcoRI and XhoI to liberate the cloned inserts. The inserts were sequenced using T7 and SP6 universal primers (Invitrogen).

Reverse-transcriptase PCR was used to amplify TmHKT8-A. This was undertaken using primers that were external to the coding sequence named 5primeUTRFor (5'-AGAAGTCTCTACACAACTTACAG-3') (SEQ ID NO:76) and 3primeUTRRev (5'-GATCATTGAGAAATATG-CAGTCC-3') (SEQ ID NO:77) using a Qiagen® OneStep RT-PCR Kit as per the manufacturer's instructions. DNA fragments of the appropriate size were amplified from *T. monococcum* and Line 149. These fragments were cut out and purified using a Qiagen gel extraction Kit® according to the manufacturer's instructions. The fragments were ligated into the pGEM-T Vector using the pGEM-T easy vector system 1 Kit® (Promega).

For heterologous expression, the protein coding sequences of TmHKT8-A and TaHKT8-D were amplified with and without their stop codons using the following primers:
Full Coding Sequence:

```
Topo5start:
                                          (SEQ ID NO: 78)
CACCTAGAAATGGGTTCTTTGCATGTC AstopcodonR:
                                          (SEQ ID NO: 79)
TTATATTATCCTCCATGCCTGGCC (for TmHKT8-A)

DstopcodonR:
                                          (SEQ ID NO: 80)
TTATACTATCCTCCATGCCTCGCC (for TaHKT8-D)
```

Coding Sequence without Stop Codon:

```
Topo5start:
CACCTAGAAATGGGTTCTTTGCATGTC    (SEQ ID NO: 78)

CutoffstopA:
TATTATCCTCCATGCCTGGCC          (SEQ ID NO: 81)

DstopcodonR:
TACTATCCTCCATGCCTCGCC          (SEO ID NO: 82)
```

The full coding sequence of each of the HKT8-A and -D gene members was ligated into pENTR-CR8 and transformed into *E. coli* as per manufacturers instructions. Purified plasmid DNAs of pENTR-CR8 containing each of the TmHKT8-A and the TaHKT8-D gene members were sequenced to confirm the presence and sequence of the insert. The plasmid DNAs were then used in Gateway Recombinase reactions to transfer each of the inserts into a Gateway enabled *Xenopus laevis* oocyte expression vector called pGEMHE. Similarly, the coding sequences of each of the TmHKT8-A and TaHKT8-D sequences, minus their stop codons, were transferred into a Gateway enabled yeast (*Saccharomyces cerevisiae*) expression vector pYES-DEST-52 which contains a C-terminal HIS tag.

Yeast transformed with pYES-DEST-52 plus either TmHKT8-A or TaHKT8-D were grown in synthetic complete growth media minus uracil (SC-URA). Expression of the HKT8 genes in the yeast was driven by a galactose-inducible promoter. When grown on SC-URA plates with galactose, yeast expressing the HKT8 genes grew slower than yeast transformed with an empty pYES-DEST-52 vector. When grown on media with increasing levels of NaCl (50 mM and 200 mM), growth of yeast expressing the HKT8 genes was significantly slower than the growth of the control yeast. Yeast expressing TaHKT8-D grew slower than yeast expressing TmHKT8-A indicating that the D genome member may be a stronger $Na^+$ transporter in yeast. From these data, it was concluded that the two genes encoded active $Na^+$ transporters.

The TaHKT8-B and TmHKT7-A2 (Nax1) coding sequences will also be transferred to pYES-DEST-52 and pGEM-HE for heterologous expression in yeast and *Xenopus* oocytes respectively.

Example 17

Immuno-Localization of HKT8 in Wheat

TmHKT8-A and TaHKT8-D proteins will be isolated and purified from cultures of the transformed yeast using the HIS tag sequences according to standard methods and used in a Western blot to produce and test an HKT8 antibody. The HKT8 antibody will then be used in immuno-localize the HKT8 protein in wheat roots. It is expected that HKT8 will be expressed in wheat roots and particularly in the upper roots. Strong expression is predicted in the xylem parenchyma cells lining the xylem in the vascular bundles.

Example 18

Expression of Wheat HKT8 in Transformed Plants Using Native Promoters

The TmHKT8-A and TaHKT8-D promoters will be put into constructs so that they are driving the expression of $Na^+$ transporter coding regions when transformed into barley, to provide synthetic salt tolerance genes which will be expressed in the same plant tissues as the genes the promoters were obtained from. The TmHKT8-A and TaHKT8-D promoters were isolated from *Triticum monococcum* and *Triticum tauschii* bacterial artificial chromosome (BAC) libraries using gene probes and hybridisation under stringent conditions. Sequences of the promoter regions are provided in SEQ ID NO's 97 and 98.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

This application claims priority from U.S. 60/830,754 and U.S. 60/847,765, the entire contents of which are incorporated herein by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Abdullah et al. (1986) Biotechnology 4:1087.
Almeida and Allshire (2005) TRENDS Cell Biol 15: 251-258.
Bonnett et al. (2005) Molecular Breeding, 15: 75-85.
Bourque (1995) Plant Sci. 105: 125-149.

Byrt et al. (2007) Plant Physiol 143:1918-1928.
Capecchi (1980) Cell 22:479-488.
Cheng et al. (1996) Plant Cell Rep. 15:653-657.
Clapp (1993) Clin. Perinatol. 20:155-168.
Comai et al. (2004) Plant J 37: 778-786.
Curiel et al. (1992) Hum. Gen. Ther. 3:147-154.
Czechowski et al. (2005) Plant Physiol. 139: 5-17.
Davenport et al. (2005) Plant Physiol 137: 807-818.
Dubcovsky et al. (1996) Theoretical and Applied Genetics 92: 448-454.
Durell et al. (1999) Channel. Biophys. J. 77: 789-807.
Dvořák and Gorham (1992) Genome 35: 639-646.
Dvořák et al. (1994) Theoretical and. Applied Genetics 87: 872-877.
Eagles et al. (2001) Aust. J. Agric. Res. 52:1 349-1356.
Eglitis et al. (1988) Biotechniques 6:608-614.
Endo and Gill (1996) J Heredity 87: 295-307.
Francois et al. (1986) Agronomy Journal 78:1053-1058.
Fujimura et al. (1985) Plant Tissue Culture Letters 2:74.
Garciadeblas et al. (2003) Plant J. 34: 788-801.
Garthwaite et al. (2005) J Experimental Botany 56:2365-2378.
Gleave (1992) Plant Mol. Biol. 20: 1203-1207.
Gorham et al. (1987) Theoretical and Applied Genetics 74:584-548.
Gorham et al. (1990) Planta 180, 590-597.
Graham et al. (1973) Virology 54:536-539.
Grant et al. (1995) Plant Cell Rep. 15:254-258.
Harayama (1998). Trends Biotechnol 16: 76-82.
Haseloff and Gerlach (1988) Nature 334:585-591.
Henikoff et al. (2004) Plant Physiol 135: 630-636.
Husain et al. (2003) Australian Journal of Agricultural Research 54:589-597.
Koorneef and Stam (2001) Plant Physiology 125:156-159.
Koziel et al. (1996) Plant Mol. Biol. 32:393-405.
Kramer (1983) Physiol Plant 58: 549-555.
Kramer et al. (1977) Ann Bot 41: 1031-1040.
Kumar et al. (2004) Brief Bioinform 5:150-163.
Jacoby (1964) Plant Physiol 39: 445-449.
Johanson and Cheeseman (1983) Plant Physiol 73: 153-158.
Lacan and Durand (1996) Plant Physiol 110: 705-711.
Lacerda et al. (2003) Env Exp Bot 49: 107-120.
Lagudah et al. (1991) Genome, 34: 387-395.
Langridge et al. (2001). Aust J Agric Res 52: 1043-1077.
Law et al. (1981) Philosophy Transactions Royal Society of London, 292: 509-518.
Law et al. (1987) In Wheat breeding its scientific basis (Ed, Lupin, F. G. H.) Chapman & Hall.
Lemieux (2000). Current Genomics 1: 301-311.
Lindsay et al. (2004) Functional Plant Biology 31: 1105-1114.
Liu et al. (1992) Theoretical and Applied Genetics, 83: 305-312.
Lu et al. (1993) J. Exp. Med. 178:2089-2096.
Maas and Grieve (1990) Crop Science 30:1309-1313.
Mäser et al. (2002) Proc. Natl. Acad. Sci. USA 99: 6428-6433.
Matsushita and Matoh (1991) Physiol Plant 83: 170-176.
Miller (1987) Plant Physiology 85:164-166.
Millar and Waterhouse (2005) Funct Integr Genomics 5:129-135.
Munns et al. (1995) Australian Journal of Plant Physiology 22:561-569.
Munns et al. (2000) Australian Journal of Agricultural Research 51: 69-74.
Munns et al. (2002) Plant and Soil 247:93-105.
Munns et al. (2003) Australian Journal of Agricultural Research 54: 627-635.
Munns and James (2003) Plant and Soil 253:201-218.
Murray et al. (2004) Plant Cell Rep. 22: 397-402.
Needleman and Wunsch (1970) J. Mol. Biol. 48:443-453.
Nicholas et al. (1997) EMBNEW.NEWS 4:14.
Pasquinelli et al. (2005) Curr Opin Genet Develop 15: 200-205.
Pellegrineschi et al. (2002) Genome 45:421-430.
Perriman et al. (1992) Gene 113: 157-163.
Pitman (1988) Whole plants. In "Solute transport in plant cells and tissues." Eds.
Baker and Hall. Longman Scientific & Technical, Harlow. p 346-391.
Pitman and Läuchli (2002) In 'Salinity:environment-plants-molecules'. (Ed. A. Lauchli and U. Luttge) pp. 3-20. (Kluwer Academic: Dordrecht, The Netherlands).
Platten et al. (2006) TRENDS Plant Sci 11:372-374.
Rawson et al. (1988) Australian Journal of Agricultural Research 39:759-772.
Ren et al. (2005) Nat Genet 37: 1141-1146.
Rengasamy (2002) Australian Journal of Experimental Agriculture 42:351-361.
Rivelli et al. (2002) Functional Plant Biology 29:1065-1074.
Roder et al. (1998) Genetics, 149: 2007-2023.
Rose et al. (2003). Nucleic Acids Res 31: 3763-3766.
Rus et al. (2004). Plant Physiology 136: 2500-2511.
Sambrook et al. (1989) Molecular Cloning A Laboratory Manual, Cold Spring Harbor Laboratory Press.
Schaefer (1995) Anal Biochem 227: 255-273.
Schachtman et al. (1992) Theor Appl Genet 84: 714-719.
Senior (1998) Biotech. Genet. Engin. Revs. 15: 79-119.
Shah et al. (1987) Journal of Experimental Botany 38:254-269.
Sharp et al. (2001) Aust J Agric Res 52: 1357-1366.
Shippy et al. (1999) Mol. Biotech. 12: 117-129.
Shone et al. (1969) Planta 86: 301-314.
Slade and Knauf (2005) Transgenic Res 14: 109-115.
Smith et al. (2000) Nature 407: 319-320.
Shone et al. (1969) Planta 86: 301-314.
Somers et al. (2004) Theor Appl Genet 109:1105-1114.
Storey (1995) Aust J Plant Physiol 22: 101-114.
Tester and Davenport (2003) Ann Bot (Lond) 91: 503-527.
The (1973) PhD Thesis, University of Sydney, Australia.
Thompson et al. (1997) Nucl. Acids Res. 25: 4876-4882.
Toriyama et al. (1986) Theor. Appl. Genet. 205:34.
Wagner et al. (1992) Proc. Natl. Acad. Sci. USA 89:6099-6103.
Waterhouse et al. (1998) Proc. Natl. Acad. Sci. USA 95: 13959-13964.

The invention claimed is:

1. A wheat plant other than a *Triticum monococcum* wheat plant which is homozygous for a Nax2 gene that encodes a Nax2 polypeptide comprising amino acids whose sequence is at least 95% identical to the sequence set forth in SEQ ID NO: 1 and confers enhanced tolerance to saline and/or sodic soils, and/or reduced sodium accumulation in an aerial part of the wheat plant in comparison to a wheat plant that is not homozygous for the Nax2 gene.

2. The wheat plant of claim 1 which is *durum* wheat.

3. The wheat plant of claim 2 which has a genetic background comprising less than 50% of the genetic background of *durum* Line 149, *durum* Line 5049, or of the cultivar Tamaroi.

4. The wheat plant of claim 1 which is hexaploid wheat.

5. The wheat plant of claim 1, wherein the gene is on chromosome 5A or chromosome 4A.

6. The wheat plant of claim 1, wherein the gene encodes a polypeptide which comprises a cysteine residue at a position corresponding to amino acid number 232 of SEQ ID NO:1 and/or an aspartic acid residue at a position corresponding to amino acid number 294 of SEQ ID NO:1.

7. The wheat plant of claim 1 which further comprises an allele of a Nax1 gene, and/or an allele of a Kna1 gene, which confers enhanced tolerance to saline and/or sodic soils, and/or reduced sodium accumulation in an aerial part of the wheat plant in comparison to a wheat plant that is not homozygous for the Nax2 gene nor comprises a Nax1 and/or Kna1 gene.

8. The wheat plant of claim 7 which is characterized by a sheath:blade ratio of $Na^+$ concentration in leaf 3 of at least 1.5 when grown for at least 10 days in a hydroponic system using a growth medium having a NaCl concentration of 50 mM.

9. The wheat plant of claim 1, wherein the gene encodes a polypeptide that transports sodium across a cell membrane and out of the xylem of a plant to a greater extent than it transports potassium.

10. A method of obtaining a wheat plant, the method comprising;
  i) crossing two wheat plants of the same species of which at least one wheat plant comprises a Nax2 locus comprising an allele that encodes a Nax2 polypeptide comprising amino acids whose sequence is at least 95% identical to the sequence set forth as SEQ ID NO: 1 and confers enhanced tolerance to saline and/or sodic soils, and/or which confers reduced sodium accumulation in an aerial part of the wheat plant, and
  ii) screening progeny wheat plants from the cross for the presence or absence of said Nax2 locus by detecting a nucleic acid molecule of the wheat plant, wherein the nucleic acid molecule is linked to, and/or comprises at least a part of, said Nax2 locus comprising the allele that confers enhanced tolerance to saline and/or sodic soils, and/or that confers reduced sodium accumulation in an aerial part of the wheat plant, wherein progeny with said allele have enhanced tolerance to saline and/or sodic soils, and/or have reduced sodium accumulation in an aerial part of the wheat plant, when compared to progeny lacking said allele.

11. The method of claim 10, wherein the wheat plants of the same species of step i) are hexaploid wheat plants.

12. The method of claim 11, wherein the cross is between a *durum* wheat plant comprising said allele and a hexaploid wheat plant lacking said allele.

13. The method of claim 10, wherein step i) comprises crossing a first parent wheat plant with a second parent wheat plant, wherein the second wheat plant comprises a Nax2 locus which comprises the allele, and wherein the method further comprises backcrossing the progeny of the cross of step i) with wheat plants of the same genotype as the first parent wheat plant for a sufficient number of times to produce a wheat plant with a majority of the genotype of the first parent but comprising said allele.

14. A process of producing wheat grain, the process comprising;
   i) growing a wheat plant of claim 1, and
   ii) harvesting the wheat grain from the wheat plant.

15. Wheat grain other than *Triticum monococcum* wheat grain produced by the process of claim 14, wherein the wheat grain is homozygous for a Nax2 gene that encodes a Nax2 polypeptide comprising an amino acids whose sequence is at least 95% identical to the sequence set forth as SEQ ID NO: 1 and confers enhanced tolerance to saline and/or sodic soils, and/or reduced sodium accumulation in an aerial part of a wheat plant in comparison to a wheat plant that is not homozygous for the Nax2 gene.

16. A process of producing flour, wholemeal, starch or other product obtained from wheat grain, the process comprising;
   i) obtaining wheat grain of claim 15, and
   ii) extracting the flour, wholemeal, starch or other product from the wheat grain.

17. A process for making a food product, the process comprising processing the wheat grain produced by the process of claim 14 with another ingredient so as to make the food product.

* * * * *

UNITED STATES PATENT AND TRADEMARK OFFICE
CERTIFICATE OF CORRECTION

PATENT NO. : 8,536,429 B2  Page 1 of 1
APPLICATION NO. : 12/309157
DATED : September 17, 2013
INVENTOR(S) : Platten et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1286 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 165

<210> SEQ ID NO 1
<211> LENGTH: 517
<212> TYPE: PRT
<213> ORGANISM: Triticum monococcum

<400> SEQUENCE: 1

```
Met Gly Ser Leu His Val Ser Asn Ala Thr Gln His Ser Lys Leu
1               5                   10                  15

Glu Arg Ala Tyr Gln Leu Leu Val Phe His Val His Pro Phe Trp Leu
            20                  25                  30

Gln Leu Leu Tyr Phe Val Ser Ile Ser Phe Phe Gly Phe Val Ile Leu
        35                  40                  45

Lys Ala Leu Pro Met Lys Thr Ser Thr Val Pro Arg Pro Met Asp Leu
50                  55                  60

Asp Leu Ile Phe Met Ser Val Ser Ala Thr Thr Val Ser Ser Met Val
65                  70                  75                  80

Ala Val Glu Met Glu Ser Phe Ser Asn Pro Gln Leu Leu Leu Leu Thr
                85                  90                  95

Leu Leu Met Leu Leu Gly Gly Glu Val Phe Thr Ser Met Leu Gly Leu
            100                 105                 110

His Phe Thr Tyr Val Lys Ser Lys Lys Glu Ala Gln Ala Pro His
        115                 120                 125

Asp His Asp Asp Gly Asp Lys Gly Lys Pro Ala Pro Ser Cys Ser Leu
130                 135                 140

Lys Leu Ala Ala Thr Thr Cys Met Asp Asp Val Asp Arg Val Glu Gln
145                 150                 155                 160

Gly Phe Lys Asp Gln Pro Arg Tyr Asp Arg Ala Phe Leu Thr Arg Leu
                165                 170                 175

Leu Leu Phe Ile Val Leu Gly Tyr His Val Val His Leu Ala Gly
            180                 185                 190

Tyr Ser Leu Met Leu Val Tyr Leu Ser Val Val Ser Gly Ala Gly Ala
        195                 200                 205

Val Leu Thr Gly Lys Gly Ile Ser Leu His Thr Phe Ser Val Phe Thr
210                 215                 220

Val Val Ser Thr Phe Ala Asn Cys Gly Phe Val Pro Asn Asn Glu Gly
225                 230                 235                 240

Met Val Ala Phe Arg Ser Phe Pro Gly Leu Leu Leu Leu Val Met Pro
                245                 250                 255

His Val Leu Leu Gly Asn Thr Leu Phe Pro Val Phe Leu Arg Leu Ala
            260                 265                 270

Ile Trp Ala Leu Arg Arg Val Thr Arg Arg Pro Glu Leu Gly Glu Leu
        275                 280                 285

Arg Ser Thr Gly Tyr Asp His Leu Leu Thr Ser Arg His Thr Trp Phe
290                 295                 300

Leu Ala Phe Thr Val Ala Ala Phe Met Leu Ala Gln Leu Ser Leu Phe
305                 310                 315                 320

Cys Ala Met Glu Trp Gly Ser Asp Gly Leu Asn Gly Leu Thr Ala Ala
                325                 330                 335

Gln Lys Leu Val Ala Ala Leu Phe Met Ser Val Asn Ser Arg His Thr
            340                 345                 350

Gly Glu Met Val Val Asp Ile Ser Thr Val Ser Ser Ala Val Val Val
        355                 360                 365
```

```
Leu Tyr Val Val Met Met Tyr Leu Pro Pro Tyr Thr Thr Phe Leu Pro
    370                 375                 380

Val Glu Asp Asp Ser Asp Gln Gln Val Gly Ala Asp Gln His Asp His
385                 390                 395                 400

Lys Arg Ile Thr Ser Ile Cys His Lys Leu Leu Met Ser Pro Leu Ser
                405                 410                 415

Cys Leu Ala Ile Phe Ile Ala Val Val Cys Ile Thr Glu Arg Arg Gln
                420                 425                 430

Ile Ser Asp Asp Pro Leu Asn Phe Asn Val Leu Asn Ile Thr Val Glu
            435                 440                 445

Val Ile Ser Ala Tyr Gly Asn Val Gly Phe Ser Thr Gly Tyr Ser Cys
        450                 455                 460

Gly Arg Gln Val Thr Pro Asp Asp Gly Asp Cys Arg Asp Thr Trp Val
465                 470                 475                 480

Gly Phe Ser Gly Lys Trp Ser Trp Gln Gly Lys Leu Ala Leu Ile Ala
                485                 490                 495

Val Met Phe Tyr Gly Arg Leu Lys Lys Phe Ser Ile His Gly Gly Gln
            500                 505                 510

Ala Trp Arg Ile Ile
        515

<210> SEQ ID NO 2
<211> LENGTH: 518
<212> TYPE: PRT
<213> ORGANISM: Triticum turgidum

<400> SEQUENCE: 2

Met Gly Ser Leu His Val Ser Cys Ser Thr Thr Gln His Ser Lys Leu
1               5                   10                  15

Gln Arg Val Tyr Gln Leu Leu Phe Phe His Val His Pro Phe Trp Leu
            20                  25                  30

His Phe Leu Tyr Phe Val Thr Ile Ser Phe Leu Gly Phe Val Ile Leu
        35                  40                  45

Lys Ala Leu Pro Met Lys Thr Ser Met Val Ser Arg Pro Ile Asp Leu
    50                  55                  60

Asp Leu Ile Phe Thr Ser Val Ser Ala Thr Thr Val Ser Ser Met Val
65                  70                  75                  80

Ala Val Glu Met Glu Ser Phe Ser Asn Pro Gln Leu Leu Leu Leu Thr
                85                  90                  95

Ile Leu Met Leu Leu Gly Gly Glu Val Phe Thr Ser Met Leu Gly Leu
            100                 105                 110

Tyr Phe Thr Tyr Ile Lys Ser Lys Lys Lys Glu Ala Pro His Asp His
        115                 120                 125

Gly Asp Gly Gly Gly Lys Val Glu Pro Ala Pro Ser Ser Leu Glu Leu
    130                 135                 140

Pro Ala Thr Thr Phe Met Asp Asp Ser Thr Ala Gln Asn Gln Met Glu
145                 150                 155                 160

Gln Gly Phe Asn Lys Glu Gln Pro Arg Tyr Gly Arg Ala Phe Leu Thr
                165                 170                 175

Arg Leu Leu Leu Phe Ile Val Leu Gly Tyr His Val Val Val His Leu
            180                 185                 190

Ala Gly Tyr Ser Leu Met Leu Leu Tyr Leu Ser Val Val Ser Gly Ala
        195                 200                 205

Arg Ala Val Leu Ala Gly Lys Gly Ile Ser Leu His Thr Phe Ser Val
    210                 215                 220
```

```
Phe Thr Val Val Ser Thr Phe Ala Asn Gly Gly Phe Val Pro Asn Asn
225                 230                 235                 240

Glu Gly Met Val Val Phe Arg Ser Phe Pro Gly Leu Leu Leu Leu Val
                245                 250                 255

Met Pro His Val Leu Leu Gly Asn Thr Leu Phe Pro Val Phe Leu Arg
            260                 265                 270

Leu Ala Ile Trp Ala Leu Arg Arg Val Thr Arg Pro Glu Leu Gly
        275                 280                 285

Gln Leu Gln Ser Ile Gly Tyr Gly His Leu Leu Thr Ser Arg His Thr
    290                 295                 300

Cys Phe Leu Ala Phe Thr Val Ala Thr Phe Val Leu Ala Gln Leu Ser
305                 310                 315                 320

Leu Phe Cys Ala Met Glu Trp Gly Ser Asn Gly Leu His Gly Leu Thr
                325                 330                 335

Ala Ala Gln Lys Leu Val Ala Ala Leu Phe Met Ser Val Asn Ser Arg
            340                 345                 350

His Thr Gly Glu Met Val Val Asp Leu Ser Thr Met Ser Ser Ala Val
        355                 360                 365

Val Val Leu Tyr Val Val Met Met Tyr Leu Pro Pro Tyr Thr Thr Phe
    370                 375                 380

Leu Pro Val Glu Asp Asp Ser Asp Gln Val Gly Ala Asp Gln His
385                 390                 395                 400

His Gln Lys Arg Val Thr Ser Ile Trp Arg Lys Leu Leu Met Ser Pro
                405                 410                 415

Leu Ser Phe Leu Ala Ile Phe Ile Ala Val Val Cys Ile Thr Glu Arg
            420                 425                 430

Arg Gln Ile Ser Asp Asp Pro Leu Asn Phe Asn Val Leu Asn Ile Thr
        435                 440                 445

Val Glu Val Ile Ser Ala Tyr Gly Asn Val Gly Phe Ser Thr Gly Tyr
    450                 455                 460

Ser Cys Ala Arg Gln Val Thr Ala Asp Gly Gly Cys Arg Asp Thr Trp
465                 470                 475                 480

Val Gly Phe Ser Gly Lys Trp Ser Trp Gln Gly Lys Leu Val Leu Ile
                485                 490                 495

Ala Val Met Phe Tyr Gly Arg Leu Lys Lys Phe Gly Met His Gly Gly
            500                 505                 510

Glu Ala Trp Arg Ile Val
        515

<210> SEQ ID NO 3
<211> LENGTH: 514
<212> TYPE: PRT
<213> ORGANISM: Triticum turgidum

<400> SEQUENCE: 3

Met Gly Ser Leu Leu His Val Ser Phe Ser Ala Thr Gln His Ser Lys
1               5                   10                  15

Leu His Arg Ala Tyr Gln Leu Leu Phe His Val Pro Phe Trp
                20                  25                  30

Leu Gln Leu Leu Tyr Phe Val Ser Ile Ser Phe Phe Gly Phe Val Ile
            35                  40                  45

Leu Lys Ala Leu Pro Met Lys Thr Gly Met Pro Met Asp Leu Asp Leu
        50                  55                  60

Ile Phe Thr Ser Val Ser Ala Thr Val Ser Ser Met Val Ala Val
65                  70                  75                  80
```

```
Glu Met Glu Ser Phe Ser Asn Pro Gln Leu Leu Leu Thr Leu Leu
                 85                  90                  95
Met Leu Leu Gly Gly Glu Val Phe Thr Ser Met Leu Gly Leu His Phe
            100                 105                 110
Thr Tyr Leu Lys Ser Lys Thr Lys Glu Ala Gln Ala Pro His Glu His
            115                 120                 125
Asp Asp Ala Asp Lys Gly Lys Pro Ala Pro Ser Ser Ser Leu Gln Leu
130                 135                 140
Thr Ala Thr Thr Cys Met Asp Asp Val Asn Arg Val Glu Gln Gly Phe
145                 150                 155                 160
Lys Asp Gln Pro Arg Tyr Asp Arg Ala Phe Leu Thr Arg Leu Leu Leu
                165                 170                 175
Phe Ile Val Leu Gly Tyr His Val Val His Leu Ala Gly Tyr Ser
            180                 185                 190
Leu Met Leu Val Tyr Leu Ser Val Val Ser Gly Ala Arg Ala Val Leu
            195                 200                 205
Ala Gly Lys Gly Ile Ser Leu His Thr Phe Ser Val Phe Thr Val Val
            210                 215                 220
Ser Thr Phe Ala Asn Gly Gly Phe Met Pro Asn Asn Glu Glu Met Val
225                 230                 235                 240
Ala Phe Arg Ser Phe Pro Gly Leu Leu Leu Val Met Pro His Val
                245                 250                 255
Leu Leu Gly Asn Thr Leu Phe Pro Val Phe Leu Arg Leu Ala Ile Trp
            260                 265                 270
Ala Leu Arg Arg Val Thr Arg Arg Pro Glu Leu Gly Glu Leu Gln Ser
            275                 280                 285
Ile Gly Tyr Asp His Leu Leu Thr Ser Arg His Thr Cys Phe Leu Ala
            290                 295                 300
Phe Thr Val Ala Met Phe Val Leu Ala Gln Leu Ser Leu Phe Cys Ala
305                 310                 315                 320
Met Glu Trp Gly Ser Asp Gly Leu His Gly Leu Thr Ala Ala Gln Lys
                325                 330                 335
Leu Val Thr Ala Leu Phe Met Ser Val Asn Ser Arg His Thr Gly Glu
            340                 345                 350
Met Val Val Asp Leu Ser Thr Val Ser Ser Ala Val Val Val Leu Tyr
            355                 360                 365
Val Val Met Met Tyr Leu Pro Pro Tyr Thr Thr Phe Leu Pro Val Glu
            370                 375                 380
Asp Asp Ser Asp Gln Gln Val Gly Ala Asp Gln His His Gln Lys Arg
385                 390                 395                 400
Val Thr Ile Ile Trp Arg Lys Leu Leu Met Ser Pro Leu Ser Cys Leu
                405                 410                 415
Ala Ile Phe Ile Ala Val Val Cys Ile Thr Glu Arg Arg Gln Ile Ser
            420                 425                 430
Asp Asp Pro Leu Asn Phe Lys Val Leu Asn Ile Thr Val Glu Val Ile
            435                 440                 445
Ser Ala Tyr Gly Asn Val Gly Phe Ser Thr Gly Tyr Ser Cys Gly Arg
            450                 455                 460
Gln Val Thr Pro Asp Gly Gly Cys Arg Asp Thr Trp Val Gly Phe Ser
465                 470                 475                 480
Gly Lys Trp Ser Trp Gln Gly Lys Leu Val Leu Ile Ala Val Met Phe
                485                 490                 495
Tyr Gly Arg Leu Lys Lys Phe Ser Met His Gly Gly Glu Ala Trp Met
```

```
                500             505             510
Ile Val

<210> SEQ ID NO 4
<211> LENGTH: 518
<212> TYPE: PRT
<213> ORGANISM: Triticum aestivum

<400> SEQUENCE: 4

Met Gly Ser Leu His Val Ser Cys Ser Thr Thr Gln His Ser Lys Leu
1               5                   10                  15

Gln Arg Val Tyr Gln Leu Leu Phe Phe His Val His Pro Phe Trp Leu
            20                  25                  30

His Phe Leu Tyr Phe Val Thr Ile Ser Phe Leu Gly Phe Val Ile Leu
        35                  40                  45

Lys Ala Leu Pro Met Lys Thr Ser Met Val Ser Arg Pro Ile Asp Leu
    50                  55                  60

Asp Leu Ile Phe Thr Ser Val Ser Ala Thr Thr Val Ser Ser Met Val
65                  70                  75                  80

Ala Val Glu Met Glu Ser Phe Ser Asn Pro Gln Leu Leu Leu Leu Thr
                85                  90                  95

Ile Leu Met Leu Leu Gly Gly Glu Val Phe Thr Ser Met Leu Gly Leu
            100                 105                 110

Tyr Phe Thr Tyr Ile Lys Ser Lys Lys Glu Ala Pro His Asp His
        115                 120                 125

Gly Asp Gly Gly Gly Lys Val Glu Pro Ala Pro Ser Ser Leu Glu Leu
    130                 135                 140

Pro Ala Thr Thr Phe Met Asp Asp Ser Thr Ala Gln Asn Gln Met Glu
145                 150                 155                 160

Gln Gly Phe Asn Lys Glu Gln Pro Arg Tyr Gly Arg Ala Phe Leu Thr
                165                 170                 175

Arg Leu Leu Leu Phe Ile Val Leu Gly Tyr His Val Val His Leu
            180                 185                 190

Ala Gly Tyr Ser Leu Met Leu Leu Tyr Leu Ser Val Val Ser Gly Ala
        195                 200                 205

Arg Ala Val Leu Ala Gly Lys Gly Ile Ser Leu His Thr Phe Ser Val
    210                 215                 220

Phe Thr Val Val Ser Thr Phe Ala Asn Gly Gly Phe Val Pro Asn Asn
225                 230                 235                 240

Glu Gly Met Val Val Phe Arg Ser Phe Pro Gly Leu Leu Leu Leu Val
                245                 250                 255

Met Pro His Val Leu Leu Gly Asn Thr Leu Phe Pro Val Phe Leu Arg
            260                 265                 270

Leu Ala Ile Trp Ala Leu Arg Arg Val Thr Arg Arg Pro Glu Leu Gly
        275                 280                 285

Gln Leu Gln Ser Ile Gly Tyr Gly His Leu Leu Thr Ser Arg His Thr
    290                 295                 300

Cys Phe Leu Ala Phe Thr Val Ala Thr Phe Val Leu Ala Gln Leu Ser
305                 310                 315                 320

Leu Phe Cys Ala Met Glu Trp Gly Ser Asn Gly Leu His Gly Leu Thr
                325                 330                 335

Ala Ala Gln Lys Leu Val Ala Ala Leu Phe Met Ser Val Asn Ser Arg
            340                 345                 350

His Thr Gly Glu Met Val Val Asp Leu Ser Thr Met Ser Ser Ala Val
        355                 360                 365
```

```
Val Val Leu Tyr Val Val Met Met Tyr Leu Pro Pro Tyr Thr Thr Phe
    370                 375                 380

Leu Pro Val Glu Asp Asp Ser Asp Gln Gln Val Gly Ala Asp Gln His
385                 390                 395                 400

His Gln Lys Arg Val Thr Ser Ile Trp Arg Lys Leu Leu Met Ser Pro
                405                 410                 415

Leu Ser Phe Leu Ala Ile Phe Ile Ala Val Val Cys Ile Thr Glu Arg
                420                 425                 430

Arg Gln Ile Ser Asp Asp Pro Leu Asn Phe Asn Val Leu Asn Ile Thr
                435                 440                 445

Val Glu Val Ile Ser Ala Tyr Gly Asn Val Gly Phe Ser Thr Gly Tyr
                450                 455                 460

Ser Cys Ala Arg Gln Val Thr Ala Asp Gly Gly Cys Arg Asp Thr Trp
465                 470                 475                 480

Val Gly Phe Ser Gly Lys Trp Ser Trp Gln Gly Lys Leu Val Leu Ile
                485                 490                 495

Ala Val Met Phe Tyr Gly Arg Leu Lys Lys Phe Gly Met His Gly Gly
                500                 505                 510

Glu Ala Trp Arg Ile Val
                515

<210> SEQ ID NO 5
<211> LENGTH: 514
<212> TYPE: PRT
<213> ORGANISM: Triticum aestivum

<400> SEQUENCE: 5

Met Gly Ser Leu Leu His Val Ser Phe Ser Ala Thr Gln His Ser Lys
1               5                   10                  15

Leu His Arg Ala Tyr Gln Leu Leu Phe Phe His Val His Pro Phe Trp
                20                  25                  30

Leu Gln Leu Leu Tyr Phe Val Ser Ile Ser Phe Phe Gly Phe Val Ile
                35                  40                  45

Leu Lys Ala Leu Pro Met Lys Thr Gly Met Pro Met Asp Leu Asp Leu
    50                  55                  60

Ile Phe Thr Ser Val Ser Ala Thr Thr Val Ser Ser Met Val Ala Val
65                  70                  75                  80

Glu Met Glu Ser Phe Ser Asn Pro Gln Leu Leu Leu Thr Leu Leu
                85                  90                  95

Met Leu Leu Gly Gly Glu Val Phe Thr Ser Met Leu Gly Leu His Phe
                100                 105                 110

Thr Tyr Leu Lys Ser Lys Thr Lys Glu Ala Gln Ala Pro His Glu His
                115                 120                 125

Asp Asp Ala Asp Lys Gly Lys Pro Ala Pro Ser Ser Ser Leu Gln Leu
    130                 135                 140

Thr Ala Thr Thr Cys Met Asp Asp Val Asn Arg Val Glu Gln Gly Phe
145                 150                 155                 160

Lys Asp Gln Pro Arg Tyr Asp Arg Ala Phe Leu Thr Arg Leu Leu Leu
                165                 170                 175

Phe Ile Val Leu Gly Tyr His Val Val His Leu Ala Gly Tyr Ser
                180                 185                 190

Leu Met Leu Val Tyr Leu Ser Val Ser Gly Ala Arg Ala Val Leu
                195                 200                 205

Ala Gly Lys Gly Ile Ser Leu His Thr Phe Ser Val Phe Thr Val Val
    210                 215                 220
```

Ser Thr Phe Ala Asn Gly Gly Phe Met Pro Asn Asn Glu Glu Met Val
225                 230                 235                 240

Ala Phe Arg Ser Phe Pro Gly Leu Leu Leu Leu Val Met Pro His Val
            245                 250                 255

Leu Leu Gly Asn Thr Leu Phe Pro Val Phe Leu Arg Leu Ala Ile Trp
            260                 265                 270

Ala Leu Arg Arg Val Thr Arg Arg Pro Glu Leu Gly Glu Leu Gln Ser
            275                 280                 285

Ile Gly Tyr Asp His Leu Leu Thr Ser Arg His Thr Cys Phe Leu Ala
        290                 295                 300

Phe Thr Val Ala Met Phe Val Leu Ala Gln Leu Ser Leu Phe Cys Ala
305                 310                 315                 320

Met Glu Trp Gly Ser Asp Gly Leu His Gly Leu Thr Ala Ala Gln Lys
                325                 330                 335

Leu Val Thr Ala Leu Phe Met Ser Val Asn Ser Arg His Thr Gly Glu
            340                 345                 350

Met Val Val Asp Leu Ser Thr Val Ser Ser Ala Val Val Val Leu Tyr
        355                 360                 365

Val Val Met Met Tyr Leu Pro Pro Tyr Thr Thr Phe Leu Pro Val Glu
    370                 375                 380

Asp Asp Ser Asp Gln Gln Val Gly Ala Asp Gln His His Gln Lys Arg
385                 390                 395                 400

Val Thr Ile Ile Trp Arg Lys Leu Leu Met Ser Pro Leu Ser Cys Leu
            405                 410                 415

Ala Ile Phe Ile Ala Val Val Cys Ile Thr Glu Arg Arg Gln Ile Ser
            420                 425                 430

Asp Asp Pro Leu Asn Phe Lys Val Leu Asn Ile Thr Val Glu Val Ile
            435                 440                 445

Ser Ala Tyr Gly Asn Val Gly Phe Ser Thr Gly Tyr Ser Cys Gly Arg
        450                 455                 460

Gln Val Thr Pro Asp Gly Gly Cys Arg Asp Thr Trp Val Gly Phe Ser
465                 470                 475                 480

Gly Lys Trp Ser Trp Gln Gly Lys Leu Val Leu Ile Ala Val Met Phe
                485                 490                 495

Tyr Gly Arg Leu Lys Lys Phe Ser Met His Gly Gly Glu Ala Trp Met
            500                 505                 510

Ile Val

<210> SEQ ID NO 6
<211> LENGTH: 516
<212> TYPE: PRT
<213> ORGANISM: Triticum aestivum

<400> SEQUENCE: 6

Met Gly Ser Leu His Val Ser Ser Ser Ala Thr Gln His Ser Lys Leu
1               5                   10                  15

Glu Arg Ala Tyr Gln Leu Leu Val Phe His Val His Pro Phe Trp Leu
            20                  25                  30

Gln Leu Leu Tyr Phe Val Ser Ile Ser Phe Phe Gly Leu Val Ile Leu
            35                  40                  45

Lys Ala Leu Pro Met Lys Thr Ser Thr Val Pro Arg Pro Met Asp Leu
        50                  55                  60

Asp Leu Ile Phe Thr Ser Val Ser Ala Thr Thr Val Ser Ser Met Val
65                  70                  75                  80

```
Ala Val Glu Met Glu Ser Phe Ser Asn Pro Gln Leu Leu Leu Thr
             85                  90                  95

Leu Leu Met Leu Leu Gly Gly Glu Val Phe Thr Ser Met Leu Gly Leu
            100                 105                 110

His Phe Thr Tyr Val Lys Ser Lys Lys Glu Ala Gln Ala Pro His
            115                 120                 125

Asp His Asp Asp Gly Asp Lys Gly Lys Pro Ala Pro Ser Ser Ser Leu
            130                 135                 140

Glu Leu Ala Val Thr Thr Gly Met Asp Asp Val Asp Arg Val Glu Gln
145                 150                 155                 160

Gly Phe Lys Asp Gln Pro Arg Tyr Asp Arg Ala Phe Leu Thr Arg Leu
                165                 170                 175

Leu Leu Phe Ile Val Leu Gly Tyr His Val Val Val His Leu Ala Gly
                180                 185                 190

Tyr Ser Leu Met Leu Val Tyr Leu Ser Val Val Ser Gly Ala Arg Ala
                195                 200                 205

Val Leu Thr Gly Lys Gly Ile Ser Leu His Thr Phe Ser Val Phe Thr
            210                 215                 220

Val Val Ser Thr Phe Ala Asn Cys Gly Phe Val Pro Asn Asn Glu Gly
225                 230                 235                 240

Met Ile Ala Phe Arg Ser Phe Pro Gly Leu Leu Leu Val Met Pro
                245                 250                 255

His Val Leu Leu Gly Asn Thr Leu Phe Pro Val Phe Leu Arg Leu Ala
                260                 265                 270

Ile Trp Ala Leu Arg Arg Val Thr Arg Arg Pro Glu Leu Gly Glu Leu
            275                 280                 285

Arg Ser Ile Gly Tyr Asp His Leu Leu Thr Ser Arg His Thr Trp Phe
            290                 295                 300

Leu Ala Phe Thr Val Ala Ala Phe Val Leu Ala Gln Leu Ser Leu Phe
305                 310                 315                 320

Cys Ala Met Glu Trp Gly Ser Asn Gly Leu Arg Gly Leu Thr Ala Val
                325                 330                 335

Gln Lys Leu Val Ala Gly Leu Phe Met Ser Val Asn Ser Arg His Thr
            340                 345                 350

Gly Glu Met Val Val Asp Leu Ser Thr Val Ser Ser Ala Leu Val Val
            355                 360                 365

Leu Tyr Val Val Met Met Tyr Leu Pro Pro Tyr Thr Thr Phe Leu Pro
            370                 375                 380

Val Glu Asp Asp Ser Asp Gln Gln Val Gly Ala Asp Gln Arg Asp Gln
385                 390                 395                 400

Lys Arg Ile Thr Ser Met Trp Arg Lys Leu Leu Met Ser Pro Leu Ser
                405                 410                 415

Cys Leu Ala Ile Phe Ile Ala Val Val Cys Ile Thr Glu Arg Arg Gln
                420                 425                 430

Ile Ser Asp Asp Pro Leu Asn Phe Asn Val Leu Asn Ile Thr Val Glu
            435                 440                 445

Val Ile Ser Ala Tyr Gly Asn Val Gly Phe Ser Thr Gly Tyr Ser Cys
            450                 455                 460

Gly Arg Gln Val Thr Pro Asp Gly Gly Cys Arg Asp Thr Trp Val Gly
465                 470                 475                 480

Phe Ser Gly Lys Trp Ser Trp Gln Gly Lys Leu Ala Leu Ile Ala Val
                485                 490                 495

Met Phe Tyr Gly Arg Leu Lys Lys Phe Ser Met His Gly Gly Glu Ala
                500                 505                 510
```

```
Trp Arg Ile Val
515

<210> SEQ ID NO 7
<211> LENGTH: 516
<212> TYPE: PRT
<213> ORGANISM: Aegilops tauschii

<400> SEQUENCE: 7

Met Gly Ser Leu His Val Ser Ser Ala Thr Gln His Ser Lys Leu
1               5                   10                  15

Glu Arg Ala Tyr Gln Leu Leu Val Phe His Val His Pro Phe Trp Leu
                20                  25                  30

Gln Leu Leu Tyr Phe Val Ser Ile Ser Phe Phe Gly Leu Val Ile Leu
            35                  40                  45

Lys Ala Leu Pro Met Lys Thr Ser Thr Val Pro Arg Pro Met Asp Leu
        50                  55                  60

Asp Leu Ile Phe Thr Ser Val Ser Ala Thr Thr Val Ser Ser Met Val
65                  70                  75                  80

Ala Val Glu Met Glu Ser Phe Ser Asn Pro Gln Leu Leu Leu Leu Thr
                85                  90                  95

Leu Leu Met Leu Leu Gly Gly Glu Val Phe Thr Ser Met Leu Gly Leu
            100                 105                 110

His Phe Thr Tyr Val Lys Ser Lys Lys Glu Ala Gln Ala Pro His
        115                 120                 125

Asp His Asp Asp Gly Asp Lys Gly Lys Pro Ala Pro Ser Ser Ser Leu
        130                 135                 140

Glu Leu Ala Val Thr Thr Gly Met Asp Asp Val Asp Arg Val Glu Gln
145                 150                 155                 160

Gly Phe Lys Asp Gln Pro Arg Tyr Asn Arg Ala Phe Leu Thr Arg Leu
                165                 170                 175

Leu Leu Phe Ile Val Leu Gly Tyr His Val Val His Leu Ala Gly
            180                 185                 190

Tyr Ser Leu Met Leu Val Tyr Leu Ser Val Val Ser Gly Ala Arg Ala
            195                 200                 205

Val Leu Thr Gly Lys Gly Ile Ser Leu His Thr Phe Ser Val Phe Thr
210                 215                 220

Val Val Ser Thr Phe Ala Asn Cys Gly Phe Val Pro Asn Asn Glu Gly
225                 230                 235                 240

Met Ile Ala Phe Arg Ser Phe Pro Gly Leu Leu Leu Val Met Pro
                245                 250                 255

His Val Leu Leu Gly Asn Thr Leu Phe Pro Val Phe Leu Arg Leu Ala
            260                 265                 270

Ile Trp Ala Leu Arg Arg Val Thr Arg Arg Pro Glu Leu Gly Glu Leu
        275                 280                 285

Arg Ser Ile Gly Tyr Asp His Leu Leu Thr Ser Arg His Thr Trp Phe
        290                 295                 300

Leu Ala Phe Thr Val Ala Ala Phe Val Leu Ala Gln Leu Ser Leu Phe
305                 310                 315                 320

Cys Ala Met Glu Trp Gly Ser Asn Gly Leu Arg Gly Leu Thr Ala Val
                325                 330                 335

Gln Lys Leu Val Ala Gly Leu Phe Met Ser Val Asn Ser Arg His Thr
            340                 345                 350

Gly Glu Met Val Val Asp Leu Ser Thr Val Ser Ser Ala Leu Val Val
            355                 360                 365
```

-continued

```
Leu Tyr Val Val Met Met Tyr Leu Pro Pro Tyr Thr Thr Phe Leu Pro
    370                 375                 380

Val Glu Asp Asp Ser Asp Gln Gln Val Gly Ala Asp Gln Arg Asp Gln
385                 390                 395                 400

Lys Arg Ile Thr Ser Met Trp Arg Lys Leu Leu Met Ser Pro Leu Ser
                405                 410                 415

Cys Leu Ala Ile Phe Ile Ala Val Val Cys Ile Thr Glu Arg Arg Gln
            420                 425                 430

Ile Ser Asp Asp Pro Leu Asn Phe Asn Val Leu Asn Ile Thr Val Glu
        435                 440                 445

Val Ile Ser Ala Tyr Gly Asn Val Gly Phe Ser Thr Gly Tyr Ser Cys
    450                 455                 460

Gly Arg Gln Val Thr Pro Asp Gly Gly Cys Arg Asp Thr Trp Val Gly
465                 470                 475                 480

Phe Ser Gly Lys Trp Ser Trp Gln Gly Lys Leu Ala Leu Ile Ala Val
                485                 490                 495

Met Phe Tyr Gly Arg Leu Lys Lys Phe Ser Met His Gly Gly Glu Ala
            500                 505                 510

Trp Arg Ile Val
        515

<210> SEQ ID NO 8
<211> LENGTH: 516
<212> TYPE: PRT
<213> ORGANISM: Aegilops tauschii

<400> SEQUENCE: 8

Met Gly Ser Leu His Val Ser Ser Ser Ala Thr Gln His Ser Lys Leu
1               5                   10                  15

Glu Arg Ala Tyr Gln Leu Leu Val Phe His Val His Pro Phe Trp Leu
            20                  25                  30

Gln Leu Leu Tyr Phe Val Ser Ile Ser Phe Phe Gly Leu Val Ile Leu
        35                  40                  45

Lys Ala Leu Pro Met Lys Thr Ser Thr Val Pro Arg Pro Met Asp Leu
    50                  55                  60

Asp Leu Ile Phe Thr Ser Val Ser Ala Thr Thr Val Ser Ser Met Val
65                  70                  75                  80

Ala Val Glu Met Glu Ser Phe Ser Asn Pro Gln Leu Leu Leu Leu Thr
            85                  90                  95

Leu Leu Met Leu Leu Gly Gly Glu Val Phe Thr Ser Met Leu Gly Leu
            100                 105                 110

His Phe Thr Tyr Val Lys Ser Lys Lys Lys Glu Ala Gln Ala Pro His
        115                 120                 125

Asp His Asp Asp Gly Asp Lys Gly Lys Pro Ala Pro Ser Ser Ser Leu
    130                 135                 140

Glu Leu Ala Val Thr Thr Gly Met Asp Asp Val Asp Arg Val Glu Gln
145                 150                 155                 160

Gly Phe Lys Asp Gln Pro Arg Tyr Asn Arg Ala Phe Leu Thr Arg Leu
                165                 170                 175

Leu Leu Phe Ile Val Leu Gly Tyr His Val Val His Leu Ala Gly
            180                 185                 190

Tyr Ser Leu Met Leu Val Tyr Leu Ser Val Val Ser Gly Ala Arg Ala
        195                 200                 205

Val Leu Thr Gly Lys Gly Ile Ser Leu His Thr Phe Ser Val Phe Thr
    210                 215                 220
```

```
Val Val Ser Thr Phe Ala Asn Cys Gly Phe Val Pro Asn Asn Glu Gly
225                 230                 235                 240

Met Ile Ala Phe Arg Ser Phe Pro Gly Leu Leu Leu Val Met Pro
            245                 250                 255

His Val Leu Leu Gly Asn Thr Leu Phe Pro Val Phe Leu Arg Leu Ala
            260                 265                 270

Ile Trp Ala Leu Arg Arg Val Thr Arg Arg Pro Glu Leu Gly Glu Leu
            275                 280                 285

Arg Ser Ile Gly Tyr Asp His Leu Leu Thr Ser Arg His Thr Trp Phe
            290                 295                 300

Leu Ala Phe Thr Val Ala Ala Phe Val Leu Ala Gln Leu Ser Leu Phe
305                 310                 315                 320

Cys Ala Met Glu Trp Gly Ser Asn Gly Leu Arg Gly Leu Thr Ala Val
                325                 330                 335

Gln Lys Leu Val Ala Gly Leu Phe Met Ser Val Asn Ser Arg His Thr
            340                 345                 350

Gly Glu Met Val Val Asp Leu Ser Thr Val Ser Ser Ala Leu Val Val
            355                 360                 365

Leu Tyr Val Val Met Met Tyr Leu Pro Pro Tyr Thr Thr Phe Leu Pro
370                 375                 380

Val Glu Asp Asp Ser Asp Gln Gln Val Gly Ala Asp Gln Arg Asp Gln
385                 390                 395                 400

Lys Arg Ile Thr Ser Met Trp Arg Lys Leu Leu Met Ser Pro Leu Ser
                405                 410                 415

Cys Leu Ala Ile Phe Ile Ala Val Val Cys Ile Thr Glu Arg Arg Gln
            420                 425                 430

Ile Ser Asp Asp Pro Leu Asn Phe Asn Val Leu Asn Ile Thr Val Glu
            435                 440                 445

Val Ile Ser Ala Tyr Gly Asn Val Gly Phe Ser Thr Gly Tyr Ser Cys
            450                 455                 460

Gly Arg Gln Val Thr Pro Asp Gly Gly Cys Arg Asp Thr Trp Val Gly
465                 470                 475                 480

Phe Ser Gly Lys Trp Ser Trp Gln Gly Lys Leu Ala Leu Ile Ala Val
                485                 490                 495

Met Phe Tyr Gly Arg Leu Lys Lys Phe Ser Met His Gly Gly Glu Ala
            500                 505                 510

Trp Arg Ile Val
        515

<210> SEQ ID NO 9
<211> LENGTH: 516
<212> TYPE: PRT
<213> ORGANISM: Aegilops tauschii

<400> SEQUENCE: 9

Met Gly Ser Leu His Val Ser Ser Ala Thr Gln His Ile Lys Leu
1               5                   10                  15

Glu Arg Ala Tyr Gln Leu Leu Val Phe His Val His Pro Phe Trp Leu
            20                  25                  30

Gln Leu Leu Tyr Phe Val Ser Ile Ser Phe Phe Gly Leu Val Ile Leu
            35                  40                  45

Lys Ala Leu Pro Met Lys Thr Ser Val Pro Arg Pro Met Asp Leu
50                  55                  60

Asp Leu Ile Phe Thr Ser Val Ser Ala Thr Thr Val Ser Ser Met Val
65                  70                  75                  80
```

```
Ala Val Glu Met Glu Ser Phe Ser Asn Pro Gln Leu Leu Leu Thr
                85                  90                  95
Leu Leu Met Leu Leu Gly Gly Glu Val Phe Thr Ser Met Leu Gly Leu
            100                 105                 110
His Phe Thr Tyr Val Lys Ser Lys Lys Glu Ala Gln Ala Pro His
            115                 120                 125
Asp His Asp Asp Gly Asp Lys Gly Lys Pro Ala Pro Ser Ser Ser Leu
        130                 135                 140
Glu Leu Ala Val Thr Thr Gly Met Asp Asp Val Asp Arg Val Glu Gln
145                 150                 155                 160
Gly Phe Lys Asp Gln Pro Arg Tyr Asp Arg Ala Phe Leu Thr Arg Leu
                165                 170                 175
Leu Leu Phe Ile Val Leu Gly Tyr His Val Val Val His Leu Ala Gly
            180                 185                 190
Tyr Ser Leu Met Leu Val Tyr Leu Ser Val Val Ser Gly Ala Arg Ala
        195                 200                 205
Val Leu Thr Gly Lys Gly Ile Ser Leu His Thr Phe Ser Val Phe Thr
        210                 215                 220
Val Val Ser Thr Phe Ala Asn Cys Gly Phe Val Pro Asn Asn Glu Gly
225                 230                 235                 240
Met Ile Ala Phe Arg Ser Phe Pro Gly Leu Leu Leu Val Met Pro
                245                 250                 255
His Val Leu Leu Gly Asn Thr Leu Phe Pro Val Phe Leu Arg Leu Ala
            260                 265                 270
Ile Trp Ala Leu Arg Arg Val Thr Arg Arg Pro Glu Leu Gly Glu Leu
        275                 280                 285
Arg Ser Ile Gly Tyr Asp His Leu Leu Thr Ser Arg His Thr Trp Phe
        290                 295                 300
Leu Ala Phe Thr Val Ala Ala Phe Val Leu Ala Gln Leu Ser Leu Phe
305                 310                 315                 320
Cys Ala Met Glu Trp Gly Ser Asn Gly Leu Arg Gly Leu Thr Ala Val
                325                 330                 335
Gln Lys Leu Val Ala Gly Leu Phe Met Ser Val Asn Ser Arg His Thr
            340                 345                 350
Gly Glu Met Val Val Asp Leu Ser Thr Val Ser Ser Ala Leu Val Val
        355                 360                 365
Leu Tyr Val Val Met Met Tyr Leu Pro Pro Tyr Thr Thr Phe Leu Pro
        370                 375                 380
Val Glu Asp Asp Ser Asp Gln Gln Val Gly Ala Asp Gln Arg Asp Gln
385                 390                 395                 400
Lys Arg Ile Thr Ser Met Trp Arg Lys Leu Leu Met Ser Pro Leu Ser
                405                 410                 415
Cys Leu Ala Ile Phe Ile Ala Val Val Cys Ile Thr Glu Arg Arg Gln
            420                 425                 430
Ile Ser Asp Asp Pro Leu Asn Phe Asn Val Leu Asn Ile Thr Val Glu
        435                 440                 445
Val Ile Ser Ala Tyr Gly Asn Val Gly Phe Ser Thr Gly Tyr Ser Cys
        450                 455                 460
Gly Arg Gln Val Thr Pro Asp Gly Gly Cys Arg Asp Thr Trp Val Gly
465                 470                 475                 480
Phe Ser Gly Lys Trp Ser Trp Gln Gly Lys Leu Ala Leu Ile Ala Val
                485                 490                 495
Met Phe Tyr Gly Arg Leu Lys Lys Phe Ser Met Tyr Gly Gly Glu Ala
```

Trp Arg Ile Val
515

<210> SEQ ID NO 10
<211> LENGTH: 1554
<212> TYPE: DNA
<213> ORGANISM: Triticum monococcum

<400> SEQUENCE: 10

| | | | | | |
|---|---|---|---|---|---|
| atgggttctt | tgcatgtctc | ctcgaatgcc | actcaacata | gcaagcttga | gagggcttac | 60 |
| caactcctgg | ttttccatgt | gcacccgttc | tggctccagc | tcttgtactt | tgtatccatc | 120 |
| tccttcttcg | gtttcgtgat | cctcaaagcc | ctccccatga | agaccagcac | ggtcccgagg | 180 |
| cccatggatt | tggacctgat | cttcatgtcg | gtgtcggcga | cgacggtgtc | gagcatggtg | 240 |
| gccgtggaga | tggagtcctt | ctccaacccc | caactcctcc | tcctgaccct | cctcatgctc | 300 |
| ctcggtggcg | aggtgttcac | gagcatgctt | gggctgcact | tcacctacgt | caagtccaag | 360 |
| aagaaagaag | cacaagcacc | ccacgaccat | gacgatggtg | acaaaggcaa | accagcacca | 420 |
| tcatgtagcc | taaagctcgc | tgctaccacc | tgcatggatg | acgtcgatcg | tgtggagcaa | 480 |
| gggtttaagg | accagccccg | ttacgatcgc | gccttcctca | ccaggttgct | tctgttcata | 540 |
| gtgctgggct | atcacgtggt | ggtgcacctc | gccggctact | ccctgatgct | ggtctacctg | 600 |
| agcgtggtct | ccggcgcggg | ggctgtgctc | accggcaagg | ggatcagcct | gcacacttc | 660 |
| tccgtcttca | ccgtcgtctc | gacgtttgcc | aactgcggct | tcgtcccgaa | caacgaaggg | 720 |
| atggtcgcct | tccggtcttt | cccgggcctc | ctgctcctcg | tcatgccgca | cgtcctcctc | 780 |
| ggcaacacgc | tcttccccgt | cttcctcagg | ctggccatct | gggctctccg | gagggtcacg | 840 |
| aggaggcccg | agctcggtga | gctgcggagc | accgggtacg | accacctgct | gacaagccgg | 900 |
| cacacgtggt | tcttggcttt | caccgtggcc | gcgttcatgc | tagctcagct | gtcgctcttc | 960 |
| tgcgccatgg | agtggggctc | cgacgggctg | aacgggctca | ccgccgcgca | gaagctcgtc | 1020 |
| gcggcactgt | tcatgtcggt | caactcaagg | cacaccggtg | agatggtcgt | ggacatttcc | 1080 |
| actgtgtcgt | cagccgtcgt | ggtgctctac | gtggtcatga | tgtacctacc | accttacact | 1140 |
| acatttctac | cagtggaaga | cgacagtgac | caacaagtgg | agcagatcag | cacgaccac | 1200 |
| aaaaggataa | caagcatatg | ccacaagctg | ctcatgtcgc | cgctctcgtg | cctggccatc | 1260 |
| ttcatcgccg | ttgtgtgcat | caccgagcgc | cggcagatct | ccgatgaccc | cctcaacttc | 1320 |
| aacgtcctca | acatcactgt | cgaagttatc | agtgcgtacg | gaaacgtggg | gtttagcacc | 1380 |
| gggtacagct | gcggccggca | ggtgacgcct | gacgacggcg | actgcaggga | cacgtgggtt | 1440 |
| ggcttctctg | ggaagtggag | ctggcaaggg | aagctggctc | tcattgctgt | catgttctac | 1500 |
| ggcaggctca | agaagttcag | cattcatggc | ggccaggcat | ggaggataat | ataa | 1554 |

<210> SEQ ID NO 11
<211> LENGTH: 1557
<212> TYPE: DNA
<213> ORGANISM: Triticum turgidum

<400> SEQUENCE: 11

| | | | | | |
|---|---|---|---|---|---|
| atgggttctc | tgcatgtctc | ctgcagtacc | actcaacata | gcaagcttca | gagggtttac | 60 |
| caactcctgt | ttttccatgt | gcacccgttc | tggctccatt | tcttgtactt | tgtaaccatc | 120 |
| tccttcttag | gtttcgtgat | cctgaaagcc | ctgcccatga | agaccagcat | ggtctcgagg | 180 |
| cccatagacc | ttgacctgat | cttcaccctcg | gtgtcggcca | ccacggtgtc | gagcatggtg | 240 |

```
gccgtggaga tggagtcctt ctccaacccc cagctcctac tcctgaccat ccttatgctc    300
ctcggcggcg aggtgttcac cagcatgctt ggcctttact ttacctacat caagtccaag    360
aagaaagaag cccccatga ccatggtgat ggtggtggca agtcgaacc agcaccgtct      420 agcctagagc tccctgctac caccttcatg gacgatagca ctgcacagaa ccagatggag    480
caagggttca acaaggagca gccccgatac ggccgagcct tcctcaccag gttgctcctg    540
ttcatagtgc tgggctatca cgtggtggtg cacctcgccg gctactccct gatgctgctc    600
tacctgagcg tcgtctccgg cgcaagggct gtgctcgccg gcaaggggat cagcctgcac    660
accttctccg tattcaccgt cgtctcgaca ttcgccaatg gtggcttcgt gccgaacaac    720
gaagggatgg tcgtcttccg gtccttcccg ggctcctgc tcctcgtcat gccgcacgtc     780
ctcctcggca acacgctctt ccctgtcttc tcaggctgg ccatctgggc tctccggagg     840
gtcaccagga ggcccgagct cggccagctg cagagcatcg gctatggtca cctgctgacg    900
agccggcaca cctgcttctt ggctttcacc gtggccacgt tcgtgctggc gcagctgtcg    960
ctcttctgcg ccatggagtg gggctccaac gggctgcacg ggctcaccgc cgcgcagaag    1020
ctcgttgcgg cactgttcat gtcggtcaac tctaggcaca ccggcgagat ggtcgtggac    1080 cttt ccacca tgtcgtcagc cgttgtggtg ctctacgtgg tcatgatgta cctaccacct    1140
tacactacat ttctaccagt ggaagacgac agtgaccaac aagtgggagc agatcagcac    1200
caccagaaaa gggtaacaag catatggcgg aagctgctca tgtcgccgct ctcgttcttg    1260
gccatcttca tcgccgtcgt gtgcatcacg gagcggcggc agatctccga tgaccccctc    1320
aacttcaacg tcctcaacat caccgtcgag gttatcagtg cgtacggaaa cgtggggttt    1380
agcaccgggt acagctgtgc ccggcaggtg actgccgacg gcggctgcag ggatacgtgg    1440
gttggcttct ctgggaagtg gagctggcaa gggaagctgg ttctcattgc tgtcatgttc    1500
tacggcagac tcaagaagtt cggcatgcat ggtggcgagg catggaggat agtataa      1557
```

<210> SEQ ID NO 12  
<211> LENGTH: 1545  
<212> TYPE: DNA  
<213> ORGANISM: Triticum turgidum

<400> SEQUENCE: 12

```
atgggctctt tgctgcatgt ctccttcagt gccactcaac atagcaagct tcatcgggct    60
taccaactcc tgttttttcca tgtgcacccg ttctggctcc agctcttgta ctttgtatcc    120
atctccttct tcggcttcgt gatcctcaaa gccctgccca tgaagaccgg catgcccatg    180
gacctggacc tgatctttac gtcagtatcg cgacgacgg tgtcgagcat ggtggctgtg    240
gagatggagt ccttctccaa ccccagctc ctactcctga ccctcctcat gctcctcggc    300
ggcgaggtgt tcacgagcat gcttggcctg cacttcacct acctcaagtc caagacgaaa   360
gaagcacaag cccccacga gcatgacgat gctgacaaag gcaaaccagc accatcatct    420
agcctacagc tcaccgctac cacctgcatg gatgatgtca atcgtgtgga gcaagggttt    480
aaggaccagc cccgttacga tcgtgccttc ctcaccaggt tgctcttgtt catagtgctg    540
ggctatcacg tggtggtgca cctcgccggc tactccctga tgctggtcta cctgagcgtc    600
gtctccggcg cgagggctgt gctcgccggc aaggggatca gcctgcacac cttctccgtc    660
ttcaccgtcg tctcgacgtt cgccaacggt ggcttcatgc caacaatga agagatggtc    720 gcctttcggt ccttcccggg cctcctgctc ctcgtcatgc cgcacgtact cctcggcaac    780
acgctcttcc ctgtcttcct caggctggcc atctgggctc tccggagggt caccaggagg    840
```

```
cccgagctcg gcgagctgca gagcatcggc tacgaccacc tgctgacgag ccggcacacc      900
tgcttcttgg ctttcactgt ggccatgttc gtgctggcgc agctgtcgct cttctgcgca      960
atggagtggg gctccgacgg gctgcatggg ctcaccgccg cgcagaagct cgtcacggca     1020
ctgttcatgt cggtcaactc caggcacaca ggcgagatgg tcgtggacct ttccacggtg     1080
tcgtcagccg ttgtggtgct ctacgtggtc atgatgtacc taccacctta cactacattt     1140
ctaccagtgg aagacgacag cgaccaacaa gtgggagcag atcagcacca ccagaaaagg     1200
gtaacaatca tatggcggaa gctgctcatg tcaccgctct cgtgcttggc catcttcatc     1260
gctgtcgtgt gcatcacgga gcggcggcag atctccgatg accccctcaa cttcaaagtc     1320
ctcaacatca ccgtcgaggt tatcagtgcg tacggaaacg tggggtttag caccgggtac     1380
agctgtggcc ggcaggtgac gcccgacggc ggctgcaggg atacgtgggt tggcttctct     1440
gggaagtgga gctggcaagg gaagctggtt ctcattgctg tcatgttcta cggcaggctc     1500
aagaagttca gcatgcatgg tggcgaggca tggatgatag tataa                     1545

<210> SEQ ID NO 13
<211> LENGTH: 1557
<212> TYPE: DNA
<213> ORGANISM: Triticum aestivum

<400> SEQUENCE: 13
atgggttctc tgcatgtctc ctgcagtacc actcaacata gcaagcttca gagggtttac       60
caactcctgt ttttccatgt gcacccgttc tggctccatt tcttgtactt tgtaaccatc      120
tccttcttag gtttcgtgat cctgaaagcc ctgcccatga agaccagcat ggtctcgagg      180
cccatagacc ttgacctgat cttcacctcg gtgtcggcca ccacggtgtc gagcatggtg      240
gccgtggaga tggagtcctt ctccaacccc cagctcctac tcctgaccat ccttatgctc      300
ctcggcggcg aggtgttcac cagcatgctt ggcctttact ttacctacat caagtccaag      360
aagaaagaag ccccccatga ccatggtgat ggtggtggca aagtcgaacc agcaccgtct      420
agcctagagc tccctgctac caccttcatg gacgatagca ctgcacagaa ccagatggag      480
caagggttca acaaggagca gccccgatac ggccgagcct tcctcaccag gttgctcctg      540
ttcatagtgc tgggctatca cgtggtggtg cacctcgccg gctactccct gatgctgctc      600
tacctgagcg tcgtctccgg cgcaagggct gtgctcgccg gcaaggggat cagcctgcac      660
accttctccg tattcaccgt cgtctcgaca ttcgccaatg gtggcttcgt gccgaacaac      720
gaagggatgg tcgtcttccg gtccttcccg ggcctcctgc tcctcgtcat gccgcacgtc      780
ctcctcggca acacgctctt ccctgtcttc ctcaggctgg ccatctgggc tctccggagg      840
gtcaccagga ggcccgagct cggccagctg cagagcatcg gctatggtca cctgctgacg      900
agccggcaca cctgcttctt ggcttttacc gtggccacgt tcgtgctggc gcagctgtcg      960
ctcttctgcg ccatggagtg gggctccaac gggctgcacg gctcaccgc cgcgcagaag     1020 ctcgttgcgg cactgttcat gtcggtcaac tctaggcaca ccggcgagat ggtcgtggac     1080 cttccacca tgtcgtcagc cgttgtggtg ctctacgtgg tcatgatgta cctaccacct     1140
tacactacat ttctaccagt ggaagacgac agtgaccaac aagtgggagc agatcagcac     1200
caccagaaaa gggtaacaag catatggcgg aagctgctca tgtcgccgct ctcgttcttg     1260
gccatcttca tcgccgtcgt gtgcatcacg gagcggcggc agatctccga tgacccctc     1320 aacttcaacg tcctcaacat caccgtcgag gttatcagtg cgtacggaaa cgtggggttt     1380
agcaccgggt acagctgtgc ccggcaggtg actgccgacg gcggctgcag ggatacgtgg     1440
```

```
gttggcttct ctgggaagtg gagctggcaa gggaagctgg ttctcattgc tgtcatgttc    1500
tacggcagac tcaagaagtt cggcatgcat ggtggcgagg catggaggat agtataa       1557
```

<210> SEQ ID NO 14
<211> LENGTH: 1545
<212> TYPE: DNA
<213> ORGANISM: Triticum aestivum

<400> SEQUENCE: 14

```
atgggctctt tgctgcatgt ctccttcagt gccactcaac atagcaagct tcatcgggct      60
taccaactcc tgttttcca tgtgcacccg ttctggctcc agctcttgta ctttgtatcc      120
atctccttct tcggcttcgt gatcctcaaa gccctgccca tgaagaccgg catgcccatg     180
gacctggacc tgatctttac gtcagtatcg gcgacgacgg tgtcgagcat ggtggctgtg     240
gagatggagt ccttctccaa cccccagctc ctactcctga ccctcctcat gctcctcggc     300
ggcgaggtgt tcacgagcat gcttggcctg cacttcacct acctcaagtc caagacgaaa     360
gaagcacaag cccccacga gcatgacgat gctgacaaag caaaccagc accatcatct       420 agcctacagc tcaccgctac cacctgcatg gatgatgtca tcgtgtgga gcaagggttt      480 aaggaccagc cccgttacga tcgtgccttc ctcaccaggt tgctcttgtt catagtgctg     540
ggctatcacg tggtggtgca cctgccggc tactccctga tgctggtcta cctgagcgtc      600
gtctccggcg cgagggctgt gctcgccggc aaggggatca gcctgcacac cttctccgtc     660
ttcaccgtcg tctcgacgtt cgccaacggt ggcttcatgc caacaatga agagatggtc      720 gcctttcggt ccttcccggg cctcctgctc ctcgtcatgc cgcacgtact cctcggcaac     780 acgtcttcc ctgtcttcct caggctggcc atctgggctc tccggagggt caccaggagg      840
cccgagctcg gcgagctgca gagcatcggc tacgaccacc tgctgacgag ccggcacacc     900
tgcttcttgg ctttcactgt ggccatgttc gtgctggcgc agctgtcgct cttctgcgca     960
atggagtggg gctccgacgg gctgcatggg ctcaccgccg cgcagaagct cgtcacggca    1020
ctgttcatgt cggtcaactc caggcacaca ggcgagatgg tcgtggacct ttccacggtg    1080
tcgtcagccg ttgtggtgct ctacgtggtc atgatgtacc taccacctta cactacattt    1140
ctaccagtgg aagacgacag cgaccaacaa gtgggagcag atcagcacca ccagaaaagg    1200
gtaacaatca tatggcggaa gctgctcatg tcaccgctct cgtgcttggc catcttcatc    1260
gctgtcgtgt gcatcacgga gcggcggcag atctccgatg accccctcaa cttcaaagtc    1320
ctcaacatca ccgtcgaggt tatcagtgcg tacgaaacg tggggtttag caccgggtac     1380
agctgtggcc ggcaggtgac gcccgacggc ggctgcaggg atacgtgggt tggcttctct    1440
gggaagtgga gctggcaagg gaagctggtt ctcattgctg tcatgttcta cggcaggctc    1500
aagaagttca gcatgcatgg tggcgaggca tggatgatag tataa                    1545
```

<210> SEQ ID NO 15
<211> LENGTH: 1551
<212> TYPE: DNA
<213> ORGANISM: Triticum aestivum

<400> SEQUENCE: 15

```
atgggttctt tgcatgtctc ctcgagtgcc actcaacata gcaagcttga gagggcttac      60
caactcctgg ttttccatgt gcaccgttc tggctccagc tcttgtactt tgtatccatc      120
tccttcttcg gttggtgat cctcaaagcc ctccccatga agaccagcac ggtcccgagg       180
cccatggatt tggacctgat cttcacgtcg gtctcggcga ccacggtgtc gagcatggtg      240
```

```
gccgtggaga tggagtcctt ctccaacccc cagctcctac tcctgaccct cctcatgctc    300
ctcggcggcg aggtgttcac gagcatgctt ggcctgcact tcacctacgt caagtccaag    360
aagaaagaag cacaagcacc ccacgaccat gacgatggtg acaaaggcaa accagcacca    420
tcatctagcc tagagctcgc tgttaccacc ggcatggatg acgtcgatcg tgtggagcaa    480
gggtttaagg accagcccg ttacgatcgc gccttcctca ccaggttgct tctgttcata     540
gtgctgggct atcacgtggt ggtgcacctc gccggctact ccttgatgct ggtctacctg    600
agcgtggtct ccggcgcgag ggctgtgctc accggcaagg ggatcagcct gcacaccttc    660
tccgtcttca ccgtcgtctc gacgttcgcc aactgcggct tcgtcccgaa caacgaaggg    720
atgatcgcct tccggtcctt cccggggcctc ctgctcctag tcatgccgca cgtcctcctc   780
ggcaacacac tcttccccgt cttcctcagg ctggccatct gggctctccg gagagtcacc    840
aggaggcccg agctcggtga gctgaggagc atcggctacg accacctgct gacgagccgg    900
cacacgtggt tcttggcttt caccgtggcg gcgttcgtgc tagcgcagct gtcgctcttc    960
tgcgccatgg agtggggctc caacgggctg cgcgggctca ccgccgtgca gaagctcgtt   1020
gcgggactgt tcatgtcggt caactccagg cacaccggtg agatggtggt ggaccttttcc  1080 accgtgtcgt cggccctcgt ggtgctctat gtggtcatga tgtacctacc accttacact   1140
acatttctac cagtggaaga cgacagtgac caacaagtgg gagcagatca gcgcgaccag   1200
aaaaggataa caagcatgtg gcggaagctg ctcatgtcgc cgctctcgtg cttggccatc   1260
ttcatcgccg tggtgtgcat cacggagcgg cggcagatct ccgatgaccc cctcaacttc   1320
aacgtcctca acatcaccgt cgaggttatc agtgcgtacg gaaacgtggg gttcagcacc   1380
gggtacagct gtggccggca ggtgacgccc gacggcggct gcagggacac gtgggttggc    1440
ttctctggga agtggagttg gcaagggaag ctggctctca ttgctgtcat gttctacggc    1500
aggctcaaga agttcagcat gcatggtggc gaggcatgga ggatagtata a            1551
```

<210> SEQ ID NO 16
<211> LENGTH: 1551
<212> TYPE: DNA
<213> ORGANISM: Aegilops tauschii

<400> SEQUENCE: 16

```
atgggttctt tgcatgtctc ctcgagtgcc actcaacata gcaagcttga gagggcttac     60
caactcctgg ttttccatgt gcacccgttc tggctccagc tcttgtactt tgtatccatc    120
tccttcttcg gtttggtgat cctcaaagcc ctccccatga agaccagcac ggtcccgagg    180
cccatggatt tggacctgat cttcacgtcg gtctcggcga ccacggtgtc gagcatggtg    240
gccgtggaga tggagtcctt ctccaacccc cagctcctac tcctgaccct cctcatgctc    300
ctcggcggcg aggtgttcac gagcatgctt ggcctgcact tcacctacgt caagtccaag    360
aagaaagaag cacaagcacc ccacgaccat gacgatggtg acaaaggcaa accagcacca    420
tcatctagcc tagagctcgc tgttaccacc ggcatggatg acgtcgatcg tgtggagcaa    480
gggtttaagg accagcccg ttacaatcgc gccttcctca ccaggttgct tctgttcata     540
gtgctgggct atcacgtggt ggtgcacctc gccggctact ccttgatgct ggtctacctg    600
agcgtggtct ccggcgcgag ggctgtgctc accggcaagg ggatcagcct gcacaccttc    660
tccgtcttca ccgtcgtctc gacgttcgcc aactgcggct tcgtcccgaa caacgaaggg    720
atgatcgcct tccggtcctt cccggggcctc ctgctcctag tcatgccgca cgtcctcctc   780
ggcaacacac tcttccccgt cttcctcagg ctggccatct gggctctccg gagagtcacc    840
```

| aggaggcccg agctcggtga gctgaggagc atcggctacg accacctgct gacgagccgg | 900 |
| cacacgtggt tcttggcttt caccgtggcg gcgttcgtgc tagcgcagct gtcgctcttc | 960 |
| tgcgccatgg agtggggctc caacgggctg cgcgggctca ccgccgtgca gaagctcgtt | 1020 |
| gcgggactgt tcatgtcggt caactccagg cacaccggtg agatggtggt ggacctttcc | 1080 |
| accgtgtcgt cggccctcgt ggtgctctat gtggtcatga tgtacctacc accttacact | 1140 |
| acatttctac cagtggaaga cgacagtgac caacaagtgg gagcagatca gcgcgaccag | 1200 |
| aaaaggataa caagcatgtg gcggaagctg ctcatgtcgc cgctctcgtg cttggccatc | 1260 |
| ttcatcgccg tggtgtgcat cacggagcgg cggcagatct ccgatgaccc cctcaacttc | 1320 |
| aacgtcctca acatcaccgt cgaggttatc agtgcgtacg gaaacgtggg gttcagcacc | 1380 |
| gggtacagct gtggccggca ggtgacgccc gacgcggct gcagggacac gtgggttggc | 1440 |
| ttctctggga agtggagttg gcaagggaag ctggctctca ttgctgtcat gttctacggc | 1500 |
| aggctcaaga agttcagcat gcatggtggc gaggcatgga ggatagtata a | 1551 |

<210> SEQ ID NO 17
<211> LENGTH: 1551
<212> TYPE: DNA
<213> ORGANISM: Aegilops tauschii

<400> SEQUENCE: 17

| atgggttctt tgcatgtctc ctcgagtgcc actcaacata gcaagcttga gagggcttac | 60 |
| caactcctgg ttttccatgt gcacccgttc tggctccagc tcttgtactt tgtatccatc | 120 |
| tccttcttcg gtttggtgat cctcaaagcc ctccccatga agaccagcac ggtcccgagg | 180 |
| cccatggatt tggacctgat cttcacgtcg gtctcggcga ccacggtgtc gagcatggtg | 240 |
| gccgtggaga tggagtcctt ctccaacccc cagctcctac tcctgaccct cctcatgctc | 300 |
| ctcggcggcg aggtgttcac gagcatgctt ggcctgcact tcacctacgt caagtccaag | 360 |
| aagaaagaag cacaagcacc ccacgaccat gacgatggtg acaaaggcaa accagcacca | 420 |
| tcatctagcc tagagctcgc tgttaccacc ggcatggatg acgtcgatcg tgtggagcaa | 480 |
| gggtttaagg accagccccg ttacaatcgc gccttcctca ccaggttgct tctgttcata | 540 |
| gtgctgggct atcacgtggt ggtgcaccctc gccggctact ccttgatgct ggtctacctg | 600 |
| agcgtggtct ccggcgcgag ggctgtgctc accggcaagg ggatcagcct gcacaccttc | 660 |
| tccgtcttca ccgtcgtctc gacgttcgcc aactgcggct tcgtcccgaa caacgaaggg | 720 |
| atgatcgcct tccggtcctt cccgggcctc ctgctcctag tcatgccgca cgtcctcctc | 780 |
| ggcaacacac tcttccccgt cttcctcagg ctggccatct gggctctccg gagagtcacc | 840 |
| aggaggcccg agctcggtga gctgaggagc atcggctacg accacctgct gacgagccgg | 900 |
| cacacgtggt tcttggcttt caccgtggcg gcgttcgtgc tagcgcagct gtcgctcttc | 960 |
| tgcgccatgg agtggggctc caacgggctg cgcgggctca ccgccgtgca gaagctcgtt | 1020 |
| gcgggactgt tcatgtcggt caactccagg cacaccggtg agatggtggt ggacctttcc | 1080 |
| accgtgtcgt cggccctcgt ggtgctctat gtggtcatga tgtacctacc accttacact | 1140 |
| acatttctac cagtggaaga cgacagtgac caacaagtgg gagcagatca gcgcgaccag | 1200 |
| aaaaggataa caagcatgtg gcggaagctg ctcatgtcgc cgctctcgtg cttggccatc | 1260 |
| ttcatcgccg tggtgtgcat cacggagcgg cggcagatct ccgatgaccc cctcaacttc | 1320 |
| aacgtcctca acatcaccgt cgaggttatc agtgcgtacg gaaacgtggg gttcagcacc | 1380 |
| gggtacagct gtggccggca ggtgacgccc gacgcggct gcagggacac gtgggttggc | 1440 |

```
ttctctggga agtggagttg gcaagggaag ctggctctca ttgctgtcat gttctacggc      1500
aggctcaaga agttcagcat gcatggtggc gaggcatgga ggatagtata a               1551

<210> SEQ ID NO 18
<211> LENGTH: 1551
<212> TYPE: DNA
<213> ORGANISM: Aegilops tauschii

<400> SEQUENCE: 18
atgggttctt tgcatgtctc ctcgagtgcc actcaacata tcaagcttga gagggcttac        60
caactcctgg ttttccatgt gcacccgttc tggctccagc tcttgtactt tgtatccatc       120
tccttcttcg gtttggtgat cctcaaagcc ctccccatga agaccagcac ggtcccgagg       180
cccatggatt tggacctgat cttcacgtcg gtctcggcga ccacggtgtc gagcatggtg       240
gccgtggaga tggagtcctt ctccaacccc cagctcctac tcctgaccct cctcatgctc       300
ctcggcggcg aggtgttcac gagcatgctt ggcctgcact tcacctacgt caagtccaag       360
aagaaagaag cacaagcacc ccacgaccat gacgatggtg acaaaggcaa accagcacca       420
tcatctagcc tagagctcgc tgttaccacc ggcatggatg acgtcgatcg tgtggagcaa       480
gggtttaagg accagccccg ttacgatcgc gccttcctca ccaggttgct tctgttcata       540
gtgctgggct atcacgtggt ggtgcacctc gccggctact ccttgatgct ggtctacctg       600
agcgtggtct ccggcgcgag ggctgtgctc accggcaagg ggatcagcct gcacaccttc       660
tccgtcttca ccgtcgtctc gacgttcgcc aactgcggct tcgtcccgaa caacgaaggg       720
atgatcgcct tccggtcctt cccgggcctc ctgctcctag tcatgccgca cgtcctcctc       780
ggcaacacac tcttccccgt cttcctcagg ctggccatct gggctctccg agagtcacc       840 aggaggcccg agctcggtga gctgaggagc atcggctacg accacctgct gacgagccgg       900
cacacgtggt tcttggcttt caccgtgcg gcgttcgtgc tagcgcagct gtcgctcttc       960
tgcgccatgg agtggggctc caacgggctg cgcgggctca ccgccgtgca gaagctcgtt      1020
gcgggactgt tcatgtcggt caactccagg cacaccggtg agatggtggt ggacctttcc      1080
accgtgtcgt cggccctcgt ggtgctctat gtggtcatga tgtacctacc accttacact      1140
acatttctac cagtggaaga cgacagtgac caacaagtgg agcagatca gcgcgaccag      1200 aaaaggataa caagcatgtg gcggaagctg ctcatgtcgc cgctctcgtg cttggccatc      1260
ttcatcgccg tggtgtgcat cacggagcgg cggcagatct ccgatgaccc cctcaacttc      1320
aacgtcctca acatcaccgt cgaggttatc agtgcgtacg gaaacgtggg gttcagcacc      1380
gggtacagct gtggccggca ggtgacgccc gacggcggct gcaggacac gtgggttggc      1440 ttctctggga agtggagttg gcaagggaag ctggctctca ttgctgtcat gttctacggc      1500
aggctcaaga agttcagcat gtatggtggc gaggcatgga ggatagtata a               1551

<210> SEQ ID NO 19
<211> LENGTH: 1702
<212> TYPE: DNA
<213> ORGANISM: Triticum monococcum

<400> SEQUENCE: 19
agaacaggcc aagaagtctc tacacaactt acagtagaaa tgggttcttt gcatgtctcc        60
tcgaatgcca ctcaacatag caagcttgag agggcttacc aactcctggt tttccatgtg       120
cacccgttct ggctccagct cttgtacttt gtatccatct ccttcttcgg tttcgtgatc       180
ctcaaagccc tccccatgaa gaccagcacg gtcccgaggc ccatggattt ggacctgatc       240
```

```
ttcatgtcgg tgtcggcgac gacggtgtcg agcatggtgg ccgtggagat ggagtccttc     300
tccaaccccc aactcctcct cctgaccctc ctcatgctcc tcggtggcga ggtgttcacg     360
agcatgcttg ggctgcactt cacctacgtc aagtccaaga agaaagaagc acaagcaccc     420
cacgaccatg acgatggtga caaaggcaaa ccagcaccat catgtagcct aaagctcgct     480
gctaccacct gcatggatga cgtcgatcgt gtggagcaag ggtttaagga ccagcccgt     540 tacgatcgcg ccttcctcac caggttgctt ctgttcatag tgctgggcta tcacgtggtg     600
gtgcacctcg ccggctactc cctgatgctg gtctacctga gcgtggtctc cggcgcgggg     660
gctgtgctca ccggcaaggg gatcagcctg cacaccttct ccgtcttcac cgtcgtctcg     720
acgtttgcca actgcggctt cgtcccgaac aacgaaggga tggtcgcctt ccggtctttc     780
ccgggcctcc tgctcctcgt catgccgcac gtcctcctcg gcaacacgct cttcccgtc     840 ttcctcaggc tggccatctg ggctctccgg agggtcacga ggaggcccga gctcggtgag     900
ctgcggagca ccgggtacga ccacctgctg acaagccggc acacgtggtt cttggctttc     960
accgtggccg cgttcatgct agctcagctg tcgctcttct gcgccatgga gtgggctcc    1020 gacgggctga acgggctcac cgccgcgcag aagctcgtcg cggcactgtt catgtcggtc    1080
aactcaaggc acaccggtga gatggtcgtg gacatttcca ctgtgtcgtc agccgtcgtg    1140
gtgctctacg tggtcatgat gtacctacca ccttacacta catttctacc agtggaagac    1200
gacagtgacc aacaagtggg agcagatcag cacgaccaca aaaggataac aagcatatgc    1260
cacaagctgc tcatgtcgcc gctctcgtgc ctggccatct tcatcgccgt tgtgtgcatc    1320
accgagcgcc ggcagatctc cgatgaccCC ctcaacttca acgtcctcaa catcactgtc    1380
gaagttatca gtgcgtacgg aaacgtgggg tttagcaccg ggtacagctg cggccggcag    1440
gtgacgcctg acgacggcga ctgcagggac acgtgggttg gcttctctgg gaagtggagc    1500
tggcaaggga agctggctct cattgctgtc atgttctacg gcaggctcaa gaagttcagc    1560
attcatggcg gccaggcatg gaggataata taacctagca gactacatat ttctcaatga    1620
tctctcttca gacagagagt agctacatct cgctctagcc taaaaccacc tgaacatatt    1680
ttcattatgc cgagtacctc aa                                            1702
```

<210> SEQ ID NO 20
<211> LENGTH: 1698
<212> TYPE: DNA
<213> ORGANISM: Triticum turgidum
<400> SEQUENCE: 20

```
aggccaagaa gtctctacaa tacttaccaa cgaatgggtt ctctgcatgt ctcctgcagt      60
accactcaac atagcaagct tcagagggtt taccaactcc tgttttcca tgtgcacccg     120 ttctggctcc atttcttgta ctttgtaacc atctccttct taggtttcgt gatcctgaaa     180
gccctgccca tgaagaccag catggtctcg aggcccatag accttgacct gatcttcacc     240
tcggtgtcgg ccaccacggt gtcgagcatg gtggccgtgg agatggagtc cttctccaac     300
ccccagctcc tactcctgac catccttatg ctcctcggcg gcgaggtgtt caccagcatg     360
cttggccttt actttaccta catcaagtcc aagaagaaag aagccccca tgaccatggt     420 gatggtggtg gcaaagtcga accagcaccg tctagcctag agctccctgc taccaccttc     480
atggacgata gcactgcaca gaaccagatg gagcaagggt tcaacaagga gcagccccga     540 tacgccgag ccttcctcac caggttgctt ctgttcatag tgctgggcta tcacgtggtg     600
gtgcacctcg ccggctactc cctgatgctg ctctacctga gcgtcgtctc cggcgcaagg     660
```

```
gctgtgctcg ccggcaaggg gatcagcctg cacaccttct ccgtattcac cgtcgtctcg      720
acattcgcca atggtggctt cgtgccgaac aacgaaggga tggtcgtctt ccggtccttc      780
ccgggcctcc tgctcctcgt catgccgcac gtcctcctcg gcaacacgct cttccctgtc      840
ttcctcaggc tggccatctg ggctctccgg agggtcacca ggaggcccga gctcggccag      900
ctgcagagca tcggctatgg tcacctgcta cgagccggc acacctgctt cttggctttc       960
accgtggcca cgttcgtgct ggcgcagctg tcgctcttct gcgccatgga gtggggctcc     1020
aacgggctgc acgggctcac cgccgcgcag aagctcgttg cggcactgtt catgtcggtc     1080
aactctaggc acaccggcga gatggtcgtg gacctttcca ccatgtcgtc agccgttgtg     1140
gtgctctacg tggtcatgat gtacctacca ccttacacta catttctacc agtggaagac     1200
gacagtgacc aacaagtggg agcagatcag caccaccaga aaagggtaac aagcatatgg     1260
cggaagctgc tcatgtcgcc gctctcgttc ttggccatct tcatcgccgt cgtgtgcatc     1320
acggagcggc ggcagatctc cgatgacccc ctcaacttca cgtcctcaa catcaccgtc      1380 gaggttatca gtgcgtacgg aaacgtgggg tttagcaccg ggtacagctg tgcccggcag     1440
gtgactgccg acggcggctg cagggatacg tgggttggct tctctgggaa gtggagctgg     1500
caagggaagc tggttctcat tgctgtcatg ttctacggca gactcaagaa gttcggcatg     1560
catggtggcg aggcatggag gatagtataa cctagtagca gactgcatat ttctcaatga     1620
tctctcttca gacagagact agctacatct cgctctagtc taaaaccatc tgaacttatt     1680
ttcattatgc aagtacct                                                  1698

<210> SEQ ID NO 21
<211> LENGTH: 1663
<212> TYPE: DNA
<213> ORGANISM: Triticum turgidum

<400> SEQUENCE: 21
agaagtctct agaatacttg cagtagaaat gggctctttg ctgcatgtct ccttcagtgc       60
cactcaacat agcaagcttc atcgggctta ccaactcctg tttttccatg tgcacccgtt      120
ctggctccag ctcttgtact ttgtatccat ctccttcttc ggcttcgtga tcctcaaagc      180
cctgcccatg aagaccggca tgcccatgga cctggacctg atctttacgt cagtatcggc      240
gacgacggtg tcgagcatgg tggctgtgga gatggagtcc ttctccaacc cccagctcct      300
actcctgacc ctcctcatgc tcctcggcgg cgaggtgttc acgagcatgc ttggcctgca      360
cttcacctac ctcaagtcca agacgaaaga agcacaagcc cccacgagc atgacgatgc       420 tgacaaaggc aaaccagcac catcatctag cctacagctc accgctacca cctgcatgga      480
tgatgtcaat cgtgtggagc aagggtttaa ggaccagccc cgttacgatc gtgccttcct      540
caccaggttg ctcttgttca tagtgctggg ctatcacgtg gtggtgcacc tcgccggcta      600
ctccctgatg ctggtctacc tgagcgtcgt ctccggcgcg agggctgtgc tcgccggcaa      660
ggggatcagc ctgcacacct tctccgtctt caccgtcgtc tcgacgttcg ccaacggtgg      720
cttcatgccc aacaatgaag agatggtcgc ctttcggtcc ttcccgggcc tcctgctcct      780
cgtcatgccg cacgtactcc tcggcaacac gctcttccct gtcttcctca ggctggccat      840
ctgggctctc cggagggtca ccaggaggcc cgagctcggc gagctgcaga gcatcggcta      900
cgaccacctg ctgacgagcc ggcacacctg cttcttggct ttcactgtgg ccatgttcgt      960
gctggcgcag ctgtcgctct tctgcgcaat ggagtgggc tccgacgggc tgcatgggct     1020
caccgccgcg cagaagctcg tcacggcact gttcatgtcg gtcaactcca ggcacacagg     1080
```

| | |
|---|---|
| cgagatggtc gtggaccttt ccacggtgtc gtcagccgtt gtggtgctct acgtggtcat | 1140 |
| gatgtaccta ccaccttaca ctacatttct accagtggaa gacgacagcg accaacaagt | 1200 |
| gggagcagat cagcaccacc agaaaagggt aacaatcata tggcggaagc tgctcatgtc | 1260 |
| accgctctcg tgcttggcca tcttcatcgc tgtcgtgtgc atcacggagc ggcggcagat | 1320 |
| ctccgatgac cccctcaact tcaaagtcct caacatcacc gtcgaggtta tcagtgcgta | 1380 |
| cggaaacgtg gggtttagca ccgggtacag ctgtggccgg caggtgacgc ccgacggcgg | 1440 |
| ctgcagggat acgtgggttg gcttctctgg gaagtggagc tggcaaggga agctggttct | 1500 |
| cattgctgtc atgttctacg gcaggctcaa gaagttcagc atgcatggtg gcgaggcatg | 1560 |
| gatgatagta taacctagta gcagactgca tatttctcaa tgatctctct tcagacagag | 1620 |
| actagctaca tctcgctcta gtcaaaaacc atctgaacat att | 1663 |

<210> SEQ ID NO 22
<211> LENGTH: 1698
<212> TYPE: DNA
<213> ORGANISM: Triticum aestivum

<400> SEQUENCE: 22

| | |
|---|---|
| aggccaagaa stctctacaa tacttaccaa cgaatgggtt ctctgcatgt ctcctgcagt | 60 |
| accactcaac atagcaagct tcagagggtt taccaactcc tgttttttcca tgtgcacccg | 120 |
| ttctggctcc atttcttgta ctttgtaacc atctccttct taggtttcgt gatcctgaaa | 180 |
| gccctgccca tgaagaccag catggtctcg aggcccatag accttgacct gatcttcacc | 240 |
| tcggtgtcgg ccaccacggt gtcgagcatg gtggccgtgg agatggagtc cttctccaac | 300 |
| ccccagctcc tactcctgac catccttatg ctcctcggcg gcgaggtgtt caccagcatg | 360 |
| cttggccttt actttaccta catcaagtcc aagaagaaag aagcccccca tgaccatggt | 420 |
| gatggtggtg gcaaagtcga accagcaccg tctagcctag agctccctgc taccaccttc | 480 |
| atggacgata gcactgcaca gaaccagatg gagcaagggt tcaacaagga gcagccccga | 540 |
| tacgccgag ccttcctcac caggttgctc tgttcatag tgctgggcta tcacgtggtg | 600 |
| gtgcacctcg ccggctactc cctgatgctg ctctacctga gcgtcgtctc cggcgcaagg | 660 |
| gctgtgctcg ccggcaaggg gatcagcctg cacaccttct ccgtattcac cgtcgtctcg | 720 |
| acattcgcca atggtggctt cgtgccgaac aacgaaggga tggtcgtctt ccggtccttc | 780 |
| ccgggcctcc tgctcctcgt catgccgcac gtcctcctcg gcaacacgct cttccctgtc | 840 |
| ttcctcaggc tggccatctg ggctctccgg agggtcacca ggaggcccga gctcggccag | 900 |
| ctgcagagca tcggctatgg tcacctgctg acgagccggc acacctgctt cttggctttc | 960 |
| accgtggcca cgttcgtgct ggcgcagctg tcgctcttct gcgccatgga gtggggctcc | 1020 |
| aacgggctgc acgggctcac cgccgcgcag aagctcgttg cggcactgtt catgtcggtc | 1080 |
| aactctaggc acaccggcga gatggtcgtg gaccttttcca ccatgtcgtc agccgttgtg | 1140 |
| gtgctctacg tggtcatgat gtacctacca ccttacacta catttctacc agtggaagac | 1200 |
| gacagtgacc aacaagtggg agcagatcag caccaccaga aaagggtaac aagcatatgg | 1260 |
| cggaagctgc tcatgtcgcc gctctcgttc ttggccatct tcatcgccgt cgtgtgcatc | 1320 |
| acggagcggc ggcagatctc cgatgacccc ctcaacttca cgtcctcaa catcaccgtc | 1380 |
| gaggttatca gtgcgtacgg aaacgtgggg tttagcaccg ggtacagctg tgcccggcag | 1440 |
| gtgactgccg acgcggctg cagggatacg tgggttggct tctctgggaa gtggagctgg | 1500 |
| caagggaagc tggttctcat tgctgtcatg ttctacggca gactcaagaa gttcggcatg | 1560 |

| | |
|---|---|
| catggtggcg aggcatggag gatagtataa cctagtagca gactgcatat ttctcaatga | 1620 |
| tctctcttca gacagagact agctacatct cgctctagtc taaaaccatc tgaacttatt | 1680 |
| ttcattatgc aagtacct | 1698 |

<210> SEQ ID NO 23
<211> LENGTH: 1660
<212> TYPE: DNA
<213> ORGANISM: Triticum aestivum

<400> SEQUENCE: 23

| | |
|---|---|
| gaagtctcta gaatacttgc agtagaaatg ggctctttgc tgcatgtctc cttcagtgcc | 60 |
| actcaacata gcaagcttca tcgggcttac caactcctgt ttttccatgt gcacccgttc | 120 |
| tggctccagc tcttgtactt tgtatccatc tccttcttcg gcttcgtgat cctcaaagcc | 180 |
| ctgcccatga agaccggcat gcccatggac ctggacctga tctttacgtc agtatcggcg | 240 |
| acgacggtgt cgagcatggt ggctgtggag atggagtcct tctccaaccc ccagctccta | 300 |
| ctcctgaccc tcctcatgct cctcggcggc gaggtgttca cgagcatgct tggcctgcac | 360 |
| ttcacctacc tcaagtccaa gacgaaagaa gcacaagccc ccacgagca tgacgatgct | 420 |
| gacaaaggca aaccagcacc atcatctagc ctacagctca ccgctaccac ctgcatggat | 480 |
| gatgtcaatc gtgtggagca agggtttaag gaccagcccc gttacgatcg tgccttcctc | 540 |
| accaggttgc tcttgttcat agtgctgggc tatcacgtgg tggtgcacct cgccggctac | 600 |
| tccctgatgc tggtctacct gagcgtcgtc tccggcgcga gggctgtgct cgccggcaag | 660 |
| gggatcagcc tgcacacctt ctccgtcttc accgtcgtct cgacgttcgc caacggtggc | 720 |
| ttcatgccca acaatgaaga gatggtcgcc tttcggtcct tcccgggcct cctgctcctc | 780 |
| gtcatgccgc acgtactcct cggcaacacg ctcttccctg tcttcctcag gctggccatc | 840 |
| tgggctctcc ggagggtcac caggaggccc gagctcggcg agctgcagag catcggctac | 900 |
| gaccacctgc tgacgagccg gcacacctgc ttcttggctt tcactgtggc catgttcgtg | 960 |
| ctggcgcagc tgtcgctctt ctgcgcaatg gagtggggct ccgacgggct gcatgggctc | 1020 |
| accgccgcgc agaagctcgt cacggcactg ttcatgtcgg tcaactccag gcacacaggc | 1080 |
| gagatggtcg tggaccttc cacggtgtcg tcagccgttg tggtgctcta cgtggtcatg | 1140 |
| atgtacctac caccttacac tacatttcta ccagtggaag acgacagcga ccaacaagtg | 1200 |
| ggagcagatc agcaccacca gaaaagggta acaatcatat ggcggaagct gctcatgtca | 1260 |
| ccgctctcgt gcttggccat cttcatcgct gtcgtgtgca tcacggagcg gcggcagatc | 1320 |
| tccgatgacc cctcaacttt caaagtcctc aacatcaccg tcgaggttat cagtgcgtac | 1380 |
| ggaaacgtgg ggtttagcac cgggtacagc tgtggccggc aggtgacgcc cgacggcggc | 1440 |
| tgcagggata cgtgggttgg cttctctggg aagtggagct ggcaagggaa gctggttctc | 1500 |
| attgctgtca tgttctacgg caggctcaag aagttcagca tgcatggtgg cgaggcatgg | 1560 |
| atgatagtat aacctagtag cagactgcat atttctcaat gatctctctt cagacagaga | 1620 |
| ctagctacat ctcgctctag tcaaaaacca tctgaacata | 1660 |

<210> SEQ ID NO 24
<211> LENGTH: 1702
<212> TYPE: DNA
<213> ORGANISM: Triticum aestivum

<400> SEQUENCE: 24

| | |
|---|---|
| agaacaggcc aagaagtctc tacacaactt acagtagaaa tgggttcttt gcatgtctcc | 60 |

```
tcgagtgcca ctcaacatag caagcttgag agggcttacc aactcctggt tttccatgtg    120
cacccgttct ggctccagct cttgtacttt gtatccatct ccttcttcgg tttggtgatc    180
ctcaaagccc tccccatgaa gaccagcacg gtcccgaggc ccatggattt ggacctgatc    240
ttcacgtcgg tctcggcgac cacggtgtcg agcatggtgg ccgtggagat ggagtccttc    300
tccaaccccc agctcctact cctgaccctc tcatgctcc tcggcggcga ggtgttcacg     360
agcatgcttg gcctgcactt cacctacgtc aagtccaaga agaaagaagc acaagcaccc    420
cacgaccatg acgatggtga caaaggcaaa ccagcaccat catctagcct agagctcgct    480
gttaccaccg gcatggatga cgtcgatcgt gtggagcaag ggtttaagga ccagccccgt    540
tacgatcgcg ccttcctcac caggttgctt ctgttcatag tgctgggcta tcacgtggtg    600
gtgcacctcg ccggctactc cttgatgctg gtctacctga gcgtggtctc cggcgcgagg    660
gctgtgctca ccggcaaggg gatcagcctg cacaccttct ccgtcttcac cgtcgtctcg    720
acgttcgcca actgcggctt cgtcccgaac aacgaaggga tgatcgcctt ccggtccttc    780
ccgggcctcc tgctcctagt catgccgcac gtcctcctcg gcaacacact cttccccgtc    840
ttcctcaggc tggccatctg ggctctccgg agagtcacca ggaggcccga gctcggtgag    900
ctgaggagca tcggctacga ccacctgctg acgagccggc acacgtggtt cttggctttc    960
accgtggcgc gttcgtgct agcgcagctg tcgctcttct cgccatggag gtggggctcc    1020
aacgggctgc gcgggctcac cgccgtgcag aagctcgttg cgggactgtt catgtcggtc    1080
aactccaggc acaccggtga gatggtggtg gacctttcca ccgtgtcgtc ggccctcgtg    1140
gtgctctatg tggtcatgat gtacctacca ccttacacta catttctacc agtggaagac    1200
gacagtgacc aacaagtggg agcagatcag cgcgaccaga aaaggataac aagcatgtgg    1260
cggaagctgc tcatgtcgcc gctctcgtgc ttggccatct tcatcgccgt ggtgtgcatc    1320
acggagcggg gcagatctc cgatgacccc ctcaacttca acgtcctcaa catcaccgtc     1380
gaggttatca gtgcgtacgg aaacgtgggg ttcagcaccg ggtacagctg tggccggcag    1440
gtgacgcccg acggcggctg cagggacacg tgggttggct tctctgggaa gtggagttgg    1500
caagggaagc tggctctcat tgctgtcatg ttctacggca ggctcaagaa gttcagcatg    1560
catggtggcg aggcatggag gatagtataa cctagtagca gactgcatat ttctcaatga    1620
tctctcttca gacagagact agctacatct cgctctagcc taaaaccatc tgaacatatt    1680
tccattatgc cgagtacctc aa                                            1702

<210> SEQ ID NO 25
<211> LENGTH: 1431
<212> TYPE: DNA
<213> ORGANISM: Triticum turgidum

<400> SEQUENCE: 25
agaagtctct agaatacttg cagtagaaat gggctctttg ctgcatgtct cctcgagtgc     60
cactcaacat agcaagcttc atcgggctta ccaactcctg ttttttccatg tgcacccgtt   120 ctggctccag ctcttgtact ttgtatccat ctcctccttc ggtttcgtga tcctcaaagc    180
cctgcccatg aagaccggca tgcccatgga cctggacctg atcttcacgt cggtatcggc    240
gacgacggtg tcgagcatgg tggctgtgga gatggagtcc ttctccaacc ccagctcct    300 actcctcacc ctcctcatgc tcctcggcgg cgaggtgttc accagcatgc ttggcctgca    360
cttcacctac ctcaagtcca agaagaaaga agcacaagcc cccacgagc atgacgatgc    420 tgacaaaggc aaaccagcac catcatctag cctacagctc accgctacca cctgcatgga    480
```

```
tgatgtcgat cgtgtggagc aagggtttaa ggaccagccc cgttacgatc gtgccttcct    540
caccaggttg ctcatgttca tagtgcttgg ctatcacgtg gtggtgcacc tcgccggcta    600
ctccttgatg ctggtctacc tgagcgtcgt ctccggcgca agggctgtgc tcgccggcaa    660
ggggatcagc ctgcacacct tctccgcctt caccgtcgtc tcgacattcg ccaacggtgg    720
cttcgcgccg aacaacgaag ggatggtcgc cttccggtcc ttcccgggcc tcctgctcct    780
cgtcatgccg cacgtcctcc tcggcaacac gctcttccct gttttcctca gctcggcggt    840
ggcgccgtac gtgaggggc cacaccctgg agacgtgtgc tgcctcttca gacatgccac    900
cacaccttaa ggtacctacc accttacact acatttctac cagtggaaga cgacagtgac    960
caacaagtgg gagcagatca gcaccaccag aaaagggtaa caagcatatg gcggaagctg   1020
ctcatgtcgc cgctctcgtt cttggccatc ttcatcgccg tcgtgtgcat cacggagcgg   1080
cggcagatct ccgatgaccc cctcaacttc aacgtcctca acatcaccgt cgaggttatc   1140
agtgcgtacg gaaacgtggg gtttagcacc gggtacagct gtgcccggca ggtgactgcc   1200
gacggcggct gcagggatac gtgggttggc ttctctggga agtggagctg caagggaag   1260 ctggttctca ttgctgtcat gttctacggc agactcaaga agttcggcat gcatggtggc   1320
gaggcatgga ggatagtata acctagtagc agactgcata tttctcaatg atctctcttc   1380
agacagagac tagctacatc tcgctctagt caaaaaccat ctgaacatat t            1431
```

<210> SEQ ID NO 26
<211> LENGTH: 554
<212> TYPE: PRT
<213> ORGANISM: Oryza sativa

<400> SEQUENCE: 26

```
Met Ser Ser Leu Asp Ala Thr Thr Pro Arg Tyr Asp Glu Phe Lys Arg
1               5                  10                  15

Ile Tyr His Leu Phe Leu Phe His Ala His Pro Phe Trp Leu Gln Leu
            20                  25                  30

Leu Tyr Phe Leu Phe Ile Ser Leu Leu Gly Phe Leu Met Leu Lys Ala
        35                  40                  45

Leu Pro Met Lys Thr Ser Met Val Pro Arg Pro Met Asp Leu Asp Leu
    50                  55                  60

Ile Phe Thr Ser Val Ser Ala Thr Thr Val Ser Ser Met Val Ala Val
65                  70                  75                  80

Glu Met Glu Ser Phe Ser Asn Ser Gln Leu Leu Leu Ile Thr Leu Leu
                85                  90                  95

Met Leu Leu Gly Gly Glu Val Phe Thr Ser Ile Leu Gly Leu Tyr Phe
            100                 105                 110

Thr Asn Ala Lys Tyr Ser Ser Lys Met Ile Ala Thr Leu Pro Asp Asp
        115                 120                 125

Asp Asp His Gly Gly Ser Gly Lys Pro Pro Pro Thr Thr Ser Pro
    130                 135                 140

Ser Ser Thr Leu Val Glu Leu Glu Leu Ala Pro Pro Met Asp Val Val
145                 150                 155                 160

Val Val Asn Pro Thr Thr Thr Ala Thr Thr His Asp Glu Val Glu Leu
                165                 170                 175

Gly Leu Gly Arg Arg Asn Lys Arg Gly Cys Thr Cys Thr Thr Thr His
            180                 185                 190

Thr Ser Ser Ser Ser Ala Ser Lys Thr Thr Thr Thr Arg Leu Leu
        195                 200                 205
```

```
Met Phe Val Val Met Gly Tyr His Ala Val His Val Ala Gly Tyr
210                 215                 220

Thr Ala Ile Val Val Tyr Leu Ser Ala Val Gly Ala Gly Ala Val
225                 230                 235                 240

Val Ala Gly Lys Gly Ile Ser Ala His Thr Phe Ala Ile Phe Thr Val
                245                 250                 255

Val Ser Thr Phe Ala Asn Cys Gly Phe Val Pro Thr Asn Glu Gly Met
                260                 265                 270

Val Ser Phe Arg Ser Phe Pro Gly Leu Leu Leu Val Met Pro His
                275                 280                 285

Val Leu Leu Gly Asn Thr Leu Phe Pro Val Phe Leu Arg Leu Ala Ile
                290                 295                 300

Ala Ala Leu Glu Arg Val Thr Gly Trp Pro Glu Leu Gly Glu Leu Leu
305                 310                 315                 320

Ile Arg Arg Arg Gly Gly Glu Gly Tyr His His Leu Leu Pro
                325                 330                 335

Ser Ser Arg Thr Arg Phe Leu Ala Leu Thr Val Ala Val Leu Val Val
                340                 345                 350

Ala Gln Leu Ala Leu Phe Cys Ala Met Glu Trp Gly Ser Asp Gly Leu
                355                 360                 365

Arg Gly Leu Thr Ala Gly Gln Lys Leu Val Gly Ala Leu Phe Met Ala
370                 375                 380

Val Asn Ser Arg His Ser Gly Glu Met Val Leu Asp Leu Ser Thr Val
385                 390                 395                 400

Ser Ser Ala Val Val Leu Tyr Val Val Met Met Tyr Leu Pro Pro
                405                 410                 415

Tyr Thr Thr Phe Val Pro Val Gln Asp Lys His Gln Gln Thr Gly Ala
                420                 425                 430

Gln Ser Gly Gln Glu Gly Ser Ser Ser Ser Ile Trp Gln Lys Leu
                435                 440                 445

Leu Met Ser Pro Leu Ser Cys Leu Ala Ile Phe Ile Val Ile Cys
450                 455                 460

Ile Thr Glu Arg Arg Gln Ile Ala Asp Asp Pro Ile Asn Tyr Ser Val
465                 470                 475                 480

Leu Asn Ile Val Val Glu Val Ile Ser Ala Tyr Gly Asn Val Gly Phe
                485                 490                 495

Ser Thr Gly Tyr Ser Cys Ala Arg Gln Val Arg Pro Asp Gly Ser Cys
                500                 505                 510

Arg Asp Leu Trp Val Gly Phe Ser Gly Lys Trp Ser Lys Gln Gly Lys
                515                 520                 525

Leu Thr Leu Met Ala Val Met Phe Tyr Gly Arg Leu Lys Lys Phe Ser
530                 535                 540

Leu His Gly Gly Gln Ala Trp Lys Ile Glu
545                 550

<210> SEQ ID NO 27
<211> LENGTH: 500
<212> TYPE: PRT
<213> ORGANISM: Oryza sativa

<400> SEQUENCE: 27

Met Pro Thr Ser Arg Arg Ala Leu Ala Gly Gly Ala Leu Ser Met His
1               5                   10                  15

Val Ala Tyr Phe Leu Ala Ile Ser Cys Leu Gly Tyr Gly Leu Leu Gly
                20                  25                  30
```

-continued

```
Val Leu Lys Val Arg Glu Pro Gly Ala Ala Pro Arg Ile Asp Arg
         35                  40                  45

Phe Phe Thr Ala Val Ser Ala Thr Val Ser Ser Met Ser Thr Val
 50                  55                  60

Glu Met Glu Val Phe Ser Asn Gly Gln Leu Val Val Leu Thr Val Leu
 65                  70                  75                  80

Met Leu Leu Gly Gly Glu Val Phe Val Ser Leu Val Gly Leu Ala Ser
                 85                  90                  95

Lys Trp Ser Lys Leu Arg Ser Asp Ala Met Asp Arg Ser Arg Arg Val
                 100                 105                 110

Glu Ser His Gly Asp Val Ala Leu Ala Asp Ile Asp Gly Gly Asp Val
                 115                 120                 125

Glu Asn Pro Thr Ser Ser Gly Glu Glu Ala Ala Ser Arg Arg Arg Pro
 130                 135                 140

Met Asp Ala Asp Thr Leu Arg His Asn Ala Val Arg Ala Leu Phe Tyr
 145                 150                 155                 160

Ile Val Leu Ala Ile Phe Ala Val Val His Val Val Gly Ala Val Ala
                 165                 170                 175

Val Ala Ala Tyr Val Leu Ala Ser Pro Gly Ala Arg Arg Thr Leu Gly
                 180                 185                 190

Asp Lys Ser Leu Asn Thr Trp Thr Phe Ala Val Phe Thr Thr Val Ser
                 195                 200                 205

Thr Phe Ser Asn Cys Gly Phe Met Pro Thr Asn Glu Asn Met Val Val
 210                 215                 220

Phe Lys Arg Asp Ala Pro Leu Gln Leu Leu Val Pro Gln Val Leu
 225                 230                 235                 240

Ala Gly Asn Thr Leu Phe Ala Pro Leu Leu Ala Ala Cys Val Trp Ala
                 245                 250                 255

Ala Ala Ala Thr Arg Arg Glu Glu Leu Val Glu Met Ala Arg Glu
                 260                 265                 270

Gly Gly Arg Ala Ala Ala Ala Gly Tyr Ala His Leu Met Pro Ala Arg
                 275                 280                 285

Arg Cys Trp Met Leu Ala Ala Thr Val Ala Ala Phe Val Ala Val Leu
 290                 295                 300

Met Ala Leu Val Cys Gly Met Glu Trp Gly Gly Ala Leu Gln Gly Met
 305                 310                 315                 320

Ser Pro Trp Glu Lys Val Val Asn Ala Leu Phe Leu Ala Val Asn Ala
                 325                 330                 335

Arg His Thr Gly Glu Ser Thr Val Asp Leu Ser Ile Leu Ala Pro Ala
                 340                 345                 350

Ile Leu Val Leu Phe Val Leu Met Met Tyr Leu Pro Pro Tyr Thr Thr
                 355                 360                 365

Trp Phe Pro Phe Glu Glu Asn Ser Thr Thr Lys Asp Ser Asn Ala Glu
 370                 375                 380

Asn Gln Gly Ile Arg Leu Leu Glu Ser Thr Leu Leu Ser Gln Leu Ser
 385                 390                 395                 400

Tyr Leu Thr Ile Phe Val Ile Ala Ile Cys Ile Thr Glu Arg Arg Lys
                 405                 410                 415

Leu Lys Glu Asp Pro Leu Asn Phe Ser Val Leu Ser Ile Val Val Glu
                 420                 425                 430

Val Val Ser Ala Tyr Gly Asn Val Gly Phe Ser Met Gly Tyr Ser Cys
                 435                 440                 445

Ser Arg Gln Ile Asn Pro Asp His Leu Cys Thr Asp Lys Trp Thr Gly
 450                 455                 460
```

```
Phe Val Gly Arg Trp Ser Asp Ser Gly Lys Leu Ile Leu Ile Phe Val
465                 470                 475                 480

Met Phe Phe Gly Arg Leu Lys Lys Phe Ser Met Lys Gly Gly Lys Ala
            485                 490                 495

Trp Lys Leu Ser
            500

<210> SEQ ID NO 28
<211> LENGTH: 19
<212> TYPE: DNA
<213> ORGANISM: Artificial
<220> FEATURE:
<223> OTHER INFORMATION: Oligonucleotide primer

<400> SEQUENCE: 28
catccctacg ccactctgc                                              19

<210> SEQ ID NO 29
<211> LENGTH: 21
<212> TYPE: DNA
<213> ORGANISM: Artificial
<220> FEATURE:
<223> OTHER INFORMATION: Oligonucleotide primer

<400> SEQUENCE: 29
aatggtatct attccgaccc g                                           21

<210> SEQ ID NO 30
<211> LENGTH: 18
<212> TYPE: DNA
<213> ORGANISM: Artificial
<220> FEATURE:
<223> OTHER INFORMATION: Oligonucleotide primer

<400> SEQUENCE: 30
gcttgagacc ggcacagt                                               18

<210> SEQ ID NO 31
<211> LENGTH: 20
<212> TYPE: DNA
<213> ORGANISM: Artificial
<220> FEATURE:
<223> OTHER INFORMATION: Oligonucleotide primer

<400> SEQUENCE: 31
cgagaccttg agggtctaga                                             20

<210> SEQ ID NO 32
<211> LENGTH: 21
<212> TYPE: DNA
<213> ORGANISM: Artificial
<220> FEATURE:
<223> OTHER INFORMATION: Oligonucleotide primer

<400> SEQUENCE: 32
catcaccgtc gaggttatca g                                           21

<210> SEQ ID NO 33
<211> LENGTH: 17
<212> TYPE: DNA
<213> ORGANISM: Artificial
<220> FEATURE:
<223> OTHER INFORMATION: Oligonucleotide primer

<400> SEQUENCE: 33
```

-continued ttgaggtact cggcata                                                    17

<210> SEQ ID NO 34
<211> LENGTH: 21
<212> TYPE: DNA
<213> ORGANISM: Artificial
<220> FEATURE:
<223> OTHER INFORMATION: Oligonucleotide primer

<400> SEQUENCE: 34
catcaccgtc gaggttatca g                                               21

<210> SEQ ID NO 35
<211> LENGTH: 17
<212> TYPE: DNA
<213> ORGANISM: Artificial
<220> FEATURE:
<223> OTHER INFORMATION: Oligonucleotide primer

<400> SEQUENCE: 35
ttgaggtact cggcata                                                    17

<210> SEQ ID NO 36
<211> LENGTH: 24
<212> TYPE: DNA
<213> ORGANISM: Artificial
<220> FEATURE:
<223> OTHER INFORMATION: Oligonucleotide primer

<400> SEQUENCE: 36
gctgtcaacg atacgctacg taac                                            24

<210> SEQ ID NO 37
<211> LENGTH: 22
<212> TYPE: DNA
<213> ORGANISM: Artificial
<220> FEATURE:
<223> OTHER INFORMATION: Oligonucleotide primer

<400> SEQUENCE: 37
cgctacgtaa cggcatgaca gt                                              22

<210> SEQ ID NO 38
<211> LENGTH: 21
<212> TYPE: DNA
<213> ORGANISM: Artificial
<220> FEATURE:
<223> OTHER INFORMATION: Oligonucleotide primer

<400> SEQUENCE: 38
cgactggagc acgaggacac t                                               21

<210> SEQ ID NO 39
<211> LENGTH: 21
<212> TYPE: DNA
<213> ORGANISM: Artificial
<220> FEATURE:
<223> OTHER INFORMATION: Oligonucleotide primer

<400> SEQUENCE: 39
ctggagcacg aggacactga c                                               21

<210> SEQ ID NO 40
<211> LENGTH: 19
<212> TYPE: DNA
<213> ORGANISM: Artificial
<220> FEATURE:

<223> OTHER INFORMATION: Oligonucleotide primer

<400> SEQUENCE: 40
tcatagtgct gggctatca                                                        19

<210> SEQ ID NO 41
<211> LENGTH: 19
<212> TYPE: DNA
<213> ORGANISM: Artificial
<220> FEATURE:
<223> OTHER INFORMATION: Oligonucleotide primer

<400> SEQUENCE: 41
tggtcgcctt ccggtcttt                                                        19

<210> SEQ ID NO 42
<211> LENGTH: 18
<212> TYPE: DNA
<213> ORGANISM: Artificial
<220> FEATURE:
<223> OTHER INFORMATION: Oligonucleotide primer

<400> SEQUENCE: 42
tgagcctgcc gtagaaca                                                         18

<210> SEQ ID NO 43
<211> LENGTH: 18
<212> TYPE: DNA
<213> ORGANISM: Artificial
<220> FEATURE:
<223> OTHER INFORMATION: Oligonucleotide primer

<400> SEQUENCE: 43
ccagagaagc caacccac                                                         18

<210> SEQ ID NO 44
<211> LENGTH: 18
<212> TYPE: DNA
<213> ORGANISM: Artificial
<220> FEATURE:
<223> OTHER INFORMATION: Oligonucleotide primer

<400> SEQUENCE: 44
cacgacggct gacgacac                                                         18

<210> SEQ ID NO 45
<211> LENGTH: 17
<212> TYPE: DNA
<213> ORGANISM: Artificial
<220> FEATURE:
<223> OTHER INFORMATION: Oligonucleotide primer

<400> SEQUENCE: 45
ctccggagag cccagat                                                          17

<210> SEQ ID NO 46
<211> LENGTH: 21
<212> TYPE: DNA
<213> ORGANISM: Artificial
<220> FEATURE:
<223> OTHER INFORMATION: Oligonucleotide primer

<400> SEQUENCE: 46
cgtgatagcc cagcactatg a                                                     21

<210> SEQ ID NO 47

```
<211> LENGTH: 21
<212> TYPE: DNA
<213> ORGANISM: Artificial
<220> FEATURE:
<223> OTHER INFORMATION: Oligonucleotide primer

<400> SEQUENCE: 47
aggccaagaa gtctctacac a                                             21

<210> SEQ ID NO 48
<211> LENGTH: 19
<212> TYPE: DNA
<213> ORGANISM: Artificial
<220> FEATURE:
<223> OTHER INFORMATION: Oligonucleotide primer

<400> SEQUENCE: 48
aggtactcgg cataatgaa                                                19

<210> SEQ ID NO 49
<211> LENGTH: 18
<212> TYPE: DNA
<213> ORGANISM: Artificial
<220> FEATURE:
<223> OTHER INFORMATION: Oligonucleotide primer

<400> SEQUENCE: 49
argccaagaa stctctac                                                 18

<210> SEQ ID NO 50
<211> LENGTH: 18
<212> TYPE: DNA
<213> ORGANISM: Artificial
<220> FEATURE:
<223> OTHER INFORMATION: Oligonucleotide primer

<400> SEQUENCE: 50
aggtacttgc ataatgaa                                                 18

<210> SEQ ID NO 51
<211> LENGTH: 20
<212> TYPE: DNA
<213> ORGANISM: Artificial
<220> FEATURE:
<223> OTHER INFORMATION: Oligonucleotide primer

<400> SEQUENCE: 51
agaastctct adaatacttg                                               20

<210> SEQ ID NO 52
<211> LENGTH: 21
<212> TYPE: DNA
<213> ORGANISM: Artificial
<220> FEATURE:
<223> OTHER INFORMATION: Oligonucleotide primer

<400> SEQUENCE: 52
aatatgttca gatggttttt g                                             21

<210> SEQ ID NO 53
<211> LENGTH: 21
<212> TYPE: DNA
<213> ORGANISM: Artificial
<220> FEATURE:
<223> OTHER INFORMATION: Oligonucleotide primer

<400> SEQUENCE: 53
```
aggccaagaa gtctctacac a                                             21

<210> SEQ ID NO 54
<211> LENGTH: 17
<212> TYPE: DNA
<213> ORGANISM: Artificial
<220> FEATURE:
<223> OTHER INFORMATION: Oligonucleotide primer

<400> SEQUENCE: 54
ttgaggtact cggcata                                                  17

<210> SEQ ID NO 55
<211> LENGTH: 26
<212> TYPE: DNA
<213> ORGANISM: Artificial
<220> FEATURE:
<223> OTHER INFORMATION: Oligonucleotide primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 55
gtgctgatgc tgctgggngg ngargt                                        26

<210> SEQ ID NO 56
<211> LENGTH: 24
<212> TYPE: DNA
<213> ORGANISM: Artificial
<220> FEATURE:
<223> OTHER INFORMATION: Oligonucleotide primer

<400> SEQUENCE: 56
cctgcacacc ttctccgtct tcac                                          24

<210> SEQ ID NO 57
<211> LENGTH: 21
<212> TYPE: DNA
<213> ORGANISM: Artificial
<220> FEATURE:
<223> OTHER INFORMATION: Oligonucleotide primer

<400> SEQUENCE: 57
cctaccacct tacactacat t                                             21

<210> SEQ ID NO 58
<211> LENGTH: 20
<212> TYPE: DNA
<213> ORGANISM: Artificial
<220> FEATURE:
<223> OTHER INFORMATION: Oligonucleotide primer

<400> SEQUENCE: 58
tttccgtacg cactgataac                                               20

<210> SEQ ID NO 59
<211> LENGTH: 20
<212> TYPE: DNA
<213> ORGANISM: Artificial
<220> FEATURE:
<223> OTHER INFORMATION: Oligonucleotide primer

<400> SEQUENCE: 59

```
tcagccgagc gggaaattgt                                                    20
```

<210> SEQ ID NO 60
<211> LENGTH: 18
<212> TYPE: DNA
<213> ORGANISM: Artificial
<220> FEATURE:
<223> OTHER INFORMATION: Oligonucleotide primer

<400> SEQUENCE: 60

```
cctctctgcg ccaatcgt                                                      18
```

<210> SEQ ID NO 61
<211> LENGTH: 19
<212> TYPE: DNA
<213> ORGANISM: Artificial
<220> FEATURE:
<223> OTHER INFORMATION: Oligonucleotide primer

<400> SEQUENCE: 61

```
agttctgcag tcgcttgta                                                     19
```

<210> SEQ ID NO 62
<211> LENGTH: 20
<212> TYPE: DNA
<213> ORGANISM: Artificial
<220> FEATURE:
<223> OTHER INFORMATION: Oligonucleotide primer

<400> SEQUENCE: 62

```
ggcctggttt gcatagtatc                                                    20
```

<210> SEQ ID NO 63
<211> LENGTH: 19
<212> TYPE: DNA
<213> ORGANISM: Artificial
<220> FEATURE:
<223> OTHER INFORMATION: Oligonucleotide primer

<400> SEQUENCE: 63

```
tccttacagc gcgagtgag                                                     19
```

<210> SEQ ID NO 64
<211> LENGTH: 20
<212> TYPE: DNA
<213> ORGANISM: Artificial
<220> FEATURE:
<223> OTHER INFORMATION: Oligonucleotide primer

<400> SEQUENCE: 64

```
caagattcgg gtctgcgtat                                                    20
```

<210> SEQ ID NO 65
<211> LENGTH: 332
<212> TYPE: DNA
<213> ORGANISM: Triticum monococcum

<400> SEQUENCE: 65

```
catcaccgtc gaggttatca gtgcgtacgg aaacgtgggg tttagcaccg ggtacagctg         60
cggccggcag gtgacgcctg acgacggcga ctgcagggac acgtgggttg gcttctctgg        120
gaagtggagc tggcaaggga agctggctct cattgctgtc atgttctacg gcaggctcaa        180
gaagttcagc attcatggcg gccaggcatg gaggataata taacctagca gactacatat        240
ttctcaatga tctctcttca gacagagagt agctacatct cgctctagcc taaaaccacc        300
```

```
tgaacatatt ttcattatgc cgagtacctc aa                                   332
```

<210> SEQ ID NO 66
<211> LENGTH: 517
<212> TYPE: DNA
<213> ORGANISM: Triticum monococcum

<400> SEQUENCE: 66

```
catcaccgtc gaggttatca ggtaatcaac tagtagtaat taacaaaatg tagaagcaca     60
tgatcaattg caatttttt accatgcatg ataggtagat accattatat acaaaatctg    120
acttagctaa attgcaaatt cagtaaactt atatataggg attgcgacca ctataacgtg    180
tgtcattgtg tgagctgtgc ttgcagtgcg tacggaaacg tggggtttag caccgggtac    240
agctgcggcc ggcaggtgac gcctgacgac ggcgactgca gggacacgtg ggttggcttc    300
tctgggaagt ggagctggca agggaagctg gctctcattg ctgtcatgtt ctacggcagg    360
ctcaagaagt tcagcattca tggcggccag gcatggagga taatataacc tagcagacta    420
catatttctc aatgatctct cttcagacag agagtagcta catctcgctc tagcctaaaa    480
ccacctgaac atattttcat tatgccgagt acctcaa                             517
```

<210> SEQ ID NO 67
<211> LENGTH: 73
<212> TYPE: PRT
<213> ORGANISM: Triticum monococcum

<400> SEQUENCE: 67

```
Ile Thr Val Glu Val Ile Ser Ala Tyr Gly Asn Val Gly Phe Ser Thr
1               5                   10                  15

Gly Tyr Ser Cys Gly Arg Gln Val Thr Pro Asp Asp Gly Asp Cys Arg
            20                  25                  30

Asp Thr Trp Val Gly Phe Ser Gly Lys Trp Ser Trp Gln Gly Lys Leu
        35                  40                  45

Ala Leu Ile Ala Val Met Phe Tyr Gly Arg Leu Lys Lys Phe Ser Ile
    50                  55                  60

His Gly Gly Gln Ala Trp Arg Ile Ile
65                  70
```

<210> SEQ ID NO 68
<211> LENGTH: 23
<212> TYPE: DNA
<213> ORGANISM: Artificial
<220> FEATURE:
<223> OTHER INFORMATION: Oligonucleotide primer

<400> SEQUENCE: 68

```
gagtggggct ccgacgggct gaa                                             23
```

<210> SEQ ID NO 69
<211> LENGTH: 23
<212> TYPE: DNA
<213> ORGANISM: Artificial
<220> FEATURE:
<223> OTHER INFORMATION: Oligonucleotide primer

<400> SEQUENCE: 69

```
gccggccgtc cactgcggac tgc                                             23
```

<210> SEQ ID NO 70
<211> LENGTH: 20
<212> TYPE: DNA
<213> ORGANISM: Artificial

```
<220> FEATURE:
<223> OTHER INFORMATION: Oligonucleotide primer

<400> SEQUENCE: 70
atcgcatgat gcacgtagac                                              20

<210> SEQ ID NO 71
<211> LENGTH: 21
<212> TYPE: DNA
<213> ORGANISM: Artificial
<220> FEATURE:
<223> OTHER INFORMATION: Oligonucleotide primer

<400> SEQUENCE: 71
acatgcatgc ctacctaatg g                                            21

<210> SEQ ID NO 72
<211> LENGTH: 20
<212> TYPE: DNA
<213> ORGANISM: Artificial
<220> FEATURE:
<223> OTHER INFORMATION: Oligonucleotide primer

<400> SEQUENCE: 72
caaattacaa acgcacagcc                                              20

<210> SEQ ID NO 73
<211> LENGTH: 20
<212> TYPE: DNA
<213> ORGANISM: Artificial
<220> FEATURE:
<223> OTHER INFORMATION: Oligonucleotide primer

<400> SEQUENCE: 73
tttgtgccat tgtgtgtgtg                                              20

<210> SEQ ID NO 74
<211> LENGTH: 21
<212> TYPE: DNA
<213> ORGANISM: Artificial
<220> FEATURE:
<223> OTHER INFORMATION: Oligonucleotide primer

<400> SEQUENCE: 74
tttccatgtg cacccgttct g                                            21

<210> SEQ ID NO 75
<211> LENGTH: 24
<212> TYPE: DNA
<213> ORGANISM: Artificial
<220> FEATURE:
<223> OTHER INFORMATION: Oligonucleotide primer

<400> SEQUENCE: 75
cttgagcctg ccgtagaaca tgac                                         24

<210> SEQ ID NO 76
<211> LENGTH: 23
<212> TYPE: DNA
<213> ORGANISM: Artificial
<220> FEATURE:
<223> OTHER INFORMATION: Oligonucleotide primer

<400> SEQUENCE: 76
agaagtctct acacaactta cag                                          23
```

```
<210> SEQ ID NO 77
<211> LENGTH: 23
<212> TYPE: DNA
<213> ORGANISM: Artificial
<220> FEATURE:
<223> OTHER INFORMATION: Oligonucleotide primer

<400> SEQUENCE: 77
gatcattgag aaatatgcag tcc                                          23

<210> SEQ ID NO 78
<211> LENGTH: 27
<212> TYPE: DNA
<213> ORGANISM: Artificial
<220> FEATURE:
<223> OTHER INFORMATION: Oligonucleotide primer

<400> SEQUENCE: 78
cacctagaaa tgggttcttt gcatgtc                                      27

<210> SEQ ID NO 79
<211> LENGTH: 24
<212> TYPE: DNA
<213> ORGANISM: Artificial
<220> FEATURE:
<223> OTHER INFORMATION: Oligonucleotide primer

<400> SEQUENCE: 79
ttatattatc ctccatgcct ggcc                                         24

<210> SEQ ID NO 80
<211> LENGTH: 24
<212> TYPE: DNA
<213> ORGANISM: Artificial
<220> FEATURE:
<223> OTHER INFORMATION: Oligonucleotide primer

<400> SEQUENCE: 80
ttatactatc ctccatgcct cgcc                                         24

<210> SEQ ID NO 81
<211> LENGTH: 21
<212> TYPE: DNA
<213> ORGANISM: Artificial
<220> FEATURE:
<223> OTHER INFORMATION: Oligonucleotide primer

<400> SEQUENCE: 81
tattatcctc catgcctggc c                                            21

<210> SEQ ID NO 82
<211> LENGTH: 21
<212> TYPE: DNA
<213> ORGANISM: Artificial
<220> FEATURE:
<223> OTHER INFORMATION: Oligonucleotide primer

<400> SEQUENCE: 82
tactatcctc catgcctcgc c                                            21

<210> SEQ ID NO 83
<211> LENGTH: 510
<212> TYPE: PRT
<213> ORGANISM: Hordeum vulgare cv Golden Promise

<400> SEQUENCE: 83

Met Gly Ser Leu His Val Ser Gly Ser Thr Thr Thr Gln His Ser Arg
```

-continued

```
1               5                   10                  15
Val Gln Arg Ala Tyr Gln Leu Leu Phe Phe His Val His Pro Phe Trp
                20                  25                  30

Pro Gln Leu Leu Tyr Phe Val Ser Ile Ser Phe Phe Gly Phe Val Met
                35                  40                  45

Leu Arg Ala Leu Pro Met Lys Thr Ser Met Pro Thr Asp Leu Asp Leu
    50                  55                  60

Ile Phe Thr Ser Val Ser Ala Thr Thr Val Ser Ser Met Gln Ala Val
65                  70                  75                  80

Glu Met Glu Ser Phe Ser Asn Pro Gln Leu Leu Leu Thr Leu Leu
                85                  90                  95

Met Leu Leu Gly Gly Glu Val Phe Thr Ser Met Leu Gly Met Tyr Phe
                100                 105                 110

Thr Tyr Val Lys Ser Lys Lys Glu Ala Gln Ala Pro His Asp Asp
                115                 120                 125

Gly Ala Lys Val Lys Pro Ala Pro Ser Ser Leu Glu Leu Thr Ala Ala
    130                 135                 140

Ser Ile Cys Met Asp Asp Gly Thr Ala Gln Asp Arg Met Glu Gln Gly
145                 150                 155                 160

Phe Lys Asp Gln Pro Arg Tyr Gly Arg Ala Phe Leu Thr Arg Leu Leu
                165                 170                 175

Leu Phe Ile Val Val Gly Tyr His Ala Val Val His Leu Ala Gly Tyr
                180                 185                 190

Ser Leu Met Leu Val Tyr Leu Ser Val Val Ser Gly Ala Arg Thr Val
                195                 200                 205

Leu Ala Gly Lys Gly Ile Ser Met His Thr Phe Ser Val Phe Thr Ile
    210                 215                 220

Val Ser Thr Phe Ala Asn Cys Gly Phe Met Pro Asn Asn Glu Gly Met
225                 230                 235                 240

Ala Ser Phe Arg Ser Phe Pro Gly Leu Leu Leu Val Met Pro His
                245                 250                 255

Val Leu Leu Gly Asn Thr Leu Phe Pro Val Phe Leu Arg Leu Ala Ile
                260                 265                 270

Trp Ala Leu Gln Arg Phe Thr Lys Arg Pro Glu Leu Gly Glu Leu Arg
                275                 280                 285

Ser Ile Gly Tyr Asp His Leu Leu Thr Ser Arg His Thr Arg Phe Leu
                290                 295                 300

Ala Phe Thr Val Ala Val Phe Val Leu Ala Gln Leu Ser Leu Phe Cys
305                 310                 315                 320

Ala Met Glu Trp Gly Ser Asp Gly Leu Arg Gly Leu Thr Ala Ala Gln
                325                 330                 335

Lys Leu Val Ala Ala Leu Phe Met Ser Val Asn Ser Arg His Ala Gly
                340                 345                 350

Glu Met Val Val Asp Leu Ser Thr Val Ser Ser Ala Val Val Val Val
                355                 360                 365

Tyr Met Val Met Met Tyr Leu Pro Pro Tyr Thr Thr Phe Leu Pro Val
                370                 375                 380

Glu Asp Ser Asn Gln Gln Val Gly Thr Asp Gln Lys Arg Thr Ser Ile
385                 390                 395                 400

Trp His Lys Leu Leu Met Ser Pro Leu Ser Cys Ile Ala Ile Phe Ile
                405                 410                 415

Val Val Val Cys Ile Thr Glu Arg Arg Gln Ile Ser Asp Pro Leu
                420                 425                 430
```

```
Asn Phe Asn Val Leu Asn Ile Ala Val Glu Val Ile Ser Ala Tyr Gly
        435                 440                 445

Asn Val Gly Phe Ser Thr Gly Tyr Ser Cys Gly Arg Gln Val Thr Pro
450                 455                 460

Asp Gly Ser Cys Arg Asp Ala Trp Val Gly Phe Ser Gly Lys Trp Ser
465                 470                 475                 480

Arg Glu Gly Lys Leu Ala Leu Ile Ala Val Met Phe Tyr Gly Arg Leu
                485                 490                 495

Lys Lys Phe Ser Met His Gly Gly Gln Ala Trp Arg Ile Val
                500                 505                 510

<210> SEQ ID NO 84
<211> LENGTH: 435
<212> TYPE: PRT
<213> ORGANISM: Hordeum vulgare cv Halcyon

<400> SEQUENCE: 84

Ile Ser Phe Phe Gly Phe Val Met Leu Arg Ala Leu Pro Met Lys Thr
1               5                   10                  15

Ser Met Pro Thr Asp Leu Asp Leu Ile Phe Thr Ser Val Ser Ala Thr
                20                  25                  30

Thr Val Ser Ser Met Gln Ala Val Glu Met Glu Ser Phe Ser Asn Pro
            35                  40                  45

Gln Leu Leu Leu Leu Thr Leu Met Leu Leu Gly Gly Glu Val Phe
    50                  55                  60

Thr Ser Met Leu Gly Met Tyr Phe Thr Tyr Val Lys Ser Lys Lys Lys
65              70                  75                  80

Glu Ala Gln Ala Pro His Asp Asp Gly Ala Lys Val Lys Pro Ala Pro
                85                  90                  95

Ser Ser Leu Glu Leu Thr Ala Ala Ser Ile Cys Met Asp Asp Gly Thr
            100                 105                 110

Ala Gln Asp Arg Met Lys Gln Gly Phe Lys Asp Gln Pro Arg Tyr Gly
        115                 120                 125

Arg Ala Phe Leu Thr Arg Leu Leu Leu Phe Ile Val Val Gly Tyr His
130                 135                 140

Ala Val Val His Leu Ala Gly Tyr Ser Leu Met Leu Val Tyr Leu Ser
145                 150                 155                 160

Val Val Ser Gly Ala Arg Thr Val Leu Ala Gly Lys Gly Ile Ser Met
                165                 170                 175

His Thr Phe Ser Val Phe Thr Ile Val Ser Thr Phe Ala Asn Cys Gly
            180                 185                 190

Phe Met Pro Asn Asn Glu Gly Met Ala Ser Phe Arg Ser Phe Pro Gly
        195                 200                 205

Leu Leu Leu Leu Val Met Pro His Val Leu Leu Gly Asn Thr Leu Phe
210                 215                 220

Pro Val Phe Leu Arg Leu Ala Ile Trp Ala Leu Gln Arg Phe Thr Lys
225                 230                 235                 240

Arg Pro Glu Leu Gly Glu Leu Arg Ser Ile Gly Tyr Asp His Leu Leu
                245                 250                 255

Thr Ser Arg His Thr Arg Phe Leu Ala Phe Thr Val Ala Val Phe Val
            260                 265                 270

Leu Ala Gln Leu Ser Leu Phe Cys Ala Met Glu Trp Gly Ser Asp Gly
        275                 280                 285

Leu Arg Gly Leu Thr Ala Ala Gln Lys Leu Val Ala Ala Leu Phe Met
290                 295                 300
```

```
Ser Val Asn Ser Arg His Ala Gly Glu Met Val Val Asp Leu Ser Thr
305                 310                 315                 320

Val Ser Ser Ala Val Val Val Tyr Met Val Met Tyr Leu Pro
            325                 330                 335

Pro Tyr Thr Thr Phe Gln Pro Val Glu Asp Ser Asn Gln Gln Val Gly
            340                 345                 350

Thr Asp Gln Lys Arg Thr Ser Ile Trp His Lys Leu Leu Met Ser Pro
            355                 360                 365

Leu Ser Cys Ile Ala Ile Phe Ile Val Val Cys Ile Thr Glu Arg
370             375                 380

Arg Gln Ile Ser Asp Asp Pro Leu Asn Phe Asn Val Leu Asn Ile Ala
385             390                 395                 400

Val Glu Val Ile Ser Ala Tyr Gly Asn Val Gly Phe Ser Thr Gly Tyr
                405                 410                 415

Ser Cys Gly Arg Gln Val Thr Pro Asp Gly Ser Cys Arg Asp Ala Trp
                420                 425                 430

Val Gly Phe
        435

<210> SEQ ID NO 85
<211> LENGTH: 510
<212> TYPE: PRT
<213> ORGANISM: Hordeum vulgare cv Morex

<400> SEQUENCE: 85

Met Gly Ser Leu His Val Ser Gly Ser Thr Thr Gln His Ser Arg
1               5                   10                  15

Val Gln Arg Ala Tyr Gln Leu Leu Phe Phe His Val His Pro Phe Trp
                20                  25                  30

Pro Gln Leu Leu Tyr Phe Val Ser Ile Ser Phe Phe Gly Phe Val Met
            35                  40                  45

Leu Arg Ala Leu Pro Met Lys Thr Asn Met Pro Thr Asp Leu Asp Leu
    50                  55                  60

Ile Phe Thr Ser Val Ser Ala Thr Thr Val Ser Ser Met Gln Ala Val
65                  70                  75                  80

Glu Met Glu Ser Phe Ser Asn Pro Gln Leu Leu Leu Thr Leu Leu
                85                  90                  95

Met Leu Leu Gly Gly Glu Val Phe Thr Ser Met Leu Gly Met Tyr Phe
            100                 105                 110

Thr Tyr Val Lys Ser Lys Lys Lys Glu Ala Gln Ala Pro His Asp Asp
            115                 120                 125

Gly Ala Lys Val Lys Pro Ala Pro Ser Ser Leu Glu Leu Thr Ala Ala
    130                 135                 140

Ser Ile Cys Met Asp Asp Gly Thr Ala Gln Asp Arg Met Glu Gln Gly
145             150                 155                 160

Phe Lys Asp Gln Pro Arg Tyr Gly Arg Ala Phe Leu Thr Arg Leu Leu
                165                 170                 175

Leu Phe Ile Val Val Gly Tyr His Ala Val His Pro Ala Gly Tyr
            180                 185                 190

Ser Leu Met Leu Val Tyr Leu Ser Val Val Ser Gly Ala Arg Thr Val
            195                 200                 205

Leu Ala Gly Lys Gly Ile Ser Met His Thr Phe Ser Val Phe Thr Ile
    210                 215                 220

Val Ser Thr Phe Ala Asn Cys Gly Phe Met Pro Asn Asn Glu Gly Met
225                 230                 235                 240
```

```
Ala Ser Phe Arg Ser Phe Pro Gly Leu Leu Leu Val Met Pro His
            245                 250                 255

Val Leu Leu Gly Asn Thr Leu Phe Pro Val Phe Leu Arg Leu Ala Ile
            260                 265                 270

Trp Ala Leu Gln Arg Phe Thr Lys Arg Pro Glu Leu Gly Glu Leu Arg
            275                 280                 285

Ser Ile Gly Tyr Asp His Leu Leu Thr Ser Arg His Thr Arg Phe Leu
            290                 295                 300

Ala Phe Thr Val Ala Val Phe Val Leu Ala Gln Leu Ser Leu Phe Cys
305                 310                 315                 320

Ala Met Glu Trp Gly Ser Asp Gly Leu Arg Gly Leu Thr Ala Ala Gln
            325                 330                 335

Lys Leu Val Ala Ala Leu Phe Met Ser Val Asn Ser Arg His Ala Gly
            340                 345                 350

Glu Met Val Val Asp Leu Ser Thr Val Ser Ser Ala Val Val Val Val
            355                 360                 365

Tyr Met Val Met Met Tyr Leu Pro Pro Tyr Thr Thr Phe Leu Pro Val
            370                 375                 380

Glu Asp Ser Asn Gln Gln Val Gly Thr Asp Gln Lys Arg Thr Ser Ile
385                 390                 395                 400

Trp His Lys Leu Leu Met Ser Pro Leu Ser Cys Ile Ala Ile Phe Val
            405                 410                 415

Val Val Val Cys Ile Thr Glu Arg Arg Gln Ile Ser Asp Asp Pro Leu
            420                 425                 430

Asn Phe Asn Val Leu Ser Ile Ala Val Glu Val Ile Ser Ala Tyr Gly
            435                 440                 445

Asn Val Gly Phe Ser Thr Gly Tyr Ser Cys Gly Arg Gln Val Thr Pro
            450                 455                 460

Asp Gly Ser Cys Arg Asp Ala Trp Val Gly Phe Ser Gly Lys Trp Ser
465                 470                 475                 480

Arg Glu Gly Lys Leu Ala Leu Ile Ala Val Met Phe Tyr Gly Arg Leu
            485                 490                 495

Lys Lys Phe Ser Met His Gly Gly Gln Ala Trp Arg Ile Val
            500                 505                 510

<210> SEQ ID NO 86
<211> LENGTH: 460
<212> TYPE: PRT
<213> ORGANISM: Hordeum intercedens

<400> SEQUENCE: 86

Leu Gln Leu Leu Tyr Phe Val Ser Ile Ser Phe Phe Gly Phe Val Ile
1               5                   10                  15

Leu Arg Ala Leu Pro Met Lys Thr Ser Met Pro Thr Asp Leu Asp Leu
            20                  25                  30

Ile Phe Thr Ser Val Ser Ala Met Thr Val Ser Ser Met Glu Ala Val
            35                  40                  45

Glu Met Glu Ser Phe Ser Asn Pro Gln Leu Leu Leu Thr Leu Leu
            50                  55                  60

Met Leu Leu Gly Gly Glu Val Phe Thr Ser Met Leu Gly Leu Tyr Phe
65                  70                  75                  80

Thr Tyr Val Lys Ser Lys Lys Glu Ala Pro Ala Pro His Asp Asp
            85                  90                  95

Gly Ala Lys Val Lys Pro Ala Pro Ser Ser Leu Glu Leu Thr Ala Thr
            100                 105                 110
```

```
Ile Phe Met Asp Asp Gly Thr Ala Gln Asp His Met Glu Gln Gly Phe
            115                 120                 125

Lys Asp Gln Pro Arg Tyr Gly Arg Ala Phe Leu Thr Arg Leu Leu Leu
130                 135                 140

Phe Ile Val Leu Gly Tyr His Ala Ala Val His Leu Ala Gly Tyr Ser
145                 150                 155                 160

Leu Met Leu Val Tyr Leu Ser Val Val Ser Gly Ala Arg Val Val Leu
                165                 170                 175

Ala Gly Lys Gly Ile Ser Met His Thr Phe Ser Val Phe Thr Val Val
            180                 185                 190

Ser Thr Phe Ala Asn Cys Gly Phe Val Pro Thr Asn Glu Gly Met Ala
            195                 200                 205

Ser Phe Arg Ser Phe Pro Gly Leu Leu Leu Leu Val Met Pro His Val
210                 215                 220

Leu Leu Gly Asn Thr Leu Phe Pro Val Phe Leu Arg Leu Thr Ile Trp
225                 230                 235                 240

Ala Leu Gln Arg Val Thr Lys Arg Pro Glu Leu Gly Glu Leu Arg Ser
                245                 250                 255

Ile Gly Tyr Asp His Leu Leu Thr Ser Arg His Thr Arg Phe Leu Ala
            260                 265                 270

Phe Thr Val Ala Ala Phe Val Leu Ala Gln Leu Ser Leu Phe Cys Ala
            275                 280                 285

Met Glu Trp Gly Ser Asp Gly Leu His Gly Leu Thr Ala Ala Gln Lys
            290                 295                 300

Leu Ile Ala Ala Leu Phe Met Ser Val Asn Ser Arg His Ala Gly Glu
305                 310                 315                 320

Met Val Val Asp Leu Ser Thr Val Ser Ser Ala Val Val Val Val Phe
                325                 330                 335

Val Val Met Met Tyr Leu Pro Pro Tyr Thr Thr Phe Leu Pro Val Glu
                340                 345                 350

Asp Ser Asp Glu Gln Val Gly Thr Asp Gln Tyr Asp Leu Gln Lys Arg
            355                 360                 365

Thr Ser Ile Trp Gln Lys Leu Leu Met Ser Pro Leu Ser Cys Val Ala
            370                 375                 380

Ile Phe Ile Val Val Cys Ile Thr Glu Arg Arg Gln Ile Ser Asp
385                 390                 395                 400

Asp Pro Leu Asn Phe Ser Val Leu Asn Ile Ala Val Glu Val Ile Ser
                405                 410                 415

Ala Tyr Gly Asn Val Gly Phe Ser Thr Gly Tyr Ser Cys Gly Arg Gln
            420                 425                 430

Val Lys Pro Asp Val Ala Cys Ser Asp Val Trp Val Gly Phe Ser Gly
            435                 440                 445

Lys Trp Ser Arg Glu Gly Lys Leu Ala Leu Val Ala
450                 455                 460

<210> SEQ ID NO 87
<211> LENGTH: 460
<212> TYPE: PRT
<213> ORGANISM: Hordeum murinum ssp. glaucum

<400> SEQUENCE: 87

Val Gln Ile Leu Tyr Phe Val Ser Ile Ser Phe Phe Gly Phe Val Ile
1               5                   10                  15

Leu Lys Ala Leu Pro Met Lys Thr Ser Lys Pro Met Asp Leu Asp Leu
            20                  25                  30
```

```
Ile Phe Thr Ser Val Ser Ala Thr Thr Val Ser Ser Met Val Ala Val
        35                  40                  45

Glu Met Glu Ser Phe Ser Asn Pro Gln Leu Leu Val Leu Thr Leu Leu
 50                  55                  60

Met Leu Leu Gly Gly Glu Val Phe Thr Ser Met Leu Gly Leu His Val
 65                  70                  75                  80

Ser Tyr Ile Lys Ser Lys Lys Glu Ala His Ala Pro His Glu His
                85                  90                  95

Asp Asp Asp Gly Asp Lys Gly Lys Pro Ala Pro Ser Ser Leu Glu
                100                 105                 110

Leu Ile Ala Thr Cys Met Asp Val Asp His Val Glu Gln Gly Phe
            115                 120                 125

Lys Asp Gln Pro Arg Tyr Asp Gly Ala Phe Leu Thr Arg Leu Leu Leu
 130                 135                 140

Cys Ile Val Leu Gly Tyr His Val Val His Leu Ala Gly Tyr Ser
 145                 150                 155                 160

Leu Val Leu Val Tyr Leu Ser Val Val Ser Gly Ala Arg Val Val Leu
                165                 170                 175

Thr Gly Lys Gly Ile Ser Val His Thr Phe Ser Ile Phe Thr Ile Val
                180                 185                 190

Ser Thr Phe Thr Asn Cys Gly Phe Val Pro Thr Asn Glu Gly Met Ile
        195                 200                 205

Ala Phe Arg Ser Phe Pro Gly Leu Leu Leu Val Met Pro His Val
 210                 215                 220

Leu Leu Gly Asn Thr Leu Phe Pro Val Phe Leu Arg Leu Ala Ile Trp
 225                 230                 235                 240

Ala Leu Arg Gly Val Thr Arg Arg Pro Glu Leu Gly Glu Leu Arg Ser
                245                 250                 255

Ile Gly Tyr Asp His Leu Leu Thr Ser Arg His Thr Trp Phe Leu Ala
                260                 265                 270

Phe Thr Val Ala Ala Phe Val Leu Leu Gln Leu Ser Leu Phe Cys Ala
        275                 280                 285

Met Glu Trp Gly Ser Asp Gly Leu Arg Gly Leu Thr Ala Ala Gln Lys
 290                 295                 300

Leu Val Ala Ala Leu Phe Met Ser Ile Asn Ser Arg His Thr Gly Glu
305                 310                 315                 320

Met Val Val Asp Leu Ser Thr Val Ser Ser Val Val Val Leu Tyr
                325                 330                 335

Val Val Met Met Tyr Leu Pro Pro Tyr Thr Thr Phe Leu Leu Val Glu
                340                 345                 350

Asp Asn Asp Gln Gln Val Gly Ala Asp Gln Asn Asp Gln Lys Lys Ile
                355                 360                 365

Thr Ser Ile Trp Gln Lys Leu Leu Met Ser Pro Leu Ser Cys Leu Ala
 370                 375                 380

Ile Phe Ile Ala Val Val Cys Ile Thr Glu Arg Arg Gln Ile Ser Glu
385                 390                 395                 400

Asp Pro Leu Asn Phe Asn Val Leu Asn Ile Thr Val Glu Val Ile Ser
                405                 410                 415

Ala Tyr Gly Asn Val Gly Phe Ser Thr Gly Tyr Ser Cys Gly Arg Gln
                420                 425                 430

Val Thr Pro Asp Gly Gly Cys Arg Asp Thr Trp Val Gly Phe Ser Gly
                435                 440                 445

Lys Trp Ser Trp Gln Gly Lys Leu Ala Leu Met Ala
 450                 455                 460
```

<210> SEQ ID NO 88
<211> LENGTH: 471
<212> TYPE: PRT
<213> ORGANISM: Hordeum marinum ssp. gussoneanum

<400> SEQUENCE: 88

```
Leu Gln Leu Leu Tyr Phe Val Ser Ile Ser Phe Phe Gly Phe Val Met
1               5                   10                  15

Leu Lys Ala Leu Pro Met Lys Thr Ser Met Pro Thr Asp Leu Asp Leu
            20                  25                  30

Ile Phe Thr Ser Val Ser Ala Met Thr Val Ser Ser Met Gln Ala Val
        35                  40                  45

Glu Met Glu Ser Phe Ser Asn Pro Gln Leu Leu Leu Thr Leu Leu
50                  55                  60

Met Leu Leu Gly Gly Glu Val Phe Thr Ser Ile Leu Gly Leu Tyr Phe
65                  70                  75                  80

Thr Tyr Val Lys Ser Lys Lys Glu Ala Gln Ala Pro His Asp Asp
                85                  90                  95

Gly Ala Lys Val Lys Pro Ala Pro Ser Ser Leu Glu Leu Thr Ala Thr
            100                 105                 110

Val Cys Met Asp Asp Gly Thr Val Gln Asp His Met Glu Gln Gly Phe
        115                 120                 125

Lys Asp Gln Pro Arg Tyr Gly Arg Ala Phe Leu Thr Arg Leu Leu Leu
130                 135                 140

Phe Ile Val Ile Gly Tyr His Ala Val Val His Leu Ala Gly Tyr Ser
145                 150                 155                 160

Leu Met Leu Val Tyr Leu Ser Val Val Ser Gly Ala Arg Val Val Leu
                165                 170                 175

Ala Gly Lys Gly Ile Ser Met His Thr Phe Ser Val Phe Thr Ile Val
            180                 185                 190

Ser Thr Phe Ala Asn Cys Gly Phe Ile Pro Asn Asn Glu Gly Met Ala
        195                 200                 205

Ser Phe Arg Ser Phe Pro Gly Phe Leu Leu Val Met Pro His Val
210                 215                 220

Leu Leu Gly Asn Thr Leu Phe Pro Val Phe Leu Arg Leu Thr Ile Trp
225                 230                 235                 240

Ala Leu Gln Arg Val Thr Lys Arg Pro Glu Leu Gly Glu Leu Arg Ser
                245                 250                 255

Ile Gly Tyr Asp His Leu Leu Thr Ser Arg His Thr Arg Phe Leu Ala
            260                 265                 270

Phe Thr Val Ala Ala Phe Val Leu Ala Gln Leu Ser Phe Phe Cys Ala
        275                 280                 285

Met Glu Trp Gly Ser Asp Gly Leu Arg Gly Leu Thr Ala Ala Gln Lys
290                 295                 300

Leu Val Ala Ala Leu Phe Met Ser Val Asn Ser Arg His Ala Gly Glu
305                 310                 315                 320

Met Val Val Asp Leu Ala Asn Val Ser Ala Val Val Val Tyr
                325                 330                 335

Val Val Met Met Tyr Leu Pro Pro Tyr Thr Thr Phe Leu Pro Val Glu
            340                 345                 350

Asp Ser Asp Lys Gln Val Gly Thr Asp Gln Tyr Asp Leu Gln Lys Arg
        355                 360                 365

Thr Ser Leu Trp Gln Lys Leu Leu Met Ser Pro Leu Ser Cys Ile Ala
370                 375                 380
```

```
Ile Phe Ile Val Val Cys Ile Thr Glu Arg Arg Gln Ile Ser Asp
385                 390                 395                 400

Asp Pro Leu Asn Phe Ser Val Leu Asn Ile Ala Val Glu Val Ile Ser
            405                 410                 415

Ala Tyr Gly Asn Val Gly Phe Ser Thr Gly Tyr Ser Cys Gly Arg Gln
            420                 425                 430

Val Thr Pro Asp Gly Ala Cys Ser Asp Leu Trp Val Gly Phe Ser Gly
            435                 440                 445

Lys Trp Ser Arg Glu Gly Lys Leu Ala Leu Ile Ala Val Met Phe Tyr
            450                 455                 460

Gly Arg Leu Lys Leu Ser Trp
465                 470

<210> SEQ ID NO 89
<211> LENGTH: 460
<212> TYPE: PRT
<213> ORGANISM: Hordeum marinum ssp. gussoneanum

<400> SEQUENCE: 89

Leu Gln Leu Leu Tyr Phe Val Ser Ile Ser Phe Phe Gly Phe Val Met
1               5                   10                  15

Leu Lys Ala Leu Pro Met Lys Thr Ser Met Pro Thr Asp Leu Asp Leu
            20                  25                  30

Ile Phe Thr Ser Val Ser Ala Met Thr Val Ser Ser Met Gln Ala Val
            35                  40                  45

Glu Met Glu Ser Phe Ser Asn Pro Gln Leu Leu Leu Thr Leu Leu
50                  55                  60

Met Leu Leu Gly Gly Glu Val Phe Thr Ser Ile Leu Gly Leu Tyr Phe
65                  70                  75                  80

Thr Tyr Val Lys Ser Lys Lys Glu Ala Gln Ala Pro His Asp Asp
                85                  90                  95

Gly Ala Lys Val Lys Pro Ala Pro Ser Thr Leu Glu Leu Thr Ala Thr
            100                 105                 110

Val Cys Met Asp Asp Gly Thr Val Gln Asp His Met Glu Gln Gly Phe
            115                 120                 125

Lys Asp Gln Pro Arg Tyr Gly Arg Ala Phe Leu Thr Arg Leu Leu Leu
130                 135                 140

Phe Ile Val Leu Gly Tyr His Ala Val Val His Leu Ala Gly Tyr Ser
145                 150                 155                 160

Leu Met Leu Val Tyr Leu Ser Val Val Ser Gly Ala Arg Val Val Leu
                165                 170                 175

Ala Gly Lys Gly Ile Ser Met His Thr Phe Ser Ile Phe Thr Ile Val
            180                 185                 190

Ser Thr Phe Ala Asn Cys Gly Phe Ile Pro Asn Asn Glu Gly Met Ala
            195                 200                 205

Ser Phe Arg Ser Phe Pro Gly Phe Leu Leu Leu Val Met Pro His Val
            210                 215                 220

Leu Leu Gly Asn Thr Leu Phe Pro Val Phe Leu Arg Leu Thr Ile Trp
225                 230                 235                 240

Ala Leu Gln Arg Val Thr Lys Arg Pro Glu Leu Gly Glu Leu Arg Ser
                245                 250                 255

Ile Gly Tyr Asp His Leu Leu Thr Ser Arg Arg Thr Arg Phe Leu Ala
            260                 265                 270

Phe Thr Val Ala Ala Phe Val Leu Ala Gln Leu Ser Leu Phe Cys Ala
            275                 280                 285
```

```
Met Glu Trp Gly Ser Asp Arg Leu Arg Gly Leu Thr Ala Ala Gln Lys
    290                 295                 300
Leu Val Ala Ala Leu Phe Met Ser Val Asn Ser Arg His Ala Gly Glu
305                 310                 315                 320
Met Val Val Asp Leu Ala Asn Val Ser Ser Ala Val Val Val Val Tyr
                325                 330                 335
Val Val Met Met Tyr Leu Pro Pro Tyr Thr Thr Phe Leu Pro Val Glu
            340                 345                 350
Asp Ser Asp Gln Gln Val Gly Thr Tyr Gln Tyr Asp Leu Gln Lys Arg
        355                 360                 365
Thr Ser Ile Trp Gln Lys Leu Leu Met Ser Pro Leu Ser Cys Ile Ala
    370                 375                 380
Ile Phe Ile Val Val Cys Ile Thr Glu Arg Arg Gln Ile Ser Asp
385                 390                 395                 400
Asp Pro Leu Asn Phe Ser Val Leu Asn Ile Thr Val Glu Val Ile Ser
                405                 410                 415
Ala Tyr Gly Asn Val Gly Phe Ser Thr Gly Tyr Ser Cys Asp Arg Gln
            420                 425                 430
Val Thr Pro Asp Gly Ala Cys Ser Asp Val Trp Val Gly Phe Ser Gly
        435                 440                 445
Lys Trp Ser Arg Glu Gly Lys Leu Ala Leu Ile Ala
    450                 455                 460

<210> SEQ ID NO 90
<211> LENGTH: 1530
<212> TYPE: DNA
<213> ORGANISM: Hordeum vulgare cv Golden Promise

<400> SEQUENCE: 90
atgggttctt tgcatgtctc cggcagtacc actactcaac atagcagggt tcagagggct     60
taccaactct tgttttttcca tgtgcacccg ttctggcccc agctcctcta ctttgtgtcc   120
atctccttt tcggcttcgt catgctgaga gccctcccca tgaagaccag catgcccacg     180
gacctagacc tgatcttcac gtcggtgtcg gcgacgacgg tgtcgagcat gcaggcggtg   240
gagatggagt ccttctccaa ccccagctc ctcctcctaa ccctcctcat gcttcttggt    300
ggcgaggtgt tcactagcat gcttggcatg tacttcacct acgtcaagtc caagaaaaaa   360
gaagcacaag caccacatga tgatggtgcc aaagtgaaac cagcaccatc tagcctagag   420
ctcacggccg ctagcatctg catggacgac ggcactgcac aggaccgtat ggagcaaggg   480
ttcaaggacc agccccgtta cggccgggcc ttcctcacca ggttgctcct gttcatagtg   540
gtcggctatc acgcggtggt gcacctggcc ggttactccc tgatgctggt ctacctgagc   600
gtcgtgtccg gcgcgaggac ggtgctcgcc ggcaagggga tcagcatgca caccttctcc   660
gtcttcacca tcgtctcgac gttcgcaaac tgcggcttca tgccgaacaa cgaagggatg   720
gcctccttcc ggtccttccc gggactcctc ctactcgtca tgccccacgt cctcctcgga   780
aacacgctct ccccgtcttc ctcaggctg gcgatctggg ctctccagcg gttcaccaag   840
aggcctgaac tcggtgagct gcggagcatc ggctacgacc acctcctgac gagccggcat   900
acaaggttct tggcttttcac cgtggccgtg ttcgtgctgg cgcagctgtc gctcttctgc   960
gccatggagt ggggctccga cgggctgcgc gggctcaccg ccgcgcaaaa gctcgtcgcg  1020
gctctcttca tgtcggtcaa ctcgaggcac gccggcgaga tggtcgtgga cctctccacc  1080
gtgtcgtcgg ccgtcgtggt ggtctacatg gtcatgatgt acctaccacc ttatactaca  1140
```

```
tttctaccag tggaagacag taaccaacaa gtgggaacag atcagaaaag gacaagcata    1200
tggcacaagc ttctcatgtc gcccctctcg tgcatagcca tcttcatcgt cgtcgtgtgc    1260
atcaccgaga gacggcagat ctccgatgac ccactcaact tcaacgtcct caacatcgcc    1320
gtcgaggtta tcagtgcgta cggcaacgtg gggttcagca cggggtacag ctgcggccgg    1380
caggtgacgc ccgacggcag ctgcagggac gcgtgggttg gcttctccgg gaagtggagc    1440
agggaaggga agctcgccct catagccgtc atgttctacg gcaggctcaa gaagttcagc    1500
atgcatggcg gccaggcatg gaggatagtg                                     1530

<210> SEQ ID NO 91
<211> LENGTH: 1307
<212> TYPE: DNA
<213> ORGANISM: Hordeum vulgare cv Halcyon

<400> SEQUENCE: 91
atctcctttt tcggcttcgt catgctgaga gccctcccca tgaagaccag catgcccacg      60
gacctagacc tgatcttcac gtcggtgtcg gcgacgacgg tgtcgagcat gcaggcggtg     120
gagatggagt ccttctccaa cccccagctc ctcctcctaa ccctcctcat gcttcttggt     180
ggcgaggtgt tcactagcat gcttggcatg tacttcacct acgtcaagtc caagaaaaaa     240
gaagcacaag caccacatga tgatggtgcc aaagtgaaac cagcaccatc tagcctagag     300
ctcacggccg ctagcatctg catggacgac ggcactgcac aggaccgtat gaagcaaggg     360
ttcaaggacc agccccgtta cggccgggcc ttcctcacca ggttgctcct gttcatagtg     420
gtcggctatc acgcggtggt gcacctggcc ggttactccc tgatgctggt ctacctgagc     480
gtcgtgtccg gcgcgaggac ggtgctcgcc ggcaagggga tcagcatgca caccttctcc     540
gtcttcacca tcgtctcgac gttcgcaaac tgcggcttca tgccgaacaa cgaagggatg     600
gcctccttcc ggtccttccc gggactcctc ctactcgtca tgccccacgt cctcctcgga     660
aacacgctct tccccgtctt cctcaggctg gcgatctggg ctctccagcg gttcaccaag     720
aggcctgaac tcggtgagct gcggagcatc ggctacgacc acctcctgac gagccggcat     780
acaaggttct tggcttcac cgtggccgtg ttcgtgctgg cgcagctgtc gctcttctgc     840
gccatggagt ggggctccga cgggctgcgc gggctcaccg ccgcgcagaa gctcgtcgcg     900
gctctcttca tgtcggtcaa ctcgaggcac gccggcgaga tggtcgtgga cctctccacc     960
gtgtcgtcgg ccgtcgtggt ggtctacatg gtcatgatgt acctaccacc ttatactaca    1020
tttcaaccag tggaagacag taaccaacaa gtgggaacag atcagaaaag gacaagcata    1080
tggcacaagc ttctcatgtc gcccctctcg tgcatagcca tcttcatcgt cgtcgtgtgc    1140
atcaccgaga gacggcagat ctccgatgac ccactcaact tcaacgtcct caacatcgcc    1200
gtcgaggtta tcagtgcgta cggcaacgtg gggttcagca cggggtacag ctgcggccgg    1260
caggtgacgc ccgacggcag ctgcagggac gcgtgggttg gcttctc                  1307

<210> SEQ ID NO 92
<211> LENGTH: 1530
<212> TYPE: DNA
<213> ORGANISM: Hordeum vulgare cv Morex

<400> SEQUENCE: 92
atgggttctt tgcatgtctc cggcagtacc actactcaac atagcagggt tcagagggct      60
taccaactct tgttttttcca gtgcacccg ttctggcccc agctcctcta ctttgtgtcc     120
atctcctttt tcggcttcgt catgctgaga gccctcccca tgaagaccaa catgcccacg     180
```

| | |
|---|---|
| gacctagacc tgatcttcac gtcggtgtcg gcgacgacgg tgtcgagcat gcaggcggtg | 240 |
| gagatggagt ccttctccaa cccccagctc ctcctcctaa ccctcctcat gcttcttggt | 300 |
| ggcgaggtgt tcactagcat gcttggcatg tacttcacct acgtcaagtc caagaaaaaa | 360 |
| gaagcacaag cacccatga tgatggtgcc aaagtgaaac cagcaccatc tagcctagag | 420 |
| ctcacggccg ctagcatctg catggacgac ggcactgcac aggaccgtat ggagcaaggg | 480 |
| ttcaaggacc agccccgtta cggccgggcc ttcctcacca ggttgctcct gttcatagtg | 540 |
| gtcggctatc acgcggtggt gcacccggcc ggttactccc tgatgctggt ctacctgagc | 600 |
| gtcgtgtccg gcgcgaggac ggtgctcgcc ggcaagggga tcagcatgca caccttctcc | 660 |
| gtcttcacca tcgtctcgac gttcgcaaac tgcggcttca tgccgaacaa cgaagggatg | 720 |
| gcctccttcc ggtccttccc gggactcctc ctactcgtca tgcccacgt cctcctcgga | 780 |
| aacacgctct ccccgtctt cctcaggctg gcgatctggg ctctccagcg gttcaccaag | 840 |
| aggcctgaac tcggtgagct gcggagcatc ggctacgacc acctcctgac aagccggcat | 900 |
| acaaggttct tggctttcac cgtggccgtg ttcgtgctgg cgcagctgtc gctcttctgc | 960 |
| gccatggagt ggggctccga cgggctgcgc gggctcaccg ccgcgcagaa gctcgtcgcg | 1020 |
| gctctcttca tgtcggtcaa ctcgaggcac gccggcgaga tggtcgtgga cctctccacc | 1080 |
| gtgtcgtcgg ccgtcgtggt ggtctacatg gtcatgatgt acctaccacc ttatactaca | 1140 |
| tttctaccag tggaagacag taaccaacaa gtgggaacag atcagaaaag gacaagcata | 1200 |
| tggcacaagc ttctcatgtc gcccctctcg tgcatagcca tcttcgtcgt cgtcgtgtgc | 1260 |
| atcaccgaga gacggcagat ctccgatgac ccactcaact tcaacgtcct cagcatcgcc | 1320 |
| gtcgaggtta tcagtgcgta cggcaacgtg gggttcagca cggggtacag ctgcggccgg | 1380 |
| caggtgacgc ccgacggcag ttgcagggac gcgtgggttg gcttctccgg gaagtggagc | 1440 |
| agggaaggga agctcgccct catagccgtc atgttctacg gcaggctcaa gaaattcagc | 1500 |
| atgcatggcg gccaggcatg gaggatagtg | 1530 |

<210> SEQ ID NO 93
<211> LENGTH: 1380
<212> TYPE: DNA
<213> ORGANISM: Hordeum intercedens

<400> SEQUENCE: 93

| | |
|---|---|
| ctccagctcc tgtactttgt gtccatctcc ttcttcggct tcgtcatcct gagagccctc | 60 |
| cccatgaaga ccagcatgcc cacgacctg gacctgatct tcacgtcggt gtcggcgatg | 120 |
| acggtgtcga gcatggaggc cgtggagatg gagtccttct ccaaccccca actcctactc | 180 |
| ctaaccctcc tcatgcttct tggcggcgag gtgttcacta gcatgcttgg attgtacttc | 240 |
| acctacgtca gtccaagaa aaaggaagca ccggcacccc atgacgatgg tgccaaagtc | 300 |
| aaaccggcac catctagcct agagctcacg gctaccatct catggacga cggcaccgca | 360 |
| caggaccata tggagcaagg gttcaaggac cagccccgtt acggccgggc cttcctcacc | 420 |
| aggttgctcc tgttcatagt gctcggctat cacgcggcgg tgcacctggc cggttactcc | 480 |
| ctgatgctgg tctacctgag cgtcgtctcc ggcgcgaggg tggtgctcgc cggcaagggg | 540 |
| atcagcatgc acaccttctc cgtcttcacc gtcgtctcga cattcgcgaa ttgcggcttc | 600 |
| gtgccgacca acgaagggat ggcctccttc cggtccttcc cgggcctcct cctcctcgtc | 660 |
| atgcccacg tcctcctcgg aaacacgctc ttccccgtct tcctcaggct gacgatctgg | 720 |
| gctctccaga gagtcaccaa gaggcctgaa ctcggtgagc tgcggagcat cggctacgac | 780 |

| cacctcctga cgagccggca cacaaggttc ttagcgttca ccgtggccgc gttcgtgctg | 840 |
| gcgcagctgt cgctcttctg cgccatggag tggggctccg acgggctgca cgggctcacc | 900 |
| gccgcgcaga agctcatcgc tgcgctcttc atgtcggtca actcgaggca cgccggcgag | 960 |
| atggtcgtgg acctctccac cgtatcgtca gccgtcgtgg tggtcttcgt ggtcatgatg | 1020 |
| tacctaccac cttacaccac atttctacca gtggaagaca gtgacgaaca agtgggaaca | 1080 |
| gatcagtacg acctgcagaa aaggacaagc atctggcaga agctgctcat gtcgcccctc | 1140 |
| tcgtgcgtag ccatcttcat cgtcgtcgtg tgcatcaccg agaggcggca gatctccgat | 1200 |
| gatcccctca acttcagcgt cctcaacatc gccgtcgagg ttatcagtgc gtacggcaac | 1260 |
| gtggggttca gcacggggta cagctgcggg cggcaggtga agcccgacgt cgcctgcagc | 1320 |
| gacgtgtggg ttgggttctc cgggaagtgg agcagggaag ggaagctcgc cctcgtagcc | 1380 |

<210> SEQ ID NO 94
<211> LENGTH: 1380
<212> TYPE: DNA
<213> ORGANISM: Hordeum murinum ssp. glaucum

<400> SEQUENCE: 94

| gtccagatct tgtactttgt atccatctcc ttcttcggtt tcgtgatcct caaagccctc | 60 |
| cccatgaaga ccagcaagcc catggacctg gacctgatct tcacgtcggt gtcggcgacg | 120 |
| acggtttcga gcatggtggc cgtggagatg gagtccttct ccaaccccca gctcctagtc | 180 |
| ctgaccctcc tcatgctcct cggcggcgag gtgttcacga gcatgcttgg cctgcacgtc | 240 |
| agctacatca agtccaagaa gaaagaagca catgcacccc atgagcatga tgatgatggt | 300 |
| gacaaaggca aaccagcacc atcgtctagc ctagagctca ttgctacctg catggacgac | 360 |
| gtcgatcatg tggagcaagg gtttaaggac cagccccgtt acgatggcgc cttcctcacc | 420 |
| aggttgcttc tgtgcatagt gctgggatat cacgtggtgg tgcacctcgc cggctactca | 480 |
| ctggtgttgg tctacttgag cgtcgtgtcc ggcgcgaggg tggtgctcac cggcaaaggg | 540 |
| atcagcgtgc acaccttctc catcttcacc atcgtgtcga cgttcaccaa ctgcggcttc | 600 |
| gtgccgacca acgaagggat gatcgccttc cggtccttcc caggcctcct actcctcgtc | 660 |
| atgccccacg tcctcctcgg caacacgctc tttcctgtct tcctcaggct ggccatctgg | 720 |
| gctctccggg gggtcaccag gaggcccgag ctcggcgagc tgcggagcat cggctacgac | 780 |
| cacctgctca cgagccggca cacgtggttc ttggctttca ccgtggccgc attcgtgctg | 840 |
| ttgcagctgt cgcttttctg cgccatggag tggggctccg acgggctgcg cgggctcact | 900 |
| gccgcgcaga agctcgtcgc ggcattattc atgtcgatca actccaggca caccggcgag | 960 |
| atggttgtgg acctctccac cgtgtcgtca gtcgtcgtgg tgctctacgt ggtcatgatg | 1020 |
| tacctaccac cttacactac atttctacta gtggaagaca atgaccaaca agtgggagca | 1080 |
| gatcagaacg accagaaaaa gataacaagc atatggcaga agctgctcat gtctccgctc | 1140 |
| tcgtgcttgg ccatcttcat cgccgtcgtg tgcatcacgg agcggcggca gatctccgag | 1200 |
| gacccccctca acttcaacgt cctcaacatc actgtggagg ttatcagtgc gtacggcaac | 1260 |
| gtggggttca gcaccggtta cagctgcggc cggcaggtga cgccggacgg cggctgcagg | 1320 |
| gacacctggg ttggcttctc tgggaagtgg agctggcaag ggaagctggc tctcatggct | 1380 |

<210> SEQ ID NO 95
<211> LENGTH: 1415
<212> TYPE: DNA
<213> ORGANISM: Hordeum marinum ssp. gussoneanum

<400> SEQUENCE: 95

```
ctccagctcc tgtactttgt gtccatctct ttcttcggct tcgtcatgct gaaagccctc    60
cccatgaaga ccagcatgcc gacggacctg gacctgatct tcacgtccgt gtcggcgatg   120
acggtgtcga gcatgcaggc cgtggagatg gagtccttct ccaaccccca gctcctactc   180
cttaccctcc tcatgcttct cggcggcgag gtgttcacca gcatccttgg cctgtacttc   240
acctacgtca agtccaagaa aaagaggca caggcacccc atgatgacgg tgccaaagtc   300
aaaccagcac catcaagcct agagctcacg gctaccgtct gcatggacga cggcaccgta   360
caggaccata tggagcaagg gttcaaggac cagccccgtt acggccgggc cttcctcacc   420
aggttgctcc tgttcatcgt gatcggttac cacgcggtgg tgcacctggc cggctactcc   480
ctgatgctgg tctacctgag cgtcgtgtcc ggcgcgaggg tggtgctcgc cggcaagggg   540
atcagcatgc acaccttctc ggtcttcacc atcgtctcga cgttcgcgaa ctgcggcttc   600
ataccgaaca acgaagggat ggcctccttc cggtccttcc cgggcttcct cctcctcgtc   660
atgccgcacg tcctcctggg aaacacgctc ttccccgtct tcctgaggct gacgatctgg   720
gctctccaga gagtcaccaa gaggcctgag ctcggtgagc tgcggagcat cggctacgac   780
cacctcctga cgagccggca cacaaggttc ttagcgttca ccgtggccgc gttcgtgctg   840
gcgcagctgt cgttcttctg cgccatggaa tggggctccg acgggctgcg cgggctcacc   900
gccgcgcaga agctcgtcgc tgcactcttc atgtcggtca actcgaggca cgccggcgag   960
atggtcgtgg acctcgccaa cgtatcggcg gccgtcgtcg tggtctacgt ggtcatgatg  1020
tacctaccac cttacactac gtttctacca gtggaagaca gtgacaaaca agtgggaaca  1080
gatcagtacg acctgcagaa aaggacaagc ctctggcaga agctgctcat gtcgcccctc  1140
tcgtgcatag ccatcttcat cgtcgtcgtg tgcatcaccg agaggcggca gatctccgat  1200
gaccccctca actttagcgt cctcaacatc gccgtcgagg ttatcagtgc gtacggcaac  1260
gtggggttca gcacgggtta cagctgcggc cggcaggtga cgcccgacgg cgcctgcagc  1320
gacctgtggg ttggcttctc cgggaagtgg agcagggaag ggaagctcgc cctcatagcc  1380
gtcatgttct acggcaggct caagctctca tggct                              1415
```

<210> SEQ ID NO 96
<211> LENGTH: 1380
<212> TYPE: DNA
<213> ORGANISM: Hordeum marinum ssp. gussoneanum

<400> SEQUENCE: 96

```
ctccagctcc tgtactttgt gtccatctct ttcttcggct tcgtcatgct gaaagccctc    60
cccatgaaga ccagcatgcc gacggacctg gacctgatct tcacgtccgt gtcggcgatg   120
acggtgtcga gcatgcaggc cgtggagatg gagtccttct ccaaccccca gctcctactc   180
cttaccctcc tcatgcttct cggcggcgag gtgttcacca gcatccttgg cctgtacttc   240
acctacgtca agtccaagaa aaagaagca caggcacccc atgatgacgg tgccaaagtc   300
aaaccagcac catctacgct agagctcacg gctaccgtct gcatggacga cggcaccgta   360
caggaccata tggagcaagg gttcaaggac cagccccgtt acggccgggc cttcctcacc   420
aggttgctcc tgttcatcgt gctcggctac cacgcggtgg tgcacctggc cggctactcc   480
ctgatgctgg tctacctgag cgtcgtgtcc ggcgcgaggg tggtgctcgc cggcaagggg   540
atcagcatgc acaccttctc gatcttcacc atcgtctcga cgttcgcgaa ctgcggcttc   600
ataccgaaca acgaagggat ggcctccttc cggtccttcc cgggcttcct cctcctcgtc   660
```

```
atgccgcacg tcctcctggg aaacacgctc ttccccgtct tcctcaggct gacgatctgg      720
gctctccaga gagtcaccaa gaggcctgag ctcggtgagc tgcggagcat cggctacgac      780
cacctcctga cgagccggcg cacaaggttc ttagcgttca ccgtggccgc gttcgtgctg      840
gcgcagctgt cgctcttctg cgccatggag tggggctccg acaggctgcg cgggctcacc      900
gccgcgcaga agctcgtcgc tgcactcttc atgtcggtca actcgaggca cgccggcgag      960
atggtcgtgg acctcgccaa cgtatcgtcg gccgtcgtcg tggtctacgt ggtcatgatg     1020
tacctgccac cttacaccac atttctaccg gtggaagaca gtgaccaaca gtgggaaca      1080 tatcagtacg acctgcagaa aaggacaagc atctggcaga agctgctcat gtcgcccctc     1140
tcgtgcatag ccatcttcat cgtcgtcgtg tgcatcaccg agaggcggca gatctccgat     1200 gacccctca actttagcgt cctcaacatc accgtcgagg ttatcagtgc gtacggcaac     1260
gtggggttca gcacggggta cagctgcgac cggcaagtga cgcccgacgg cgcctgcagc     1320
gacgtgtggg ttggcttctc cggaaagtgg agcagggaag ggaagctcgc cctcatagcc     1380
```

<210> SEQ ID NO 97
<211> LENGTH: 1048
<212> TYPE: DNA
<213> ORGANISM: Triticum monococcum

<400> SEQUENCE: 97

```
cagatgttcg catacactca accctaagaa tgcctgcaca cacacacaca cacacacaca       60
cacacacaca cacacacaca cactcctact aaaggcacat cgccgaaagg cctgaaatga      120
atgcaagaaa acacgaccat caatgtcaag tctagaactt gaatcctggt gggttatttc      180
catcacaaac aaagaaacca tttgagttac cctcagttcg ctatgccaac attaattaac      240
aatagcaaac ttgtttcatt atatttgtca taatataatt tctaaatata tagtcaaaat      300
aatttcaaat atttatgaac caagggagca ccgtgctacg gtaacataca tgcattactt      360
tggaggagct agttgtaggt agctctaaac atgtattttc atagtttata attttcggca      420 tgtatttct atcttctatg tgtatatctt tttcaggatt ctgtgtgtat atgtgtatat      480
gtacttttcg ttgcacttag tacaacacaa gtcaggtggt gccctgagc tccttctctt      540 cacgatgcca cgctcacacc ctacgatcca tatccaatgg agcaaggcat cgcacccggt      600
gggcaccaac cgactcttgt tcgttacggg tgatatggac gtggaactta tcactcacac      660
gcaaaagaaa aaaacttat cactcgattc cattttttct tccacaagtc tgctcttctg      720
ggagtaccta attttcgtca tatgatatgc ctcgcaaaaa agatatgcct cccacgagct      780
cccattgtgc gctagctttt gcgattagat tcagtaatta agacactata atgtcgttac      840
agggagtaaa gcaacatcaa cggacaaatt tttacagacc tcacgggatg gctgtcgta      900 gcagatctat ttggataaag aattcagata tttcttgtag tccgtcgtct gtctagcatt      960
ttgcgtcacc cccctttttg ggtataataa tccagtagtt tcgatgctcc aacagaacag     1020
cagaagtctt tacacaacta cagtagaa                                         1048
```

<210> SEQ ID NO 98
<211> LENGTH: 1027
<212> TYPE: DNA
<213> ORGANISM: Triticum aestivum

<400> SEQUENCE: 98

```
ttgcagatgt tcgcatacac tcaaccataa gaatgcatgc acacacacac tcctactaaa       60
tgcacatcgc cgaaaggcct gaaatgaatg caagaaaatg cgaccaccag tgtcaagtct      120
```

```
agaacttgaa ccctggtggg ttatttccat cacaagcaac ctaaccattt gagttaccct      180
cagctcgcta tgccaacatt aattaacaat agcaaacttg tttcactata tttatcataa      240
tataatttct agatatatag tcaaaataat ttcaaatatt tatgaatgaa gggagcacca      300
tgctatggta atatagatgc attactttgg aggagctagt tgtaggtagc tctaaacatg      360
tattttcata gtttctaatt tttggcatgt attttctatc ttctatgtgt atatcttttt      420
cgggattctg tatgtatatg tgtatatgta cttttcgttg cacttagtac aacacaagtc      480
aggtggttgc cctgagctcc ttctcttcat gatgccacgc tcacaccta cgatacatat       540 ccaacggagc ggggcatcgc acccgtgggg caccaactga ctcttgttcg ttaccggtga      600
tacggacgtg gaacttatca ctcacccgca aaaaaaaag ttatcactcg attccattgt       660
ttcttccaca gtctgctct cttgtaggag tacctaattt tcgtcatatg atatgcctcg       720 caaaaagat atgcctccca cgagctccca ttgtgcgcta gcttttgcga ttagattcag       780
taattaagac actataatgt cgttgcaggg agtaaagcaa catcaacgga caaatttta       840 cagacctcac gggatgggct gtcgtagcag atctatttgg aaaaagaaat tagagatttt      900
ctttgtagtc cgtccgtttg tctagcattt ttgcgtccac ccccctttt tgggtataat       960 aatccattag tctctgattg cctccaacaa aacagaccaa gaagtctcta cacaacttac      1020
agtagaa                                                                1027

<210> SEQ ID NO 99
<211> LENGTH: 795
<212> TYPE: DNA
<213> ORGANISM: Triticum aestivum

<400> SEQUENCE: 99
tggtcatgat gtaagtagtc ctttcatccc ttttttactc cgcatataag atttgtctga       60
agttgaactt tataaaattt aactgatctt gtaaataaaa atatcaccat tcacacagta      120
cgaaatcata ccattagatg cgacgtgaat taaatattca tatcaatata tttttagttt      180
tgcagatgtt gatattttt catataaata tgtggtgaaa ctttatgaac ttttttttccc      240 ctccactcca tatagatttt atatacatag tgaaaatgac cggagggagt acgttaaata      300
ccttcactcc atcaattcta gatagtgata accataaact ctctcatatc atgctcgtgc      360
ctacacacta cgaacaggta cctaccacct tacactacat ttctaccagt ggaagacgac      420
agcgaccaac aagtgggagc agatcagcac caccagaaaa gggtaacaat catatggcgg      480
aagctgctca tgtcaccgct ctcgtgcttg gccatcttca tcgctgtcgt gtgcatcacg      540
gagcggcggc agatctccga tgaccccctc aacttcaaag tcctcaacat caccgtcgag      600
gttatcaggt aatcccctac ttaacaaaac gtataagcac atgatcaatt gcaatattct      660
taccatacat gatcgatacc attatacatg aaatccgaga cttacccaaa ttgcaaattc      720
agtcaactta catatagcta tcgccaccac tataacgtat gacattgtgt gaactgtgct      780
tgcagtgcgt acgga                                                       795

<210> SEQ ID NO 100
<211> LENGTH: 777
<212> TYPE: DNA
<213> ORGANISM: Triticum aestivum

<400> SEQUENCE: 100
tggtcatgat gtaagtagtc ccttcatccc ttttttactc cgcaaataag atttgtctga       60
aatcgaactt tataaaattt aactaatctt gtaaatgtac gaaatcatac cattagatgc      120
```

```
ggcgtgaatt aaattttcat atcaatatat ttttagtttt gcagatgttg atattttttc    180
atataaatat gtggtgaaac tttatgaagg cttttcccc tccactccat atatagattt    240
tatatacgta gtgaaaatga caggagggag tacgttaaat accttcactc catccattct    300
agatagtgat aaccataaac tctctcatat catgctcgtg cctacacact acgaacaggt    360
acctaccacc ttacactaca tttctaccag tggaagacga cagtgaccaa caagtgggag    420
cagatcagca ccaccagaaa agggtaacaa gcatatggcg gaagctgctc atgtcgccgc    480
tctcgttctt ggccatcttc atcgccgtcg tgtgcatcac ggagcggcgg cagatctccg    540
atgaccccct caacttcaac gtcctcaaca tcaccgtcga ggttatcagg taatccccta    600
cttaacaaaa gcgtataagc acatgatcaa ttgcaatatt cttaccatac atgatcgata    660
ccattagacg tgaaatcgga gacttaccca aattggaaat tcagtcaact tacatatagc    720
tatcgccacc actataacgt gtgacattgt gtgaactgtg cttgcagtgc gtacgga    777

<210> SEQ ID NO 101
<211> LENGTH: 787
<212> TYPE: DNA
<213> ORGANISM: Triticum aestivum

<400> SEQUENCE: 101
tggtcatgat gtgagtactt cctcaagtcc attttactcc gcatataaag tttgtctgaa    60
gtcgaacttt ataaaattta actaattttg taaagaaac atcaccattc acacagtacg    120
aaatcatacc attagatgcg tcatgaatta aattttcata tcatatattt ttagttttgc    180
agatgttgat attttttcat ataaatatgt ggttaaactt tctgaacttt ttccctcca    240 ctccatatac atttatata cagagtgaaa atgaccggag ggagtacgtt acatacctcc    300
actcgatcga ttcagatagt gataaccata aactctctca tatcatgctc gtgcctatac    360
actacgaaca ggtacctacc acctacact acatttctac cagtggaaga cgacagtgac    420
caacaagtgg gagcagatca gcgcgaccag aaaaggataa caagcatgtg gcggaagctg    480
ctcatgtcgc cgctctcgtg cttggccatc ttcatcgccg tggtgtgcat cacggagcgg    540
cggcagatct ccgatgaccc cctcaacttc aacgtcctca acatcaccgt cgaggttatc    600
aggtaatcca ctacttaaca aaacgtataa gcacatgatc aattgcaata ttcttaccat    660
gcatgatcga taccattata cacaaaacct tacttaccca aattgcaaat tcaatcagca    720
tacatatagc tattgcgacc actataacgt gtggcattgt gtgaactgtg cttgcagtgc    780
gtacgga    787

<210> SEQ ID NO 102
<211> LENGTH: 751
<212> TYPE: DNA
<213> ORGANISM: Triticum monococcum

<400> SEQUENCE: 102
tggtcatgat gtaagtagtc cttcagtcca ttttactccg cgtataagat tgtcaatttt    60
tatagaaaaa aaatctaacc attcacacta cagaatcaat ctaaccattc acactacaga    120
atcaatatca ttagatgtgt tattatttaa ttatcatatt ttatacttta atattgcaga    180
tgttgatttt ttgtcatata aatatggtca aactaaataa acctttataa tgtttgactt    240
cagacaatct tacactcctt cgattctaga tagtgataac catcaactct ctcatatcat    300
gctcttgccc acacactacg agcaggtacc taccacctta cactacattt ctaccagtgg    360
aagacgacag tgaccaacaa gtgggagcag atcagcacga ccacaaaagg ataacaagca    420
```

```
tatgccacaa gctgctcatg tcgccgctct cgtgcctggc catcttcatc gccgttgtgt    480
gcatcaccga gcgccggcag atctccgatg accccctcaa cttcaacgtc ctcaacatca    540
ctgtcgaagt tatcaggtaa tcaactagta gtaattaaca aaatgtagaa gcacatgatc    600
aattgcaatt tttttaccat gcatgatagg tagataccat tatatacaaa atctgactta    660
gctaaattgc aaattcagta aacttatata taggtattgc gaccactata acgtgtgtca    720
ttgtgtgagc tgtgcttgca gtgcgtacgg a                                   751
```

<210> SEQ ID NO 103
<211> LENGTH: 26
<212> TYPE: PRT
<213> ORGANISM: Triticum monococcum

<400> SEQUENCE: 103

Ser Leu His Thr Phe Ser Val Phe Thr Val Val Ser Thr Phe Ala Asn
1               5                   10                  15

Cys Gly Phe Val Pro Asn Asn Glu Gly Met
            20                  25

<210> SEQ ID NO 104
<211> LENGTH: 26
<212> TYPE: PRT
<213> ORGANISM: Triticum aestivum

<400> SEQUENCE: 104

Ser Leu His Thr Phe Ser Val Phe Thr Val Val Ser Thr Phe Ala Asn
1               5                   10                  15

Cys Gly Phe Val Pro Asn Asn Glu Gly Met
            20                  25

<210> SEQ ID NO 105
<211> LENGTH: 26
<212> TYPE: PRT
<213> ORGANISM: Triticum turgidum

<400> SEQUENCE: 105

Ser Leu His Thr Phe Ser Val Phe Thr Val Val Ser Thr Phe Ala Asn
1               5                   10                  15

Gly Gly Phe Val Pro Asn Asn Glu Gly Met
            20                  25

<210> SEQ ID NO 106
<211> LENGTH: 26
<212> TYPE: PRT
<213> ORGANISM: Triticum turgidum

<400> SEQUENCE: 106

Ser Leu His Thr Phe Ser Val Phe Thr Val Val Ser Thr Phe Ala Asn
1               5                   10                  15

Gly Gly Phe Met Pro Asn Asn Glu Glu Met
            20                  25

<210> SEQ ID NO 107
<211> LENGTH: 26
<212> TYPE: PRT
<213> ORGANISM: Triticum turgidum

<400> SEQUENCE: 107

Ser Leu His Thr Phe Ser Ala Phe Thr Val Val Ser Thr Phe Ala Asn
1               5                   10                  15

Gly Gly Phe Ala Pro Asn Asn Glu Gly Met

<210> SEQ ID NO 108
<211> LENGTH: 26
<212> TYPE: PRT
<213> ORGANISM: Oryza sativa

<400> SEQUENCE: 108

Ser Ala His Thr Phe Ala Ile Phe Thr Val Val Ser Thr Phe Ala Asn
1               5                   10                  15

Cys Gly Phe Val Pro Thr Asn Glu Gly Met
            20                  25

<210> SEQ ID NO 109
<211> LENGTH: 26
<212> TYPE: PRT
<213> ORGANISM: Triticum turgidum

<400> SEQUENCE: 109

Ser Val Trp Thr Phe Ala Val Phe Thr Thr Val Ser Thr Phe Ser Ser
1               5                   10                  15

Cys Gly Phe Met Pro Asn Asn Glu Asn Met
            20                  25

<210> SEQ ID NO 110
<211> LENGTH: 26
<212> TYPE: PRT
<213> ORGANISM: Oryza sativa

<400> SEQUENCE: 110

Asn Thr Trp Thr Phe Ala Val Phe Thr Thr Val Ser Thr Phe Ser Asn
1               5                   10                  15

Cys Gly Phe Met Pro Thr Asn Glu Asn Met
            20                  25

<210> SEQ ID NO 111
<211> LENGTH: 26
<212> TYPE: PRT
<213> ORGANISM: Triticum monococcum

<400> SEQUENCE: 111

Gly Leu Phe Leu Phe Ser Val Phe Thr Ala Ile Ser Ser Val Ala Asn
1               5                   10                  15

Cys Gly Phe Thr Pro Val Asn Glu Asn Met
            20                  25

<210> SEQ ID NO 112
<211> LENGTH: 26
<212> TYPE: PRT
<213> ORGANISM: Oryza sativa

<400> SEQUENCE: 112

Gly Ile Ile Val Phe Ser Val Phe Thr Ala Ile Ser Ser Val Gly Asn
1               5                   10                  15

Cys Gly Phe Thr Pro Val Asn Glu Asn Met
            20                  25

<210> SEQ ID NO 113
<211> LENGTH: 26
<212> TYPE: PRT
<213> ORGANISM: Triticum turgidum

<400> SEQUENCE: 113

-continued

Lys Met Trp Thr Phe Ser Ile Phe Thr Ala Val Ser Ser Phe Ala Asn
1               5                   10                  15

Cys Gly Phe Thr Pro Leu Asn Asp Ser Met
            20                  25

<210> SEQ ID NO 114
<211> LENGTH: 26
<212> TYPE: PRT
<213> ORGANISM: Oryza sativa

<400> SEQUENCE: 114

Lys Ile Trp Thr Phe Ser Ile Phe Thr Ala Val Ser Ser Phe Ala Asn
1               5                   10                  15

Cys Gly Phe Thr Pro Val Asn Asp Asn Met
            20                  25

<210> SEQ ID NO 115
<211> LENGTH: 26
<212> TYPE: PRT
<213> ORGANISM: Oryza sativa

<400> SEQUENCE: 115

Asn Met Tyr Thr Phe Cys Ile Phe Thr Ala Val Ser Ser Phe Ala Asn
1               5                   10                  15

Cys Gly Phe Thr Pro Leu Asn Ser Asn Met
            20                  25

<210> SEQ ID NO 116
<211> LENGTH: 26
<212> TYPE: PRT
<213> ORGANISM: Aegilops tauschii

<400> SEQUENCE: 116

Ser Pro Leu Thr Phe Ser Val Phe Thr Val Ser Thr Phe Ala Asn
1               5                   10                  15

Cys Gly Phe Val Pro Thr Asn Glu Asn Met
            20                  25

<210> SEQ ID NO 117
<211> LENGTH: 26
<212> TYPE: PRT
<213> ORGANISM: Eucalyptus camaldulensis

<400> SEQUENCE: 117

Lys Met Met Thr Phe Ser Ile Phe Thr Thr Val Ser Thr Phe Ala Ser
1               5                   10                  15

Cys Gly Phe Val Pro Thr Asn Glu Asn Met
            20                  25

<210> SEQ ID NO 118
<211> LENGTH: 26
<212> TYPE: PRT
<213> ORGANISM: Eucalyptus camaldulensis

<400> SEQUENCE: 118

Lys Met Val Thr Phe Ser Val Phe Thr Val Ser Thr Phe Ala Ser
1               5                   10                  15

Cys Gly Phe Val Pro Thr Asn Glu Asn Met
            20                  25

<210> SEQ ID NO 119
<211> LENGTH: 26
<212> TYPE: PRT

<213> ORGANISM: Suaeda maritima

<400> SEQUENCE: 119

Lys Thr Phe Thr Phe Ser Ile Phe Ser Val Val Ser Thr Phe Ala Ser
1               5                   10                  15

Cys Gly Phe Thr Pro Thr Asn Glu Asn Met
            20                  25

<210> SEQ ID NO 120
<211> LENGTH: 26
<212> TYPE: PRT
<213> ORGANISM: Mesembryanthemum crystallinum

<400> SEQUENCE: 120

Lys Ser Ile Thr Phe Ala Ile Phe Thr Ser Val Ser Thr Phe Ser Ser
1               5                   10                  15

Cys Gly Phe Val Pro Thr Asn Glu Asn Met
            20                  25

<210> SEQ ID NO 121
<211> LENGTH: 26
<212> TYPE: PRT
<213> ORGANISM: Populus tenuiflora

<400> SEQUENCE: 121

Lys Ile Gln Thr Phe Ser Val Phe Thr Thr Val Ser Thr Phe Ser Asn
1               5                   10                  15

Cys Gly Phe Val Pro Thr Asn Glu Asn Met
            20                  25

<210> SEQ ID NO 122
<211> LENGTH: 26
<212> TYPE: PRT
<213> ORGANISM: Mesembryanthemum crystallinum

<400> SEQUENCE: 122

Glu Met His Leu Phe Ser Leu Phe Val Thr Val Ser Thr Phe Ser Asn
1               5                   10                  15

Cys Gly Phe Ile Pro Thr Asn Glu Asn Met
            20                  25

<210> SEQ ID NO 123
<211> LENGTH: 26
<212> TYPE: PRT
<213> ORGANISM: Hordeum vulgare

<400> SEQUENCE: 123

Asn Ile Val Leu Phe Ser Leu Ser Val Thr Val Ala Ser Ile Ala Asn
1               5                   10                  15

Gly Gly Leu Val Pro Thr Asn Glu Asn Met
            20                  25

<210> SEQ ID NO 124
<211> LENGTH: 26
<212> TYPE: PRT
<213> ORGANISM: Triticum aestivum

<400> SEQUENCE: 124

Asn Ile Val Leu Phe Ser Leu Ser Val Thr Val Ala Ser Cys Ala Asn
1               5                   10                  15

Ala Gly Leu Val Pro Thr Asn Glu Asn Met
            20                  25

<210> SEQ ID NO 125
<211> LENGTH: 26
<212> TYPE: PRT
<213> ORGANISM: Phragmites australis

<400> SEQUENCE: 125

Asn Val Ala Leu Phe Ser Val Ser Val Thr Val Ser Ser Phe Ala Asn
1               5                   10                  15

Gly Gly Leu Val Pro Thr Asn Glu Asn Met
            20                  25

<210> SEQ ID NO 126
<211> LENGTH: 26
<212> TYPE: PRT
<213> ORGANISM: Oryza sativa

<400> SEQUENCE: 126

Asn Ile Ala Leu Phe Ser Phe Ser Val Thr Val Ser Ser Phe Ala Asn
1               5                   10                  15

Gly Gly Leu Val Pro Thr Asn Glu Asn Met
            20                  25

<210> SEQ ID NO 127
<211> LENGTH: 26
<212> TYPE: PRT
<213> ORGANISM: Oryza sativa

<400> SEQUENCE: 127

Asn Ala Ile Leu Phe Ser Phe Ser Val Thr Val Ser Ser Phe Ala Asn
1               5                   10                  15

Val Gly Leu Val Pro Thr Asn Glu Asn Met
            20                  25

<210> SEQ ID NO 128
<211> LENGTH: 26
<212> TYPE: PRT
<213> ORGANISM: Triticum monococcum

<400> SEQUENCE: 128

Asn Thr Met Leu Phe Ser Ile Ser Val Thr Val Ser Ser Phe Thr Asn
1               5                   10                  15

Gly Gly Leu Ile Pro Thr Asn Glu Ser Met
            20                  25

<210> SEQ ID NO 129
<211> LENGTH: 26
<212> TYPE: PRT
<213> ORGANISM: Triticum aestivum

<400> SEQUENCE: 129

Asn Thr Met Leu Phe Ser Ile Ser Val Thr Val Ser Ser Phe Thr Asn
1               5                   10                  15

Gly Gly Leu Ile Pro Thr Asn Glu Ser Met
            20                  25

<210> SEQ ID NO 130
<211> LENGTH: 26
<212> TYPE: PRT
<213> ORGANISM: Triticum aestivum

<400> SEQUENCE: 130

Asn Thr Met Leu Phe Ser Ile Ser Val Thr Val Ser Ser Phe Thr Asn
1               5                   10                  15

```
Gly Gly Leu Ile Pro Thr Asn Glu Ser Met
            20                  25

<210> SEQ ID NO 131
<211> LENGTH: 26
<212> TYPE: PRT
<213> ORGANISM: Triticum turgidum

<400> SEQUENCE: 131

Asn Thr Met Leu Phe Ser Ile Ser Val Thr Val Ser Ser Phe Thr Asn
1               5                   10                  15

Gly Gly Leu Ile Pro Thr Asn Glu Ser Met
            20                  25

<210> SEQ ID NO 132
<211> LENGTH: 26
<212> TYPE: PRT
<213> ORGANISM: Oryza sativa

<400> SEQUENCE: 132

Asn Lys Ala Leu Phe Ser Ile Ser Val Thr Val Ser Ser Phe Thr Asn
1               5                   10                  15

Gly Gly Leu Leu Pro Thr Asn Glu Ser Met
            20                  25

<210> SEQ ID NO 133
<211> LENGTH: 26
<212> TYPE: PRT
<213> ORGANISM: Oryza sativa

<400> SEQUENCE: 133

Asn Lys Ala Leu Phe Ser Ile Ser Val Thr Val Ser Ser Phe Thr Asn
1               5                   10                  15

Gly Gly Leu Leu Pro Thr Asn Glu Ser Met
            20                  25

<210> SEQ ID NO 134
<211> LENGTH: 13
<212> TYPE: PRT
<213> ORGANISM: Triticum monococcum

<400> SEQUENCE: 134

Gly Tyr Asp His Leu Leu Thr Ser Arg His Thr Trp Phe
1               5                   10

<210> SEQ ID NO 135
<211> LENGTH: 13
<212> TYPE: PRT
<213> ORGANISM: Triticum aestivum

<400> SEQUENCE: 135

Gly Tyr Asp His Leu Leu Thr Ser Arg His Trp Thr Phe
1               5                   10

<210> SEQ ID NO 136
<211> LENGTH: 13
<212> TYPE: PRT
<213> ORGANISM: Triticum turgidum

<400> SEQUENCE: 136

Gly Tyr Asp His Leu Leu Thr Ser Arg His Thr Cys Phe
1               5                   10
```

<210> SEQ ID NO 137
<211> LENGTH: 13
<212> TYPE: PRT
<213> ORGANISM: Triticum turgidum

<400> SEQUENCE: 137

Gly Tyr Gly His Leu Leu Thr Ser Arg His Thr Cys Phe
1               5                   10

<210> SEQ ID NO 138
<211> LENGTH: 13
<212> TYPE: PRT
<213> ORGANISM: Oryza sativa

<400> SEQUENCE: 138

Gly Tyr His His Leu Leu Pro Ser Ser Arg Thr Arg Phe
1               5                   10

<210> SEQ ID NO 139
<211> LENGTH: 13
<212> TYPE: PRT
<213> ORGANISM: Oryza sativa

<400> SEQUENCE: 139

Gly Tyr Asp His Leu Leu Pro Ser Ser Arg Thr Arg Phe
1               5                   10

<210> SEQ ID NO 140
<211> LENGTH: 13
<212> TYPE: PRT
<213> ORGANISM: Oryza sativa

<400> SEQUENCE: 140

Gly Tyr Ala His Leu Met Pro Ala Arg Arg Cys Trp Met
1               5                   10

<210> SEQ ID NO 141
<211> LENGTH: 13
<212> TYPE: PRT
<213> ORGANISM: Triticum turgidum

<400> SEQUENCE: 141

Gly Tyr Tyr His Leu Leu Pro Ala Arg Arg Cys Ala Met
1               5                   10

<210> SEQ ID NO 142
<211> LENGTH: 13
<212> TYPE: PRT
<213> ORGANISM: Suaeda maritima

<400> SEQUENCE: 142

Glu Tyr His His Leu Leu Ser Ser Lys His Ser Arg Phe
1               5                   10

<210> SEQ ID NO 143
<211> LENGTH: 13
<212> TYPE: PRT
<213> ORGANISM: Mesembryanthemum crystallinum

<400> SEQUENCE: 143

Ala Tyr His His Leu Leu Pro Thr Lys His Ser Lys Tyr
1               5                   10

<210> SEQ ID NO 144
<211> LENGTH: 13
<212> TYPE: PRT

<213> ORGANISM: Eucalyptus camaldulensis

<400> SEQUENCE: 144

Gly Tyr Lys His Leu Leu Pro Ser Leu Tyr Ser Ser Leu
1               5                   10

<210> SEQ ID NO 145
<211> LENGTH: 13
<212> TYPE: PRT
<213> ORGANISM: Eucalyptus camaldulensis

<400> SEQUENCE: 145

Gly Tyr Lys His Leu Leu Pro Ser Leu Tyr Ser Ser Leu
1               5                   10

<210> SEQ ID NO 146
<211> LENGTH: 13
<212> TYPE: PRT
<213> ORGANISM: Populus tenuiflora

<400> SEQUENCE: 146

Gly Tyr Gly His Leu Leu Ser Phe Ser His Ser Cys Leu
1               5                   10

<210> SEQ ID NO 147
<211> LENGTH: 13
<212> TYPE: PRT
<213> ORGANISM: Mesembryanthemum crystallinum

<400> SEQUENCE: 147

Gly Tyr Gly Leu Phe Phe Ser Gln Val Asp Ala Leu Leu
1               5                   10

<210> SEQ ID NO 148
<211> LENGTH: 13
<212> TYPE: PRT
<213> ORGANISM: Aegilops tauschii

<400> SEQUENCE: 148

Gly Tyr Ser His Leu Leu Ser Val Arg Leu Cys Val Leu
1               5                   10

<210> SEQ ID NO 149
<211> LENGTH: 13
<212> TYPE: PRT
<213> ORGANISM: Oryza sativa

<400> SEQUENCE: 149

Gly Tyr Lys His Leu Met Ser Thr Arg Glu Ser Val Tyr
1               5                   10

<210> SEQ ID NO 150
<211> LENGTH: 13
<212> TYPE: PRT
<213> ORGANISM: Oryza sativa

<400> SEQUENCE: 150

Gly Tyr Arg Tyr Leu Gln Leu Gln Lys Asn Ser Val Asn
1               5                   10

<210> SEQ ID NO 151
<211> LENGTH: 13
<212> TYPE: PRT
<213> ORGANISM: Oryza sativa

<400> SEQUENCE: 151

```
Gly Tyr Lys His Leu His Val Arg Arg Asn Ser Val Tyr
1               5                   10

<210> SEQ ID NO 152
<211> LENGTH: 13
<212> TYPE: PRT
<213> ORGANISM: Triticum turgidum

<400> SEQUENCE: 152

Gly Tyr Arg His Leu Gln Pro His Lys Asn Ser Val Gln
1               5                   10

<210> SEQ ID NO 153
<211> LENGTH: 13
<212> TYPE: PRT
<213> ORGANISM: Triticum turgidum

<400> SEQUENCE: 153

Gly Tyr Arg His Leu Gln Pro His Lys Asn Ser Val Gln
1               5                   10

<210> SEQ ID NO 154
<211> LENGTH: 13
<212> TYPE: PRT
<213> ORGANISM: Oryza sativa

<400> SEQUENCE: 154

Gly Phe Ser His Leu Leu Pro Asn Leu Gln Thr Ile Phe
1               5                   10

<210> SEQ ID NO 155
<211> LENGTH: 13
<212> TYPE: PRT
<213> ORGANISM: Oryza sativa

<400> SEQUENCE: 155

Gly Phe Ser His Leu Leu Pro Asn Leu Gln Thr Ile Phe
1               5                   10

<210> SEQ ID NO 156
<211> LENGTH: 13
<212> TYPE: PRT
<213> ORGANISM: Oryza sativa

<400> SEQUENCE: 156

Gln Tyr Asp Tyr Leu Leu Pro Lys Leu Pro Thr Ala Phe
1               5                   10

<210> SEQ ID NO 157
<211> LENGTH: 13
<212> TYPE: PRT
<213> ORGANISM: Oryza sativa

<400> SEQUENCE: 157

Gln Tyr Asp Tyr Leu Leu Pro Lys Leu Pro Thr Ala Phe
1               5                   10

<210> SEQ ID NO 158
<211> LENGTH: 13
<212> TYPE: PRT
<213> ORGANISM: Triticum aestivum

<400> SEQUENCE: 158

Arg Phe Ala Asn Leu Leu Ala Arg Leu Pro Thr Val Phe
1               5                   10
```

<210> SEQ ID NO 159
<211> LENGTH: 13
<212> TYPE: PRT
<213> ORGANISM: Hordeum vulgare

<400> SEQUENCE: 159

His Phe Gly Asn Leu Leu Pro Arg Leu Pro Thr Val Phe
1               5                   10

<210> SEQ ID NO 160
<211> LENGTH: 25
<212> TYPE: DNA
<213> ORGANISM: Artificial
<220> FEATURE:
<223> OTHER INFORMATION: AloI Enzyme Recognition Site
<220> FEATURE:
<221> NAME/KEY: misc_feature
<222> LOCATION: (1)..(12)
<223> OTHER INFORMATION: Each n is a, t, g, or c, individually.
<220> FEATURE:
<221> NAME/KEY: misc_feature
<222> LOCATION: (17)..(22)
<223> OTHER INFORMATION: Each n is a, t, g, or c, individually.

<400> SEQUENCE: 160
nnnnnnnnnn nngaacnnnn nntcc                                          25

<210> SEQ ID NO 161
<211> LENGTH: 26
<212> TYPE: DNA
<213> ORGANISM: Artificial
<220> FEATURE:
<223> OTHER INFORMATION: BaeI Enzyme Recognition Site
<220> FEATURE:
<221> NAME/KEY: misc_feature
<222> LOCATION: (1)..(15)
<223> OTHER INFORMATION: Each n is a, t, g, or c, individually.
<220> FEATURE:
<221> NAME/KEY: misc_feature
<222> LOCATION: (18)..(21)
<223> OTHER INFORMATION: Each n is a, t, g, or c, individually.

<400> SEQUENCE: 161
nnnnnnnnnn nnnnnacnnn ngtayc                                         26

<210> SEQ ID NO 162
<211> LENGTH: 24
<212> TYPE: DNA
<213> ORGANISM: Artificial
<220> FEATURE:
<223> OTHER INFORMATION: BcgI Enzyme Recognition Site
<220> FEATURE:
<221> NAME/KEY: misc_feature
<222> LOCATION: (1)..(12)
<223> OTHER INFORMATION: Each n is a, t, g, or c, individually.
<220> FEATURE:
<221> NAME/KEY: misc_feature
<222> LOCATION: (16)..(21)
<223> OTHER INFORMATION: Each n is a, t, g, or c, individually.

<400> SEQUENCE: 162
nnnnnnnnnn nncgannnnn ntgc                                           24

<210> SEQ ID NO 163
<211> LENGTH: 23
<212> TYPE: DNA
<213> ORGANISM: Artificial
<220> FEATURE:
<223> OTHER INFORMATION: BsaXI Enzyme Recognition Site
<220> FEATURE:

```
<221> NAME/KEY: misc_feature
<222> LOCATION: (1)..(12)
<223> OTHER INFORMATION: Each n is a, t, g, or c, individually.
<220> FEATURE:
<221> NAME/KEY: misc_feature
<222> LOCATION: (15)..(19)
<223> OTHER INFORMATION: Each n is a, t, g, or c, individually.

<400> SEQUENCE: 163
nnnnnnnnnn nnacnnnnnc tcc                                             23

<210> SEQ ID NO 164
<211> LENGTH: 10
<212> TYPE: DNA
<213> ORGANISM: Artificial
<220> FEATURE:
<223> OTHER INFORMATION: BsmAI Enzyme Recognition Site
<220> FEATURE:
<221> NAME/KEY: misc_feature
<222> LOCATION: (6)..(10)
<223> OTHER INFORMATION: Each n is a, t, g, or c, individually.

<400> SEQUENCE: 164 gtctcnnnnn                                                            10

<210> SEQ ID NO 165
<211> LENGTH: 24
<212> TYPE: DNA
<213> ORGANISM: Artificial
<220> FEATURE:
<223> OTHER INFORMATION: PpiI Enzyme Recognition Site
<220> FEATURE:
<221> NAME/KEY: misc_feature
<222> LOCATION: (1)..(12)
<223> OTHER INFORMATION: Each n is a, t, g, or c, individually.
<220> FEATURE:
<221> NAME/KEY: misc_feature
<222> LOCATION: (17)..(21)
<223> OTHER INFORMATION: Each n is a, t, g, or c, individually.

<400> SEQUENCE: 165
nnnnnnnnnn nngaacnnnn nctc                                            24
```